(12) United States Patent
Koehn et al.

(10) Patent No.: US 11,304,418 B2
(45) Date of Patent: Apr. 19, 2022

(54) SUBSTITUTED N-(-1,3,4-OXADIAZOLE-2-YL)ARYL CARBOXAMIDES AND THE USE THEREOF AS HERBICIDES

(71) Applicant: Bayer CropScience Aktiengesellschaft, Monheim am Rhein (DE)

(72) Inventors: Arnim Koehn, Klein-Winternheim (DE); Hartmut Ahrens, Langen (DE); Christian Waldraff, Bad Vilbel (DE); Ralf Braun, Ramberg (DE); Stephen David Lindell, Eppstein (DE); Anu Bheemaiah Machettira, Frankfurt am Main (DE); Elmar Gatzweiler, Bad Nauheim (DE); Christopher Hugh Rosinger, Hofheim (DE); Hansjoerg Dietrich, Liederbach am Taunus (DE)

(73) Assignee: Bayer CropScience Aktiengesellschaft

( * ) Notice: Subject to any disclaimer, the term of this patent is extended or adjusted under 35 U.S.C. 154(b) by 249 days.

(21) Appl. No.: 16/497,814

(22) PCT Filed: Mar. 22, 2018

(86) PCT No.: PCT/EP2018/057268
§ 371 (c)(1),
(2) Date: Sep. 26, 2019

(87) PCT Pub. No.: WO2018/177871
PCT Pub. Date: Oct. 4, 2018

(65) Prior Publication Data
US 2021/0076680 A1    Mar. 18, 2021

(30) Foreign Application Priority Data

Mar. 30, 2017 (EP) .................... 17163727

(51) Int. Cl.
*A01N 43/82* (2006.01)
*C07D 271/113* (2006.01)

(52) U.S. Cl.
CPC .......... *A01N 43/82* (2013.01); *C07D 271/113* (2013.01)

(58) Field of Classification Search
CPC .......................... A01N 43/82; C07D 271/113
See application file for complete search history.

(56) References Cited

U.S. PATENT DOCUMENTS

| | | | |
|---|---|---|---|
| 8,288,316 B2 | 10/2012 | Koehn et al. | |
| 8,481,749 B2 | 7/2013 | Braun et al. | |
| 9,101,141 B2 | 8/2015 | Koehn et al. | |
| 2014/0080705 A1* | 3/2014 | Koehn | A01N 43/82 504/105 |
| 2018/0360046 A1* | 12/2018 | Kordes | C07D 271/07 |

FOREIGN PATENT DOCUMENTS

| | | |
|---|---|---|
| CN | 1126208 A * | 7/1996 |
| EP | 0 173 657 A2 | 3/1986 |
| WO | 2011/035874 A1 | 3/2011 |
| WO | 2012/028579 A1 | 3/2012 |
| WO | 2012/126932 A1 | 9/2012 |
| WO | 2013/083859 A2 | 6/2013 |
| WO | 2014/113467 A1 | 7/2014 |
| WO | 2014/144710 A1 | 9/2014 |
| WO | 2014/184015 A1 | 11/2014 |
| WO | 2017/102275 A1 | 6/2017 |

OTHER PUBLICATIONS

PCT International Search Report for PCT/EP2018/057268, dated May 11, 2018.

* cited by examiner

*Primary Examiner* — Mina Haghighatian
*Assistant Examiner* — Nathan W Schlientz
(74) *Attorney, Agent, or Firm* — McBee Moore & Vanik IP, LLC

(57) ABSTRACT

Disclosed are N-(1,3,4-oxadiazole-2-yl)aryl carboxamides of formula (I) or the salts (I) thereof as well as the use thereof as herbicides.

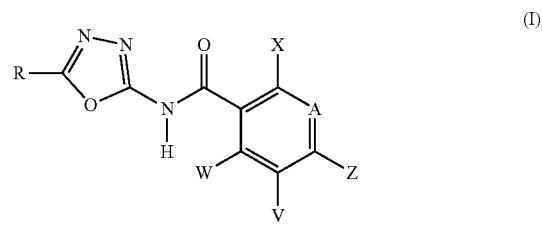

16 Claims, No Drawings

SUBSTITUTED N-(-1,3,4-OXADIAZOLE-2-YL)ARYL CARBOXAMIDES AND THE USE THEREOF AS HERBICIDES

CROSS-REFERENCE TO RELATED APPLICATIONS

This application is the National Stage entry of International Application No. PCT/EP2018/057268, filed 22 Mar. 2018, which claims priority to European Patent Application No. 17163727.5, filed 30 Mar. 2017.

BACKGROUND

Field

The invention relates to the technical field of the herbicides, in particular the field of the heterocyclically substituted arylcarboxamides for the selective control of broad-leaved weeds and weed grasses in crops of useful plants.

Description of Related Art

The herbicidal action of heterocyclically substituted arylcarboxamides is known.

According to the heterocyclic moiety of these compounds, the herbicides of the prior art can be divided into tetrazole- and triazole-substituted arylcarboxamides and oxadiazole-substituted arylcarboxamides.

Document WO 2012/028579 A1 discloses N-(tetrazol-4-yl)benzamides and N-(triazol-3-yl)benzamides which are substituted in the 2-, 3- and 4-position of the phenyl ring and have herbicidal action.

Document WO 2014/184015 A1, too, discloses N-(tetrazol-4-yl)benzamides and N-(triazol-3-yl)benzamides having herbicidal action, and the compounds disclosed in document WO 2014/184015 are substituted at the phenyl ring in position 2, 3, 4 and also in position 5 and 6.

Document WO 2011/035874 A1 discloses oxadiazole-substituted benzamide compounds, namely N-(1,2,5-oxadiazol-3-yl)phenylbenzamides, which are substituted in the 2-, 3- and 4-position of the phenyl ring and have herbicidal action. Further N-(1,2,5-oxadiazol-3-yl)phenylbenzamides are known from EP 0 173 657 A1.

Document WO 2012/126932 A1, too, discloses N-(1,3,4-oxadiazol-2-yl)benzamides, where the benzyl (aryl moiety) is likewise in each case only substituted in position 2, 3 and 4, i.e. the compounds with herbicidal activity known from WO 2012/126932 A1 are not substituted in positions 5 and 6 of the phenyl moiety.

A further document, WO 2017/102275 A1, which, with respect to the present application, is a document according to Art. 54 (3) EPC, discloses further N-(1,3,4-oxadiazol-2-yl)benzamides with the alternative $Q^4$=1,3,4-oxadiazol-2-yl. The compounds claimed in WO 2017/102275 A1 are distinguished by a phenyl substituent, referred to as $R^2$, which has a diamide structure. The two compounds specified in WO 2017/102275 A1 in a list (Table IV, page 113) were excluded from the scope of the present invention.

Moreover, the starting material used in WO 2017/102275 A1, namely 3-amino-4-bromo-6-fluoro-2-methyl-N-(5-methyl-1,3,4-oxadiazol-2-yl)benzamide, was excluded from the scope of the present invention. This compound, disclosed in connection with Example 3 in WO 2017/102275 A1, has an amino group in the position of the radical Y of the present invention, instead of a radical with diamide structure.

In addition to the three compounds mentioned above, the scope of the present invention excludes six further commercially available compounds. For these six compounds, no use of the compounds as herbicide was found in the prior art.

However, the known N-(1,3,4-oxadiazol-2-yl)benzamides frequently have insufficient herbicidal activity.

SUMMARY

Accordingly, it is an object of the present invention to provide further N-(1,3,4-oxadiazol-2-yl)benzamides having improved herbicidal activity.

The object is achieved by N-(1,3,4-oxadiazol-2-yl)arylcarboxamides according to claim 1, i.e. by N-(1,3,4-oxadiazol-2-yl)arylcarboxamides of the formula (I) or salts thereof

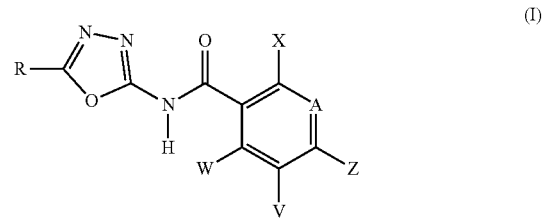

(I)

where the substituents have the following meanings:
A represents N or C—Y,
R represents hydrogen, halogen, $(C_1-C_6)$-alkyl, $R^1O$—$(C_1-C_6)$-alkyl, $CH_2R^6$, $(C_3-C_7)$-cycloalkyl, halo-$(C_1-C_6)$-alkyl, $(C_1-C_6)$-alkoxy-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $OR^1$, $NHR^1$, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfenyl, methylsulfinyl, methylsulfonyl
or
represents heteroaryl, heterocyclyl, benzyl or phenyl, in each case substituted by s radicals selected from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl,
X represents nitro, halogen, cyano, formyl, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR_1R_2$, $P(O)(OR^5)_2$, $CH_2P(O)(OR^5)_2$, $(C_1-C_6)$-alkyl-heteroaryl, $(C_1-C_6)$-alkyl-heterocyclyl,
where the two last-mentioned radicals are each independently of one another substituted by s radicals selected from the group consisting of halogen, $(C_1-C_6)$-alkyl, halo-$(C_1-C_6)$-alkyl, $S(O)_n$—$(C_1-C_6)$-alkyl, $(C_1-C_6)$-alkoxy, halo-$(C_1-C_6)$-alkoxy, and where heterocyclyl carries n oxo groups, Y represents hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $O(CH_2)_2$—$NH(CO)NMe_2$, $O(CH_2)_2$—$NH(CO)NHCO_2Et$, $OC(O)N(R^1)_2$, $CO(NOR^1)R^1$, $NR^1SO_2R^2$, $NR^1COR^1$, $OR^1$, $OSO_2R^2$, $S(O)_nR^2$, $SO_2OR^1$, $SO_2N(R^1)_2$, $N=S(O)_nR^7R^8$, $S(R^9)=NR^{10}$, $S(O)(R^9)=NR^{10}$, $(C_1-C_6)$-alkyl-$S(O)_nR^2$, $C(R^{11})=NOR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-CN, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, $(C_1-C_6)$-alkyl-phenyl, $(C_1-C_6)$-alkyl-heteroaryl, $(C_1-C_6)$-alkyl-heterocyclyl, phenyl, heteroaryl or heterocyclyl, where the last 6 radicals are each independently of one another substituted by s radicals selected from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries n oxo groups, Z represents hydrogen, nitro, halogen, cyano, thiocyanato, $(C_1-C_6)$-alkyl, $(C_1-C_6)$-alkoxy, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^1(R^1ON=)C$, $R^1O(O)C$, $(R^1)_2N(O)C$, $R^1O$, $(R^1)_2N$, $R^1(O)C(R^1)N$, $R^2(O)_2S(R^1)N$, $R^2O(O)C(R^1)N$, $(R^1)_2N(O)C(R^1)N$, $R^2(O)_nS$, $R^1O(O)_2S$, $(R^1)_2N(O)_2S$, $(R^5O)_2(O)P$, $R^1(O)C$—$(C_1-C_6)$-alkyl, $R^1O(O)C$—$(C_1-C_6)$-alkyl, $(R^1)_2N(O)C$—$(C_1-C_6)$-alkyl, NC—$(C_1-C_6)$-alkyl, $R^1O$—$(C_1-C_6)$-alkyl, $(R^1)_2N$—$(C_1-C_6)$-alkyl, $R^1(O)C(R^1)N$—$(C_1-C_6)$-alkyl, $R^2(O)_2S(R^1)N$—$(C_1-C_6)$-alkyl, $R^2O(O)C(R^1)N$—$(C_1-C_6)$-alkyl, $(R^1)_2N(O)C(R^1)N$—$(C_1-C_6)$-alkyl, $R^2(O)_nS$—$(C_1-C_6)$-alkyl, $R^1O(O)_2S$—$(C_1-C_6)$-alkyl, $(R^1)_2N(O)_2S$—$(C_1-C_6)$-alkyl, $(R^5O)_2(O)P$—$(C_1-C_6)$-alkyl, phenyl, heteroaryl, heterocyclyl, phenyl-$(C_1-C_6)$-alkyl, heteroaryl-$(C_1-C_6)$-alkyl, heterocyclyl-$(C_1-C_6)$-alkyl, where the six last-mentioned radicals are each independently of one another substituted by s radicals selected from the group consisting of halogen, nitro, cyano, thiocyanato, $(C_1-C_6)$-alkyl, halo-$(C_1-C_6)$-alkyl, $R^1O$, $(R^1)_2N$, $R^2(O)_nS$, $R^1O(O)_2S$, $(R^1)_2N(O)_2S$ and $R^1O$—$(C_1-C_6)$-alkyl, and where heterocyclyl carries n oxo groups, with the proviso that at least one of the radicals Y and Z does not represent hydrogen, i.e. that in the positions of the radicals Y and Z of the compound (1) either only Y or only Z may represent hydrogen, V and W independently of one another are selected from the group consisting of hydrogen, cyano-$S^1$, halogen, nitro, $(C_1-C_8)$-alkyl, $(C_3-C_7)$-cycloalkyl, $(C_3-C_7)$-cycloalkyl-$(C_1-C_4)$-alkyl, where the $(C_3-C_7)$-cycloalkyl groups in the two abovementioned radicals are unsubstituted or partially or fully halogenated by a halogen selected from the group consisting of fluorine, chlorine, bromine and iodine, $(C_2-C_8)$-alkenyl, $(C_2-C_8)$-alkynyl, $(C_1-C_8)$-haloalkyl, $(C_1-C_3)$-alkylamino, $(C_1-C_3)$-dialkylamino, $(C_1-C_3)$-alkylamino-$S(O)_n(C_1-C_3)$-alkylcarbonyl, $(C_1-C_8)$-alkoxy, $(C_1-C_4)$-alkoxy-$(C_1-C_4)$-alkyl, $(C_1-C_4)$-alkoxy-$(C_1-C_4)$-alkoxy-$S^1$, $(C_1-C_4)$-alkylthio-$(C_1-C_4)$-alkyl, $(C_1-C_4)$-alkylthio-$(C_1-C_4)$-alkylthio-$S^1$, $(C_2-C_6)$-alkenyloxy, $(C_2-C_6)$-alkynyloxy, $(C_1-C_6)$-haloalkoxy, $(C_1-C_4)$-haloalkoxy-$(C_1-C_4)$-alkyl, $(C_1-C_4)$-haloalkoxy-$(C_1-C_4)$-alkoxy-$S^1$, $S^2$—$S(O)_n$—$S_1$, phenoxy-$S^1$ and heterocyclyloxy-$S^1$, where heterocyclyloxy represents a 5- or 6-membered monocyclic ring or an 8-, 9- or 10-membered bicyclic saturated or partially unsaturated or aromatic heterocycle attached via oxygen which has 1, 2, 3 or 4 heteroatoms as ring atoms selected from the group consisting of O, N and S, and where the cyclic groups in the case of phenoxy and heterocyclyloxy are unsubstituted or substituted by 1, 2, 3 or 4 identical or different radicals selected from the group $S^3$, with the proviso that in each case at least one of the radicals V and W does not represent hydrogen, i.e. that in the positions of the radicals V and W of the compound (1) either only V or only W may represent hydrogen, $S^1$ represents a covalent bond or $(C_1-C_4)$-alkanediyl, $S^2$ represents $(C_1-C_6)$-alkyl, $(C_3-C_7)$-cycloalkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, phenyl or heterocyclyl, where heterocyclyl represents a 5- or 6-membered monocyclic saturated or partially unsaturated or aromatic heterocycle which 1, 2, 3 or 4 heteroatoms as ring atoms selected from the group consisting of O, N and S, where phenyl and heterocyclyl are unsubstituted or substituted by 1, 2, 3 or 4 identical or different radicals selected from the group consisting of halogen, $(C_1-C_6)$-alkyl, $(C_1-C_4)$-haloalkyl, $(C_1-C_4)$-alkoxy and $(C_1-C_4)$-haloalkoxy, $S^3$ represents halogen, nitro, $(C_1-C_6)$-alkyl, $(C_3-C_7)$-cycloalkyl, $(C_3-C_7)$-halocycloalkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_1-C_4)$-alkoxy-$(C_1-C_4)$-alkyl, $(C_1-C_4)$-alkylthio-$(C_1-C_4)$-alkyl, $(C_1-C_4)$-haloalkoxy-$(C_1-C_4)$-alkyl, $(C_1-C_4)$-alkoxy-$(C_1-C_4)$-alkoxy, $(C_3-C_7)$-cycloalkoxy or $(C_1-C_6)$-haloalkyloxy, $R^1$ represents hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkyl-heteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, $(C_1-C_6)$-alkyl-$NR^3$-heterocyclyl, where the abovementioned radicals $R^1$, except for hydrogen, are substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and where heterocyclyl carries n oxo groups, $R^2$ represents $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkyl-heteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, $(C_1-C_6)$-alkyl-$NR^3$-heterocyclyl, where the abovementioned radicals $R^2$ are substituted by s radicals from the group consisting of cyano, halogen, nitro, thiocyanato, $OR^3$, $S(O)_nR^4$, $N(R^3)_2$, $NR^3OR^3$, COR$^3$, OCOR$^3$, SCOR$^4$, NR$^3$COR$^3$, NR$^3$SO$_2$R$^4$, CO$_2$R$^3$, COSR$^4$, CON(R$^3$)$_2$ and (C$_1$-C$_4$)-alkoxy-(C$_2$-C$_6$)-alkoxycarbonyl, and where heterocyclyl carries n oxo groups, R$^3$ represents hydrogen, (C$_1$-C$_6$)-alkyl, (C$_2$-C$_6$)-alkenyl, (C$_2$-C$_6$)-alkynyl, (C$_3$-C$_6$)-cycloalkyl or (C$_3$-C$_6$)-cycloalkyl-(C$_1$-C$_6$)-alkyl, R$^4$ represents (C$_1$-C$_6$)-alkyl, (C$_2$-C$_6$)-alkenyl or (C$_2$-C$_6$)-alkynyl, R$^5$ represents methyl or ethyl, R$^6$ represents acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, (C$_1$-C$_6$)-alkoxy, (C$_3$-C$_6$)-cycloalkyl, or represents heteroaryl, heterocyclyl or phenyl, in each case substituted by s radicals from the group consisting of methyl, ethyl, methoxy, trifluoromethyl and halogen, R$^7$ and R$^8$ each independently of one another represent (C$_1$-C$_6$)-alkyl, halo-(C$_1$-C$_6$)-alkyl, (C$_3$-C$_6$)-cycloalkyl, (C$_3$-C$_6$)-cycloalkyl-(C$_1$-C$_6$)-alkyl, (C$_1$-C$_6$)-alkoxy-(C$_1$-C$_6$)-alkyl, phenyl, heteroaryl or heterocyclyl, where the three last-mentioned radicals are each substituted by s radicals from the group consisting of nitro, halogen, cyano, thiocyanato, (C$_1$-C$_6$)-alkyl, halo-(C$_1$-C$_6$)-alkyl, (C$_3$-C$_6$)-cycloalkyl, R$^1$O(O)C, (R$^1$)$_2$N(O)C, R$^1$O, (R$^1$)$_2$N, R$^2$(O)$_n$S, R$^1$O(O)$_2$S, (R$^1$)$_2$N(O)$_2$S and R$^1$O—(C$_1$-C$_6$)-alkyl, and where heterocyclyl carries n oxo groups, or R$^7$ and R$^8$ together with the sulfur atom to which they are attached form a 3- or 8-membered unsaturated, partially saturated or saturated ring which, in addition to the carbon atoms and in addition to the sulfur atom of the sulfoximino group, in each case contains m ring members from the group consisting of N(R$^1$), O and S(O), where this ring is in each case substituted by s radicals from the group consisting of nitro, halogen, cyano, thiocyanato, (C$_1$-C$_6$)-alkyl, halo-(C$_1$-C$_6$)-alkyl, (C$_3$-C$_6$)-cycloalkyl, R$^1$O(O)C, (R$^1$)$_2$N(O)C, R$^1$O, (R$^1$)$_2$N, R$^2$(O)$_n$S, R$^1$O(O)$_2$S, (R$^1$)$_2$N(O)$_2$S and R$^1$O—(C$_1$-C$_6$)-alkyl, and where this ring carries n oxo groups, R$^9$ represents (C$_1$-C$_6$)-alkyl substituted by s radicals from the group consisting of halogen, (C$_3$-C$_6$)-cycloalkyl and R$^{11}$O, R$^{10}$ represents hydrogen, cyano, R$^{11}$(O)C or (R$^{11}$)$_2$N(O)C, R$^{11}$ represents hydrogen, (C$_1$-C$_6$)-alkyl or halo-(C$_1$-C$_6$)-alkyl, R$^{12}$ represents hydrogen, cyano, (C$_1$-C$_6$)-alkyl, (C$_3$-C$_6$)-cycloalkyl, halo-(C$_1$-C$_6$)-alkyl, OR$^8$, SR$^8$ or NR$^8$R$^9$, m represents 0, 1 or 2, n represents 0, 1 or 2, and s represents 0, 1, 2 or 3, with the proviso that the compounds 4-bromo-3[[(diethylamino)carbonyl]amino]-6-fluoro-2-methyl-N-(5-methyl-1,3,4-oxadiazol-2-yl)benzamide, 4-bromo-3[[(ethylmethylamino)carbonyl]amino]-6-fluoro-2-methyl-N-(5-methyl-1,3,4-oxadiazol-2-yl)benzamide, and 3-amino-4-bromo-6-fluoro-2-methyl-N-(5-methyl-1,3,4-oxadiazol-2-yl)benzamide, and also 4-bromo-2,6-difluoro-2-N-(5-methyl-1,3,4-oxadiazol-2-yl) benzamide, 4-bromo-2,6-difluoro-2-N-(5-cyclopropyl-1,3,4-oxadiazol-2-yl)benzamide, 3-amino-6-fluoro-2-methyl-N-(5-methyl-1,3,4-oxadiazol-2-yl)benzamide, 2-amino-6-fluoro-2-N-(5-methyl-1,3,4-oxadiazol-2-yl)-3 nitrobenzamide, 2,6-difluoro-N-(5-methyl-1,3,4-oxadiazol-2-yl)-3 nitrobenzamide, and 3-amino-2,6-difluoro-N-(5-methyl-1,3,4-oxadiazol-2-yl) benzamide are excluded.

DETAILED DESCRIPTION OF A PREFERRED EMBODIMENT

The N-(1,3,4-oxadiazol-2-yl)arylcarboxamides of the invention differ from the known N-(1,3,4-oxadiazol-2-yl) arylcarboxamides in particular by the additional substituents in positions 5 and 6 of the phenyl moiety.

The core of the invention relates to the surprising discovery that, in the case of the N-(1,3,4-oxadiazol-2-yl)arylcarboxamides, the phenyl substituents in positions 5 and 6 of the phenyl are, in combination with the other substituents, of unexpectedly high relevance for the herbicidal activity.

In the formula (I) and all the formulae which follow, alkyl radicals having more than two carbon atoms may be straight-chain or branched. Alkyl radicals are, for example, methyl, ethyl, n-propyl or isopropyl, n-, iso-, t- or 2-butyl, pentyls, hexyls such as n-hexyl, isohexyl and 1,3-dimethylbutyl. Halogen is fluorine, chlorine, bromine or iodine.

Heterocyclyl is a saturated, partly saturated or fully unsaturated cyclic radical which contains 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydrofuranyl, dihydrofuranyl and oxetanyl.

Heteroaryl is an aromatic cyclic radical which contains 3 to 6 ring atoms, of which 1 to 4 are from the group of oxygen, nitrogen and sulfur, and which may additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

If a group is polysubstituted by radicals, this should be understood to mean that this group is substituted by one or more identical or different radicals selected from the radicals mentioned.

Depending on the nature of the substituents and the manner in which they are attached, the compounds of the general formula (I) may be present as stereoisomers. If, for example, one or more asymmetric carbon atoms are present, enantiomers and diastereomers may occur. Stereoisomers likewise occur when n is 1 (sulfoxides). Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention also relates to all the stereoisomers and mixtures thereof that are encompassed by the general formula (I) but are not defined specifically.

Preference is given to compounds of the general formula (in which A represents N or C—Y, where R represents hydrogen, halogen, $(C_1-C_4)$-alkyl, halo-$(C_1-C_4)$-alkyl or $(C_1-C_4)$-alkoxy-$(C_1-C_4)$-alkyl, X represents nitro, halogen, cyano, $(C_1-C_6)$-alkyl, halo-$(C_1-C_6)$-alkyl, $(C_3-C_6)$-cycloalkyl, $OR^1$, $S(O)_nR^2$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkyl-heteroaryl, $(C_1-C_6)$-alkyl-heterocyclyl, where the two last-mentioned radicals are each substituted by s radicals selected from the group consisting of halogen, $(C_1-C_6)$-alkyl, halo-$(C_1-C_6)$-alkyl, $S(O)_n$—$(C_1-C_6)$-alkyl, $(C_1-C_6)$-alkoxy, halo-$(C_1-C_6)$-alkoxy, and where heterocyclyl carries n oxo groups, Y represents hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COR^1$, $C(O)N(R^1)_2$, $OC(O)N(R^1)_2$, $CO(NOR^1)R^1$, $NR^1SO_2R^2$, $NR^1COR^1$, $OR^1$, $OSO_2R^2$, $S(O)_nR^2$, $SO_2OR^1$, $SO_2N(R^1)_2$, $N=S(O)_nR^7R^8$, $S(R^9)=NR^{10}$, $S(O)(R^9)=NR^{10}$, $(C_1-C_6)$-alkyl-$S(O)_nR_2$, $C(R^{11})=NOR^{12}$, $(C_1-C_6)$-alkyl-$OR^1$, $(C_1-C_6)$-alkyl-$OCOR^1$, $(C_1-C_6)$-alkyl-$OSO2R^2$, $(C_1-C_6)$-alkyl-$CO_2R^1$, $(C_1-C_6)$-alkyl-CN, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, $(C_1-C_6)$-alkyl-phenyl, $(C_1-C_6)$-alkyl-heteroaryl, $(C_1-C_6)$-alkyl-heterocyclyl, phenyl, heteroaryl or heterocyclyl, where the six last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries n oxo groups, Z represents hydrogen, nitro, halogen, cyano, $(C_1-C_6)$-alkyl, $(C_1-C_6)$-alkoxy, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^1(R^1ON=)C$, $R^1O(O)C$, $(R^1)_2N(O)C$, $R^1O$, $(R^1)_2N$, $R^1(O)C(R^1)N$, $R^2(O)_2S(R^1)N$, $R^2O(O)C(R^1)N$, $(R^1)_2N(O)C(R^1)N$, $R^2(O)_nS$, $R^1O(O)_2S$, $(R^1)_2N(O)_2S$, $(R^5O)_2(O)P$, $R^1(O)C$—$(C_1-C_6)$-alkyl, $R^1O(O)C$—$(C_1-C_6)$-alkyl, $(R^1)_2N(O)C$—$(C_1-C_6)$-alkyl, NC—$(C_1-C_6)$-alkyl, $R^1O$—$(C_1-C_6)$-alkyl, $(R^1)_2N$—$(C_1-C_6)$-alkyl, $R^1(O)C(R^1)N$—$(C_1-C_6)$-alkyl, $R^2(O)_2S(R^1)N$—$(C_1-C_6)$-alkyl, $R^2O(O)C(R^1)N$—$(C_1-C_6)$-alkyl, $(R^1)_2N(O)C(R^1)N$—$(C_1-C_6)$-alkyl, $R^2(O)_nS$—$(C_1-C_6)$-alkyl, $R^1O(O)_2S$—$(C_1-C_6)$-alkyl, $(R^1)_2N(O)_2S$—$(C_1-C_6)$-alkyl, $(R^5O)_2(O)P$—$(C_1-C_6)$-alkyl, phenyl, heteroaryl, heterocyclyl, phenyl-$(C_1-C_6)$-alkyl, heteroaryl-$(C_1-C_6)$-alkyl, heterocyclyl-$(C_1-C_6)$-alkyl, where the six last-mentioned radicals are each substituted by s radicals selected from the group consisting of halogen, nitro, cyano, thiocyanato, $(C_1-C_6)$-alkyl, halo-$(C_1-C_6)$-alkyl, $R^1O$, $(R^1)_2N$, $R^2(O)_nS$, $R^1O(O)_2S$, $(R^1)_2N(O)_2S$ and $R^1O$—$(C_1-C_6)$-alkyl, and where heterocyclyl carries n oxo groups, with the proviso that at least one of the radicals Y and Z does not represent hydrogen, V represents hydrogen, halogen, cyano, nitro, $(C_1-C_4)$-alkyl or $(C_1-C_4)$-haloalkyl, W represents halogen, cyano, nitro, $(C_1-C_4)$-alkyl or $(C_1-C_4)$-haloalkyl, where $R^1$ to $R^{12}$ and m, n and s are each independently of one another as defined in claim 1, with the proviso that the compounds 3-amino-4-bromo-6-fluoro-2-methyl-N-(5-methyl-1,3,4-oxadiazol-2-yl)benzamide, 4-bromo-2,6-difluoro-2-N-(5-methyl-1,3,4-oxadiazol-2-yl)benzamide, 4-bromo-2,6-difluoro-2-N-(5-cyclopropyl-1,3,4-oxadiazol-2-yl)benzamide, 3-amino-6-fluoro-2-methyl-N-(5-methyl-1,3,4-oxadiazol-2-yl)benzamide, 2-amino-6-fluoro-2-N-(5-methyl-1,3,4-oxadiazol-2-yl)-3 nitrobenzamide, 2,6-difluoro-N-(5-methyl-1,3,4-oxadiazol-2-yl)-3 nitrobenzamide, and 3-amino-2,6-difluoro-N-(5-methyl-1,3,4-oxadiazol-2-yl)benzamide are excluded, where $R^1$ to $R^{12}$ and m, n and s are each independently of one another as defined above.

Particular preference is given to compounds of the general formula (I) in which A represents N or C—Y, where R represents hydrogen, methyl, ethyl, trifluoromethyl, methoxymethyl or halogen, X represents nitro, fluorine, chlorine, bromine, iodine, methyl, ethyl, n-propyl, isopropyl, cyclopropyl, trifluoromethyl, difluoromethyl, chlorodifluoromethyl, dichlorofluoromethyl, methoxy, ethoxy, methylsulfanyl, methylsulfinyl, methylsulfonyl, ethylsulfanyl, ethylsulfinyl, ethylsulfonyl, methoxymethyl, ethoxymethyl, methoxyethyl, methoxyethoxymethyl, cyclopropylmethoxy, methylthiomethyl, methylsulfinylmethyl or methylsulfonylmethyl, Y represents hydrogen, nitro, fluorine, chlorine, bromine, iodine, cyano, $(C_1-C_6)$-alkyl, halo-$(C_1-C_6)$-alkyl, $OR^1$, $S(O)_nR^2$, $SO_2N(R^1)_2$, $N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkyl-phenyl, $(C_1-C_6)$-alkyl-heteroaryl, $(C_1-C_6)$-alkyl-heterocyclyl, phenyl, heteroaryl or heterocyclyl, where the six last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries n oxo groups, Z represents hydrogen, nitro, cyano, fluorine, chlorine, bromine or iodine, methyl, ethyl, n-propyl, isopropyl, cyclopropyl, trifluoromethyl, difluoromethyl, chlorodifluoromethyl, dichlorofluoromethyl, trichloromethyl, pentafluoroethyl, heptafluoroisopropyl, methoxy, ethoxy, methylsulfanyl, methylsulfinyl, methylsulfonyl, ethylsulfanyl, ethylsulfinyl, ethylsulfonyl or 1H-1,2,4-triazol-1-yl, with the proviso that at least one of the radicals Y and Z does not represent hydrogen, V represents hydrogen, fluorine, methyl or trifluoromethyl ($CF_3$), W represents fluorine, where $R^1$ to $R^{12}$ and m, n and s are each independently of one another as defined above.

Very particular preference is given to N-(1,3,4-oxadiazol-2-yl)arylcarboxamides of the formula (I) in which A represents C—Y, where V represents hydrogen,
W represents fluorine
and the radicals
R, X, Y and Z as well as the radicals $R^1$ to $R^{12}$ and also m, n and s are each independently of one another as defined above.

Even more preference is given to N-(1,3,4-oxadiazol-2-yl)arylcarboxamides of the formula (I) in which A represents C—Y, where R represents hydrogen, methyl, ethyl, trifluoromethyl, methoxymethyl or chlorine, X represents nitro, fluorine, chlorine, bromine, iodine, methyl, ethyl, n-propyl, isopropyl, cyclopropyl, trifluoromethyl, difluoromethyl, chlorodifluoromethyl, dichlorofluoromethyl, methoxy, ethoxy, methylsulfanyl, methylsulfinyl, methylsulfonyl, ethylsulfanyl, ethylsulfinyl, ethylsulfonyl, methoxymethyl, ethoxymethyl, methoxyethyl, methoxyethoxymethyl, cyclopropylmethoxy, methylthiomethyl, methylsulfinylmethyl or methylsulfonylmethyl, Y represents hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $OC(O)N(R^1)_2$, $CO(NOR^1)R^1$, $NR^1SO_2R^2$, $NR^1COR^1$, $OR^1$, $OSO_2R^2$, $S(O)_nR^2$, $SO_2OR^1$, $SO_2N(R^1)_2$, $N{=}S(O)_nR^7R^8$, $S(R^9){=}NR^{10}$, $S(O)(R^9){=}NR^{10}$, $(C_1-C_6)$-alkyl-$S(O)_nR_2$, $C(R^{11}){=}NOR^{12}$, $(C_1-C_6)$-alkyl-$OR^1$, $(C_1-C_6)$-alkyl-$OCOR^1$, $(C_1-C_6)$-alkyl-$OSO2R^2$, $(C_1-C_6)$-alkyl-$CO_2R^1$, $(C_1-C_6)$-alkyl-CN, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, $(C_1-C_6)$-alkyl-phenyl, $(C_1-C_6)$-alkyl-heteroaryl, $(C_1-C_6)$-alkyl-heterocyclyl, phenyl, heteroaryl or heterocyclyl, where the last 6 radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries n oxo groups, Z represents hydrogen, nitro, halogen, cyano, $(C_1-C_6)$-alkyl, $(C_1-C_6)$-alkoxy, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^1(R^1ON{=})C$, $R^1O(O)C$, $(R^1)_2N(O)C$, $R^1O$, $(R^1)_2N$, $R^1(O)C(R^1)N$, $R^2(O)_2S(R^1)N$, $R^2O(O)C(R^1)N$, $(R^1)_2N(O)C(R^1)N$, $R^2(O)_nS$, $R^1O(O)_2S$, $(R^1)_2N(O)_2S$, $(R^5O)_2(O)P$, $R^1(O)C$—$(C_1-C_6)$-alkyl, $R^1O(O)C$—$(C_1-C_6)$-alkyl, $(R^1)_2N(O)C$—$(C_1-C_6)$-alkyl, $NC$—$(C_1-C_6)$-alkyl, $R^1O$—$(C_1-C_6)$-alkyl, $(R^1)_2N$—$(C_1-C_6)$-alkyl, $R^1(O)C(R^1)N$—$(C_1-C_6)$-alkyl, $R^2(O)_2S(R^1)N$—$(C_1-C_6)$-alkyl, $R^2O(O)C(R^1)N$—$(C_1-C_6)$-alkyl, $(R^1)_2N(O)C(R^1)N$—$(C_1-C_6)$-alkyl, $R^2(O)_nS$—$(C_1-C_6)$-alkyl, $R^1O(O)_2S$—$(C_1-C_6)$-alkyl, $(R^1)_2N(O)_2S$—$(C_1-C_6)$-alkyl, $(R^5O)_2(O)P$—$(C_1-C_6)$-alkyl, phenyl, heteroaryl, heterocyclyl, phenyl-$(C_1-C_6)$-alkyl, heteroaryl-$(C_1-C_6)$-alkyl, heterocyclyl-$(C_1-C_6)$-alkyl, where the six last-mentioned radicals are each substituted by s radicals from the group consisting of halogen, nitro, cyano, thiocyanato, $(C_1-C_6)$-alkyl, halo-$(C_1-C_6)$-alkyl, $R^1O$, $(R^1)_2N$, $R^2(O)_nS$, $R^1O(O)_2S$, $(R^1)_2N(O)_2S$ and $R^1O$—$(C_1-C_6)$-alkyl, and where heterocyclyl carries n oxo groups, with the proviso that at least one of the radicals Y and Z does not represent hydrogen, V represents hydrogen,
W represents fluorine and
$R^1$ to $R^{12}$ and m, n and s are each independently of one another as defined in claim 1,
with the proviso that the compounds
3-amino-4-bromo-6-fluoro-2-methyl-N-(5-methyl-1,3,4-oxadiazol-2-yl)benzamide,
4-bromo-2,6-difluoro-2-N-(5-methyl-1,3,4-oxadiazol-2-yl) benzamide,
4-bromo-2,6-difluoro-2-N-(5-cyclopropyl-1,3,4-oxadiazol-2-yl)benzamide,
3-amino-6-fluoro-2-methyl-N-(5-methyl-1,3,4-oxadiazol-2-yl)benzamide,
2-amino-6-fluoro-2-N-(5-methyl-1,3,4-oxadiazol-2-yl)-3 nitrobenzamide,
2,6-difluoro-N-(5-methyl-1,3,4-oxadiazol-2-yl)-3 nitrobenzamide, and
3-amino-2,6-difluoro-N-(5-methyl-1,3,4-oxadiazol-2-yl) benzamide
are excluded.

Even more particular preference is given to N-(1,3,4-oxadiazol-2-yl)arylcarboxamides of the formula (I) in which A represents C—Y, where R represents hydrogen, methyl, ethyl, trifluoromethyl, methoxymethyl or chlorine, X represents nitro, fluorine, chlorine, bromine, iodine, methyl, ethyl, n-propyl, isopropyl, cyclopropyl, trifluoromethyl, difluoromethyl, chlorodifluoromethyl, dichlorofluoromethyl, methoxy, ethoxy, methylsulfanyl, methylsulfinyl, methylsulfonyl, ethylsulfanyl, ethylsulfinyl, ethylsulfonyl, methoxymethyl, ethoxymethyl, methoxyethyl, methoxyethoxymethyl, cyclopropylmethoxy, methylthiomethyl, methylsulfinylmethyl or methylsulfonylmethyl, Y represents hydrogen, nitro, fluorine, chlorine, bromine, iodine, cyano, $(C_1-C_6)$-alkyl, halo-$(C_1-C_6)$-alkyl, $OR^1$, $S(O)_nR^2$, $SO_2N(R^1)_2$, $N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkyl-phenyl, $(C_1-C_6)$-alkyl-heteroaryl, $(C_1-C_6)$-alkyl-heterocyclyl, phenyl, heteroaryl or heterocyclyl, where the six last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and
where heterocyclyl carries n oxo groups, Z represents hydrogen, nitro, cyano, fluorine, chlorine, bromine or iodine, methyl, ethyl, n-propyl, isopropyl, cyclopropyl, trifluoromethyl, difluoromethyl, chlorodifluoromethyl, dichlorofluoromethyl, trichloromethyl, pentafluoroethyl, heptafluoroisopropyl, methoxy, ethoxy, methylsulfanyl, methylsulfinyl or methylsulfonyl, ethylsulfanyl, ethylsulfinyl, ethylsulfonyl or 1H-1,2,4-triazol-1-yl,
with the proviso that at least one of the radicals Y and Z does not represent hydrogen, V represents hydrogen,
W represents fluorine and
$R^1$ to $R^{12}$ and m, n and s are each independently of one another as defined above, where in particular for the radicals $R^1$ and $R^2$:

$R^1$ represents hydrogen, $(C_1-C_6)$-alkyl or $(C_1-C_6)$-haloalkyl, where the above-mentioned radicals $R^1$, except for hydrogen, are substituted by s radicals from the group consisting of cyano, halogen and nitro, $R^2$ represents $(C_1-C_6)$-alkyl or $(C_1-C_6)$-haloalkyl, where the above-mentioned radicals R² are substituted by
s radicals from the group consisting of cyano, halogen,
nitro and
s represents 0, 1, 2 or 3,
with the proviso that the compounds
3-amino-4-bromo-6-fluoro-2-methyl-N-(5-methyl-1,3,4-oxadiazol-2-yl)benzamide,
4-bromo-2,6-difluoro-2-N-(5-methyl-1,3,4-oxadiazol-2-yl) benzamide,
3-amino-6-fluoro-2-methyl-N-(5-methyl-1,3,4-oxadiazol-2-yl)benzamide,
2,6-difluoro-N-(5-methyl-1,3,4-oxadiazol-2-yl)-3 nitrobenzamide, and
3-amino-2,6-difluoro-N-(5-methyl-1,3,4-oxadiazol-2-yl) benzamide
are excluded.

A particular aspect of the invention relates to N-(1,3,4-oxadiazol-2-yl)arylcarboxamides of the formula (I) in which the substituents have the following meaning:
A represents C—Y,
R represents hydrogen, methyl, ethyl, trifluoromethyl or methoxymethyl,
X represents fluorine, chlorine, bromine, iodine, methyl, ethyl, n-propyl, isopropyl or cyclopropyl,
Y represents $S(O)_nR^2$,
Z represents trifluoromethyl, difluoromethyl or pentafluoroethyl,
V represents hydrogen,
W represents fluorine and
R² represents $(C_1-C_6)$-alkyl, $(C_1-C_6)$-haloalkyl,
where the above-mentioned radicals R² are substituted by s radicals from the group consisting of cyano, halogen, nitro,
n represents 0, 1 or 2,
s represents 0, 1,2 or 3.

With respect to the generically defined substituent Y=S(O)$_n$R² where n=0, n=1 or n=2, most preference is given to the radicals methylsulfanyl (SMe), methylsulfinyl (methyl sulfoxide (SOMe)), methylsulfonyl (SO₂Me), ethylsulfanyl (SEt), ethylsulfinyl (ethyl sulfoxide (SOEt)) and ethylsulfonyl (SO₂Et) where R²=methyl (Me) or R²=ethyl (Et).

Utmost preference is given to the three methyl-substituted alternatives of Y, i.e. Y=SMe, Y=SOMe, Y=SO₂Me.

Accordingly, N-(1,3,4-oxadiazol-2-yl)arylcarboxamides of the formula (I) in which the substituents have the following meaning:
A represents C—Y,
R represents methyl,
X represents chlorine or methyl,
Y represents SMe, SOMe or SO₂Me,
Z represents trifluoromethyl or chlorine,
V represents hydrogen,
W represents fluorine,
are particularly preferred in the context of the particular aspect mentioned above.

The following tabular compilation specifically discloses six of the compounds of the general formula (I) which are most preferred according to the aspect mentioned above in which, as shown in the formula below, A represents CY, X represents chlorine or methyl, Y represents methylsulfanyl, methylsulfinyl or methylsulfonyl, Z represents trifluoromethyl, V represents hydrogen, W represents fluorine and R represents methyl:

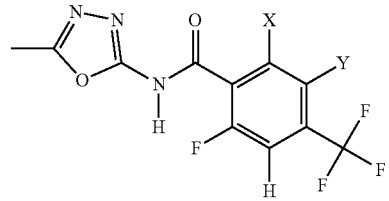

| No. | X | Y | Compound |
|---|---|---|---|
| 2-143 | Cl | SMe | 2-chloro-6-fluoro-N-(5-methyl-1,3,4-oxadiazol-2-yl)-3-(methylsulfanyl)-4-(trifluoromethyl)benzamide |
| 2-144 | Cl | S(O)Me | 2-chloro-6-fluoro-N-(5-methyl-1,3,4-oxadiazol-2-yl)-3-(methylsulfinyl)-4-(trifluoromethyl)benzamide |
| 2-145 | Cl | SO₂Me | 2-chloro-6-fluoro-N-(5-methyl-1,3,4-oxadiazol-2-yl)-3-(methylsulfonyl)-4-(trifluoromethyl)benzamide |
| 2-359 | Me | SMe | 6-fluoro-2-methyl-N-(5-methyl-1,3,4-oxadiazol-2-yl)-3-(methylsulfanyl)-4-(trifluoromethyl)benzamide |
| 2-360 | Me | S(O)Me | 6-fluoro-2-methyl-N-(5-methyl-1,3,4-oxadiazol-2-yl)-3-(methylsulfinyl)-4-(trifluoromethyl)benzamide |
| 2-361 | Me | SO₂Me | 6-fluoro-2-methyl-N-(5-methyl-1,3,4-oxadiazol-2-yl)-3-(methylsulfonyl)-4-(trifluoromethyl)benzamide |

Moreover, preference is given to N-(1,3,4-oxadiazol-2-yl)arylcarboxamides of the formula (I) in which A represents C—Y, where
R represents hydrogen, methyl, ethyl, trifluoromethyl or methoxymethyl,
X represents F, Cl, Br, CH₃, ethyl, n-propyl, isopropyl, CF₃, O—CH₂-cyclopropyl, SMe or SO₂Me,
Y represents H, F, Cl, Me, ethyl, propyl, isopropyl, CH₂OMe, CH₂OEt, CH₂OCH₂CHF₂, CH₂OCH₂CF₃, CH₂OCH₂CF₂CHF₂, CH₂O-c-pentyl, CH₂O-tetrahydrofuran-3-yl, CH₂OCH₂-tetrahydrofuran-2-yl, CH₂OCH₂-tetrahydrofuran-3-yl, CH₂PO(OMe)₂, COOMe, CONMe₂, CONMe(OMe), NH₂, NHMe, NMe₂, NHEt, NH(CH₂)₂OMe, NH(CH₂)₂OEt, OH, OMe, OEt, OiPr, O(CH₂)₂OMe, O(CH₂)₃OMe, O(CH₂)₄OMe, OCH₂CHF₂, OCH₂(CO)NMe₂, O(CH₂)₂—(CO)—NMe₂, O(CH₂)₂—NH(CO)NMe₂, O(CH₂)₂—NH(CO)NHCO₂Et, O(CH₂)₂—NHCO₂Me, O(CH₂)₂—NHSO₂Me, OCH₂—NHSO₂cPr, O(CH₂)₂NHSO₂Me, O(CH₂)-5-2,4-dimethyl-2,4-dihydro-3H-1,2,4-triazol-3-one, O(CH₂)-3,5-dimethyl-1,2-oxazol-4-yl, O(CH₂)-5-pyrrolidin-2-one, O(CH₂)₂—O(3,5-di-methoxypyrimidin-2-yl, SMe, SEt, S(CH₂)₂OMe, SO(CH₂)₂OMe, SO₂(CH₂)₂OMe, S(O)Me, S(O)Et, SO₂Me, SO₂Et, SO₂(CH₂)₂OMe,
4,5-dihydro-1,2-oxazol-3 yl, 5-cyanomethyl-4,5-dihydro-1,2-oxazol-3-yl, [1,4]dioxan-2-ylmethoxy, pyrazol-1-yl, 4-methoxylpyrazol-1-yl, 1,2,3-triazol-1-yl, 5-(methoxymethyl)-4,5-dihydro-1,2-oxazol-3-yl or 5-cyanomethyl-4,5-dihydro-1,2-oxazol-3-yl and
Z represents F, Cl, Br, I, CF₃, NO₂, SMe, SEt, SOMe, SOEt, SO₂Me, SO₂Et, pyrazol-1-yl or 1H-1,2,4-triazol-1-yl,
with the proviso that the compounds
3-amino-4-bromo-6-fluoro-2-methyl-N-(5-methyl-1,3,4-oxadiazol-2-yl)benzamide, and also
4-bromo-2,6-difluoro-2-N-(5-methyl-1,3,4-oxadiazol-2-yl) benzamide,
are excluded.

Alternatively, preference is given to N-(1,3,4-oxadiazol-2-yl)arylcarboxamides of the formula (I) in which A represents N (instead of C—Y), where V represents hydrogen, W represents fluorine, Z represents $CF_3$, and the radicals R, X and Y as well as the radicals $R^1$ to $R^2$ and also m, n and s are each independently of one another as defined above.

In all the formulae specified hereinafter, the substituents and symbols have the same meaning as described in formula (I), unless defined differently.

Compounds according to the invention can be prepared, for example, by the method shown in scheme 1, by base-catalyzed reaction of a benzoyl or nicotinoyl chloride (II) with a 2-amino-1,3,4-oxadiazole (III):

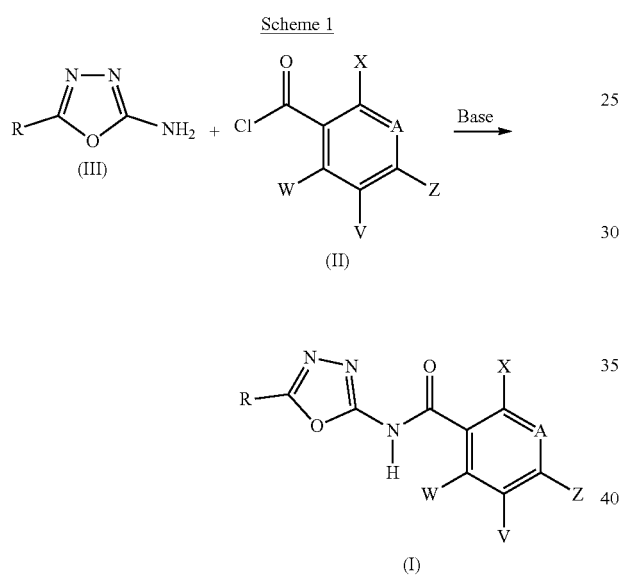

The benzoyl chlorides of the formula (II) or the parent benzoic acids thereof are known in principle and can be prepared, for example, by the methods described in U.S. Pat. No. 6,376,429 B1, EP 1 585 742 A1, WO2014/184015, WO2014/184016, WO2013/083859 and EP 1202 978 A1.

Compounds according to the invention can also be prepared by the method described in scheme 2, by reacting a benzoic or nicotinic acid of the formula (IV) with a 2-amino-1,3,4-oxadiazole (III):

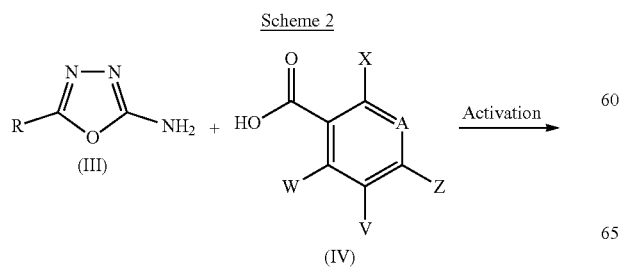

For the activation, it is possible to use dehydrating reagents which are typically used for amidation reactions, for example 1,1'-carbonyldiimidazole (CDI), dicyclohexylcarbodiimide (DCC), 2,4,6-tripropyl-1,3,5,2,4,6-trioxatriphosphinane 2,4,6-trioxide (T3P), etc.

Inventive compounds can also be prepared by the method described in scheme 3, by cyclizing a compound of the formula V:

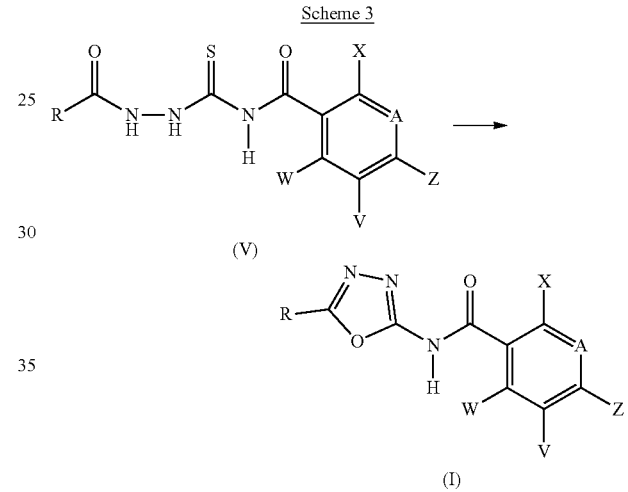

The cyclization can be performed by the methods described in Synth. Commun. 31 (12), 1907-1912 (2001) or in Indian J. Chem., Section B: Organic Chemistry Including Medicinal Chemistry; Vol. 43 (10), 2170-2174 (2004).

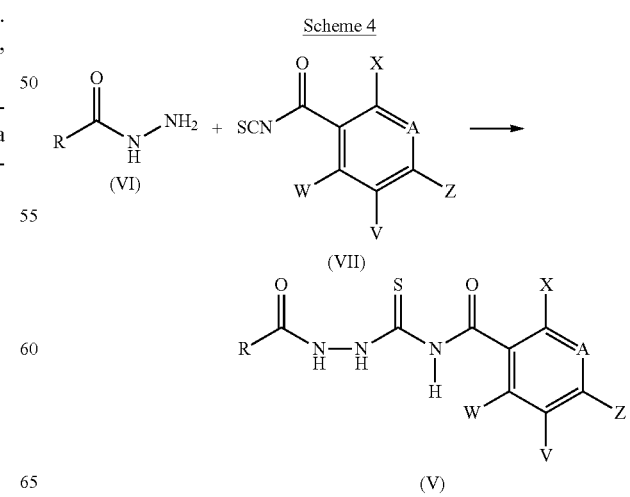

The compound of the formula V used in scheme 3 can be prepared by reaction of an acyl isocyanate of the formula VII with a hydrazide of the formula VI by the method described in Synth. Commun. 25(12), 1885-1892 (1995).

It may be appropriate to alter the sequence of the reaction steps. For instance, benzoic acids bearing a sulfoxide cannot be converted directly to their acid chlorides. One option here is first to prepare the amide at the thioether stage, and then to oxidize the thioether to the sulfoxide.

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor: Gunther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB113AZ, England, or MultiPROBE Automated Workstations from Perkin Elmer, Waltham, Mass. 02451, USA. For the parallelized purification of compounds of the general formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be obtained, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, compounds of the general formula (I) and salts thereof can be prepared completely or partially by solid-phase-supported methods. For this purpose, individual intermediates or all intermediates in the synthesis or a synthesis adapted for the corresponding procedure are bound to a synthesis resin. Solid-phase-supported synthesis methods are described adequately in the technical literature, for example Barry A. Bunin in "The Combinatorial Index", Academic Press, 1998 and Combinatorial Chemistry—Synthesis, Analysis, Screening (editor: Gunther Jung), Wiley, 1999. The use of solid-phase-supported synthesis methods permits a number of protocols, which are known from the literature and which for their part may be performed manually or in an automated manner. The reactions can be performed, for example, by means of IRORI technology in microreactors from Nexus Biosystems, 12140 Community Road, Poway, Calif. 92064, USA.

Both in the solid and in the liquid phase, the implementation of individual or several synthesis steps may be supported by the use of microwave technology. The specialist literature describes a series of experimental protocols, for example in Microwaves in Organic and Medicinal Chemistry (editors: C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

The compounds of the formula (I) according to the invention (and/or salts thereof), referred to collectively as "compounds according to the invention" hereinafter, have excellent herbicidal efficacy against a broad spectrum of economically important monocotyledonous and dicotyledonous annual harmful plants. The active ingredients also have good control over perennial harmful plants which are difficult to control and produce shoots from rhizomes, root stocks or other perennial organs.

The present invention therefore also provides a method for controlling unwanted plants or for regulating the growth of plants, preferably in plant crops, in which one or more compound(s) of the invention is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The compounds of the invention can be deployed, for example, prior to sowing (if appropriate also by incorporation into the soil), prior to emergence or after emergence. Specific examples of some representatives of the monocotyledonous and dicotyledonous weed flora which can be controlled by the compounds of the invention are as follows, though the enumeration is not intended to impose a restriction to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds of the invention are applied to the soil surface before germination, either the emergence of the weed seedlings is prevented completely or the weeds grow until they have reached the cotyledon stage, but then they stop growing and ultimately die completely after three to four weeks have passed.

If the active compounds are applied post-emergence to the green parts of the plants, growth stops after the treatment, and the harmful plants remain at the growth stage at the time of application, or they die completely after a certain time, so that in this manner competition by the weeds, which is harmful to the crop plants, is eliminated very early and in a sustained manner.

Although the compounds of the invention have outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* in particular *Zea* and *Triticum,* will be damaged to a negligible extent only, if at all, depending on the structure of the particular compound of the invention and its application rate. For these reasons, the present compounds are very suitable for selective control of unwanted plant growth in plant crops such as agriculturally useful plants or ornamental plants.

In addition, the compounds of the invention (depending on their particular structure and the application rate deployed) have outstanding growth-regulating properties in crop plants. They intervene in the plants' own metabolism with regulatory effect, and can thus be used for the controlled influencing of plant constituents and to facilitate harvesting, for example by triggering desiccation and stunted growth. Furthermore, they are also suitable for the general control and inhibition of unwanted vegetative growth without killing the plants in the process. Inhibition of vegetative growth plays a major role for many mono- and dicotyledonous crops since, for example, this can reduce or completely prevent lodging.

By virtue of their herbicidal and plant growth regulatory properties, the active compounds can also be used to control harmful plants in crops of genetically modified plants or plants modified by conventional mutagenesis. In general, the transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or those with a different fatty acid composition in the harvested material.

It is preferable, with respect to transgenic crops, to use the compounds of the invention in economically important transgenic crops of useful plants and ornamentals, for example of cereals such as wheat, barley, rye, oats, millet/sorghum, rice and corn or else crops of sugar beet, cotton, soybean, oilseed rape, potato, tomato, peas and other types of vegetable. Preferably, the compounds of the invention can be used as herbicides in crops of useful plants which are resistant, or have been made resistant by genetic engineering, to the phytotoxic effects of the herbicides.

Preference is given to the use of the compounds according to the invention or salts thereof in economically important transgenic crops of useful plants and ornamentals, for example of cereals such as wheat, barley, rye, oats, millet/sorghum, rice, cassava and corn, or else crops of sugar beet, cotton, soybean, oilseed rape, potato, tomato, peas and other types of vegetable. Preferably, the compounds of the invention can be used as herbicides in crops of useful plants which are resistant, or have been made resistant by genetic engineering, to the phytotoxic effects of the herbicides.

Conventional ways of producing novel plants which have modified properties in comparison to existing plants consist, for example, in traditional cultivation methods and the generation of mutants.

Alternatively, novel plants with modified properties can be generated with the aid of recombinant methods (see, for example, EP-A-0221044, EP-A-0131624). For example, there have been descriptions in several cases of:

genetic modifications of crop plants for the purpose of modifying the starch synthesized in the plants (e.g. WO 92/11376, WO 92/14827, WO 91/19806), transgenic crop plants which are resistant to particular herbicides of the glufosinate type (cf., for example, EP-A-0242236, EP-A-242246) or glyphosate type (WO 92/00377) or the sulfonylurea type (EP-A-0257993, U.S. Pat. No. 5,013,659), transgenic crop plants, for example cotton, capable of producing *Bacillus thuringiensis* toxins (Bt toxins), which make the plants resistant to particular pests (EP-A-0142924, EP-A-0193259).

transgenic crop plants having a modified fatty acid composition (WO 91/13972), genetically modified crop plants with novel constituents or secondary metabolites, for example novel phytoalexins, which bring about an increased disease resistance (EPA 309862, EPA0464461), genetically modified plants having reduced photorespiration, which have higher yields and higher stress tolerance (EPA 0305398), transgenic crop plants which produce pharmaceutically or diagnostically important proteins ("molecular pharming"), transgenic crop plants which feature higher yields or better quality, transgenic crop plants which feature a combination, for example, of the abovementioned novel properties ("gene stacking").

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431.

For such genetic manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. To join the DNA fragments with one another, adapters or linkers can be placed onto the fragments, see, for example, Sambrook et al., 1989, Molecular Cloning, A Laboratory Manual, 2nd edition, Cold Spring Harbor Laboratory Press, Cold Spring Harbor, N.Y., or Winnacker "Gene und Klone" [Genes and clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227, Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

The compounds of the invention can be used with preference in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active compounds.

When the active compounds of the invention are employed in transgenic crops, not only do the effects towards harmful plants observed in other crops occur, but frequently also effects which are specific to the application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the compounds of the invention as herbicides for control of harmful plants in transgenic crop plants.

The compounds of the invention can be applied in the form of wettable powders, emulsifiable concentrates, sprayable solutions, dusting products or granules in the customary formulations. The invention therefore also provides herbicidal and plant-growth-regulating compositions which comprise the compounds of the invention.

The compounds of the invention can be formulated in various ways, according to the biological and/or physico-chemical parameters required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], Volume 7, C. Hanser Verlag Munich, 4th Ed. 1986, Wade van Valkenburg, "Pesticide Formulations", Marcel Dekker, N.Y., 1973, K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesellschaft, Stuttgart 1976; Winnacker-Küchler, "Chemische Technologie" [Chemical Engineering], volume 7, C. Hanser Verlag Munich, 4th Ed. 1986.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tank mix. Suitable safeners are, for example, mefenpyr-diethyl, cyprosulfamide, isoxadifen-ethyl, cloquintocet-mexyl and dichlormid.

Wettable powders are preparations uniformly dispersible in water which, alongside the active ingredient apart from a diluent or inert substance, also comprise surfactants of an ionic and/or non-ionic type (wetting agent, dispersant), e.g. polyethoxylated alkylphenols, polyethoxylated fatty alcohols, polyethoxylated fatty amines, fatty alcohol poly glycolethersulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the herbicidally active compounds are finely ground, for example in customary apparatuses such as hammer mills, blower mills and air-jet mills, and simultaneously or subsequently mixed with the formulation auxiliaries.

Emulsifiable concentrates are produced by dissolving the active compound in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active compound with finely distributed solids, for example talc, natural clays, such as kaolin, bentonite and pyrophyllite, or diatomaceous earth. Suspension concentrates may be water- or oil-based. They may be prepared, for example, by wet-grinding by means of commercial bead mills and optional addition of surfactants as have, for example, already been listed above for the other formulation types. Emulsions, for example oil-in-water emulsions (EW), can be produced, for example, by means of stirrers, colloid mills and/or static mixers using aqueous organic solvents and optionally surfactants as already listed above, for example, for the other formulation types. Granules can be produced either by spraying the active compound onto adsorptive granular inert material or by applying active compound concentrates to the surface of carriers, such as sand, kaolinites or granular inert material, by means of adhesives, for example polyvinyl alcohol, sodium polyacrylate or else mineral oils. Suitable active compounds can also be granulated in the manner customary for the production of fertilizer granules—if desired as a mixture with fertilizers. Water-dispersible granules are produced generally by the customary processes such as spray-drying, fluidized-bed granulation, pan granulation, mixing with high-speed mixers and extrusion without solid inert material. For the production of pan, fluidized-bed, extruder and spray granules, see e.g. processes in "Spray-Drying Handbook" 3rd Ed. 1979, G. Goodwin Ltd., London, J. E. Browning, "Agglomeration", Chemical and Engineering 1967, pages 147 ff.; "Perry's Chemical Engineer's Handbook", 5th Ed., McGraw-Hill, New York 1973, pp. 8-57. For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations contain generally 0.1 to 99% by weight, especially 0.1 to 95% by weight, of compounds of the invention.

In wettable powders, the active compound concentration is, for example, about 10 to 90% by weight, the remainder to 100% by weight consisting of customary formulation constituents. In emulsifiable concentrates, the active compound concentration may be about 1% to 90% and preferably 5% to 80% by weight. Dust-type formulations contain 1% to 30% by weight of active ingredient, preferably usually 5% to 20% by weight of active ingredient; sprayable solutions contain about 0.05% to 80% by weight, preferably 2% to 50% by weight of active ingredient. In the case of water-dispersible granules, the active compound content depends partially on whether the active compound is in liquid or solid form and on which granulation auxiliaries, fillers, etc., are used. In the water-dispersible granules, the content of active compound is, for example, between 1% and 95% by weight, preferably between 10% and 80% by weight.

In addition, the active compound formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tank mix.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as are described in, for example, Weed Research 26 (1986) 441-445 or "The Pesticide Manual", 15th edition, The British Crop Protection Council and the Royal Soc. of Chemistry, 2009 and the literature cited therein. Examples of known herbicides or plant growth regulators which can be combined with the inventive compounds include the active ingredients which follow (the compounds are designated by the common name according to the International Organization for Standardization (ISO) or by the chemical name or by the code number) and always encompass all use forms, such as acids, salts, esters and isomers, such as stereoisomers and optical isomers. These include, by way of example, one use form and in some cases also a plurality of use forms:
acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryne, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumicloracpentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. 0-(2,4-dimethyl-6-nitrophenyl)O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, 1H, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron esters, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl} oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e. 1-ethoxy-3-methyl-1-oxobut-3-en-2-yl 5-[2-chlor-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triafamone, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds

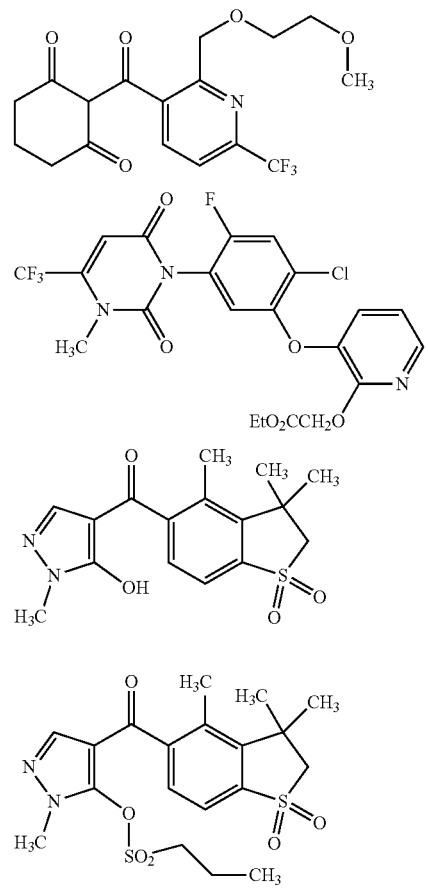

-continued

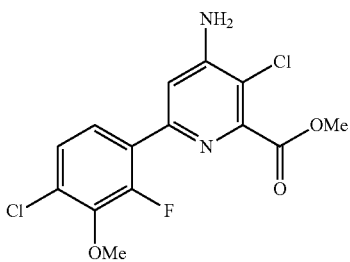

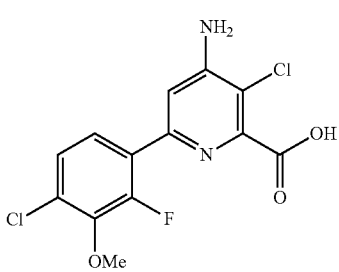

For application, the formulations in commercial form are, if appropriate, diluted in a customary manner, for example in the case of wettable powders, emulsifiable concentrates, dispersions and water-dispersible granules with water. Dust-type preparations, granules for soil application or granules for scattering and sprayable solutions are not normally diluted further with other inert substances prior to application.

The required application rate of the compounds of the formula (I) varies with the external conditions, including, inter alia, temperature, humidity and the type of herbicide used. It can vary within wide limits, for example between 0.001 and 1.0 kg/ha or more of active substance, but it is preferably between 0.005 and 750 g/ha.

The examples which follow illustrate the invention.

A. CHEMICAL EXAMPLES

Preparation of 2,4-dichloro-6-fluoro-N-(5-methyl-1,3,4-oxadiazol-2-yl)-3-(methylsulfanyl)benzamide Ex. No. 2-242

1. Preparation of 1,3-dichloro-5-fluoro-2-(methylsulfanyl)benzene

Under an atmosphere of nitrogen and at 0° C., 9.5 g (67 mmol) of methyl iodide are added to a mixture of 11.0 g (55.8 mmol) of 2,6-dichloro-4-fluorobenzenethiol and 11.6 g (84 mmol) of K2CO3 in 50 ml of DMF. After 12 h of stirring at room temperature, the reaction mixture is poured onto ice and then extracted with tert-butyl methyl ether. The organic phase is washed twice with water and once with sat. NaCl solution, dried over sodium sulfate and concentrated. Yield: 10.55 g (90%); slightly yellowish oil.

2. Preparation of 2,4-dichloro-6-fluoro-3-(methylsulfanyl)benzoic acid

At −78° C., 20 ml (50 mmol) of a 2.5 M nBuLi solution are added dropwise to a solution of 10.55 g (50 mmol) of 1,3-dichloro-5-fluoro-2-(methylsulfanyl)benzoline in 100 ml of THF (abs.). After 1 h of stirring at −78° C., an excess of $CO_2$ is passed through. The reaction mixture is subsequently allowed to warm to room temperature and then poured into 500 ml of a 1 M aqueous sodium hydroxide solution. The mixture is then washed with t-butyl methyl ether. The aqueous phase is acidified to pH 4 using a 2 M HCl solution and then extracted with t-butyl methyl ether. The organic phase is dried over sodium sulfate, filtered and concentrated. Yield: 10 g (39 mmol; 78%). $^1$H-NMR (40 MHz; DMSO-$d_6$): 7.63 ppm (d, 1H); 2.42 (s, 3H).

3. 2,4-Dichloro-6-fluoro-N-(5-methyl-1,3,4-oxadiazol-2-yl)-3-(methylsulfanyl)benzamide (Ex. No. 2-242)

At 0° C., 448 mg (0.309 ml, 3.53 mmol) of oxalyl chloride are added dropwise to a solution of 600 mg (2.35 mmol) of 2,4-dichloro-6-fluoro-3-(methylsulfanyl)benzoic acid and 326 mg (3.29 mmol) of 2-amino-5-methyl-1,3,4-oxadiazole in 20 ml of pyridine. After 1 h at 0° C., the reaction mixture is warmed to room temperature and stirred at room temperature for 14 h. The mixture is then concentrated and 20 ml each of dichloromethane and water are added to the residue. After separation of the phases, the organic phase is dried over sodium sulfate, filtered and concentrated. The residue is purified by column chromatography (silica gel, heptane/ethyl acetate).

Yield: 165 mg (90% pure; 19%) 1H-NMR (40 MHz; DMSO-$d^6$): 12.59 ppm (bs, 1H), 7.86 ppm (d, 1H); 2.41 ppm (s, 3H).

Preparation of 2,4-dichloro-6-fluoro-N-(5-methyl-1,3,4-oxadiazol-2-yl)-3-(methylsulfinyl)benzamide Ex. No. 2-243

At 0° C., 107 mg (0.465 mmol) meta-chloroperbenzoic acid are added to a solution of 115 mg (0.274 mmol) of 2,4-dichloro-6-fluoro-N-(5-methyl-1,3,4-oxadiazol-2-yl)-3-(methylsulfanyl)benzamide (Ex. No. 2-242) in 20 ml of dichloromethane. After 2 days of stirring at room temperature, an aqueous bisulfite solution is added. Following extraction, the organic phase is concentrated and purified by column chromatography (HPLC; acetonitrile/water).

Yield: 32 mg (95% pure; 31%) H-NMR (40 MHz; DMSO-$d_6$): 11.60 ppm (bs, 1H), 7.24 ppm (d, 1H); 3.07 ppm (s, 3H).

The abbreviations used mean:

| | | | |
|---|---|---|---|
| Et = ethyl | Me = methyl | n-Pr = n-propyl | i-Pr = isopropyl |
| c-Pr = cyclopropyl | Ph = phenyl | Ac = acetyl | Bz = benzoyl |

TABLE 1

Compounds of the general formula (I) in which A represents CY, W represents fluorine and V and R represent hydrogen

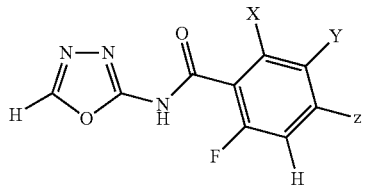

| No. | X | Y | Z | Physical data (¹H-NMR, DMSO-$d_6$, 400 MHz) |
|---|---|---|---|---|
| 1-1 | F | H | Cl | |
| 1-2 | F | H | SO$_2$Me | |
| 1-3 | F | H | SO$_2$Et | |
| 1-4 | F | H | CF$_3$ | |
| 1-5 | F | H | NO$_2$ | |
| 1-6 | Cl | H | Br | |
| 1-7 | Cl | H | SMe | |
| 1-8 | Cl | H | SOMe | |
| 1-9 | Cl | H | SO$_2$Me | |
| 1-10 | Cl | H | SO$_2$CH$_2$Cl | |
| 1-11 | Cl | H | SEt | |
| 1-12 | Cl | H | SO$_2$Et | |
| 1-13 | Cl | H | CF$_3$ | |
| 1-14 | Cl | H | NO$_2$ | |
| 1-15 | Cl | H | pyrazol-1-yl | |
| 1-16 | Cl | H | 1H-1,2,4-triazol-1-yl | |
| 1-17 | Br | H | Cl | |
| 1-18 | Br | H | Br | |
| 1-19 | Br | H | SO$_2$Me | |
| 1-20 | Br | H | SO$_2$Et | |
| 1-21 | Br | H | CF$_3$ | |
| 1-22 | SO$_2$Me | H | Cl | |
| 1-23 | SO$_2$Me | H | Br | |
| 1-24 | SO$_2$Me | H | SMe | |
| 1-25 | SO$_2$Me | H | SOMe | |
| 1-26 | SO$_2$Me | H | SO$_2$Me | |
| 1-27 | SO$_2$Me | H | SO$_2$Et | |
| 1-28 | SO$_2$Me | H | CF$_3$ | |
| 1-29 | SO$_2$Et | H | Cl | |
| 1-30 | SO$_2$Et | H | Br | |
| 1-31 | SO$_2$Et | H | SMe | |
| 1-32 | SO$_2$Et | H | SOMe | |
| 1-33 | SO$_2$Et | H | SO$_2$Me | |
| 1-34 | SO$_2$Et | H | CF$_3$ | |
| 1-35 | NO$_2$ | H | F | |
| 1-36 | NO$_2$ | H | Cl | |
| 1-37 | NO$_2$ | H | Br | |
| 1-38 | NO$_2$ | H | I | |
| 1-39 | NO$_2$ | H | CN | |
| 1-40 | NO$_2$ | H | SO$_2$Me | |
| 1-41 | NO$_2$ | H | SO$_2$Et | |
| 1-42 | NO$_2$ | H | CF$_3$ | |
| 1-43 | Me | H | Cl | |
| 1-44 | Me | H | Br | |
| 1-45 | Me | H | SMe | |
| 1-46 | Me | H | SO$_2$Me | |
| 1-47 | Me | H | SO$_2$CH$_2$Cl | |
| 1-48 | Me | H | SEt | |
| 1-49 | Me | H | SO$_2$Et | |
| 1-50 | Me | H | CF$_3$ | |
| 1-51 | CH$_2$SO$_2$Me | H | CF$_3$ | |
| 1-52 | Et | H | Cl | |
| 1-53 | Et | H | Br | |
| 1-54 | Et | H | SMe | |
| 1-55 | Et | H | SO$_2$Me | |
| 1-56 | Et | H | SO$_2$CH$_2$Cl | |
| 1-57 | Et | H | SEt | |
| 1-58 | Et | H | SO$_2$Et | |
| 1-59 | Et | H | CF$_3$ | |
| 1-60 | CF$_3$ | H | Cl | |
| 1-61 | CF$_3$ | H | Br | |
| 1-62 | CF$_3$ | H | SO$_2$Me | |

TABLE 1-continued

Compounds of the general formula (I) in which A represents CY, W represents fluorine and V and R represent hydrogen

| No. | X | Y | Z | Physical data ($^1$H-NMR, DMSO-$d_6$, 400 MHz) |
|---|---|---|---|---|
| 1-63 | CF$_3$ | H | SO$_2$Et | |
| 1-64 | CF$_3$ | H | CF$_3$ | |
| 1-65 | NO$_2$ | NH$_2$ | F | |
| 1-66 | NO$_2$ | NHMe | F | |
| 1-67 | NO$_2$ | NMe$_2$ | F | |
| 1-68 | NO$_2$ | Me | Cl | |
| 1-69 | NO$_2$ | NH$_2$ | Cl | |
| 1-70 | NO$_2$ | NHMe | Cl | |
| 1-71 | NO$_2$ | NMe$_2$ | Cl | |
| 1-72 | NO$_2$ | NH$_2$ | Br | |
| 1-73 | NO$_2$ | NHMe | Br | |
| 1-74 | NO$_2$ | NMe$_2$ | Br | |
| 1-75 | NO$_2$ | NH$_2$ | CF$_3$ | |
| 1-76 | NO$_2$ | NMe$_2$ | CF$_3$ | |
| 1-77 | NO$_2$ | NH$_2$ | SO$_2$Me | |
| 1-78 | NO$_2$ | NH$_2$ | SO$_2$Et | |
| 1-79 | NO$_2$ | NHMe | SO$_2$Me | |
| 1-80 | NO$_2$ | NMe$_2$ | SO$_2$Me | |
| 1-81 | NO$_2$ | NMe$_2$ | SO$_2$Et | |
| 1-82 | NO$_2$ | NH$_2$ | 1H-1,2,4-triazol-1-yl | |
| 1-83 | NO$_2$ | NHMe | 1H-1,2,4-triazol-1-yl | |
| 1-84 | NO$_2$ | NMe$_2$ | 1H-1,2,4-triazol-1-yl | |
| 1-85 | Me | SMe | H | |
| 1-86 | Me | SOMe | H | |
| 1-87 | Me | SO$_2$Me | H | |
| 1-88 | Me | SEt | H | |
| 1-89 | Me | SOEt | H | |
| 1-90 | Me | SO$_2$Et | H | |
| 1-91 | Me | S(CH$_2$)$_2$OMe | H | |
| 1-92 | Me | SO(CH$_2$)$_2$OMe | H | |
| 1-93 | Me | SO$_2$(CH$_2$)$_2$OMe | H | |
| 1-94 | Me | F | F | |
| 1-95 | Me | F | Cl | |
| 1-96 | Me | SEt | F | |
| 1-97 | Me | SOEt | F | |
| 1-98 | Me | SO$_2$Et | F | |
| 1-99 | Me | Me | Cl | |
| 1-100 | Me | F | Cl | |
| 1-101 | Me | Cl | Cl | |
| 1-102 | Me | NH$_2$ | Cl | |
| 1-103 | Me | NHMe | Cl | |
| 1-104 | Me | NMe$_2$ | Cl | |
| 1-105 | Me | O(CH$_2$)$_2$OMe | Cl | |
| 1-106 | Me | O(CH$_2$)$_3$OMe | Cl | |
| 1-107 | Me | O(CH$_2$)$_4$OMe | Cl | |
| 1-108 | Me | OCH$_2$CONMe$_2$ | Cl | |
| 1-109 | Me | O(CH$_2$)$_2$—CO—NMe$_2$ | Cl | |
| 1-110 | Me | O(CH$_2$)$_2$—NH(CO)NMe$_2$ | Cl | |
| 1-111 | Me | O(CH$_2$)$_2$—NH(CO)NHCO$_2$Et | Cl | |
| 1-112 | Me | O(CH$_2$)$_2$—NHCO$_2$Me | Cl | |
| 1-113 | Me | OCH$_2$—NHSO$_2$cPr | Cl | |
| 1-114 | Me | O(CH$_2$)-5-2,4-dimethyl-2,4-dihydro-3H-1,2,4-triazol-3-one | Cl | |
| 1-115 | Me | O(CH$_2$)-3,5-dimethyl-1,2-oxazol-4-yl | Cl | |
| 1-116 | Me | SMe | Cl | |
| 1-117 | Me | SOMe | Cl | |
| 1-118 | Me | SO$_2$Me | Cl | |
| 1-119 | Me | SEt | Cl | |
| 1-120 | Me | SOEt | Cl | |

TABLE 1-continued

Compounds of the general formula (I) in which A represents CY, W represents fluorine and V and R represent hydrogen

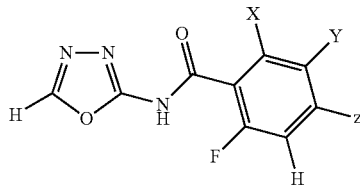

| No. | X | Y | Z | Physical data (¹H-NMR, DMSO-$d_6$, 400 MHz) |
|---|---|---|---|---|
| 1-121 | Me | $SO_2Et$ | Cl | |
| 1-122 | Me | $S(CH_2)_2OMe$ | Cl | |
| 1-123 | Me | $SO(CH_2)_2OMe$ | Cl | |
| 1-124 | Me | $SO_2(CH_2)_2OMe$ | Cl | |
| 1-125 | Me | $NH_2$ | Br | |
| 1-126 | Me | NHMe | Br | |
| 1-127 | Me | $NMe_2$ | Br | |
| 1-128 | Me | $OCH_2(CO)NMe_2$ | Br | |
| 1-129 | Me | $O(CH_2)$-5-pyrrolidin-2-one | Br | |
| 1-130 | Me | SMe | Br | |
| 1-131 | Me | SOMe | Br | |
| 1-132 | Me | $SO_2Me$ | Br | |
| 1-133 | Me | SEt | Br | |
| 1-134 | Me | SOEt | Br | |
| 1-135 | Me | $SO_2Et$ | Br | |
| 1-136 | Me | SMe | I | |
| 1-137 | Me | SOMe | I | |
| 1-138 | Me | $SO_2Me$ | I | |
| 1-139 | Me | SEt | I | |
| 1-140 | Me | SOEt | I | |
| 1-141 | Me | $SO_2Et$ | I | |
| 1-142 | Me | Cl | $CF_3$ | |
| 1-143 | Me | SMe | $CF_3$ | |
| 1-144 | Me | SOMe | $CF_3$ | |
| 1-145 | Me | $SO_2Me$ | $CF_3$ | |
| 1-146 | Me | SEt | $CF_3$ | |
| 1-147 | Me | SOEt | $CF_3$ | |
| 1-148 | Me | $SO_2Et$ | $CF_3$ | |
| 1-149 | Me | $S(CH_2)_2OMe$ | $CF_3$ | |
| 1-150 | Me | $SO(CH_2)_2OMe$ | $CF_3$ | |
| 1-151 | Me | $SO_2(CH_2)_2OMe$ | $CF_3$ | |
| 1-152 | Me | Me | $SO_2Me$ | |
| 1-153 | Me | 4,5-dihydro-1,2-oxazol-3-yl | $SO_2Me$ | |
| 1-154 | Me | 4,5-dihydro-1,2-oxazol-3-yl | $SO_2Et$ | |
| 1-155 | Me | 5-cyanomethyl-4,5-dihydro-1,2-oxazol-3-yl | $SO_2Me$ | |
| 1-156 | Me | 5-cyanomethyl-4,5-dihydro-1,2-oxazol-3-yl | $SO_2Et$ | |
| 1-157 | Me | $NH_2$ | $SO_2Me$ | |
| 1-158 | Me | NHMe | $SO_2Me$ | |
| 1-159 | Me | $NMe_2$ | $SO_2Me$ | |
| 1-160 | Me | $NH(CH_2)_2OMe$ | $SO_2Me$ | |
| 1-161 | Me | pyrazol-1-yl | $SO_2Me$ | |
| 1-162 | Me | OH | $SO_2Me$ | |
| 1-163 | Me | OMe | $SO_2Me$ | |
| 1-164 | Me | OMe | $SO_2Et$ | |
| 1-165 | Me | OEt | $SO_2Me$ | |
| 1-166 | Me | OEt | $SO_2Et$ | |
| 1-167 | Me | OiPr | $SO_2Me$ | |
| 1-168 | Me | OiPr | $SO_2Et$ | |
| 1-169 | Me | $O(CH_2)_2OMe$ | $SO_2Me$ | |
| 1-170 | Me | $O(CH_2)_2OMe$ | $SO_2Et$ | |
| 1-171 | Me | $O(CH_2)_3OMe$ | $SO_2Me$ | |
| 1-172 | Me | $O(CH_2)_3OMe$ | $SO_2Et$ | |
| 1-173 | Me | $O(CH_2)_4OMe$ | $SO_2Me$ | |
| 1-174 | Me | $O(CH_2)_4OMe$ | $SO_2Et$ | |
| 1-175 | Me | $O(CH_2)_2NHSO2Me$ | $SO_2Me$ | |
| 1-176 | Me | $O(CH_2)_2NHSO2Me$ | $SO_2Et$ | |

TABLE 1-continued

Compounds of the general formula (I) in which A represents CY, W represents fluorine and V and R represent hydrogen

| No. | X | Y | Z | Physical data ($^1$H-NMR, DMSO-$d_6$, 400 MHz) |
|---|---|---|---|---|
| 1-177 | Me | OCH$_2$(CO)NMe$_2$ | SO$_2$Me | |
| 1-178 | Me | OCH$_2$(CO)NMe$_2$ | SO$_2$Et | |
| 1-179 | Me | [1,4]dioxan-2-ylmethoxy | SO$_2$Me | |
| 1-180 | Me | [1,4]dioxan-2-ylmethoxy | SO$_2$Et | |
| 1-181 | Me | O(CH$_2$)$_2$—O-(3,5-dimethoxypyrimidin-2-yl) | SO$_2$Me | |
| 1-182 | Me | Cl | SO$_2$Me | |
| 1-183 | Me | SMe | SO$_2$Me | |
| 1-184 | Me | SOMe | SO$_2$Me | |
| 1-185 | Me | SO$_2$Me | SO$_2$Me | |
| 1-186 | Me | SO$_2$Me | SO$_2$Et | |
| 1-187 | Me | SEt | SO$_2$Me | |
| 1-188 | Me | SOEt | SO$_2$Me | |
| 1-189 | Me | SO$_2$Et | SO$_2$Me | |
| 1-190 | Me | S(CH$_2$)$_2$OMe | SO$_2$Me | |
| 1-191 | Me | SO(CH$_2$)$_2$OMe | SO$_2$Me | |
| 1-192 | Me | SO$_2$(CH$_2$)$_2$OMe | SO2Me | |
| 1-193 | CH$_2$SMe | OMe | SO$_2$Me | |
| 1-194 | CH$_2$OMe | OMe | SO$_2$Me | |
| 1-195 | CH$_2$O(CH$_2$)$_2$OMe | NH(CH$_2$)$_2$OEt | SO$_2$Me | |
| 1-196 | CH$_2$O(CH$_2$)$_2$OMe | NH(CH$_2$)$_3$OEt | SO$_2$Me | |
| 1-197 | CH$_2$O(CH$_2$)$_3$OMe | OMe | SO$_2$Me | |
| 1-198 | CH$_2$O(CH$_2$)$_2$OMe | NH(CH$_2$)$_2$OMe | SO$_2$Me | |
| 1-199 | CH$_2$O(CH$_2$)$_2$OMe | NH(CH$_2$)$_3$OMe | SO$_2$Me | |
| 1-200 | Et | SMe | Cl | |
| 1-201 | Et | SO$_2$Me | Cl | |
| 1-202 | Et | SMe | CF$_3$ | |
| 1-203 | Et | SO$_2$Me | CF$_3$ | |
| 1-204 | Et | F | SO$_2$Me | |
| 1-205 | Et | NH(CH$_2$)$_2$OMe | SO$_2$Me | |
| 1-206 | iPr | SO$_2$Me | CF$_3$ | |
| 1-207 | cPr | SO$_2$Me | CF$_3$ | |
| 1-208 | CF$_3$ | O(CH$_2$)$_2$OMe | F | |
| 1-209 | CF$_3$ | O(CH$_2$)$_3$OMe | F | |
| 1-210 | CF$_3$ | OCH$_2$CONMe$_2$ | F | |
| 1-211 | CF$_3$ | [1,4]dioxan-2-ylmethoxy | F | |
| 1-212 | CF$_3$ | O(CH$_2$)$_2$OMe | Cl | |
| 1-213 | CF$_3$ | O(CH$_2$)$_3$OMe | Cl | |
| 1-214 | CF$_3$ | OCH$_2$CONMe$_2$ | Cl | |
| 1-215 | CF$_3$ | [1,4]dioxan-2-ylmethoxy | Cl | |
| 1-216 | CF$_3$ | O(CH$_2$)$_2$OMe | Br | |
| 1-217 | CF$_3$ | O(CH$_2$)$_3$OMe | Br | |
| 1-218 | CF$_3$ | OCH$_2$CONMe$_2$ | Br | |
| 1-219 | CF$_3$ | [1,4]dioxan-2-ylmethoxy | Br | |
| 1-220 | CF$_3$ | O(CH$_2$)$_2$OMe | I | |
| 1-221 | CF$_3$ | O(CH$_2$)$_3$OMe | I | |
| 1-222 | CF$_3$ | OCH$_2$CONMe$_2$ | I | |
| 1-223 | CF$_3$ | [1,4]dioxan-2-ylmethoxy | I | |
| 1-224 | CF$_3$ | F | SO$_2$Me | |
| 1-225 | CF$_3$ | F | SO$_2$Et | |
| 1-226 | CF$_3$ | O(CH$_2$)$_2$OMe | SO$_2$Me | |
| 1-227 | CF$_3$ | O(CH$_2$)$_2$OMe | SO$_2$Et | |
| 1-228 | CF$_3$ | O(CH$_2$)$_3$OMe | SO$_2$Me | |
| 1-229 | CF$_3$ | O(CH$_2$)$_3$OMe | SO$_2$Et | |
| 1-230 | CF$_3$ | OCH$_2$CONMe$_2$ | SO$_2$Me | |
| 1-231 | CF$_3$ | OCH$_2$CONMe$_2$ | SO$_2$Et | |

TABLE 1-continued

Compounds of the general formula (I) in which A represents CY, W represents fluorine and V and R represent hydrogen

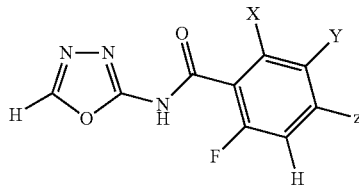

| No. | X | Y | Z | Physical data ($^1$H-NMR, DMSO-$d_6$, 400 MHz) |
|---|---|---|---|---|
| 1-232 | CF$_3$ | [1,4]dioxan-2-ylmethoxy | SO$_2$Me | |
| 1-233 | CF$_3$ | [1,4]dioxan-2-ylmethoxy | SO$_2$Et | |
| 1-234 | F | SMe | CF$_3$ | |
| 1-235 | F | SOMe | CF$_3$ | |
| 1-236 | Cl | Me | Cl | |
| 1-237 | Cl | OCH$_2$CHCH$_2$ | Cl | |
| 1-238 | Cl | OCH$_2$CHF$_2$ | Cl | |
| 1-239 | Cl | O(CH$_2$)$_2$OMe | Cl | |
| 1-240 | Cl | OCH$_2$CONMe$_2$ | Cl | |
| 1-241 | Cl | O(CH$_2$)-5-pyrrolidin-2-one | Cl | |
| 1-242 | Cl | SMe | Cl | |
| 1-243 | Cl | SOMe | Cl | |
| 1-244 | Cl | SO$_2$Me | Cl | |
| 1-245 | Cl | F | SMe | |
| 1-246 | Cl | Cl | SO$_2$Me | |
| 1-247 | Cl | COOMe | SO$_2$Me | |
| 1-248 | Cl | CONMe$_2$ | SO$_2$Me | |
| 1-249 | Cl | CONMe(OMe) | SO$_2$Me | |
| 1-250 | Cl | CH$_2$OMe | SO$_2$Me | |
| 1-251 | Cl | CH$_2$OMe | SO$_2$Et | |
| 1-252 | Cl | CH$_2$OEt | SO$_2$Me | |
| 1-253 | Cl | CH$_2$OEt | SO$_2$Et | |
| 1-254 | Cl | CH$_2$OCH$_2$CHF$_2$ | SO$_2$Me | |
| 1-255 | Cl | CH$_2$OCH$_2$CF$_3$ | SO$_2$Me | |
| 1-256 | Cl | CH$_2$OCH$_2$CF$_3$ | SO$_2$Et | |
| 1-257 | Cl | CH$_2$OCH$_2$CF$_2$CHF$_2$ | SO$_2$Me | |
| 1-258 | Cl | CH$_2$O-c-pentyl | SO$_2$Me | |
| 1-259 | Cl | CH$_2$PO(OMe)$_2$ | SO$_2$Me | |
| 1-260 | Cl | 4,5-dihydro-1,2-oxazol-3-yl | SMe | |
| 1-261 | Cl | 4,5-dihydro-1,2-oxazol-3-yl | SO$_2$Me | |
| 1-262 | Cl | 4,5-dihydro-1,2-oxazol-3-yl | SO$_2$Et | |
| 1-263 | Cl | 5-cyanomethyl-4,5-dihydro-1,2-oxazol-3-yl | SO$_2$Me | |
| 1-264 | Cl | 5-cyanomethyl-4,5-dihydro-1,2-oxazol-3-yl | SO$_2$Et | |
| 1-265 | Cl | 5-(methoxymethyl)-4,5-dihydro-1,2-oxazol-3-yl | SO$_2$Et | |
| 1-266 | Cl | 5-(methoxymethyl)-5-methyl-4,5-dihydro-1,2-oxazol-3-yl | SO$_2$Et | |
| 1-267 | Cl | CH$_2$O-tetrahydrofuran-3-yl | SO$_2$Me | |
| 1-268 | Cl | CH$_2$O-tetrahydrofuran-3-yl | SO$_2$Et | |
| 1-269 | Cl | CH$_2$OCH$_2$-tetrahydrofuran-2-yl | SO$_2$Me | |
| 1-270 | Cl | CH$_2$OCH$_2$-tetrahydrofuran-2-yl | SO$_2$Et | |
| 1-271 | Cl | CH$_2$OCH$_2$-tetrahydrofuran-3-yl | SO$_2$Me | |

TABLE 1-continued

Compounds of the general formula (I) in which A represents CY, W represents fluorine and V and R represent hydrogen

| No. | X | Y | Z | Physical data ($^1$H-NMR, DMSO-$d_6$, 400 MHz) |
|---|---|---|---|---|
| 1-272 | Cl | CH$_2$OCH$_2$-tetrahydrofuran-3-yl | SO$_2$Et | |
| 1-273 | Cl | OMe | SO$_2$Me | |
| 1-274 | Cl | OMe | SO$_2$Et | |
| 1-275 | Cl | OEt | SO$_2$Me | |
| 1-276 | Cl | OEt | SO$_2$Et | |
| 1-277 | Cl | OiPr | SO$_2$Me | |
| 1-278 | Cl | OiPr | SO$_2$Et | |
| 1-279 | Cl | O(CH$_2$)$_2$OMe | SO$_2$Me | |
| 1-280 | Cl | O(CH$_2$)$_4$OMe | SO$_2$Me | |
| 1-281 | Cl | O(CH$_2$)$_4$OMe | SO$_2$Et | |
| 1-282 | Cl | O(CH$_2$)$_3$OMe | SO$_2$Me | |
| 1-283 | Cl | O(CH$_2$)$_3$OMe | SO$_2$Et | |
| 1-284 | Cl | O(CH$_2$)$_2$OMe | SO$_2$Me | |
| 1-285 | Cl | O(CH$_2$)$_2$OMe | SO$_2$Et | |
| 1-286 | Cl | [1,4]dioxan-2-ylmethoxy | SO$_2$Me | |
| 1-287 | Cl | [1,4]dioxan-2-ylmethoxy | SO$_2$Et | |
| 1-288 | Cl | OCH$_2$(CO)NMe$_2$ | SO$_2$Me | |
| 1-289 | Cl | OCH$_2$(CO)NMe$_2$ | SO$_2$Et | |
| 1-290 | Cl | SMe | SO$_2$Me | |
| 1-291 | Cl | SOMe | SO$_2$Me | |
| 1-292 | Br | OMe | Br | |
| 1-293 | Br | O(CH$_2$)$_2$OMe | Br | |
| 1-294 | Br | O(CH$_2$)$_2$OMe | SO$_2$Me | |
| 1-295 | Br | O(CH$_2$)$_2$OMe | SO$_2$Et | |
| 1-296 | Br | O(CH$_2$)$_3$OMe | SO$_2$Me | |
| 1-297 | Br | O(CH$_2$)$_3$OMe | SO$_2$Et | |
| 1-298 | Br | O(CH$_2$)$_4$OMe | SO$_2$Me | |
| 1-299 | Br | O(CH$_2$)$_4$OMe | SO$_2$Et | |
| 1-300 | Br | [1,4]dioxan-2-ylmethoxy | SO$_2$Me | |
| 1-301 | Br | [1,4]dioxan-2-ylmethoxy | SO$_2$Et | |
| 1-302 | I | O(CH$_2$)$_2$OMe | SO$_2$Me | |
| 1-303 | I | O(CH$_2$)$_2$OMe | SO$_2$Et | |
| 1-304 | I | O(CH$_2$)$_3$OMe | SO$_2$Me | |
| 1-305 | I | O(CH$_2$)$_3$OMe | SO$_2$Et | |
| 1-306 | I | O(CH$_2$)$_4$OMe | SO$_2$Me | |
| 1-307 | I | O(CH$_2$)$_4$OMe | SO$_2$Et | |
| 1-308 | I | [1,4]dioxan-2-ylmethoxy | SO$_2$Me | |
| 1-309 | I | [1,4]dioxan-2-ylmethoxy | SO$_2$Et | |
| 1-310 | OMe | SMe | CF$_3$ | |
| 1-311 | OMe | SOMe | CF$_3$ | |
| 1-312 | OMe | SO$_2$Me | CF$_3$ | |
| 1-313 | OMe | SOEt | CF$_3$ | |
| 1-314 | OMe | SO$_2$Et | CF$_3$ | |
| 1-315 | OMe | S(CH$_2$)$_2$OMe | CF$_3$ | |
| 1-316 | OMe | SO(CH$_2$)$_2$OMe | CF$_3$ | |
| 1-317 | OMe | SO$_2$(CH$_2$)$_2$OMe | CF$_3$ | |
| 1-318 | OMe | SMe | Cl | |
| 1-319 | OMe | SOMe | Cl | |
| 1-320 | OMe | SO$_2$Me | Cl | |
| 1-321 | OMe | SEt | Cl | |
| 1-322 | OMe | SOEt | Cl | |
| 1-323 | OMe | SO2Et | Cl | |
| 1-324 | OMe | S(CH$_2$)$_2$OMe | Cl | |
| 1-325 | OMe | SO(CH$_2$)$_2$OMe | Cl | |
| 1-326 | OMe | SO$_2$(CH$_2$)$_2$OMe | Cl | |
| 1-327 | OCH$_2$c-Pr | SMe | CF$_3$ | |

TABLE 1-continued

Compounds of the general formula (I) in which A represents CY, W represents fluorine and V and R represent hydrogen

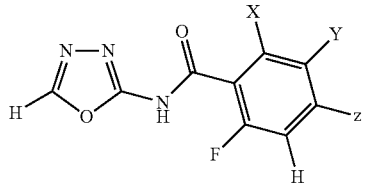

| No. | X | Y | Z | Physical data ($^1$H-NMR, DMSO-$d_6$, 400 MHz) |
|---|---|---|---|---|
| 1-328 | OCH$_2$c-Pr | SOMe | CF$_3$ | |
| 1-329 | OCH$_2$c-Pr | SO$_2$Me | CF$_3$ | |
| 1-330 | OCH$_2$c-Pr | SEt | CF$_3$ | |
| 1-331 | OCH$_2$c-Pr | SOEt | CF$_3$ | |
| 1-332 | OCH$_2$c-Pr | SO$_2$Et | CF$_3$ | |
| 1-333 | OCH$_2$c-Pr | S(CH$_2$)$_2$OMe | CF$_3$ | |
| 1-334 | OCH$_2$c-Pr | SO(CH$_2$)$_2$OMe | CF$_3$ | |
| 1-335 | OCH$_2$c-Pr | SO$_2$(CH$_2$)$_2$OMe | CF$_3$ | |
| 1-336 | OCH$_2$c-Pr | SMe | Cl | |
| 1-337 | OCH$_2$c-Pr | SOMe | Cl | |
| 1-338 | OCH$_2$c-Pr | SO$_2$Me | Cl | |
| 1-339 | OCH$_2$c-Pr | SEt | Cl | |
| 1-340 | OCH$_2$c-Pr | SOEt | Cl | |
| 1-341 | OCH$_2$c-Pr | SO$_2$Et | Cl | |
| 1-342 | OCH$_2$c-Pr | S(CH$_2$)$_2$OMe | Cl | |
| 1-343 | OCH$_2$c-Pr | SO(CH$_2$)$_2$OMe | Cl | |
| 1-344 | OCH$_2$c-Pr | SO$_2$(CH$_2$)$_2$OMe | Cl | |
| 1-345 | OCH$_2$c-Pr | SMe | SO$_2$Me | |
| 1-346 | OCH$_2$c-Pr | SOMe | SO$_2$Me | |
| 1-347 | OCH$_2$c-Pr | SO$_2$Me | SO$_2$Me | |
| 1-348 | OCH$_2$c-Pr | SEt | SO$_2$Me | |
| 1-349 | OCH$_2$c-Pr | SOEt | SO$_2$Me | |
| 1-350 | OCH$_2$c-Pr | SO$_2$Et | SO$_2$Me | |
| 1-351 | OCH$_2$c-Pr | S(CH$_2$)$_2$OMe | SO$_2$Me | |
| 1-352 | OCH$_2$c-Pr | SO(CH$_2$)$_2$OMe | SO$_2$Me | |
| 1-353 | OCH$_2$c-Pr | SO$_2$(CH$_2$)$_2$OMe | SO$_2$Me | |
| 1-354 | SO$_2$Me | F | CF$_3$ | |
| 1-355 | SO$_2$Me | NH$_2$ | CF$_3$ | |
| 1-356 | SO$_2$Me | NHEt | Cl | |
| 1-357 | SMe | SEt | F | |
| 1-358 | SMe | SMe | F | |
| 1-359 | Cl | SMe | CF$_3$ | |
| 1-360 | Cl | S(O)Me | CF$_3$ | |
| 1-361 | Cl | SO$_2$Me | CF$_3$ | |
| 1-362 | Cl | SO$_2$Me | SO$_2$Me | |

TABLE 2

Compounds of the general formula (I) in which A represents CY, V represents hydrogen, W represents fluorine and R represents methyl

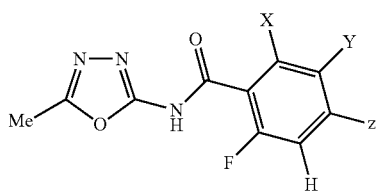

| No. | X | Y | Z | Physical data ($^1$H-NMR, DMSO-$d_6$, 400 MHz) |
|---|---|---|---|---|
| 2-1 | F | H | Cl | |
| 2-2 | F | H | SO$_2$Me | |
| 2-3 | F | H | SO$_2$Et | |
| 2-4 | F | H | CF$_3$ | |
| 2-5 | F | H | NO$_2$ | |
| 2-6 | Cl | H | Br | |

TABLE 2-continued

Compounds of the general formula (I) in which A represents
CY, V represents hydrogen, W represents fluorine and R represents methyl

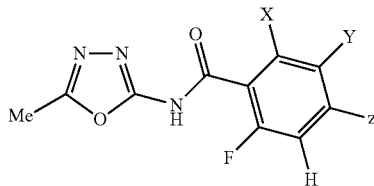

| No. | X | Y | Z | Physical data ($^1$H-NMR, DMSO-$d_6$, 400 MHz) |
|---|---|---|---|---|
| 2-7 | Cl | H | SMe | |
| 2-8 | Cl | H | SOMe | |
| 2-9 | Cl | H | SO$_2$Me | |
| 2-10 | Cl | H | SO$_2$CH$_2$Cl | |
| 2-11 | Cl | H | SEt | |
| 2-12 | Cl | H | SO$_2$Et | |
| 2-13 | Cl | H | CF$_3$ | |
| 2-14 | Cl | H | NO$_2$ | |
| 2-15 | Cl | H | pyrazol-1-yl | |
| 2-16 | Cl | H | 1H-1,2,4-triazol-1-yl | |
| 2-17 | Br | H | Cl | |
| 2-18 | Br | H | Br | |
| 2-19 | Br | H | SO$_2$Me | |
| 2-20 | Br | H | SO$_2$Et | |
| 2-21 | Br | H | CF$_3$ | |
| 2-22 | SO$_2$Me | H | Cl | |
| 2-23 | SO$_2$Me | H | Br | |
| 2-24 | SO$_2$Me | H | SMe | |
| 2-25 | SO$_2$Me | H | SOMe | |
| 2-26 | SO$_2$Me | H | SO$_2$Me | |
| 2-27 | SO$_2$Me | H | SO$_2$Et | |
| 2-28 | SO$_2$Me | H | CF$_3$ | |
| 2-29 | SO$_2$Et | H | Cl | |
| 2-30 | SO$_2$Et | H | Br | |
| 2-31 | SO$_2$Et | H | SMe | |
| 2-32 | SO$_2$Et | H | SOMe | |
| 2-33 | SO$_2$Et | H | SO$_2$Me | |
| 2-34 | SO$_2$Et | H | CF$_3$ | |
| 2-35 | NO$_2$ | H | F | |
| 2-36 | NO$_2$ | H | Cl | |
| 2-37 | NO$_2$ | H | Br | |
| 2-38 | NO$_2$ | H | I | |
| 2-39 | NO$_2$ | H | CN | |
| 2-40 | NO$_2$ | H | SO$_2$Me | |
| 2-41 | NO$_2$ | H | SO$_2$Et | |
| 2-42 | NO$_2$ | H | CF$_3$ | |
| 2-43 | Me | H | Cl | |
| 2-44 | Me | H | Br | |
| 2-45 | Me | H | SMe | |
| 2-46 | Me | H | SO$_2$Me | |
| 2-47 | Me | H | SO$_2$CH$_2$Cl | |
| 2-48 | Me | H | SEt | |
| 2-49 | Me | H | SO$_2$Et | |
| 2-50 | Me | H | CF$_3$ | |
| 2-51 | CH$_2$SO$_2$Me | H | CF$_3$ | |
| 2-52 | Et | H | Cl | |
| 2-53 | Et | H | Br | |
| 2-54 | Et | H | SMe | |
| 2-55 | Et | H | SO$_2$Me | |
| 2-56 | Et | H | SO$_2$CH$_2$Cl | |
| 2-57 | Et | H | SEt | |
| 2-58 | Et | H | SO$_2$Et | |
| 2-59 | Et | H | CF$_3$ | |
| 2-60 | CF$_3$ | H | Cl | |
| 2-61 | CF$_3$ | H | Br | |
| 2-62 | CF$_3$ | H | SO$_2$Me | |
| 2-63 | CF$_3$ | H | SO$_2$Et | |
| 2-64 | CF$_3$ | H | CF$_3$ | |
| 2-65 | NO$_2$ | NH$_2$ | F | |
| 2-66 | NO$_2$ | NHMe | F | |
| 2-67 | NO$_2$ | NMe$_2$ | F | |
| 2-68 | NO$_2$ | Me | Cl | |
| 2-69 | NO$_2$ | NH$_2$ | Cl | |

TABLE 2-continued

Compounds of the general formula (I) in which A represents
CY, V represents hydrogen, W represents fluorine and R represents methyl

| No. | X | Y | Z | Physical data ($^1$H-NMR, DMSO-$d_6$, 400 MHz) |
|---|---|---|---|---|
| 2-70 | NO$_2$ | NHMe | Cl | |
| 2-71 | NO$_2$ | NMe$_2$ | Cl | |
| 2-72 | NO$_2$ | NH$_2$ | Br | |
| 2-73 | NO$_2$ | NHMe | Br | |
| 2-74 | NO$_2$ | NMe$_2$ | Br | |
| 2-75 | NO$_2$ | NH$_2$ | CF$_3$ | |
| 2-76 | NO$_2$ | NMe$_2$ | CF$_3$ | |
| 2-77 | NO$_2$ | NH$_2$ | SO$_2$Me | |
| 2-78 | NO$_2$ | NH$_2$ | SO$_2$Et | |
| 2-79 | NO$_2$ | NHMe | SO$_2$Me | |
| 2-80 | NO$_2$ | NMe$_2$ | SO$_2$Me | |
| 2-81 | NO$_2$ | NMe$_2$ | SO$_2$Et | |
| 2-82 | NO$_2$ | NH$_2$ | 1H-1,2,4-triazol-1-yl | |
| 2-83 | NO$_2$ | NHMe | 1H-1,2,4-triazol-1-yl | |
| 2-84 | NO$_2$ | NMe$_2$ | 1H-1,2,4-triazol-1-yl | |
| 2-85 | Me | SMe | H | |
| 2-86 | Me | SOMe | H | |
| 2-87 | Me | SO$_2$Me | H | |
| 2-88 | Me | SEt | H | |
| 2-89 | Me | SOEt | H | |
| 2-90 | Me | SO$_2$Et | H | |
| 2-91 | Me | S(CH$_2$)$_2$OMe | H | |
| 2-92 | Me | SO(CH$_2$)$_2$OMe | H | |
| 2-93 | Me | SO$_2$(CH$_2$)$_2$OMe | H | |
| 2-94 | Me | F | F | |
| 2-95 | Me | F | Cl | |
| 2-96 | Me | SEt | F | |
| 2-97 | Me | SOEt | F | |
| 2-98 | Me | SO$_2$Et | F | |
| 2-99 | Me | Me | Cl | |
| 2-100 | Me | F | Cl | |
| 2-101 | Me | Cl | Cl | |
| 2-102 | Me | NH$_2$ | Cl | |
| 2-103 | Me | NHMe | Cl | |
| 2-104 | Me | NMe$_2$ | Cl | |
| 2-105 | Me | O(CH$_2$)$_2$OMe | Cl | |
| 2-106 | Me | O(CH$_2$)$_3$OMe | Cl | |
| 2-107 | Me | O(CH$_2$)$_4$OMe | Cl | |
| 2-108 | Me | OCH$_2$CONMe$_2$ | Cl | |
| 2-109 | Me | O(CH$_2$)$_2$—CO—NMe$_2$ | Cl | |
| 2-110 | Me | O(CH$_2$)$_2$—NH(CO)NMe$_2$ | Cl | |
| 2-111 | Me | O(CH$_2$)$_2$—NH(CO)NHCO$_2$Et | Cl | |
| 2-112 | Me | O(CH$_2$)$_2$—NHCO$_2$Me | Cl | |
| 2-113 | Me | O—CH$_2$—NHSO$_2$cPr | Cl | |
| 2-114 | Me | O(CH$_2$)-5-2,4-dimethyl-2,4-dihydro-3H-1,2,4-triazol-3-one | Cl | |
| 2-115 | Me | O(CH$_2$)-3,5-dimethyl-1,2-oxazol-4-yl | Cl | |
| 2-116 | Me | SMe | Cl | |
| 2-117 | Me | SOMe | Cl | |
| 2-118 | Me | SO$_2$Me | Cl | |
| 2-119 | Me | SEt | Cl | |
| 2-120 | Me | SOEt | Cl | |
| 2-121 | Me | SO$_2$Et | Cl | |
| 2-122 | Me | S(CH$_2$)$_2$OMe | Cl | |
| 2-123 | Me | SO(CH$_2$)$_2$OMe | Cl | |
| 2-124 | Me | SO$_2$(CH$_2$)$_2$OMe | Cl | |
| 2-125 | | | | |
| 2-126 | Me | NHMe | Br | |

TABLE 2-continued

Compounds of the general formula (I) in which A represents
CY, V represents hydrogen, W represents fluorine and R represents methyl

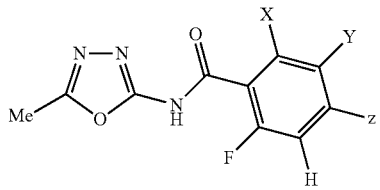

| No. | X | Y | Z | Physical data (¹H-NMR, DMSO-$d_6$, 400 MHz) |
|---|---|---|---|---|
| 2-127 | Me | NMe$_2$ | Br | |
| 2-128 | Me | O(CH$_2$)CONEt$_2$ | Br | |
| 2-129 | Me | O(CH$_2$)-5-pyrrolidin-2-one | Br | |
| 2-130 | Me | SMe | Br | |
| 2-131 | Me | SOMe | Br | |
| 2-132 | Me | SO$_2$Me | Br | |
| 2-133 | Me | SEt | Br | |
| 2-134 | Me | SOEt | Br | |
| 2-135 | Me | SO$_2$Et | Br | |
| 2-136 | Me | SMe | I | |
| 2-137 | Me | SOMe | I | |
| 2-138 | Me | SO$_2$Me | I | |
| 2-139 | Me | SEt | I | |
| 2-140 | Me | SOEt | I | |
| 2-141 | Me | SO$_2$Et | I | |
| 2-142 | Me | Cl | CF$_3$ | |
| 2-143 | Me | SMe | CF$_3$ | |
| 2-144 | Me | SOMe | CF$_3$ | |
| 2-145 | Me | SO$_2$Me | CF$_3$ | |
| 2-146 | Me | SEt | CF$_3$ | |
| 2-147 | Me | SOEt | CF$_3$ | |
| 2-148 | Me | SO$_2$Et | CF$_3$ | |
| 2-149 | Me | S(CH$_2$)$_2$OMe | CF$_3$ | |
| 2-150 | Me | SO(CH$_2$)$_2$OMe | CF$_3$ | |
| 2-151 | Me | SO$_2$(CH$_2$)$_2$OMe | CF$_3$ | |
| 2-152 | Me | Me | SO$_2$Me | |
| 2-153 | Me | 4,5-dihydro-1,2-oxazol-3-yl | SO$_2$Me | |
| 2-154 | Me | 4,5-dihydro-1,2-oxazol-3-yl | SO$_2$Et | |
| 2-155 | Me | 5-cyanomethyl-4,5-dihydro-1,2-oxazol-3-yl | SO$_2$Me | |
| 2-156 | Me | 5-cyanomethyl-4,5-dihydro-1,2-oxazol-3-yl | SO$_2$Et | |
| 2-157 | Me | NH$_2$ | SO$_2$Me | |
| 2-158 | Me | NHMe | SO$_2$Me | |
| 2-159 | Me | NMe$_2$ | SO$_2$Me | |
| 2-160 | Me | NH(CH$_2$)$_2$OMe | SO$_2$Me | |
| 2-161 | Me | pyrazol-1-yl | SO$_2$Me | |
| 2-162 | Me | OH | SO$_2$Me | |
| 2-163 | Me | OMe | SO$_2$Me | |
| 2-164 | Me | OMe | SO$_2$Et | |
| 2-165 | Me | OEt | SO$_2$Me | |
| 2-166 | Me | OEt | SO$_2$Et | |
| 2-167 | Me | OiPr | SO$_2$Me | |
| 2-168 | Me | OiPr | SO$_2$Et | |
| 2-169 | Me | O(CH$_2$)$_2$OMe | SO$_2$Me | |
| 2-170 | Me | O(CH$_2$)$_2$OMe | SO$_2$Et | |
| 2-171 | Me | O(CH$_2$)$_3$OMe | SO$_2$Me | |
| 2-172 | Me | O(CH$_2$)$_3$OMe | SO$_2$Et | |
| 2-173 | Me | O(CH$_2$)$_4$OMe | SO$_2$Me | |
| 2-174 | Me | O(CH$_2$)$_4$OMe | SO$_2$Et | |
| 2-175 | Me | O(CH$_2$)$_2$NHSO2Me | SO$_2$Me | |
| 2-176 | Me | O(CH$_2$)$_2$NHSO2Me | SO$_2$Et | |
| 2-177 | Me | OCH$_2$(CO)NMe$_2$ | SO$_2$Me | |
| 2-178 | Me | OCH$_2$(CO)NMe$_2$ | SO$_2$Et | |
| 2-179 | Me | [1,4]dioxan-2-ylmethoxy | SO$_2$Me | |
| 2-180 | Me | [1,4]dioxan-2-ylmethoxy | SO$_2$Et | |

TABLE 2-continued

Compounds of the general formula (I) in which A represents CY, V represents hydrogen, W represents fluorine and R represents methyl

| No. | X | Y | Z | Physical data ($^1$H-NMR, DMSO-d$_6$, 400 MHz) |
|---|---|---|---|---|
| 2-181 | Me | O(CH$_2$)$_2$—O-(3,5-di-methoxypyrimidin-2-yl) | SO$_2$Me | |
| 2-182 | Me | Cl | SO$_2$Me | |
| 2-183 | Me | SMe | SO$_2$Me | |
| 2-184 | Me | SOMe | SO$_2$Me | |
| 2-185 | Me | SO$_2$Me | SO$_2$Me | |
| 2-186 | Me | SO$_2$Me | SO$_2$Et | |
| 2-187 | Me | SEt | SO$_2$Me | |
| 2-188 | Me | SOEt | SO$_2$Me | |
| 2-189 | Me | SO$_2$Et | SO$_2$Me | |
| 2-190 | Me | S(CH$_2$)$_2$OMe | SO$_2$Me | |
| 2-191 | Me | SO(CH$_2$)$_2$OMe | SO$_2$Me | |
| 2-192 | Me | SO$_2$(CH$_2$)$_2$OMe | SO$_2$Me | |
| 2-193 | CH$_2$SMe | OMe | SO$_2$Me | |
| 2-194 | CH$_2$OMe | OMe | SO$_2$Me | |
| 2-195 | CH$_2$O(CH$_2$)$_2$OMe | NH(CH$_2$)$_2$OEt | SO$_2$Me | |
| 2-196 | CH$_2$O(CH$_2$)$_2$OMe | NH(CH$_2$)$_3$OEt | SO$_2$Me | |
| 2-197 | CH$_2$O(CH$_2$)$_3$OMe | OMe | SO$_2$Me | |
| 2-198 | CH$_2$O(CH$_2$)$_2$OMe | NH(CH$_2$)$_2$OMe | SO$_2$Me | |
| 2-199 | CH$_2$O(CH$_2$)$_2$OMe | NH(CH$_2$)$_3$OMe | SO$_2$Me | |
| 2-200 | Et | SMe | Cl | |
| 2-201 | Et | SO$_2$Me | Cl | |
| 2-202 | Et | SMe | CF$_3$ | |
| 2-203 | Et | SO$_2$Me | CF$_3$ | |
| 2-204 | Et | F | SO$_2$Me | |
| 2-205 | Et | NH(CH$_2$)$_2$OMe | SO$_2$Me | |
| 2-206 | iPr | SO$_2$Me | CF$_3$ | |
| 2-207 | cPr | SO$_2$Me | CF$_3$ | |
| 2-208 | CF$_3$ | O(CH$_2$)$_2$OMe | F | |
| 2-209 | CF$_3$ | O(CH$_2$)$_3$OMe | F | |
| 2-210 | CF$_3$ | OCH$_2$CONMe$_2$ | F | |
| 2-211 | CF$_3$ | [1,4]dioxan-2-ylmethoxy | F | |
| 2-212 | CF$_3$ | O(CH$_2$)$_2$OMe | Cl | |
| 2-213 | CF$_3$ | O(CH$_2$)$_3$OMe | Cl | |
| 2-214 | CF$_3$ | OCH$_2$CONMe$_2$ | Cl | |
| 2-215 | CF$_3$ | [1,4]dioxan-2-ylmethoxy | Cl | |
| 2-216 | CF$_3$ | O(CH$_2$)$_2$OMe | Br | |
| 2-217 | CF$_3$ | O(CH$_2$)$_3$OMe | Br | |
| 2-218 | CF$_3$ | OCH$_2$CONMe$_2$ | Br | |
| 2-219 | CF$_3$ | [1,4]dioxan-2-ylmethoxy | Br | |
| 2-220 | CF$_3$ | O(CH$_2$)$_2$OMe | I | |
| 2-221 | CF$_3$ | O(CH$_2$)$_3$OMe | I | |
| 2-222 | CF$_3$ | OCH$_2$CONMe$_2$ | I | |
| 2-223 | CF$_3$ | [1,4]dioxan-2-ylmethoxy | I | |
| 2-224 | CF$_3$ | F | SO$_2$Me | |
| 2-225 | CF$_3$ | F | SO$_2$Et | |
| 2-226 | CF$_3$ | O(CH$_2$)$_2$OMe | SO$_2$Me | |
| 2-227 | CF$_3$ | O(CH$_2$)$_2$OMe | SO$_2$Et | |
| 2-228 | CF$_3$ | O(CH$_2$)$_3$OMe | SO$_2$Me | |
| 2-229 | CF$_3$ | O(CH$_2$)$_3$OMe | SO$_2$Et | |
| 2-230 | CF$_3$ | OCH$_2$CONMe$_2$ | SO$_2$Me | |
| 2-231 | CF$_3$ | OCH$_2$CONMe$_2$ | SO$_2$Et | |

TABLE 2-continued

Compounds of the general formula (I) in which A represents
CY, V represents hydrogen, W represents fluorine and R represents methyl

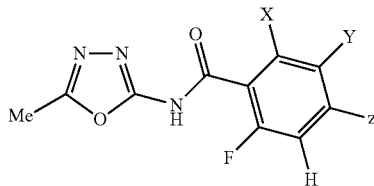

| No. | X | Y | Z | Physical data (¹H-NMR, DMSO-$d_6$, 400 MHz) |
|---|---|---|---|---|
| 2-232 | $CF_3$ | [1,4]dioxan-2-ylmethoxy | $SO_2Me$ | |
| 2-233 | $CF_3$ | [1,4]dioxan-2-ylmethoxy | $SO_2Et$ | |
| 2-234 | F | SMe | $CF_3$ | |
| 2-235 | F | SOMe | $CF_3$ | |
| 2-236 | Cl | Me | Cl | |
| 2-237 | Cl | $OCH_2CHCH_2$ | Cl | |
| 2-238 | Cl | $OCH_2CHF_2$ | Cl | |
| 2-239 | Cl | $O(CH_2)_2OMe$ | Cl | |
| 2-240 | Cl | $OCH_2(CO)NMe_2$ | Cl | |
| 2-241 | Cl | $O(CH_2)$-5-pyrrolidin-2-one | Cl | |
| 2-242 | Cl | SMe | Cl | 12.59 ppm (bs, 1H), 7.86 ppm (d, 1H); 2.41 ppm (s, 3H). |
| 2-243 | Cl | SOMe | Cl | 11.60 ppm (bs, 1H), 7.24 ppm (d, 1H); 3.07 ppm (s, 3H). |
| 2-244 | Cl | $SO_2Me$ | Cl | |
| 2-245 | Cl | F | SMe | |
| 2-246 | Cl | Cl | $SO_2Me$ | |
| 2-247 | Cl | COOMe | $SO_2Me$ | |
| 2-248 | Cl | $CONMe_2$ | $SO_2Me$ | |
| 2-249 | Cl | CONMe(OMe) | $SO_2Me$ | |
| 2-250 | Cl | $CH_2OMe$ | $SO_2Me$ | |
| 2-251 | Cl | $CH_2OMe$ | $SO_2Et$ | |
| 2-252 | Cl | $CH_2OEt$ | $SO_2Me$ | |
| 2-253 | Cl | $CH_2OEt$ | $SO_2Et$ | |
| 2-254 | Cl | $CH_2OCH_2CHF_2$ | $SO_2Me$ | |
| 2-255 | Cl | $CH_2OCH_2CF_3$ | $SO_2Me$ | |
| 2-256 | Cl | $CH_2OCH_2CF_3$ | $SO_2Et$ | |
| 2-257 | Cl | $CH_2OCH_2CF_2CHF_2$ | $SO_2Me$ | |
| 2-258 | Cl | $CH_2O$-c-pentyl | $SO_2Me$ | |
| 2-259 | Cl | $CH_2PO(OMe)_2$ | $SO_2Me$ | |
| 2-260 | Cl | 4,5-dihydro-1,2-oxazol-3-yl | SMe | |
| 2-261 | Cl | 4,5-dihydro-1,2-oxazol-3-yl | $SO_2Me$ | |
| 2-262 | Cl | 4,5-dihydro-1,2-oxazol-3-yl | $SO_2Et$ | |
| 2-263 | Cl | 5-cyanomethyl-4,5-dihydro-1,2-oxazol-3-yl | $SO_2Me$ | |
| 2-264 | Cl | 5-cyanomethyl-4,5-dihydro-1,2-oxazol-3-yl | $SO_2Et$ | |
| 2-265 | Cl | 5-(methoxymethyl)-4,5-dihydro-1,2-oxazol-3-yl | $SO_2Et$ | |
| 2-266 | Cl | 5-(methoxymethyl)-5-methyl-4,5-dihydro-1,2-oxazol-3-yl | $SO_2Et$ | |
| 2-267 | Cl | $CH_2O$-tetrahydrofuran-3-yl | $SO_2Me$ | |
| 2-268 | Cl | $CH_2O$-tetrahydrofuran-3-yl | $SO_2Et$ | |

TABLE 2-continued

Compounds of the general formula (I) in which A represents CY, V represents hydrogen, W represents fluorine and R represents methyl

| No. | X | Y | Z | Physical data ($^1$H-NMR, DMSO-$d_6$, 400 MHz) |
|---|---|---|---|---|
| 2-269 | Cl | CH$_2$OCH$_2$-tetrahydrofuran-2-yl | SO$_2$Me | |
| 2-270 | Cl | CH$_2$OCH$_2$-tetrahydrofuran-2-yl | SO$_2$Et | |
| 2-271 | Cl | CH$_2$OCH$_2$-tetrahydrofuran-3-yl | SO$_2$Me | |
| 2-272 | Cl | CH$_2$OCH$_2$-tetrahydrofuran-3-yl | SO$_2$Et | |
| 2-273 | Cl | OMe | SO$_2$Me | |
| 2-274 | Cl | OMe | SO$_2$Et | |
| 2-275 | Cl | OEt | SO$_2$Me | |
| 2-276 | Cl | OEt | SO$_2$Et | |
| 2-277 | Cl | OiPr | SO$_2$Me | |
| 2-278 | Cl | OiPr | SO$_2$Et | |
| 2-279 | Cl | O(CH$_2$)$_2$OMe | SO$_2$Me | |
| 2-280 | Cl | O(CH$_2$)$_4$OMe | SO$_2$Me | |
| 2-281 | Cl | O(CH$_2$)$_4$OMe | SO$_2$Et | |
| 2-282 | Cl | O(CH$_2$)$_3$OMe | SO$_2$Me | |
| 2-283 | Cl | O(CH$_2$)$_3$OMe | SO$_2$Et | |
| 2-284 | Cl | O(CH$_2$)$_2$OMe | SO$_2$Me | |
| 2-285 | Cl | O(CH$_2$)$_2$OMe | SO$_2$Et | |
| 2-286 | Cl | [1,4]dioxan-2-ylmethoxy | SO$_2$Me | |
| 2-287 | Cl | [1,4]dioxan-2-ylmethoxy | SO$_2$Et | |
| 2-288 | Cl | OCH$_2$(CO)NMe$_2$ | SO$_2$Me | |
| 2-289 | Cl | OCH$_2$(CO)NMe$_2$ | SO$_2$Et | |
| 2-290 | Cl | SMe | SO$_2$Me | |
| 2-291 | Cl | SOMe | SO$_2$Me | |
| 2-292 | Br | OMe | Br | |
| 2-293 | Br | O(CH$_2$)$_2$OMe | Br | |
| 2-294 | Br | O(CH$_2$)$_2$OMe | SO$_2$Me | |
| 2-295 | Br | O(CH$_2$)$_2$OMe | SO$_2$Et | |
| 2-296 | Br | O(CH$_2$)$_3$OMe | SO$_2$Me | |
| 2-297 | Br | O(CH$_2$)$_3$OMe | SO$_2$Et | |
| 2-298 | Br | O(CH$_2$)$_4$OMe | SO$_2$Me | |
| 2-299 | Br | O(CH$_2$)$_4$OMe | SO$_2$Et | |
| 2-300 | Br | [1,4]dioxan-2-ylmethoxy | SO$_2$Me | |
| 2-301 | Br | [1,4]dioxan-2-ylmethoxy | SO$_2$Et | |
| 2-302 | I | O(CH$_2$)$_2$OMe | SO$_2$Me | |
| 2-303 | I | O(CH$_2$)$_2$OMe | SO$_2$Et | |
| 2-304 | I | O(CH$_2$)$_3$OMe | SO$_2$Me | |
| 2-305 | I | O(CH$_2$)$_3$OMe | SO$_2$Et | |
| 2-306 | I | O(CH$_2$)$_4$OMe | SO$_2$Me | |
| 2-307 | I | O(CH$_2$)$_4$OMe | SO$_2$Et | |
| 2-308 | I | [1,4]dioxan-2-ylmethoxy | SO$_2$Me | |
| 2-309 | I | [1,4]dioxan-2-ylmethoxy | SO$_2$Et | |
| 2-310 | OMe | SMe | CF$_3$ | |
| 2-311 | OMe | SOMe | CF$_3$ | |
| 2-312 | OMe | SO$_2$Me | CF$_3$ | |
| 2-313 | OMe | SOEt | CF$_3$ | |
| 2-314 | OMe | SO$_2$Et | CF$_3$ | |
| 2-315 | OMe | S(CH$_2$)$_2$OMe | CF$_3$ | |
| 2-316 | OMe | SO(CH$_2$)$_2$OMe | CF$_3$ | |
| 2-317 | OMe | SO$_2$(CH$_2$)$_2$OMe | CF$_3$ | |

TABLE 2-continued

Compounds of the general formula (I) in which A represents
CY, V represents hydrogen, W represents fluorine and R represents methyl

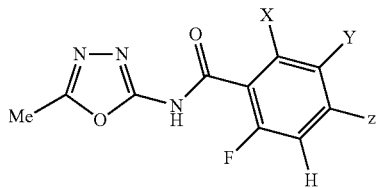

| No. | X | Y | Z | Physical data ($^1$H-NMR, DMSO-$d_6$, 400 MHz) |
|---|---|---|---|---|
| 2-318 | OMe | SMe | Cl | |
| 2-319 | OMe | SOMe | Cl | |
| 2-320 | OMe | SO$_2$Me | Cl | |
| 2-321 | OMe | SEt | Cl | |
| 2-322 | OMe | SOEt | Cl | |
| 2-323 | OMe | SO2Et | Cl | |
| 2-324 | OMe | S(CH$_2$)$_2$OMe | Cl | |
| 2-325 | OMe | SO(CH$_2$)$_2$OMe | Cl | |
| 2-326 | OMe | SO$_2$(CH$_2$)$_2$OMe | Cl | |
| 2-327 | OCH$_2$c-Pr | SMe | CF$_3$ | |
| 2-328 | OCH$_2$c-Pr | SOMe | CF$_3$ | |
| 2-329 | OCH$_2$c-Pr | SO$_2$Me | CF$_3$ | |
| 2-330 | OCH$_2$c-Pr | SEt | CF$_3$ | |
| 2-331 | OCH$_2$c-Pr | SOEt | CF$_3$ | |
| 2-332 | OCH$_2$c-Pr | SO$_2$Et | CF$_3$ | |
| 2-333 | OCH$_2$c-Pr | S(CH$_2$)$_2$OMe | CF$_3$ | |
| 2-334 | OCH$_2$c-Pr | SO(CH$_2$)$_2$OMe | CF$_3$ | |
| 2-335 | OCH$_2$c-Pr | SO$_2$(CH$_2$)$_2$OMe | CF$_3$ | |
| 2-336 | OCH$_2$c-Pr | SMe | Cl | |
| 2-337 | OCH$_2$c-Pr | SOMe | Cl | |
| 2-338 | OCH$_2$c-Pr | SO$_2$Me | Cl | |
| 2-339 | OCH$_2$c-Pr | SEt | Cl | |
| 2-340 | OCH$_2$c-Pr | SOEt | Cl | |
| 2-341 | OCH$_2$c-Pr | SO$_2$Et | Cl | |
| 2-342 | OCH$_2$c-Pr | S(CH$_2$)$_2$OMe | Cl | |
| 2-343 | OCH$_2$c-Pr | SO(CH$_2$)$_2$OMe | Cl | |
| 2-344 | OCH$_2$c-Pr | SO$_2$(CH$_2$)$_2$OMe | Cl | |
| 2-345 | OCH$_2$c-Pr | SMe | SO$_2$Me | |
| 2-346 | OCH$_2$c-Pr | SOMe | SO$_2$Me | |
| 2-347 | OCH$_2$c-Pr | SO$_2$Me | SO$_2$Me | |
| 2-348 | OCH$_2$c-Pr | SEt | SO$_2$Me | |
| 2-349 | OCH$_2$c-Pr | SOEt | SO$_2$Me | |
| 2-350 | OCH$_2$c-Pr | SO$_2$Et | SO$_2$Me | |
| 2-351 | OCH$_2$c-Pr | S(CH$_2$)$_2$OMe | SO$_2$Me | |
| 2-352 | OCH$_2$c-Pr | SO(CH$_2$)$_2$OMe | SO$_2$Me | |
| 2-353 | OCH$_2$c-Pr | SO$_2$(CH$_2$)$_2$OMe | SO$_2$Me | |
| 2-354 | SO$_2$Me | F | CF$_3$ | |
| 2-355 | SO$_2$Me | NH$_2$ | CF$_3$ | |
| 2-356 | SO$_2$Me | NHEt | Cl | |
| 2-357 | SMe | SEt | F | |
| 2-358 | SMe | SMe | F | |
| 2-359 | Cl | SMe | CF$_3$ | |
| 2-360 | Cl | S(O)Me | CF$_3$ | |
| 2-361 | Cl | SO$_2$Me | CF$_3$ | |
| 2-362 | Cl | SO$_2$Me | SO$_2$Me | |

TABLE 3

Compounds of the general formula (I) in which A represents CY, V represents hydrogen, W represents fluorine and R represents ethyl

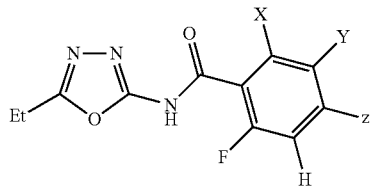

| No. | X | Y | Z | Physical data ($^1$H-NMR, DMSO-$d_6$, 400 MHz) |
|---|---|---|---|---|
| 3-1 | F | H | Cl | |
| 3-2 | F | H | SO$_2$Me | |
| 3-3 | F | H | SO$_2$Et | |
| 3-4 | F | H | CF$_3$ | |
| 3-5 | F | H | NO$_2$ | |
| 3-6 | Cl | H | Br | |
| 3-7 | Cl | H | SMe | |
| 3-8 | Cl | H | SOMe | |
| 3-9 | Cl | H | SO$_2$Me | |
| 3-10 | Cl | H | SO$_2$CH$_2$Cl | |
| 3-11 | Cl | H | SEt | |
| 3-12 | Cl | H | SO$_2$Et | |
| 3-13 | Cl | H | CF$_3$ | |
| 3-14 | Cl | H | NO$_2$ | |
| 3-15 | Cl | H | pyrazol-1-yl | |
| 3-16 | Cl | H | 1H-1,2,4-triazol-1-yl | |
| 3-17 | Br | H | Cl | |
| 3-18 | Br | H | Br | |
| 3-19 | Br | H | SO$_2$Me | |
| 3-20 | Br | H | SO$_2$Et | |
| 3-21 | Br | H | CF$_3$ | |
| 3-22 | SO$_2$Me | H | Cl | |
| 3-23 | SO$_2$Me | H | Br | |
| 3-24 | SO$_2$Me | H | SMe | |
| 3-25 | SO$_2$Me | H | SOMe | |
| 3-26 | SO$_2$Me | H | SO$_2$Me | |
| 3-27 | SO$_2$Me | H | SO$_2$Et | |
| 3-28 | SO$_2$Me | H | CF$_3$ | |
| 3-29 | SO$_2$Et | H | Cl | |
| 3-30 | SO$_2$Et | H | Br | |
| 3-31 | SO$_2$Et | H | SMe | |
| 3-32 | SO$_2$Et | H | SOMe | |
| 3-33 | SO$_2$Et | H | SO$_2$Me | |
| 3-34 | SO$_2$Et | H | CF$_3$ | |
| 3-35 | NO$_2$ | H | F | |
| 3-36 | NO$_2$ | H | Cl | |
| 3-37 | NO$_2$ | H | Br | |
| 3-38 | NO$_2$ | H | I | |
| 3-39 | NO$_2$ | H | CN | |
| 3-40 | NO$_2$ | H | SO$_2$Me | |
| 3-41 | NO$_2$ | H | SO$_2$Et | |
| 3-42 | NO$_2$ | H | CF$_3$ | |
| 3-43 | Me | H | Cl | |
| 3-44 | Me | H | Br | |
| 3-45 | Me | H | SMe | |
| 3-46 | Me | H | SO$_2$Me | |
| 3-47 | Me | H | SO$_2$CH$_2$Cl | |
| 3-48 | Me | H | SEt | |
| 3-49 | Me | H | SO$_2$Et | |
| 3-50 | Me | H | CF$_3$ | |
| 3-51 | CH$_2$SO$_2$Me | H | CF$_3$ | |
| 3-52 | Et | H | Cl | |
| 3-53 | Et | H | Br | |
| 3-54 | Et | H | SMe | |
| 3-55 | Et | H | SO$_2$Me | |
| 3-56 | Et | H | SO$_2$CH$_2$Cl | |
| 3-57 | Et | H | SEt | |
| 3-58 | Et | H | SO$_2$Et | |
| 3-59 | Et | H | CF$_3$ | |
| 3-60 | CF$_3$ | H | Cl | |

TABLE 3-continued

Compounds of the general formula (I) in which A represents CY, V represents hydrogen, W represents fluorine and R represents ethyl

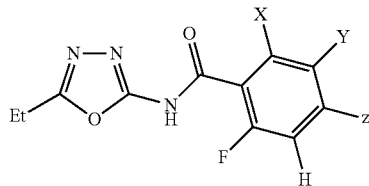

| No. | X | Y | Z | Physical data (¹H-NMR, DMSO-$d_6$, 400 MHz) |
|---|---|---|---|---|
| 3-61 | $CF_3$ | H | Br | |
| 3-62 | $CF_3$ | H | $SO_2Me$ | |
| 3-63 | $CF_3$ | H | $SO_2Et$ | |
| 3-64 | $CF_3$ | H | $CF_3$ | |
| 3-65 | $NO_2$ | $NH_2$ | F | |
| 3-66 | $NO_2$ | NHMe | F | |
| 3-67 | $NO_2$ | $NMe_2$ | F | |
| 3-68 | $NO_2$ | Me | Cl | |
| 3-69 | $NO_2$ | $NH_2$ | Cl | |
| 3-70 | $NO_2$ | NHMe | Cl | |
| 3-71 | $NO_2$ | $NMe_2$ | Cl | |
| 3-72 | $NO_2$ | $NH_2$ | Br | |
| 3-73 | $NO_2$ | NHMe | Br | |
| 3-74 | $NO_2$ | $NMe_2$ | Br | |
| 3-75 | $NO_2$ | $NH_2$ | $CF_3$ | |
| 3-76 | $NO_2$ | $NMe_2$ | $CF_3$ | |
| 3-77 | $NO_2$ | $NH_2$ | $SO_2Me$ | |
| 3-78 | $NO_2$ | $NH_2$ | $SO_2Et$ | |
| 3-79 | $NO_2$ | NHMe | $SO_2Me$ | |
| 3-80 | $NO_2$ | $NMe_2$ | $SO_2Me$ | |
| 3-81 | $NO_2$ | $NMe_2$ | $SO_2Et$ | |
| 3-82 | $NO_2$ | $NH_2$ | 1H-1,2,4-triazol-1-yl | |
| 3-83 | $NO_2$ | NHMe | 1H-1,2,4-triazol-1-yl | |
| 3-84 | $NO_2$ | $NMe_2$ | 1H-1,2,4-triazol-1-yl | |
| 3-85 | Me | SMe | H | |
| 3-86 | Me | SOMe | H | |
| 3-87 | Me | $SO_2Me$ | H | |
| 3-88 | Me | SEt | H | |
| 3-89 | Me | SOEt | H | |
| 3-90 | Me | $SO_2Et$ | H | |
| 3-91 | Me | $S(CH_2)_2OMe$ | H | |
| 3-92 | Me | $SO(CH_2)_2OMe$ | H | |
| 3-93 | Me | $SO_2(CH_2)_2OMe$ | H | |
| 3-94 | Me | F | F | |
| 3-95 | Me | F | Cl | |
| 3-96 | Me | SEt | F | |
| 3-97 | Me | SOEt | F | |
| 3-98 | Me | $SO_2Et$ | F | |
| 3-99 | Me | Me | Cl | |
| 3-100 | Me | F | Cl | |
| 3-101 | Me | Cl | Cl | |
| 3-102 | Me | $NH_2$ | Cl | |
| 3-103 | Me | NHMe | Cl | |
| 3-104 | Me | $NMe_2$ | Cl | |
| 3-105 | Me | $O(CH_2)_2OMe$ | Cl | |
| 3-106 | Me | $O(CH_2)_3OMe$ | Cl | |
| 3-107 | Me | $O(CH_2)_4OMe$ | Cl | |
| 3-108 | Me | $OCH_2CONMe_2$ | Cl | |
| 3-109 | Me | $O(CH_2)_2$—$CONMe_2$ | Cl | |
| 3-110 | Me | $O(CH_2)_2$—NH(CO)$NMe_2$ | Cl | |
| 3-111 | Me | $O(CH_2)_2$—NH(CO)$NHCO_2Et$ | Cl | |
| 3-112 | Me | $O(CH_2)_2NHCO_2Me$ | Cl | |
| 3-113 | Me | $OCH_2NHSO_2cPr$ | Cl | |
| 3-114 | Me | $O(CH_2)$-5-2,4-dimethyl-2,4-dihydro-3H-1,2,4-triazol-3-one | Cl | |

TABLE 3-continued

Compounds of the general formula (I) in which A represents CY, V represents hydrogen, W represents fluorine and R represents ethyl

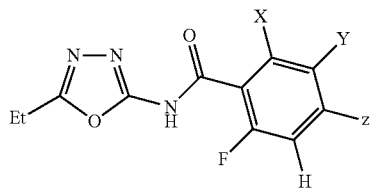

| No. | X | Y | Z | Physical data (¹H-NMR, DMSO-$d_6$, 400 MHz) |
|---|---|---|---|---|
| 3-115 | Me | O(CH$_2$)-3,5-dimethyl-1,2-oxazol-4-yl | Cl | |
| 3-116 | Me | SMe | Cl | |
| 3-117 | Me | SOMe | Cl | |
| 3-118 | Me | SO$_2$Me | Cl | |
| 3-119 | Me | SEt | Cl | |
| 3-120 | Me | SOEt | Cl | |
| 3-121 | Me | SO$_2$Et | Cl | |
| 3-122 | Me | S(CH$_2$)$_2$OMe | Cl | |
| 3-123 | Me | SO(CH$_2$)$_2$OMe | Cl | |
| 3-124 | Me | SO$_2$(CH$_2$)$_2$OMe | Cl | |
| 3-125 | Me | NH$_2$ | Br | |
| 3-126 | Me | NHMe | Br | |
| 3-127 | Me | NMe$_2$ | Br | |
| 3-128 | Me | OCH$_2$CONMe$_2$ | Br | |
| 3-129 | Me | O(CH$_2$)-5-pyrrolidin-2-one | Br | |
| 3-130 | Me | SMe | Br | |
| 3-131 | Me | SOMe | Br | |
| 3-132 | Me | SO$_2$Me | Br | |
| 3-133 | Me | SEt | Br | |
| 3-134 | Me | SOEt | Br | |
| 3-135 | Me | SO$_2$Et | Br | |
| 3-136 | Me | SMe | I | |
| 3-137 | Me | SOMe | I | |
| 3-138 | Me | SO$_2$Me | I | |
| 3-139 | Me | SEt | I | |
| 3-140 | Me | SOEt | I | |
| 3-141 | Me | SO$_2$Et | I | |
| 3-142 | Me | Cl | CF$_3$ | |
| 3-143 | Me | SMe | CF$_3$ | |
| 3-144 | Me | SOMe | CF$_3$ | |
| 3-145 | Me | SO$_2$Me | CF$_3$ | |
| 3-146 | Me | SEt | CF$_3$ | |
| 3-147 | Me | SOEt | CF$_3$ | |
| 3-148 | Me | SO$_2$Et | CF$_3$ | |
| 3-149 | Me | S(CH$_2$)$_2$OMe | CF$_3$ | |
| 3-150 | Me | SO(CH$_2$)$_2$OMe | CF$_3$ | |
| 3-151 | Me | SO$_2$(CH$_2$)$_2$OMe | CF$_3$ | |
| 3-152 | Me | Me | SO$_2$Me | |
| 3-153 | Me | 4,5-dihydro-1,2-oxazol-3-yl | SO$_2$Me | |
| 3-154 | Me | 4,5-dihydro-1,2-oxazol-3-yl | SO$_2$Et | |
| 3-155 | Me | 5-cyanomethyl-4,5-dihydro-1,2-oxazol-3-yl | SO$_2$Me | |
| 3-156 | Me | 5-cyanomethyl-4,5-dihydro-1,2-oxazol-3-yl | SO$_2$Et | |
| 3-157 | Me | NH$_2$ | SO$_2$Me | |
| 3-158 | Me | NHMe | SO$_2$Me | |
| 3-159 | Me | NMe$_2$ | SO$_2$Me | |
| 3-160 | Me | NH(CH$_2$)$_2$OMe | SO$_2$Me | |
| 3-161 | Me | Pyrazol-1-yl | SO$_2$Me | |
| 3-162 | Me | OH | SO$_2$Me | |
| 3-163 | Me | OMe | SO$_2$Me | |
| 3-164 | Me | OMe | SO$_2$Et | |
| 3-165 | Me | OEt | SO$_2$Me | |
| 3-166 | Me | OEt | SO$_2$Et | |
| 3-167 | Me | OiPr | SO$_2$Me | |
| 3-168 | Me | OiPr | SO$_2$Et | |

TABLE 3-continued

Compounds of the general formula (I) in which A represents CY, V represents hydrogen, W represents fluorine and R represents ethyl

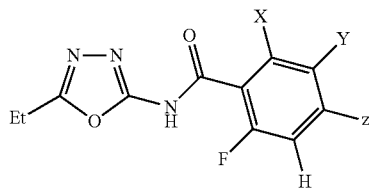

| No. | X | Y | Z | Physical data ($^1$H-NMR, DMSO-$d_6$, 400 MHz) |
|---|---|---|---|---|
| 3-169 | Me | O(CH$_2$)$_2$OMe | SO$_2$Me | |
| 3-170 | Me | O(CH$_2$)$_2$OMe | SO$_2$Et | |
| 3-171 | Me | O(CH$_2$)$_3$OMe | SO$_2$Me | |
| 3-172 | Me | O(CH$_2$)$_3$OMe | SO$_2$Et | |
| 3-173 | Me | O(CH$_2$)$_4$OMe | SO$_2$Me | |
| 3-174 | Me | O(CH$_2$)$_4$OMe | SO$_2$Et | |
| 3-175 | Me | O(CH$_2$)$_2$NHSO2Me | SO$_2$Me | |
| 3-176 | Me | O(CH$_2$)$_2$NHSO2Me | SO$_2$Et | |
| 3-177 | Me | OCH$_2$(CO)NMe$_2$ | SO$_2$Me | |
| 3-178 | Me | OCH$_2$(CO)NMe$_2$ | SO$_2$Et | |
| 3-179 | Me | [1,4]dioxan-2-ylmethoxy | SO$_2$Me | |
| 3-180 | Me | [1,4]dioxan-2-ylmethoxy | SO$_2$Et | |
| 3-181 | Me | O(CH$_2$)$_2$—O-(3,5-dimethoxypyrimidin-2-yl) | SO$_2$Me | |
| 3-182 | Me | Cl | SO$_2$Me | |
| 3-183 | Me | SMe | SO$_2$Me | |
| 3-184 | Me | SOMe | SO$_2$Me | |
| 3-185 | Me | SO$_2$Me | SO$_2$Me | |
| 3-186 | Me | SO$_2$Me | SO$_2$Et | |
| 3-187 | Me | SEt | SO$_2$Me | |
| 3-188 | Me | SOEt | SO$_2$Me | |
| 3-189 | Me | SO$_2$Et | SO$_2$Me | |
| 3-190 | Me | S(CH$_2$)$_2$OMe | SO$_2$Me | |
| 3-191 | Me | SO(CH$_2$)$_2$OMe | SO$_2$Me | |
| 3-192 | Me | SO$_2$(CH$_2$)$_2$OMe | SO2Me | |
| 3-193 | CH$_2$SMe | OMe | SO$_2$Me | |
| 3-194 | CH$_2$OMe | OMe | SO$_2$Me | |
| 3-195 | CH$_2$O(CH$_2$)$_2$OMe | NH(CH$_2$)$_2$OEt | SO$_2$Me | |
| 3-196 | CH$_2$O(CH$_2$)$_2$OMe | NH(CH$_2$)$_3$OEt | SO$_2$Me | |
| 3-197 | CH$_2$O(CH$_2$)$_3$OMe | OMe | SO$_2$Me | |
| 3-198 | CH$_2$O(CH$_2$)$_2$OMe | NH(CH$_2$)$_2$OMe | SO$_2$Me | |
| 3-199 | CH$_2$O(CH$_2$)$_2$OMe | NH(CH$_2$)$_3$OMe | SO$_2$Me | |
| 3-200 | Et | SMe | Cl | |
| 3-201 | Et | SO$_2$Me | Cl | |
| 3-202 | Et | SMe | CF$_3$ | |
| 3-203 | Et | SO$_2$Me | CF$_3$ | |
| 3-204 | Et | F | SO$_2$Me | |
| 3-205 | Et | NH(CH$_2$)$_2$OMe | SO$_2$Me | |
| 3-206 | iPr | SO$_2$Me | CF$_3$ | |
| 3-207 | cPr | SO$_2$Me | CF$_3$ | |
| 3-208 | CF$_3$ | O(CH$_2$)$_2$OMe | F | |
| 3-209 | CF$_3$ | O(CH$_2$)$_3$OMe | F | |
| 3-210 | CF$_3$ | OCH$_2$CONMe$_2$ | F | |
| 3-211 | CF$_3$ | [1,4]dioxan-2-ylmethoxy | F | |
| 3-212 | CF$_3$ | O(CH$_2$)$_2$OMe | Cl | |
| 3-213 | CF$_3$ | O(CH$_2$)$_3$OMe | Cl | |
| 3-214 | CF$_3$ | OCH$_2$CONMe$_2$ | Cl | |
| 3-215 | CF$_3$ | [1,4]dioxan-2-ylmethoxy | Cl | |
| 3-216 | CF$_3$ | O(CH$_2$)$_2$OMe | Br | |
| 3-217 | CF$_3$ | O(CH$_2$)$_3$OMe | Br | |
| 3-218 | CF$_3$ | OCH$_2$CONMe$_2$ | Br | |
| 3-219 | CF$_3$ | [1,4]dioxan-2-ylmethoxy | Br | |

TABLE 3-continued

Compounds of the general formula (I) in which A represents CY, V represents hydrogen, W represents fluorine and R represents ethyl

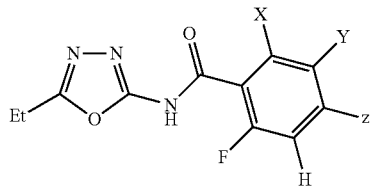

| No. | X | Y | Z | Physical data (¹H-NMR, DMSO-$d_6$, 400 MHz) |
|---|---|---|---|---|
| 3-220 | $CF_3$ | $O(CH_2)_2OMe$ | I | |
| 3-221 | $CF_3$ | $O(CH_2)_3OMe$ | I | |
| 3-222 | $CF_3$ | $OCH_2CONMe_2$ | I | |
| 3-223 | $CF_3$ | [1,4]dioxan-2-ylmethoxy | I | |
| 3-224 | $CF_3$ | F | $SO_2Me$ | |
| 3-225 | $CF_3$ | F | $SO_2Et$ | |
| 3-226 | $CF_3$ | $O(CH_2)_2OMe$ | $SO_2Me$ | |
| 3-227 | $CF_3$ | $O(CH_2)_2OMe$ | $SO_2Et$ | |
| 3-228 | $CF_3$ | $O(CH_2)_3OMe$ | $SO_2Me$ | |
| 3-229 | $CF_3$ | $O(CH_2)_3OMe$ | $SO_2Et$ | |
| 3-230 | $CF_3$ | $OCH_2CONMe_2$ | $SO_2Me$ | |
| 3-231 | $CF_3$ | $OCH_2CONMe_2$ | $SO_2Et$ | |
| 3-232 | $CF_3$ | [1,4]dioxan-2-ylmethoxy | $SO_2Me$ | |
| 3-233 | $CF_3$ | [1,4]dioxan-2-ylmethoxy | $SO_2Et$ | |
| 3-234 | F | SMe | $CF_3$ | |
| 3-235 | F | SOMe | $CF_3$ | |
| 3-236 | Cl | Me | Cl | |
| 3-237 | Cl | $OCH_2CHCH_2$ | Cl | |
| 3-238 | Cl | $OCH_2CHF_2$ | Cl | |
| 3-239 | Cl | $O(CH_2)_2OMe$ | Cl | |
| 3-240 | Cl | $OCH_2(CO)NMe_2$ | Cl | |
| 3-241 | Cl | $O(CH_2)$-5-pyrrolidin-2-one | Cl | |
| 3-242 | Cl | SMe | Cl | |
| 3-243 | Cl | SOMe | Cl | |
| 3-244 | Cl | $SO_2Me$ | Cl | |
| 3-245 | Cl | F | SMe | |
| 3-246 | Cl | Cl | $SO_2Me$ | |
| 3-247 | Cl | COOMe | $SO_2Me$ | |
| 3-248 | Cl | $CONMe_2$ | $SO_2Me$ | |
| 3-249 | Cl | CONMe(OMe) | $SO_2Me$ | |
| 3-250 | Cl | $CH_2OMe$ | $SO_2Me$ | |
| 3-251 | Cl | $CH_2OMe$ | $SO_2Et$ | |
| 3-252 | Cl | $CH_2OEt$ | $SO_2Me$ | |
| 3-253 | Cl | $CH_2OEt$ | $SO_2Et$ | |
| 3-254 | Cl | $CH_2OCH_2CHF_2$ | $SO_2Me$ | |
| 3-255 | Cl | $CH_2OCH_2CF_3$ | $SO_2Me$ | |
| 3-256 | Cl | $CH_2OCH_2CF_3$ | $SO_2Et$ | |
| 3-257 | Cl | $CH_2OCH_2CF_2CHF_2$ | $SO_2Me$ | |
| 3-258 | Cl | $CH_2O$-c-pentyl | $SO_2Me$ | |
| 3-259 | Cl | $CH_2PO(OMe)_2$ | $SO_2Me$ | |
| 3-260 | Cl | 4,5-dihydro-1,2-oxazol-3-yl | SMe | |
| 3-261 | Cl | 4,5-dihydro-1,2-oxazol-3-yl | $SO_2Me$ | |
| 3-262 | Cl | 4,5-dihydro-1,2-oxazol-3-yl | $SO_2Et$ | |
| 3-263 | Cl | 5-cyanomethyl-4,5-dihydro-1,2-oxazol-3-yl | $SO_2Me$ | |
| 3-264 | Cl | 5-cyanomethyl-4,5-dihydro-1,2-oxazol-3-yl | $SO_2Et$ | |
| 3-265 | Cl | 5-(methoxymethyl)-4,5-dihydro-1,2-oxazol-3-yl | $SO_2Et$ | |
| 3-266 | Cl | 5-(methoxymethyl)-5-methyl-4,5-dihydro-1,2-oxazol-3-yl | $SO_2Et$ | |

TABLE 3-continued

Compounds of the general formula (I) in which A represents CY, V represents hydrogen, W represents fluorine and R represents ethyl

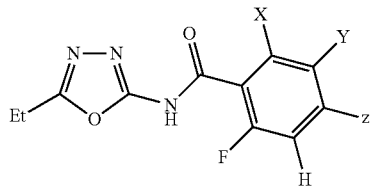

| No. | X | Y | Z | Physical data ($^1$H-NMR, DMSO-$d_6$, 400 MHz) |
|---|---|---|---|---|
| 3-267 | Cl | CH$_2$O-tetrahydrofuran-3-yl | SO$_2$Me | |
| 3-268 | Cl | CH$_2$O-tetrahydrofuran-3-yl | SO$_2$Et | |
| 3-269 | Cl | CH$_2$OCH$_2$-tetrahydrofuran-2-yl | SO$_2$Me | |
| 3-270 | Cl | CH$_2$OCH$_2$-tetrahydrofuran-2-yl | SO$_2$Et | |
| 3-271 | Cl | CH$_2$OCH$_2$-tetrahydrofuran-3-yl | SO$_2$Me | |
| 3-272 | Cl | CH$_2$OCH$_2$-tetrahydrofuran-3-yl | SO$_2$Et | |
| 3-273 | Cl | OMe | SO$_2$Me | |
| 3-274 | Cl | OMe | SO$_2$Et | |
| 3-275 | Cl | OEt | SO$_2$Me | |
| 3-276 | Cl | OEt | SO$_2$Et | |
| 3-277 | Cl | OiPr | SO$_2$Me | |
| 3-278 | Cl | OiPr | SO$_2$Et | |
| 3-279 | Cl | O(CH$_2$)$_2$OMe | SO$_2$Me | |
| 3-280 | Cl | O(CH$_2$)$_4$OMe | SO$_2$Me | |
| 3-281 | Cl | O(CH$_2$)$_4$OMe | SO$_2$Et | |
| 3-282 | Cl | O(CH$_2$)$_3$OMe | SO$_2$Me | |
| 3-283 | Cl | O(CH$_2$)$_3$OMe | SO$_2$Et | |
| 3-284 | Cl | O(CH$_2$)$_2$OMe | SO$_2$Me | |
| 3-285 | Cl | O(CH$_2$)$_2$OMe | SO$_2$Et | |
| 3-286 | Cl | [1,4]dioxan-2-ylmethoxy | SO$_2$Me | |
| 3-287 | Cl | [1,4]dioxan-2-ylmethoxy | SO$_2$Et | |
| 3-288 | Cl | OCH$_2$(CO)NMe$_2$ | SO$_2$Me | |
| 3-289 | Cl | OCH$_2$(CO)NMe$_2$ | SO$_2$Et | |
| 3-290 | Cl | SMe | SO$_2$Me | |
| 3-291 | Cl | SOMe | SO$_2$Me | |
| 3-292 | Br | OMe | Br | |
| 3-293 | Br | O(CH$_2$)$_2$OMe | Br | |
| 3-294 | Br | O(CH$_2$)$_2$OMe | SO$_2$Me | |
| 3-295 | Br | O(CH$_2$)$_2$OMe | SO$_2$Et | |
| 3-296 | Br | O(CH$_2$)$_3$OMe | SO$_2$Me | |
| 3-297 | Br | O(CH$_2$)$_3$OMe | SO$_2$Et | |
| 3-298 | Br | O(CH$_2$)$_4$OMe | SO$_2$Me | |
| 3-299 | Br | O(CH$_2$)$_4$OMe | SO$_2$Et | |
| 3-300 | Br | [1,4]dioxan-2-ylmethoxy | SO$_2$Me | |
| 3-301 | Br | [1,4]dioxan-2-ylmethoxy | SO$_2$Et | |
| 3-302 | I | O(CH$_2$)$_2$OMe | SO$_2$Me | |
| 3-303 | I | O(CH$_2$)$_2$OMe | SO$_2$Et | |
| 3-304 | I | O(CH$_2$)$_3$OMe | SO$_2$Me | |
| 3-305 | I | O(CH$_2$)$_3$OMe | SO$_2$Et | |
| 3-306 | I | O(CH$_2$)$_4$OMe | SO$_2$Me | |
| 3-307 | I | O(CH$_2$)$_4$OMe | SO$_2$Et | |
| 3-308 | I | [1,4]dioxan-2-ylmethoxy | SO$_2$Me | |
| 3-309 | I | [1,4]dioxan-2-ylmethoxy | SO$_2$Et | |
| 3-310 | OMe | SMe | CF$_3$ | |
| 3-311 | OMe | SOMe | CF$_3$ | |
| 3-312 | OMe | SO$_2$Me | CF$_3$ | |
| 3-313 | OMe | SOEt | CF$_3$ | |
| 3-314 | OMe | SO$_2$Et | CF$_3$ | |
| 3-315 | OMe | S(CH$_2$)$_2$OMe | CF$_3$ | |
| 3-316 | OMe | SO(CH$_2$)$_2$OMe | CF$_3$ | |
| 3-317 | OMe | SO$_2$(CH$_2$)$_2$OMe | CF$_3$ | |

TABLE 3-continued

Compounds of the general formula (I) in which A represents CY, V represents hydrogen, W represents fluorine and R represents ethyl

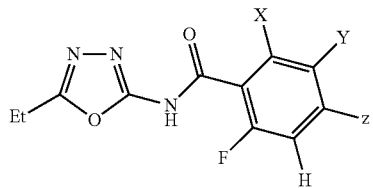

| No. | X | Y | Z | Physical data ($^1$H-NMR, DMSO-$d_6$, 400 MHz) |
|---|---|---|---|---|
| 3-318 | OMe | SMe | Cl | |
| 3-319 | OMe | SOMe | Cl | |
| 3-320 | OMe | SO$_2$Me | Cl | |
| 3-321 | OMe | SEt | Cl | |
| 3-322 | OMe | SOEt | Cl | |
| 3-323 | OMe | SO2Et | Cl | |
| 3-324 | OMe | S(CH$_2$)$_2$OMe | Cl | |
| 3-325 | OMe | SO(CH$_2$)$_2$OMe | Cl | |
| 3-326 | OMe | SO$_2$(CH$_2$)$_2$OMe | Cl | |
| 3-327 | OCH$_2$c-Pr | SMe | CF$_3$ | |
| 3-328 | OCH$_2$c-Pr | SOMe | CF$_3$ | |
| 3-329 | OCH$_2$c-Pr | SO$_2$Me | CF$_3$ | |
| 3-330 | OCH$_2$c-Pr | SEt | CF$_3$ | |
| 3-331 | OCH$_2$c-Pr | SOEt | CF$_3$ | |
| 3-332 | OCH$_2$c-Pr | SO$_2$Et | CF$_3$ | |
| 3-333 | OCH$_2$c-Pr | S(CH$_2$)$_2$OMe | CF$_3$ | |
| 3-334 | OCH$_2$c-Pr | SO(CH$_2$)$_2$OMe | CF$_3$ | |
| 3-335 | OCH$_2$c-Pr | SO$_2$(CH$_2$)$_2$OMe | CF$_3$ | |
| 3-336 | OCH$_2$c-Pr | SMe | Cl | |
| 3-337 | OCH$_2$c-Pr | SOMe | Cl | |
| 3-338 | OCH$_2$c-Pr | SO$_2$Me | Cl | |
| 3-339 | OCH$_2$c-Pr | SEt | Cl | |
| 3-340 | OCH$_2$c-Pr | SOEt | Cl | |
| 3-341 | OCH$_2$c-Pr | SO$_2$Et | Cl | |
| 3-342 | OCH$_2$c-Pr | S(CH$_2$)$_2$OMe | Cl | |
| 3-343 | OCH$_2$c-Pr | SO(CH$_2$)$_2$OMe | Cl | |
| 3-344 | OCH$_2$c-Pr | SO$_2$(CH$_2$)$_2$OMe | Cl | |
| 3-345 | OCH$_2$c-Pr | SMe | SO$_2$Me | |
| 3-346 | OCH$_2$c-Pr | SOMe | SO$_2$Me | |
| 3-347 | OCH$_2$c-Pr | SO$_2$Me | SO$_2$Me | |
| 3-348 | OCH$_2$c-Pr | SEt | SO$_2$Me | |
| 3-349 | OCH$_2$c-Pr | SOEt | SO$_2$Me | |
| 3-350 | OCH$_2$c-Pr | SO$_2$Et | SO$_2$Me | |
| 3-351 | OCH$_2$c-Pr | S(CH$_2$)$_2$OMe | SO$_2$Me | |
| 3-352 | OCH$_2$c-Pr | SO(CH$_2$)$_2$OMe | SO$_2$Me | |
| 3-353 | OCH$_2$c-Pr | SO$_2$(CH$_2$)$_2$OMe | SO$_2$Me | |
| 3-354 | SO$_2$Me | F | CF$_3$ | |
| 3-355 | SO$_2$Me | NH$_2$ | CF$_3$ | |
| 3-356 | SO$_2$Me | NHEt | Cl | |
| 3-357 | SMe | SEt | F | |
| 3-358 | SMe | SMe | F | |
| 3-359 | Cl | SMe | CF$_3$ | |
| 3-360 | Cl | S(O)Me | CF$_3$ | |
| 3-361 | Cl | SO$_2$Me | CF$_3$ | |
| 3-362 | Cl | SO$_2$Me | SO$_2$Me | |

TABLE 4

Compounds of the general formula (I) in which A represents CY, V represents hydrogen, W represents fluorine and R represents trifluoromethyl

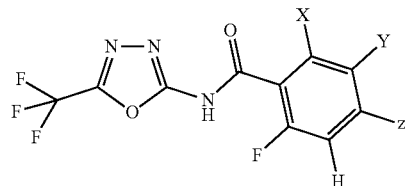

| No. | X | Y | Z | Physical data ($^1$H-NMR, DMSO-$d_6$, 400 MHz) |
|---|---|---|---|---|
| 4-1 | F | H | Cl | |
| 4-2 | F | H | SO$_2$Me | |
| 4-3 | F | H | SO$_2$Et | |
| 4-4 | F | H | CF$_3$ | |
| 4-5 | F | H | NO$_2$ | |
| 4-6 | Cl | H | Br | |
| 4-7 | Cl | H | SMe | |
| 4-8 | Cl | H | SOMe | |
| 4-9 | Cl | H | SO$_2$Me | |
| 4-10 | Cl | H | SO$_2$CH$_2$Cl | |
| 4-11 | Cl | H | SEt | |
| 4-12 | Cl | H | SO$_2$Et | |
| 4-13 | Cl | H | CF$_3$ | |
| 4-14 | Cl | H | NO$_2$ | |
| 4-15 | Cl | H | pyrazol-1-yl | |
| 4-16 | Cl | H | 1H-1,2,4-triazol-1-yl | |
| 4-17 | Br | H | Cl | |
| 4-18 | Br | H | Br | |
| 4-19 | Br | H | SO$_2$Me | |
| 4-20 | Br | H | SO$_2$Et | |
| 4-21 | Br | H | CF$_3$ | |
| 4-22 | SO$_2$Me | H | Cl | |
| 4-23 | SO$_2$Me | H | Br | |
| 4-24 | SO$_2$Me | H | SMe | |
| 4-25 | SO$_2$Me | H | SOMe | |
| 4-26 | SO$_2$Me | H | SO$_2$Me | |
| 4-27 | SO$_2$Me | H | SO$_2$Et | |
| 4-28 | SO$_2$Me | H | CF$_3$ | |
| 4-29 | SO$_2$Et | H | Cl | |
| 4-30 | SO$_2$Et | H | Br | |
| 4-31 | SO$_2$Et | H | SMe | |
| 4-32 | SO$_2$Et | H | SOMe | |
| 4-33 | SO$_2$Et | H | SO$_2$Me | |
| 4-34 | SO$_2$Et | H | CF$_3$ | |
| 4-35 | NO$_2$ | H | F | |
| 4-36 | NO$_2$ | H | Cl | |
| 4-37 | NO$_2$ | H | Br | |
| 4-38 | NO$_2$ | H | I | |
| 4-39 | NO$_2$ | H | CN | |
| 4-40 | NO$_2$ | H | SO$_2$Me | |
| 4-41 | NO$_2$ | H | SO$_2$Et | |
| 4-42 | NO$_2$ | H | CF$_3$ | |
| 4-43 | Me | H | Cl | |
| 4-44 | Me | H | Br | |
| 4-45 | Me | H | SMe | |
| 4-46 | Me | H | SO$_2$Me | |
| 4-47 | Me | H | SO$_2$CH$_2$Cl | |
| 4-48 | Me | H | SEt | |
| 4-49 | Me | H | SO$_2$Et | |
| 4-50 | Me | H | CF$_3$ | |
| 4-51 | CH$_2$SO$_2$Me | H | CF$_3$ | |
| 4-52 | Et | H | Cl | |
| 4-53 | Et | H | Br | |
| 4-54 | Et | H | SMe | |
| 4-55 | Et | H | SO$_2$Me | |
| 4-56 | Et | H | SO$_2$CH$_2$Cl | |
| 4-57 | Et | H | SEt | |
| 4-58 | Et | H | SO$_2$Et | |
| 4-59 | Et | H | CF$_3$ | |
| 4-60 | CF$_3$ | H | Cl | |
| 4-61 | CF$_3$ | H | Br | |
| 4-62 | CF$_3$ | H | SO$_2$Me | |

TABLE 4-continued

Compounds of the general formula (I) in which A represents CY, V represents hydrogen, W represents fluorine and R represents trifluoromethyl

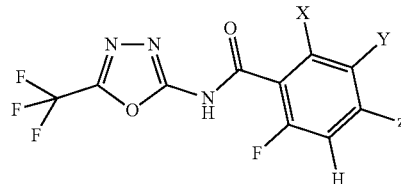

| No. | X | Y | Z | Physical data (¹H-NMR, DMSO-$d_6$, 400 MHz) |
|---|---|---|---|---|
| 4-63 | $CF_3$ | H | $SO_2Et$ | |
| 4-64 | $CF_3$ | H | $CF_3$ | |
| 4-65 | $NO_2$ | $NH_2$ | F | |
| 4-66 | $NO_2$ | NHMe | F | |
| 4-67 | $NO_2$ | $NMe_2$ | F | |
| 4-68 | $NO_2$ | Me | Cl | |
| 4-69 | $NO_2$ | $NH_2$ | Cl | |
| 4-70 | $NO_2$ | NHMe | Cl | |
| 4-71 | $NO_2$ | $NMe_2$ | Cl | |
| 4-72 | $NO_2$ | $NH_2$ | Br | |
| 4-73 | $NO_2$ | NHMe | Br | |
| 4-74 | $NO_2$ | $NMe_2$ | Br | |
| 4-75 | $NO_2$ | $NH_2$ | $CF_3$ | |
| 4-76 | $NO_2$ | $NMe_2$ | $CF_3$ | |
| 4-77 | $NO_2$ | $NH_2$ | $SO_2Me$ | |
| 4-78 | $NO_2$ | $NH_2$ | $SO_2Et$ | |
| 4-79 | $NO_2$ | NHMe | $SO_2Me$ | |
| 4-80 | $NO_2$ | $NMe_2$ | $SO_2Me$ | |
| 4-81 | $NO_2$ | $NMe_2$ | $SO_2Et$ | |
| 4-82 | $NO_2$ | $NH_2$ | 1H-1,2,4-triazol-1-yl | |
| 4-83 | $NO_2$ | NHMe | 1H-1,2,4-triazol-1-yl | |
| 4-84 | $NO_2$ | $NMe_2$ | 1H-1,2,4-triazol-1-yl | |
| 4-85 | Me | SMe | H | |
| 4-86 | Me | SOMe | H | |
| 4-87 | Me | $SO_2Me$ | H | |
| 4-88 | Me | SEt | H | |
| 4-89 | Me | SOEt | H | |
| 4-90 | Me | $SO_2Et$ | H | |
| 4-91 | Me | $S(CH_2)_2OMe$ | H | |
| 4-92 | Me | $SO(CH_2)_2OMe$ | H | |
| 4-93 | Me | $SO_2(CH_2)_2OMe$ | H | |
| 4-94 | Me | F | F | |
| 4-95 | Me | F | Cl | |
| 4-96 | Me | SEt | F | |
| 4-97 | Me | SOEt | F | |
| 4-98 | Me | $SO_2Et$ | F | |
| 4-99 | Me | Me | Cl | |
| 4-100 | Me | F | Cl | |
| 4-101 | Me | Cl | Cl | |
| 4-102 | Me | $NH_2$ | Cl | |
| 4-103 | Me | NHMe | Cl | |
| 4-104 | Me | $NMe_2$ | Cl | |
| 4-105 | Me | $O(CH_2)_2OMe$ | Cl | |
| 4-106 | Me | $O(CH_2)_3OMe$ | Cl | |
| 4-107 | Me | $O(CH_2)_4OMe$ | Cl | |
| 4-108 | Me | $OCH_2CONMe_2$ | Cl | |
| 4-109 | Me | $O(CH_2)_2-CO-NMe_2$ | Cl | |
| 4-110 | Me | $O(CH_2)_2-NH(CO)NMe_2$ | Cl | |
| 4-111 | Me | $O(CH_2)_2-NH(CO)NHCO_2Et$ | Cl | |
| 4-112 | Me | $O(CH_2)_2-NHCO_2Me$ | Cl | |
| 4-113 | Me | $OCH_2-NHSO_2cPr$ | Cl | |
| 4-114 | Me | $O(CH_2)$-5-2,4-dimethyl-2,4-dihydro-3H-1,2,4-triazol-3-one | Cl | |
| 4-115 | Me | $O(CH_2)$-3,5-dimethyl-1,2-oxazol-4-yl | Cl | |
| 4-116 | Me | SMe | Cl | |
| 4-117 | Me | SOMe | Cl | |
| 4-118 | Me | $SO_2Me$ | Cl | |
| 4-119 | Me | SEt | Cl | |

TABLE 4-continued

Compounds of the general formula (I) in which A represents CY, V represents hydrogen, W represents fluorine and R represents trifluoromethyl

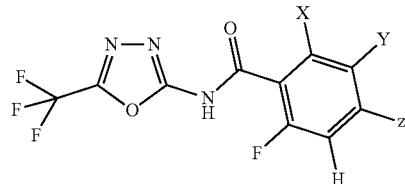

| No. | X | Y | Z | Physical data ($^1$H-NMR, DMSO-$d_6$, 400 MHz) |
|---|---|---|---|---|
| 4-120 | Me | SOEt | Cl | |
| 4-121 | Me | SO$_2$Et | Cl | |
| 4-122 | Me | S(CH$_2$)$_2$OMe | Cl | |
| 4-123 | Me | SO(CH$_2$)$_2$OMe | Cl | |
| 4-124 | Me | SO$_2$(CH$_2$)$_2$OMe | Cl | |
| 4-125 | Me | NH$_2$ | Br | |
| 4-126 | Me | NHMe | Br | |
| 4-127 | Me | NMe$_2$ | Br | |
| 4-128 | Me | OCH$_2$(CO)NMe$_2$ | Br | |
| 4-129 | Me | O(CH$_2$)-5-pyrrolidin-2-one | Br | |
| 4-130 | Me | SMe | Br | |
| 4-131 | Me | SOMe | Br | |
| 4-132 | Me | SO$_2$Me | Br | |
| 4-133 | Me | SEt | Br | |
| 4-134 | Me | SOEt | Br | |
| 4-135 | Me | SO$_2$Et | Br | |
| 4-136 | Me | SMe | I | |
| 4-137 | Me | SOMe | I | |
| 4-138 | Me | SO$_2$Me | I | |
| 4-139 | Me | SEt | I | |
| 4-140 | Me | SOEt | I | |
| 4-141 | Me | SO$_2$Et | I | |
| 4-142 | Me | Cl | CF$_3$ | |
| 4-143 | Me | SMe | CF$_3$ | |
| 4-144 | Me | SOMe | CF$_3$ | |
| 4-145 | Me | SO$_2$Me | CF$_3$ | |
| 4-146 | Me | SEt | CF$_3$ | |
| 4-147 | Me | SOEt | CF$_3$ | |
| 4-148 | Me | SO$_2$Et | CF$_3$ | |
| 4-149 | Me | S(CH$_2$)$_2$OMe | CF$_3$ | |
| 4-150 | Me | SO(CH$_2$)$_2$OMe | CF$_3$ | |
| 4-151 | Me | SO$_2$(CH$_2$)$_2$OMe | CF$_3$ | |
| 4-152 | Me | Me | SO$_2$Me | |
| 4-153 | Me | 4,5-dihydro-1,2-oxazol-3-yl | SO$_2$Me | |
| 4-154 | Me | 4,5-dihydro-1,2-oxazol-3-yl | SO$_2$Et | |
| 4-155 | Me | 5-cyanomethyl-4,5-dihydro-1,2-oxazol-3-yl | SO$_2$Me | |
| 4-156 | Me | 5-cyanomethyl-4,5-dihydro-1,2-oxazol-3-yl | SO$_2$Et | |
| 4-157 | Me | NH$_2$ | SO$_2$Me | |
| 4-158 | Me | NHMe | SO$_2$Me | |
| 4-159 | Me | NMe$_2$ | SO$_2$Me | |
| 4-160 | Me | NH(CH$_2$)$_2$OMe | SO$_2$Me | |
| 4-161 | Me | pyrazol-1-yl | SO$_2$Me | |
| 4-162 | Me | OH | SO$_2$Me | |
| 4-163 | Me | OMe | SO$_2$Me | |
| 4-164 | Me | OMe | SO$_2$Et | |
| 4-165 | Me | OEt | SO$_2$Me | |
| 4-166 | Me | OEt | SO$_2$Et | |
| 4-167 | Me | OiPr | SO$_2$Me | |
| 4-168 | Me | OiPr | SO$_2$Et | |
| 4-169 | Me | O(CH$_2$)$_2$OMe | SO$_2$Me | |
| 4-170 | Me | O(CH$_2$)$_2$OMe | SO$_2$Et | |
| 4-171 | Me | O(CH$_2$)$_3$OMe | SO$_2$Me | |
| 4-172 | Me | O(CH$_2$)$_3$OMe | SO$_2$Et | |
| 4-173 | Me | O(CH$_2$)$_4$OMe | SO$_2$Me | |
| 4-174 | Me | O(CH$_2$)$_4$OMe | SO$_2$Et | |
| 4-175 | Me | O(CH$_2$)$_2$NHSO2Me | SO$_2$Me | |
| 4-176 | Me | O(CH$_2$)$_2$NHSO2Me | SO$_2$Et | |
| 4-177 | Me | OCH$_2$(CO)NMe$_2$ | SO$_2$Me | |
| 4-178 | Me | OCH$_2$(CO)NMe$_2$ | SO$_2$Et | |

TABLE 4-continued

Compounds of the general formula (I) in which A represents CY, V represents hydrogen, W represents fluorine and R represents trifluoromethyl

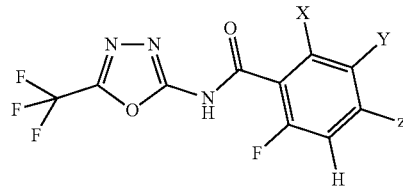

| No. | X | Y | Z | Physical data ($^1$H-NMR, DMSO-$d_6$, 400 MHz) |
|---|---|---|---|---|
| 4-179 | Me | [1,4]dioxan-2-ylmethoxy | SO$_2$Me | |
| 4-180 | Me | [1,4]dioxan-2-ylmethoxy | SO$_2$Et | |
| 4-181 | Me | O(CH$_2$)$_2$—O-(3,5-di-methoxypyrimidin-2-yl) | SO$_2$Me | |
| 4-182 | Me | Cl | SO$_2$Me | |
| 4-183 | Me | SMe | SO$_2$Me | |
| 4-184 | Me | SOMe | SO$_2$Me | |
| 4-185 | Me | SO$_2$Me | SO$_2$Me | |
| 4-186 | Me | SO$_2$Me | SO$_2$Et | |
| 4-187 | Me | SEt | SO$_2$Me | |
| 4-188 | Me | SOEt | SO$_2$Me | |
| 4-189 | Me | SO$_2$Et | SO$_2$Me | |
| 4-190 | Me | S(CH$_2$)$_2$OMe | SO$_2$Me | |
| 4-191 | Me | SO(CH$_2$)$_2$OMe | SO$_2$Me | |
| 4-192 | Me | SO$_2$(CH$_2$)$_2$OMe | SO2Me | |
| 4-193 | CH$_2$SMe | OMe | SO$_2$Me | |
| 4-194 | CH$_2$OMe | OMe | SO$_2$Me | |
| 4-195 | CH$_2$O(CH$_2$)$_2$OMe | NH(CH$_2$)$_2$OEt | SO$_2$Me | |
| 4-196 | CH$_2$O(CH$_2$)$_2$OMe | NH(CH$_2$)$_3$OEt | SO$_2$Me | |
| 4-197 | CH$_2$O(CH$_2$)$_3$OMe | OMe | SO$_2$Me | |
| 4-198 | CH$_2$O(CH$_2$)$_2$OMe | NH(CH$_2$)$_2$OMe | SO$_2$Me | |
| 4-199 | CH$_2$O(CH$_2$)$_2$OMe | NH(CH$_2$)$_3$OMe | SO$_2$Me | |
| 4-200 | Et | SMe | Cl | |
| 4-201 | Et | SO$_2$Me | Cl | |
| 4-202 | Et | SMe | CF$_3$ | |
| 4-203 | Et | SO$_2$Me | CF$_3$ | |
| 4-204 | Et | F | SO$_2$Me | |
| 4-205 | Et | NH(CH$_2$)$_2$OMe | SO$_2$Me | |
| 4-206 | iPr | SO$_2$Me | CF$_3$ | |
| 4-207 | cPr | SO$_2$Me | CF$_3$ | |
| 4-208 | CF$_3$ | O(CH$_2$)$_2$OMe | F | |
| 4-209 | CF$_3$ | O(CH$_2$)$_3$OMe | F | |
| 4-210 | CF$_3$ | OCH$_2$CONMe$_2$ | F | |
| 4-211 | CF$_3$ | [1,4]dioxan-2-ylmethoxy | F | |
| 4-212 | CF$_3$ | O(CH$_2$)$_2$OMe | Cl | |
| 4-213 | CF$_3$ | O(CH$_2$)$_3$OMe | Cl | |
| 4-214 | CF$_3$ | OCH$_2$CONMe$_2$ | Cl | |
| 4-215 | CF$_3$ | [1,4]dioxan-2-ylmethoxy | Cl | |
| 4-216 | CF$_3$ | O(CH$_2$)$_2$OMe | Br | |
| 4-217 | CF$_3$ | O(CH$_2$)$_3$OMe | Br | |
| 4-218 | CF$_3$ | OCH$_2$CONMe$_2$ | Br | |
| 4-219 | CF$_3$ | [1,4]dioxan-2-ylmethoxy | Br | |
| 4-220 | CF$_3$ | O(CH$_2$)$_2$OMe | I | |
| 4-221 | CF$_3$ | O(CH$_2$)$_3$OMe | I | |
| 4-222 | CF$_3$ | OCH$_2$CONMe$_2$ | I | |
| 4-223 | CF$_3$ | [1,4]dioxan-2-ylmethoxy | I | |
| 4-224 | CF$_3$ | F | SO$_2$Me | |
| 4-225 | CF$_3$ | F | SO$_2$Et | |
| 4-226 | CF$_3$ | O(CH$_2$)$_2$OMe | SO$_2$Me | |
| 4-227 | CF$_3$ | O(CH$_2$)$_2$OMe | SO$_2$Et | |
| 4-228 | CF$_3$ | O(CH$_2$)$_3$OMe | SO$_2$Me | |
| 4-229 | CF$_3$ | O(CH$_2$)$_3$OMe | SO$_2$Et | |
| 4-230 | CF$_3$ | OCH$_2$CONMe$_2$ | SO$_2$Me | |
| 4-231 | CF$_3$ | OCH$_2$CONMe$_2$ | SO$_2$Et | |
| 4-232 | CF$_3$ | [1,4]dioxan-2-ylmethoxy | SO$_2$Me | |

TABLE 4-continued

Compounds of the general formula (I) in which A represents CY, V represents hydrogen, W represents fluorine and R represents trifluoromethyl

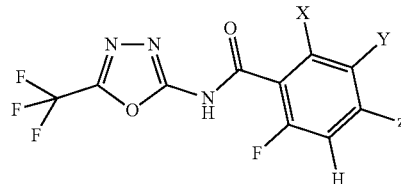

| No. | X | Y | Z | Physical data ($^1$H-NMR, DMSO-$d_6$, 400 MHz) |
|---|---|---|---|---|
| 4-233 | CF$_3$ | [1,4]dioxan-2-ylmethoxy | SO$_2$Et | |
| 4-234 | F | SMe | CF$_3$ | |
| 4-235 | F | SOMe | CF$_3$ | |
| 4-236 | Cl | Me | Cl | |
| 4-237 | Cl | OCH$_2$CHCH$_2$ | Cl | |
| 4-238 | Cl | OCH$_2$CHF$_2$ | Cl | |
| 4-239 | Cl | O(CH$_2$)$_2$OMe | Cl | |
| 4-240 | Cl | OCH$_2$CONMe$_2$ | Cl | |
| 4-241 | Cl | O(CH$_2$)-5-pyrrolidin-2-one | Cl | |
| 4-242 | Cl | SMe | Cl | |
| 4-243 | Cl | SOMe | Cl | |
| 4-244 | Cl | SO$_2$Me | Cl | |
| 4-245 | Cl | F | SMe | |
| 4-246 | Cl | Cl | SO$_2$Me | |
| 4-247 | Cl | COOMe | SO$_2$Me | |
| 4-248 | Cl | CONMe$_2$ | SO$_2$Me | |
| 4-249 | Cl | CONMe(OMe) | SO$_2$Me | |
| 4-250 | Cl | CH$_2$OMe | SO$_2$Me | |
| 4-251 | Cl | CH$_2$OMe | SO$_2$Et | |
| 4-252 | Cl | CH$_2$OEt | SO$_2$Me | |
| 4-253 | Cl | CH$_2$OEt | SO$_2$Et | |
| 4-254 | Cl | CH$_2$OCH$_2$CHF$_2$ | SO$_2$Me | |
| 4-255 | Cl | CH$_2$OCH$_2$CF$_3$ | SO$_2$Me | |
| 4-256 | Cl | CH$_2$OCH$_2$CF$_3$ | SMe | |
| 4-257 | Cl | CH$_2$OCH$_2$CF$_3$ | SO$_2$Et | |
| 4-258 | Cl | CH$_2$OCH$_2$CF$_2$CHF$_2$ | SO$_2$Me | |
| 4-259 | Cl | CH$_2$O-c-pentyl | SO$_2$Me | |
| 4-260 | Cl | CH$_2$PO(OMe)$_2$ | SO$_2$Me | |
| 4-261 | Cl | 4,5-dihydro-1,2-oxazol-3-yl | SMe | |
| 4-262 | Cl | 4,5-dihydro-1,2-oxazol-3-yl | SO$_2$Me | |
| 4-263 | Cl | 4,5-dihydro-1,2-oxazol-3-yl | SO$_2$Et | |
| 4-264 | Cl | 5-cyanomethyl-4,5-dihydro-1,2-oxazol-3-yl | SO$_2$Me | |
| 4-265 | Cl | 5-cyanomethyl-4,5-dihydro-1,2-oxazol-3-yl | SO$_2$Et | |
| 4-266 | Cl | 5-(methoxymethyl)-4,5-dihydro-1,2-oxazol-3-yl | SO$_2$Et | |
| 4-267 | Cl | 5-(methoxymethyl)-5-methyl-4,5-dihydro-1,2-oxazol-3-yl | SO$_2$Et | |
| 4-268 | Cl | CH$_2$O-tetrahydrofuran-3-yl | SO$_2$Me | |
| 4-269 | Cl | CH$_2$O-tetrahydrofuran-3-yl | SO$_2$Et | |
| 4-270 | Cl | CH$_2$OCH$_2$-tetrahydrofuran-2-yl | SO$_2$Me | |
| 4-271 | Cl | CH$_2$OCH$_2$-tetrahydrofuran-2-yl | SO$_2$Et | |
| 4-272 | Cl | CH$_2$OCH$_2$-tetrahydrofuran-3-yl | SO$_2$Me | |
| 4-273 | Cl | CH$_2$OCH$_2$-tetrahydrofuran-3-yl | SO$_2$Et | |
| 4-274 | Cl | OMe | SO$_2$Me | |
| 4-275 | Cl | OMe | SO$_2$Et | |
| 4-276 | Cl | OEt | SO$_2$Me | |
| 4-277 | Cl | OEt | SO$_2$Et | |
| 4-278 | Cl | OiPr | SO$_2$Me | |
| 4-279 | Cl | OiPr | SO$_2$Et | |

TABLE 4-continued

Compounds of the general formula (I) in which A represents CY, V represents hydrogen, W represents fluorine and R represents trifluoromethyl

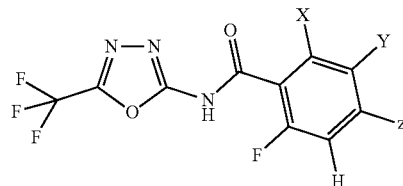

| No. | X | Y | Z | Physical data ($^1$H-NMR, DMSO-$d_6$, 400 MHz) |
|---|---|---|---|---|
| 4-280 | Cl | O(CH$_2$)$_2$OMe | SO$_2$Me | |
| 4-281 | Cl | O(CH$_2$)$_4$OMe | SO$_2$Me | |
| 4-282 | Cl | O(CH$_2$)$_4$OMe | SO$_2$Et | |
| 4-283 | Cl | O(CH$_2$)$_3$OMe | SO$_2$Me | |
| 4-284 | Cl | O(CH$_2$)$_3$OMe | SO$_2$Et | |
| 4-285 | Cl | O(CH$_2$)$_2$OMe | SO$_2$Me | |
| 4-286 | Cl | O(CH$_2$)$_2$OMe | SO$_2$Et | |
| 4-287 | Cl | [1,4]dioxan-2-ylmethoxy | SO$_2$Me | |
| 4-288 | Cl | [1,4]dioxan-2-ylmethoxy | SO$_2$Et | |
| 4-289 | Cl | OCH$_2$(CO)NMe$_2$ | SO$_2$Me | |
| 4-290 | Cl | OCH$_2$(CO)NMe$_2$ | SO$_2$Et | |
| 4-291 | Cl | SMe | SO$_2$Me | |
| 4-292 | Cl | SOMe | SO$_2$Me | |
| 4-293 | Br | OMe | Br | |
| 4-294 | Br | O(CH$_2$)$_2$OMe | Br | |
| 4-295 | Br | O(CH$_2$)$_2$OMe | SO$_2$Me | |
| 4-296 | Br | O(CH$_2$)$_2$OMe | SO$_2$Et | |
| 4-297 | Br | O(CH$_2$)$_3$OMe | SO$_2$Me | |
| 4-298 | Br | O(CH$_2$)$_3$OMe | SO$_2$Et | |
| 4-299 | Br | O(CH$_2$)$_4$OMe | SO$_2$Me | |
| 4-300 | Br | O(CH$_2$)$_4$OMe | SO$_2$Et | |
| 4-301 | Br | [1,4]dioxan-2-ylmethoxy | SO$_2$Me | |
| 4-302 | Br | [1,4]dioxan-2-ylmethoxy | SO$_2$Et | |
| 4-303 | I | O(CH$_2$)$_2$OMe | SO$_2$Me | |
| 4-304 | I | O(CH$_2$)$_2$OMe | SO$_2$Et | |
| 4-305 | I | O(CH$_2$)$_3$OMe | SO$_2$Me | |
| 4-306 | I | O(CH$_2$)$_3$OMe | SO$_2$Et | |
| 4-307 | I | O(CH$_2$)$_4$OMe | SO$_2$Me | |
| 4-308 | I | O(CH$_2$)$_4$OMe | SO$_2$Et | |
| 4-309 | I | [1,4]dioxan-2-ylmethoxy | SO$_2$Me | |
| 4-310 | I | [1,4]dioxan-2-ylmethoxy | SO$_2$Et | |
| 4-311 | OMe | SMe | CF$_3$ | |
| 4-312 | OMe | SOMe | CF$_3$ | |
| 4-313 | OMe | SO$_2$Me | CF$_3$ | |
| 4-314 | OMe | SOEt | CF$_3$ | |
| 4-315 | OMe | SO$_2$Et | CF$_3$ | |
| 4-316 | OMe | S(CH$_2$)$_2$OMe | CF$_3$ | |
| 4-317 | OMe | SO(CH$_2$)$_2$OMe | CF$_3$ | |
| 4-318 | OMe | SO$_2$(CH$_2$)$_2$OMe | CF$_3$ | |
| 4-319 | OMe | SMe | Cl | |
| 4-320 | OMe | SOMe | Cl | |
| 4-321 | OMe | SO$_2$Me | Cl | |
| 4-322 | OMe | SEt | Cl | |
| 4-323 | OMe | SOEt | Cl | |
| 4-324 | OMe | SO2Et | Cl | |
| 4-325 | OMe | S(CH$_2$)$_2$OMe | Cl | |
| 4-326 | OMe | SO(CH$_2$)$_2$OMe | Cl | |
| 4-327 | OMe | SO$_2$(CH$_2$)$_2$OMe | Cl | |
| 4-328 | OCH$_2$c-Pr | SMe | CF$_3$ | |
| 4-329 | OCH$_2$c-Pr | SOMe | CF$_3$ | |
| 4-330 | OCH$_2$c-Pr | SO$_2$Me | CF$_3$ | |
| 4-331 | OCH$_2$c-Pr | SEt | CF$_3$ | |
| 4-332 | OCH$_2$c-Pr | SOEt | CF$_3$ | |
| 4-333 | OCH$_2$c-Pr | SO$_2$Et | CF$_3$ | |
| 4-334 | OCH$_2$c-Pr | S(CH$_2$)$_2$OMe | CF$_3$ | |
| 4-335 | OCH$_2$c-Pr | SO(CH$_2$)$_2$OMe | CF$_3$ | |
| 4-336 | OCH$_2$c-Pr | SO$_2$(CH$_2$)$_2$OMe | CF$_3$ | |

TABLE 4-continued

Compounds of the general formula (I) in which A represents CY, V represents hydrogen, W represents fluorine and R represents trifluoromethyl

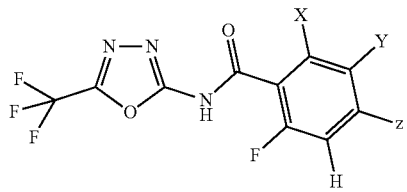

| No. | X | Y | Z | Physical data (¹H-NMR, DMSO-$d_6$, 400 MHz) |
|---|---|---|---|---|
| 4-337 | OCH$_2$c-Pr | SMe | Cl | |
| 4-338 | OCH$_2$c-Pr | SOMe | Cl | |
| 4-339 | OCH$_2$c-Pr | SO$_2$Me | Cl | |
| 4-340 | OCH$_2$c-Pr | SEt | Cl | |
| 4-341 | OCH$_2$c-Pr | SOEt | Cl | |
| 4-342 | OCH$_2$c-Pr | SO$_2$Et | Cl | |
| 4-343 | OCH$_2$c-Pr | S(CH$_2$)$_2$OMe | Cl | |
| 4-344 | OCH$_2$c-Pr | SO(CH$_2$)$_2$OMe | Cl | |
| 4-345 | OCH$_2$c-Pr | SO$_2$(CH$_2$)$_2$OMe | Cl | |
| 4-346 | OCH$_2$c-Pr | SMe | SO$_2$Me | |
| 4-347 | OCH$_2$c-Pr | SOMe | SO$_2$Me | |
| 4-348 | OCH$_2$c-Pr | SO$_2$Me | SO$_2$Me | |
| 4-349 | OCH$_2$c-Pr | SEt | SO$_2$Me | |
| 4-350 | OCH$_2$c-Pr | SOEt | SO$_2$Me | |
| 4-351 | OCH$_2$c-Pr | SO$_2$Et | SO$_2$Me | |
| 4-352 | OCH$_2$c-Pr | S(CH$_2$)$_2$OMe | SO$_2$Me | |
| 4-353 | OCH$_2$c-Pr | SO(CH$_2$)$_2$OMe | SO$_2$Me | |
| 4-354 | OCH$_2$c-Pr | SO$_2$(CH$_2$)$_2$OMe | SO$_2$Me | |
| 4-355 | SO$_2$Me | F | CF$_3$ | |
| 4-356 | SO$_2$Me | NH$_2$ | CF$_3$ | |
| 4-357 | SO$_2$Me | NHEt | Cl | |
| 4-358 | SMe | SEt | F | |
| 4-359 | SMe | SMe | F | |
| 4-360 | Cl | SMe | CF$_3$ | |
| 4-361 | Cl | S(O)Me | CF$_3$ | |
| 4-362 | Cl | SO$_2$Me | CF$_3$ | |
| 4-363 | Cl | SO$_2$Me | SO$_2$Me | |

TABLE 5

Compounds of the general formula (I) in which A represents CY, V represents hydrogen, W represents fluorine and R represents CH$_2$OMe

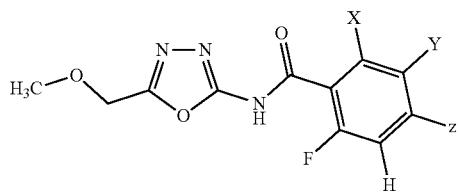

| No. | X | Y | Z | Physical data (¹H-NMR, DMSO-$d_6$, 400 MHz) |
|---|---|---|---|---|
| 5-1 | F | H | Cl | |
| 5-2 | F | H | SO$_2$Me | |
| 5-3 | F | H | SO$_2$Et | |
| 5-4 | F | H | CF$_3$ | |
| 5-5 | F | H | NO$_2$ | |
| 5-6 | Cl | H | Br | |
| 5-7 | Cl | H | SMe | |
| 5-8 | Cl | H | SOMe | |
| 5-9 | Cl | H | SO$_2$Me | |
| 5-10 | Cl | H | SO$_2$CH$_2$Cl | |
| 5-11 | Cl | H | SEt | |
| 5-12 | Cl | H | SO$_2$Et | |
| 5-13 | Cl | H | CF$_3$ | |
| 5-14 | Cl | H | NO$_2$ | |
| 5-15 | Cl | H | pyrazol-1-yl | |

TABLE 5-continued

Compounds of the general formula (I) in which A represents CY, V represents hydrogen, W represents fluorine and R represents CH₂OMe

| No. | X | Y | Z | Physical data (¹H-NMR, DMSO-d₆, 400 MHz) |
|---|---|---|---|---|
| 5-16 | Cl | H | 1H-1,2,4-triazol-1-yl | |
| 5-17 | Br | H | Cl | |
| 5-18 | Br | H | Br | |
| 5-19 | Br | H | SO₂Me | |
| 5-20 | Br | H | SO₂Et | |
| 5-21 | Br | H | CF₃ | |
| 5-22 | SO₂Me | H | Cl | |
| 5-23 | SO₂Me | H | Br | |
| 5-24 | SO₂Me | H | SMe | |
| 5-25 | SO₂Me | H | SOMe | |
| 5-26 | SO₂Me | H | SO₂Me | |
| 5-27 | SO₂Me | H | SO₂Et | |
| 5-28 | SO₂Me | H | CF₃ | |
| 5-29 | SO₂Et | H | Cl | |
| 5-30 | SO₂Et | H | Br | |
| 5-31 | SO₂Et | H | SMe | |
| 5-32 | SO₂Et | H | SOMe | |
| 5-33 | SO₂Et | H | SO₂Me | |
| 5-34 | SO₂Et | H | CF₃ | |
| 5-35 | NO₂ | H | F | |
| 5-36 | NO₂ | H | Cl | |
| 5-37 | NO₂ | H | Br | |
| 5-38 | NO₂ | H | I | |
| 5-39 | NO₂ | H | CN | |
| 5-40 | NO₂ | H | SO₂Me | |
| 5-41 | NO₂ | H | SO₂Et | |
| 5-42 | NO₂ | H | CF₃ | |
| 5-43 | Me | H | Cl | |
| 5-44 | Me | H | Br | |
| 5-45 | Me | H | SMe | |
| 5-46 | Me | H | SO₂Me | |
| 5-47 | Me | H | SO₂CH₂Cl | |
| 5-48 | Me | H | SEt | |
| 5-49 | Me | H | SO₂Et | |
| 5-50 | Me | H | CF₃ | |
| 5-51 | CH₂SO₂Me | H | CF₃ | |
| 5-52 | Et | H | Cl | |
| 5-53 | Et | H | Br | |
| 5-54 | Et | H | SMe | |
| 5-55 | Et | H | SO₂Me | |
| 5-56 | Et | H | SO₂CH₂Cl | |
| 5-57 | Et | H | SEt | |
| 5-58 | Et | H | SO₂Et | |
| 5-59 | Et | H | CF₃ | |
| 5-60 | CF₃ | H | Cl | |
| 5-61 | CF₃ | H | Br | |
| 5-62 | CF₃ | H | SO₂Me | |
| 5-63 | CF₃ | H | SO₂Et | |
| 5-64 | CF₃ | H | CF₃ | |
| 5-65 | NO₂ | NH₂ | F | |
| 5-66 | NO₂ | NHMe | F | |
| 5-67 | NO₂ | NMe₂ | F | |
| 5-68 | NO₂ | Me | Cl | |
| 5-69 | NO₂ | NH₂ | Cl | |
| 5-70 | NO₂ | NHMe | Cl | |
| 5-71 | NO₂ | NMe₂ | Cl | |
| 5-72 | NO₂ | NH₂ | Br | |
| 5-73 | NO₂ | NHMe | Br | |
| 5-74 | NO₂ | NMe₂ | Br | |
| 5-75 | NO₂ | NH₂ | CF₃ | |
| 5-76 | NO₂ | NMe₂ | CF₃ | |
| 5-77 | NO₂ | NH₂ | SO₂Me | |
| 5-78 | NO₂ | NH₂ | SO₂Et | |

TABLE 5-continued

Compounds of the general formula (I) in which A represents CY, V represents hydrogen, W represents fluorine and R represents CH₂OMe

| No. | X | Y | Z | Physical data (¹H-NMR, DMSO-d₆, 400 MHz) |
|---|---|---|---|---|
| 5-79 | NO₂ | NHMe | SO₂Me | |
| 5-80 | NO₂ | NMe₂ | SO₂Me | |
| 5-81 | NO₂ | NMe₂ | SO₂Et | |
| 5-82 | NO₂ | NH₂ | 1H-1,2,4-triazol-1-yl | |
| 5-83 | NO₂ | NHMe | 1H-1,2,4-triazol-1-yl | |
| 5-84 | NO₂ | NMe₂ | 1H-1,2,4-triazol-1-yl | |
| 5-85 | Me | SMe | H | |
| 5-86 | Me | SOMe | H | |
| 5-87 | Me | SO₂Me | H | |
| 5-88 | Me | SEt | H | |
| 5-89 | Me | SOEt | H | |
| 5-90 | Me | SO₂Et | H | |
| 5-91 | Me | S(CH₂)₂OMe | H | |
| 5-92 | Me | SO(CH₂)₂OMe | H | |
| 5-93 | Me | SO₂(CH₂)₂OMe | H | |
| 5-94 | Me | F | F | |
| 5-95 | Me | F | Cl | |
| 5-96 | Me | SEt | F | |
| 5-97 | Me | SOEt | F | |
| 5-98 | Me | SO₂Et | F | |
| 5-99 | Me | Me | Cl | |
| 5-100 | Me | F | Cl | |
| 5-101 | Me | Cl | Cl | |
| 5-102 | Me | NH₂ | Cl | |
| 5-103 | Me | NHMe | Cl | |
| 5-104 | Me | NMe₂ | Cl | |
| 5-105 | Me | O(CH₂)₂OMe | Cl | |
| 5-106 | Me | O(CH₂)₃OMe | Cl | |
| 5-107 | Me | O(CH₂)₄OMe | Cl | |
| 5-108 | Me | OCH₂CONMe₂ | Cl | |
| 5-109 | Me | O(CH₂)₂—CO—NMe₂ | Cl | |
| 5-110 | Me | O(CH₂)₂—NH(CO)NMe₂ | Cl | |
| 5-111 | Me | O(CH₂)₂—NH(CO)NHCO₂Et | Cl | |
| 5-112 | Me | O(CH₂)₂—NHCO₂Me | Cl | |
| 5-113 | Me | OCH₂—NHSO₂cPr | Cl | |
| 5-114 | Me | O(CH₂)-5-2,4-dimethyl-2,4-dihydro-3H-1,2,4-triazol-3-one | Cl | |
| 5-115 | Me | O(CH₂)-3,5-dimethyl-1,2-oxazol-4-yl | Cl | |
| 5-116 | Me | SMe | Cl | |
| 5-117 | Me | SOMe | Cl | |
| 5-118 | Me | SO₂Me | Cl | |
| 5-119 | Me | SEt | Cl | |
| 5-120 | Me | SOEt | Cl | |
| 5-121 | Me | SO₂Et | Cl | |
| 5-122 | Me | S(CH₂)₂OMe | Cl | |
| 5-123 | Me | SO(CH₂)₂OMe | Cl | |
| 5-124 | Me | SO₂(CH₂)₂OMe | Cl | |
| 5-125 | Me | NH₂ | Br | |
| 5-126 | Me | NHMe | Br | |
| 5-127 | Me | NMe₂ | Br | |
| 5-128 | Me | OCH₂(CO)NMe₂ | Br | |
| 5-129 | Me | O(CH₂)-5-pyrrolidin-2-one | Br | |
| 5-130 | Me | SMe | Br | |
| 5-131 | Me | SOMe | Br | |
| 5-132 | Me | SO₂Me | Br | |
| 5-133 | Me | SEt | Br | |
| 5-134 | Me | SOEt | Br | |
| 5-135 | Me | SO₂Et | Br | |
| 5-136 | Me | SMe | I | |

TABLE 5-continued

Compounds of the general formula (I) in which A represents CY, V represents hydrogen, W represents fluorine and R represents CH₂OMe

| No. | X | Y | Z | Physical data (¹H-NMR, DMSO-d₆, 400 MHz) |
|---|---|---|---|---|
| 5-137 | Me | SOMe | I | |
| 5-138 | Me | SO₂Me | I | |
| 5-139 | Me | SEt | I | |
| 5-140 | Me | SOEt | I | |
| 5-141 | Me | SO₂Et | I | |
| 5-142 | Me | Cl | CF₃ | |
| 5-143 | Me | SMe | CF₃ | |
| 5-144 | Me | SOMe | CF₃ | |
| 5-145 | Me | SO₂Me | CF₃ | |
| 5-146 | Me | SEt | CF₃ | |
| 5-147 | Me | SOEt | CF₃ | |
| 5-148 | Me | SO₂Et | CF₃ | |
| 5-149 | Me | S(CH₂)₂OMe | CF₃ | |
| 5-150 | Me | SO(CH₂)₂OMe | CF₃ | |
| 5-151 | Me | SO₂(CH₂)₂OMe | CF₃ | |
| 5-152 | Me | Me | SO₂Me | |
| 5-153 | Me | 4,5-dihydro-1,2-oxazol-3-yl | SO₂Me | |
| 5-154 | Me | 4,5-dihydro-1,2-oxazol-3-yl | SO₂Et | |
| 5-155 | Me | 5-cyanomethyl-4,5-dihydro-1,2-oxazol-3-yl | SO₂Me | |
| 5-156 | Me | 5-cyanomethyl-4,5-dihydro-1,2-oxazol-3-yl | SO₂Et | |
| 5-157 | Me | NH₂ | SO₂Me | |
| 5-158 | Me | NHMe | SO₂Me | |
| 5-159 | Me | NMe₂ | SO₂Me | |
| 5-160 | Me | NH(CH₂)₂OMe | SO₂Me | |
| 5-161 | Me | pyrazol-1-yl | SO₂Me | |
| 5-162 | Me | OH | SO₂Me | |
| 5-163 | Me | OMe | SO₂Me | |
| 5-164 | Me | OMe | SO₂Et | |
| 5-165 | Me | OEt | SO₂Me | |
| 5-166 | Me | OEt | SO₂Et | |
| 5-167 | Me | OiPr | SO₂Me | |
| 5-168 | Me | OiPr | SO₂Et | |
| 5-169 | Me | O(CH₂)₂OMe | SO₂Me | |
| 5-170 | Me | O(CH₂)₂OMe | SO₂Et | |
| 5-171 | Me | O(CH₂)₃OMe | SO₂Me | |
| 5-172 | Me | O(CH₂)₃OMe | SO₂Et | |
| 5-173 | Me | O(CH₂)₄OMe | SO₂Me | |
| 5-174 | Me | O(CH₂)₄OMe | SO₂Et | |
| 5-175 | Me | O(CH₂)₂NHSO2Me | SO₂Me | |
| 5-176 | Me | O(CH₂)₂NHSO2Me | SO₂Et | |
| 5-177 | Me | OCH₂(CO)NMe₂ | SO₂Me | |
| 5-178 | Me | OCH₂(CO)NMe₂ | SO₂Et | |
| 5-179 | Me | [1,4]dioxan-2-ylmethoxy | SO₂Me | |
| 5-180 | Me | [1,4]dioxan-2-ylmethoxy | SO₂Et | |
| 5-181 | Me | O(CH₂)₂—O-(3,5-dimethoxypyrimidin-2-yl) | SO₂Me | |
| 5-182 | Me | Cl | SO₂Me | |
| 5-183 | Me | SMe | SO₂Me | |
| 5-184 | Me | SOMe | SO₂Me | |
| 5-185 | Me | SO₂Me | SO₂Me | |
| 5-186 | Me | SO₂Me | SO₂Et | |
| 5-187 | Me | SEt | SO₂Me | |
| 5-188 | Me | SOEt | SO₂Me | |
| 5-189 | Me | SO₂Et | SO₂Me | |
| 5-190 | Me | S(CH₂)₂OMe | SO₂Me | |
| 5-191 | Me | SO(CH₂)₂OMe | SO₂Me | |
| 5-192 | Me | SO₂(CH₂)₂OMe | SO₂Me | |
| 5-193 | CH₂SMe | OMe | SO₂Me | |

TABLE 5-continued

Compounds of the general formula (I) in which A represents CY, V represents hydrogen, W represents fluorine and R represents CH$_2$OMe

| No. | X | Y | Z | Physical data ($^1$H-NMR, DMSO-d$_6$, 400 MHz) |
|---|---|---|---|---|
| 5-194 | CH$_2$OMe | OMe | SO$_2$Me | |
| 5-195 | CH$_2$O(CH$_2$)$_2$OMe | NH(CH$_2$)$_2$OEt | SO$_2$Me | |
| 5-196 | CH$_2$O(CH$_2$)$_2$OMe | NH(CH$_2$)$_3$OEt | SO$_2$Me | |
| 5-197 | CH$_2$O(CH$_2$)$_3$OMe | OMe | SO$_2$Me | |
| 5-198 | CH$_2$O(CH$_2$)$_2$OMe | NH(CH$_2$)$_2$OMe | SO$_2$Me | |
| 5-199 | CH$_2$O(CH$_2$)$_2$OMe | NH(CH$_2$)$_3$OMe | SO$_2$Me | |
| 5-200 | Et | SMe | Cl | |
| 5-201 | Et | SO$_2$Me | Cl | |
| 5-202 | Et | SMe | CF$_3$ | |
| 5-203 | Et | SO$_2$Me | CF$_3$ | |
| 5-204 | Et | F | SO$_2$Me | |
| 5-205 | Et | NH(CH$_2$)$_2$OMe | SO$_2$Me | |
| 5-206 | iPr | SO$_2$Me | CF$_3$ | |
| 5-207 | cPr | SO$_2$Me | CF$_3$ | |
| 5-208 | CF$_3$ | O(CH$_2$)$_2$OMe | F | |
| 5-209 | CF$_3$ | O(CH$_2$)$_3$OMe | F | |
| 5-210 | CF$_3$ | OCH$_2$CONMe$_2$ | F | |
| 5-211 | CF$_3$ | [1,4]dioxan-2-ylmethoxy | F | |
| 5-212 | CF$_3$ | O(CH$_2$)$_2$OMe | Cl | |
| 5-213 | CF$_3$ | O(CH$_2$)$_3$OMe | Cl | |
| 5-214 | CF$_3$ | OCH$_2$CONMe$_2$ | Cl | |
| 5-215 | CF$_3$ | [1,4]dioxan-2-ylmethoxy | Cl | |
| 5-216 | CF$_3$ | O(CH$_2$)$_2$OMe | Br | |
| 5-217 | CF$_3$ | O(CH$_2$)$_3$OMe | Br | |
| 5-218 | CF$_3$ | OCH$_2$CONMe$_2$ | Br | |
| 5-219 | CF$_3$ | [1,4]dioxan-2-ylmethoxy | Br | |
| 5-220 | CF$_3$ | O(CH$_2$)$_2$OMe | I | |
| 5-221 | CF$_3$ | O(CH$_2$)$_3$OMe | I | |
| 5-222 | CF$_3$ | OCH$_2$CONMe$_2$ | I | |
| 5-223 | CF$_3$ | [1,4]dioxan-2-ylmethoxy | I | |
| 5-224 | CF$_3$ | F | SO$_2$Me | |
| 5-225 | CF$_3$ | F | SO$_2$Et | |
| 5-226 | CF$_3$ | O(CH$_2$)$_2$OMe | SO$_2$Me | |
| 5-227 | CF$_3$ | O(CH$_2$)$_2$OMe | SO$_2$Et | |
| 5-228 | CF$_3$ | O(CH$_2$)$_3$OMe | SO$_2$Me | |
| 5-229 | CF$_3$ | O(CH$_2$)$_3$OMe | SO$_2$Et | |
| 5-230 | CF$_3$ | OCH$_2$CONMe$_2$ | SO$_2$Me | |
| 5-231 | CF$_3$ | OCH$_2$CONMe$_2$ | SO$_2$Et | |
| 5-232 | CF$_3$ | [1,4]dioxan-2-ylmethoxy | SO$_2$Me | |
| 5-233 | CF$_3$ | [1,4]dioxan-2-ylmethoxy | SO$_2$Et | |
| 5-234 | F | SMe | CF$_3$ | |
| 5-235 | F | SOMe | CF$_3$ | |
| 5-236 | Cl | Me | Cl | |
| 5-237 | Cl | OCH$_2$CHCH$_2$ | Cl | |
| 5-238 | Cl | OCH$_2$CHF$_2$ | Cl | |
| 5-239 | Cl | O(CH$_2$)$_2$OMe | Cl | |
| 5-240 | Cl | OCH$_2$CONMe$_2$ | Cl | |
| 5-241 | Cl | O(CH$_2$)-5-pyrrolidin-2-one | Cl | |
| 5-242 | Cl | SMe | Cl | |
| 5-243 | Cl | SOMe | Cl | |
| 5-244 | Cl | SO$_2$Me | Cl | |
| 5-245 | Cl | F | SMe | |
| 5-246 | Cl | Cl | SO$_2$Me | |
| 5-247 | Cl | COOMe | SO$_2$Me | |
| 5-248 | Cl | CONMe$_2$ | SO$_2$Me | |
| 5-249 | Cl | CONMe(OMe) | SO$_2$Me | |
| 5-250 | Cl | CH$_2$OMe | SO$_2$Me | |
| 5-251 | Cl | CH$_2$OMe | SO$_2$Et | |
| 5-252 | Cl | CH$_2$OEt | SO$_2$Me | |
| 5-253 | Cl | CH$_2$OEt | SO$_2$Et | |
| 5-254 | Cl | CH$_2$OCH$_2$CHF$_2$ | SO$_2$Me | |
| 5-255 | Cl | CH$_2$OCH$_2$CF$_3$ | SO$_2$Me | |
| 5-256 | Cl | CH$_2$OCH$_2$CF$_3$ | SO$_2$Et | |
| 5-257 | Cl | CH$_2$OCH$_2$CF$_2$CHF$_2$ | SO$_2$Me | |

TABLE 5-continued

Compounds of the general formula (I) in which A represents CY, V represents hydrogen, W represents fluorine and R represents CH₂OMe

| No. | X | Y | Z | Physical data ($^1$H-NMR, DMSO-$d_6$, 400 MHz) |
|---|---|---|---|---|
| 5-258 | Cl | CH₂O-c-pentyl | SO₂Me | |
| 5-259 | Cl | CH₂PO(OMe)₂ | SO₂Me | |
| 5-260 | Cl | 4,5-dihydro-1,2-oxazol-3-yl | SMe | |
| 5-261 | Cl | 4,5-dihydro-1,2-oxazol-3-yl | SO₂Me | |
| 5-262 | Cl | 4,5-dihydro-1,2-oxazol-3-yl | SO₂Et | |
| 5-263 | Cl | 5-cyanomethyl-4,5-dihydro-1,2-oxazol-3-yl | SO₂Me | |
| 5-264 | Cl | 5-cyanomethyl-4,5-dihydro-1,2-oxazol-3-yl | SO₂Et | |
| 5-265 | Cl | 5-(methoxymethyl)-4,5-dihydro-1,2-oxazol-3-yl | SO₂Et | |
| 5-266 | Cl | 5-(methoxymethyl)-5-methyl-4,5-dihydro-1,2-oxazol-3-yl | SO₂Et | |
| 5-267 | Cl | CH₂O-tetrahydrofuran-3-yl | SO₂Me | |
| 5-268 | Cl | CH₂O-tetrahydrofuran-3-yl | SO₂Et | |
| 5-269 | Cl | CH₂OCH₂-tetrahydrofuran-2-yl | SO₂Me | |
| 5-270 | Cl | CH₂OCH₂-tetrahydrofuran-2-yl | SO₂Et | |
| 5-271 | Cl | CH₂OCH₂-tetrahydrofuran-3-yl | SO₂Me | |
| 5-272 | Cl | CH₂OCH₂-tetrahydrofuran-3-yl | SO₂Et | |
| 5-273 | Cl | OMe | SO₂Me | |
| 5-274 | Cl | OMe | SO₂Et | |
| 5-275 | Cl | OEt | SO₂Me | |
| 5-276 | Cl | OEt | SO₂Et | |
| 5-277 | Cl | OiPr | SO₂Me | |
| 5-278 | Cl | OiPr | SO₂Et | |
| 5-279 | Cl | O(CH₂)₂OMe | SO₂Me | |
| 5-280 | Cl | O(CH₂)₄OMe | SO₂Me | |
| 5-281 | Cl | O(CH₂)₄OMe | SO₂Et | |
| 5-282 | Cl | O(CH₂)₃OMe | SO₂Me | |
| 5-283 | Cl | O(CH₂)₃OMe | SO₂Et | |
| 5-284 | Cl | O(CH₂)₂OMe | SO₂Me | |
| 5-285 | Cl | O(CH₂)₂OMe | SO₂Et | |
| 5-286 | Cl | [1,4]dioxan-2-ylmethoxy | SO₂Me | |
| 5-287 | Cl | [1,4]dioxan-2-ylmethoxy | SO₂Et | |
| 5-288 | Cl | OCH₂(CO)NMe₂ | SO₂Me | |
| 5-289 | Cl | OCH₂(CO)NMe₂ | SO₂Et | |
| 5-290 | Cl | SMe | SO₂Me | |
| 5-291 | Cl | SOMe | SO₂Me | |
| 5-292 | Br | OMe | Br | |
| 5-293 | Br | O(CH₂)₂OMe | Br | |
| 5-294 | Br | O(CH₂)₂OMe | SO₂Me | |
| 5-295 | Br | O(CH₂)₂OMe | SO₂Et | |
| 5-296 | Br | O(CH₂)₃OMe | SO₂Me | |
| 5-297 | Br | O(CH₂)₃OMe | SO₂Et | |
| 5-298 | Br | O(CH₂)₄OMe | SO₂Me | |
| 5-299 | Br | O(CH₂)₄OMe | SO₂Et | |
| 5-300 | Br | [1,4]dioxan-2-ylmethoxy | SO₂Me | |
| 5-301 | Br | [1,4]dioxan-2-ylmethoxy | SO₂Et | |
| 5-302 | I | O(CH₂)₂OMe | SO₂Me | |
| 5-303 | I | O(CH₂)₂OMe | SO₂Et | |
| 5-304 | I | O(CH₂)₃OMe | SO₂Me | |
| 5-305 | I | O(CH₂)₃OMe | SO₂Et | |
| 5-306 | I | O(CH₂)₄OMe | SO₂Me | |
| 5-307 | I | O(CH₂)₄OMe | SO₂Et | |
| 5-308 | I | [1,4]dioxan-2-ylmethoxy | SO₂Me | |
| 5-309 | I | [1,4]dioxan-2-ylmethoxy | SO₂Et | |
| 5-310 | OMe | SMe | CF₃ | |
| 5-311 | OMe | SOMe | CF₃ | |
| 5-312 | OMe | SO₂Me | CF₃ | |
| 5-313 | OMe | SOEt | CF₃ | |

TABLE 5-continued

Compounds of the general formula (I) in which A represents CY, V represents hydrogen, W represents fluorine and R represents CH$_2$OMe

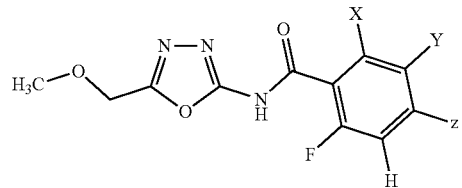

| No. | X | Y | Z | Physical data ($^1$H-NMR, DMSO-d$_6$, 400 MHz) |
|---|---|---|---|---|
| 5-314 | OMe | SO$_2$Et | CF$_3$ | |
| 5-315 | OMe | S(CH$_2$)$_2$OMe | CF$_3$ | |
| 5-316 | OMe | SO(CH$_2$)$_2$OMe | CF$_3$ | |
| 5-317 | OMe | SO$_2$(CH$_2$)$_2$OMe | CF$_3$ | |
| 5-318 | OMe | SMe | Cl | |
| 5-319 | OMe | SOMe | Cl | |
| 5-320 | OMe | SO$_2$Me | Cl | |
| 5-321 | OMe | SEt | Cl | |
| 5-322 | OMe | SOEt | Cl | |
| 5-323 | OMe | SO2Et | Cl | |
| 5-324 | OMe | S(CH$_2$)$_2$OMe | Cl | |
| 5-325 | OMe | SO(CH$_2$)$_2$OMe | Cl | |
| 5-326 | OMe | SO$_2$(CH$_2$)$_2$OMe | Cl | |
| 5-327 | OMe | H | SO$_2$Me | |
| 5-328 | OCH$_2$-c-Pr | SMe | CF$_3$ | |
| 5-329 | OCH$_2$-c-Pr | SOMe | CF$_3$ | |
| 5-330 | OCH$_2$-c-Pr | SO$_2$Me | CF$_3$ | |
| 5-331 | OCH$_2$-c-Pr | SEt | CF$_3$ | |
| 5-332 | OCH$_2$-c-Pr | SOEt | CF$_3$ | |
| 5-333 | OCH$_2$-c-Pr | SO$_2$Et | CF$_3$ | |
| 5-334 | OCH$_2$-c-Pr | S(CH$_2$)$_2$OMe | CF$_3$ | |
| 5-335 | OCH$_2$-c-Pr | SO(CH$_2$)$_2$OMe | CF$_3$ | |
| 5-336 | OCH$_2$-c-Pr | SO$_2$(CH$_2$)$_2$OMe | CF$_3$ | |
| 5-337 | OCH$_2$-c-Pr | SMe | Cl | |
| 5-338 | OCH$_2$-c-Pr | SOMe | Cl | |
| 5-339 | OCH$_2$-c-Pr | SO$_2$Me | Cl | |
| 5-340 | OCH$_2$-c-Pr | SEt | Cl | |
| 5-341 | OCH$_2$-c-Pr | SOEt | Cl | |
| 5-342 | OCH$_2$-c-Pr | SO$_2$Et | Cl | |
| 5-343 | OCH$_2$-c-Pr | S(CH$_2$)$_2$OMe | Cl | |
| 5-344 | OCH$_2$-c-Pr | SO(CH$_2$)$_2$OMe | Cl | |
| 5-345 | OCH$_2$-c-Pr | SO$_2$(CH$_2$)$_2$OMe | Cl | |
| 5-346 | OCH$_2$-c-Pr | SMe | SO$_2$Me | |
| 5-347 | OCH$_2$-c-Pr | SOMe | SO$_2$Me | |
| 5-348 | OCH$_2$-c-Pr | SO$_2$Me | SO$_2$Me | |
| 5-349 | OCH$_2$-c-Pr | SEt | SO$_2$Me | |
| 5-350 | OCH$_2$-c-Pr | SOEt | SO$_2$Me | |
| 5-351 | OCH$_2$-c-Pr | SO$_2$Et | SO$_2$Me | |
| 5-352 | OCH$_2$-c-Pr | S(CH$_2$)$_2$OMe | SO$_2$Me | |
| 5-353 | OCH$_2$-c-Pr | SO(CH$_2$)$_2$OMe | SO$_2$Me | |
| 5-354 | OCH$_2$-c-Pr | SO$_2$(CH$_2$)$_2$OMe | SO$_2$Me | |
| 5-355 | SO$_2$Me | F | CF$_3$ | |
| 5-356 | SO$_2$Me | NH$_2$ | CF$_3$ | |
| 5-357 | SO$_2$Me | NHEt | Cl | |
| 5-358 | SMe | SEt | F | |
| 5-359 | SMe | SMe | F | |
| 5-360 | F | SO$_2$Me | CF$_3$ | |
| 5-361 | Cl | SMe | CF$_3$ | |
| 5-362 | Cl | S(O)Me | CF$_3$ | |
| 5-363 | Cl | SO$_2$Me | CF$_3$ | |
| 5-364 | Cl | SO$_2$Me | SO$_2$Me | |

TABLE 6

Compounds of the general formula (I) in which A represents CY, V represents hydrogen, W represents fluorine

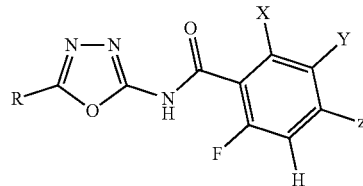

| No. | R | X | Y | Z | Physical data |
|---|---|---|---|---|---|
| 6-1 | c-Pr | NO$_2$ | H | SO$_2$Me | |
| 6-2 | c-Pr | Cl | H | SO$_2$Me | |
| 6-3 | c-Pr | SO$_2$Me | H | CF$_3$ | |
| 6-4 | c-Pr | NO$_2$ | H | OMe | |
| 6-5 | c-Pr | NO$_2$ | H | Br | |
| 6-6 | c-Pr | NO$_2$ | H | Cl | |
| 6-7 | c-Pr | NO$_2$ | H | CF$_3$ | |
| 6-8 | c-Pr | NO$_2$ | H | NO$_2$ | |
| 6-9 | c-Pr | NO$_2$ | H | Me | |
| 6-10 | c-Pr | NO$_2$ | H | F | |
| 6-11 | c-Pr | OMe | H | SO$_2$Me | |
| 6-12 | c-Pr | CF$_3$ | H | NO$_2$ | |
| 6-13 | c-Pr | CF$_3$ | H | Cl | |
| 6-14 | c-Pr | CH$_2$SO$_2$Me | H | Br | |
| 6-15 | c-Pr | Cl | CH$_2$OCH$_2$CF$_3$ | SO$_2$Me | |
| 6-16 | c-Pr | Cl | CH$_2$OCH$_2$CF$_3$ | SMe | |
| 6-17 | c-Pr | Cl | 5-cyanomethyl-4,5-dihydro-1,2-oxazol-3-yl | SO$_2$Et | |
| 6-18 | c-Pr | Cl | 4,5-dihydro-1,2-oxazol-3-yl | SO$_2$Et | |
| 6-19 | c-Pr | Cl | CH$_2$OCH$_2$-tetrahydrofuran-2-yl | SO$_2$Me | |
| 6-20 | c-Pr | Cl | SMe | Cl | |
| 6-21 | c-Pr | Cl | SMe | SO$_2$Me | |
| 6-22 | c-Pr | Cl | Me | SO$_2$Et | |
| 6-23 | c-Pr | Cl | O(CH$_2$)$_2$OMe | Cl | |
| 6-24 | c-Pr | Cl | OCH$_2$-cyclopropyl | Cl | |
| 6-25 | c-Pr | Cl | OMe | Cl | |
| 6-26 | c-Pr | Cl | NHAc | Cl | |
| 6-27 | c-Pr | Cl | OCH$_2$C(O)NMe$_2$ | Cl | |
| 6-28 | c-Pr | Cl | Cl | SO$_2$Me | |
| 6-29 | c-Pr | Cl | pyrazol-1-yl | SO$_2$Me | |
| 6-30 | c-Pr | Cl | 4-methoxypyrazol-1-yl | SO$_2$Me | |
| 6-31 | c-Pr | Cl | 1,2,3-triazol-1-yl | SO$_2$Me | |
| 6-32 | c-Pr | Cl | 1,2,3-triazol-2-yl | SO$_2$Me | |
| 6-33 | c-Pr | Cl | F | SO$_2$Me | |
| 6-34 | c-Pr | Me | SO$_2$Me | SO$_2$Me | |
| 6-35 | c-Pr | Me | SO$_2$Me | CF$_3$ | |
| 6-36 | c-Pr | Me | NMe$_2$ | SO$_2$Me | |
| 6-37 | c-Pr | Me | S(O)Me | CF$_3$ | |
| 6-38 | c-Pr | Me | SMe | CF$_3$ | |
| 6-39 | c-Pr | Me | SO$_2$CH$_2$CH$_2$OMe | CF$_3$ | |
| 6-40 | c-Pr | Me | pyrazol-1-yl | SO$_2$Me | |
| 6-41 | c-Pr | Me | 4-methoxypyrazol-1-yl | SO$_2$Me | |
| 6-42 | c-Pr | Me | 1,2,3-triazol-1-yl | SO$_2$Me | |
| 6-43 | c-Pr | Me | 1,2,3-triazol-2-yl | SO$_2$Me | |
| 6-44 | c-Pr | Me | Cl | SO$_2$Me | |
| 6-45 | c-Pr | Me | Me | SO$_2$Me | |
| 6-46 | c-Pr | Me | F | Cl | |
| 6-47 | c-Pr | Me | SO$_2$Me | Cl | |
| 6-48 | c-Pr | Me | NMe$_2$ | SO$_2$Me | |
| 6-49 | c-Pr | Me | NH(CH$_2$)$_2$OMe | SO$_2$Me | |
| 6-50 | c-Pr | CF$_3$ | F | SO$_2$CH$_3$ | |
| 6-51 | c-Pr | CF$_3$ | SMe | SO$_2$CH$_3$ | |
| 6-52 | c-Pr | CF$_3$ | SEt | SO$_2$CH$_3$ | |
| 6-53 | c-Pr | CF$_3$ | S(O)Et | SO$_2$CH$_3$ | |
| 6-54 | c-Pr | CF$_3$ | SO$_2$CH$_3$ | SO$_2$CH$_3$ | |
| 6-55 | c-Pr | CF$_3$ | OCH$_2$CH$_2$OMe | SO$_2$CH$_3$ | |
| 6-56 | c-Pr | CF$_3$ | OCH$_2$(CO)NMe$_2$ | SO2Me | |
| 6-57 | c-Pr | CF$_3$ | CH$_2$O-tetrahydrofuran-2-yl | SO$_2$Et | |
| 6-58 | c-Pr | SMe | SMe | F | |
| 6-59 | c-Pr | SMe | SEt | F | |
| 6-60 | c-Pr | SO$_2$CH$_3$ | F | Cl | |
| 6-61 | c-Pr | F | S(O)Me | CF$_3$ | |

TABLE 6-continued

Compounds of the general formula (I) in which A represents CY, V represents hydrogen, W represents fluorine

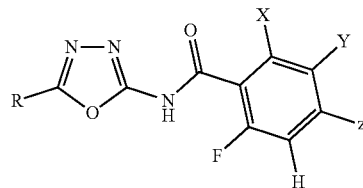

| No. | R | X | Y | Z | Physical data |
|---|---|---|---|---|---|
| 6-62 | c-Pr | F | SMe | $CF_3$ | |
| 6-63 | $CO_2Et$ | $NO_2$ | H | $SO_2Me$ | |
| 6-64 | $CO_2Et$ | Cl | H | $SO_2Me$ | |
| 6-65 | $CO_2Et$ | $SO_2Me$ | H | $CF_3$ | |
| 6-66 | $CO_2Et$ | $NO_2$ | H | OMe | |
| 6-67 | $CO_2Et$ | $NO_2$ | H | Br | |
| 6-68 | $CO_2Et$ | $NO_2$ | H | $CF_3$ | |
| 6-69 | $CO_2Et$ | $NO_2$ | H | $NO_2$ | |
| 6-70 | $CO_2Et$ | $NO_2$ | H | Cl | |
| 6-71 | $CO_2Et$ | $NO_2$ | H | Me | |
| 6-72 | $CO_2Et$ | $NO_2$ | H | F | |
| 6-73 | $CO_2Et$ | OMe | H | $SO_2Me$ | |
| 6-74 | $CO_2Et$ | $CF_3$ | H | $NO_2$ | |
| 6-75 | $CO_2Et$ | $CH_2SO_2Me$ | H | Br | |
| 6-76 | $CO_2Et$ | Cl | $CH_2OCH_2CF_3$ | $SO_2Me$ | |
| 6-77 | $CO_2Et$ | Cl | $CH_2OCH_2CF_3$ | SMe | |
| 6-78 | $CO_2Et$ | Cl | 5-cyanomethyl-4,5-dihydro-1,2-oxazol-3-yl | $SO_2Et$ | |
| 6-79 | $CO_2Et$ | Cl | 4,5-dihydro-1,2-oxazol-3-yl | $SO_2Et$ | |
| 6-80 | $CO_2Et$ | Cl | $CH_2OCH_2$-tetrahydrofuran-2-yl | $SO_2Me$ | |
| 6-81 | $CO_2Et$ | Cl | SMe | Cl | |
| 6-82 | $CO_2Et$ | Cl | SMe | $SO_2Me$ | |
| 6-83 | $CO_2Et$ | Cl | Me | $SO_2Et$ | |
| 6-84 | $CO_2Et$ | Cl | $O(CH_2)_2OMe$ | Cl | |
| 6-85 | $CO_2Et$ | Cl | $OCH_2$-cyclopropyl | Cl | |
| 6-86 | $CO_2Et$ | Cl | OMe | Cl | |
| 6-87 | $CO_2Et$ | Cl | NHAc | Cl | |
| 6-88 | $CO_2Et$ | Cl | $OCH_2C(O)NMe_2$ | Cl | |
| 6-89 | $CO_2Et$ | Cl | Cl | $SO_2Me$ | |
| 6-90 | $CO_2Et$ | Cl | pyrazol-1-yl | $SO_2Me$ | |
| 6-91 | $CO_2Et$ | Cl | 4-methoxypyrazol-1-yl | $SO_2Me$ | |
| 6-92 | $CO_2Et$ | Cl | 1,2,3-triazol-1-yl | $SO_2Me$ | |
| 6-93 | $CO_2Et$ | Cl | 1,2,3-triazol-2-yl | $SO_2Me$ | |
| 6-94 | $CO_2Et$ | Cl | F | $SO_2Me$ | |
| 6-95 | $CO_2Et$ | Me | $SO_2Me$ | $SO_2Me$ | |
| 6-96 | $CO_2Et$ | Me | $SO_2Me$ | $CF_3$ | |
| 6-97 | $CO_2Et$ | Me | $NMe_2$ | $SO_2Me$ | |
| 6-98 | $CO_2Et$ | Me | S(O)Me | $CF_3$ | |
| 6-99 | $CO_2Et$ | Me | SMe | $CF_3$ | |
| 6-100 | $CO_2Et$ | Me | $SO_2CH_2CH_2OMe$ | $CF_3$ | |
| 6-101 | $CO_2Et$ | Me | pyrazol-1-yl | $SO_2Me$ | |
| 6-102 | $CO_2Et$ | Me | 4-methoxypyrazol-1-yl | $SO_2Me$ | |
| 6-103 | $CO_2Et$ | Me | 1,2,3-triazol-1-yl | $SO_2Me$ | |
| 6-104 | $CO_2Et$ | Me | 1,2,3-triazol-2-yl | $SO_2Me$ | |
| 6-105 | $CO_2Et$ | Me | Cl | $SO_2Me$ | |
| 6-106 | $CO_2Et$ | Me | Me | $SO_2Me$ | |
| 6-107 | $CO_2Et$ | Me | Me | SMe | |
| 6-108 | $CO_2Et$ | Me | $SO_2Me$ | Cl | |
| 6-109 | $CO_2Et$ | Me | $NMe_2$ | $SO_2Me$ | |
| 6-110 | $CO_2Et$ | Me | $NH(CH_2)_2OMe$ | $SO_2Me$ | |
| 6-111 | $CO_2Et$ | $CF_3$ | F | $SO_2CH_3$ | |
| 6-112 | $CO_2Et$ | $CF_3$ | SMe | $SO_2CH_3$ | |
| 6-113 | $CO_2Et$ | $CF_3$ | SEt | $SO_2CH_3$ | |
| 6-114 | $CO_2Et$ | $CF_3$ | S(O)Et | $SO_2CH_3$ | |
| 6-115 | $CO_2Et$ | $CF_3$ | $SO_2CH_3$ | $SO_2CH_3$ | |
| 6-116 | $CO_2Et$ | $CF_3$ | $OCH_2CH_2OMe$ | $SO_2CH_3$ | |
| 6-117 | $CO_2Et$ | $CF_3$ | $OCH_2(CO)NMe_2$ | $SO2Me$ | |
| 6-118 | $CO_2Et$ | $CF_3$ | $CH_2O$-tetrahydrofuran-2-yl | $SO_2Et$ | |
| 6-119 | $CO_2Et$ | SMe | SMe | F | |
| 6-120 | $CO_2Et$ | SMe | SEt | F | |
| 6-121 | $CO_2Et$ | $SO_2CH_3$ | F | Cl | |
| 6-122 | $CO_2Et$ | F | S(O)Me | $CF_3$ | |
| 6-123 | $CO_2Et$ | F | SMe | $CF_3$ | |

TABLE 6-continued

Compounds of the general formula (I) in which A represents CY, V represents hydrogen, W represents fluorine

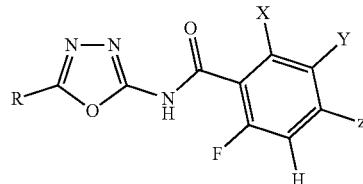

| No. | R | X | Y | Z | Physical data |
|---|---|---|---|---|---|
| 6-124 | CO$_2$Me | NO$_2$ | H | SO$_2$Me | |
| 6-125 | CO$_2$Me | Cl | H | SO$_2$Me | |
| 6-126 | CO$_2$Me | SO$_2$Me | H | CF$_3$ | |
| 6-127 | CO$_2$Me | NO$_2$ | H | OMe | |
| 6-128 | CO$_2$Me | NO$_2$ | H | Br | |
| 6-129 | CO$_2$Me | NO$_2$ | H | CF$_3$ | |
| 6-130 | CO$_2$Me | NO$_2$ | H | NO$_2$ | |
| 6-131 | CO$_2$Me | NO$_2$ | H | Cl | |
| 6-132 | CO$_2$Me | NO$_2$ | H | Me | |
| 6-133 | CO$_2$Me | NO$_2$ | H | F | |
| 6-134 | CO$_2$Me | OMe | H | SO$_2$Me | |
| 6-135 | CO$_2$Me | CF$_3$ | H | NO$_2$ | |
| 6-136 | CO$_2$Me | CH$_2$SO$_2$Me | H | Br | |
| 6-137 | CO$_2$Me | Cl | CH$_2$OCH$_2$CF$_3$ | SO$_2$Me | |
| 6-138 | CO$_2$Me | Cl | CH$_2$OCH$_2$CF$_3$ | SMe | |
| 6-139 | CO$_2$Me | Cl | 5-cyanomethyl-4,5-dihydro-1,2-oxazol-3-yl | SO$_2$Et | |
| 6-140 | CO$_2$Me | Cl | 4,5-dihydro-1,2-oxazol-3-yl | SO$_2$Et | |
| 6-141 | CO$_2$Me | Cl | CH$_2$OCH$_2$-tetrahydrofuran-2-yl | SO$_2$Me | |
| 6-142 | CO$_2$Me | Cl | SMe | Cl | |
| 6-143 | CO$_2$Me | Cl | SMe | SO$_2$Me | |
| 6-144 | CO$_2$Me | Cl | Me | SO$_2$Et | |
| 6-145 | CO$_2$Me | Cl | O(CH$_2$)$_2$OMe | Cl | |
| 6-146 | CO$_2$Me | Cl | OCH$_2$-cyclopropyl | Cl | |
| 6-147 | CO$_2$Me | Cl | OMe | Cl | |
| 6-148 | CO$_2$Me | Cl | NHAc | Cl | |
| 6-149 | CO$_2$Me | Cl | OCH$_2$C(O)NMe$_2$ | Cl | |
| 6-150 | CO$_2$Me | Cl | Cl | SO$_2$Me | |
| 6-151 | CO$_2$Me | Cl | pyrazol-1-yl | SO$_2$Me | |
| 6-152 | CO$_2$Me | Cl | 4-methoxypyrazol-1-yl | SO$_2$Me | |
| 6-153 | CO$_2$Me | Cl | 1,2,3-triazol-1-yl | SO$_2$Me | |
| 6-154 | CO$_2$Me | Cl | 1,2,3-triazol-2-yl | SO$_2$Me | |
| 6-155 | CO$_2$Me | Cl | F | SO$_2$Me | |
| 6-156 | CO$_2$Me | Me | SO$_2$Me | SO$_2$Me | |
| 6-157 | CO$_2$Me | Me | SO$_2$Me | CF$_3$ | |
| 6-158 | CO$_2$Me | Me | NMe$_2$ | SO$_2$Me | |
| 6-159 | CO$_2$Me | Me | S(O)Me | CF$_3$ | |
| 6-160 | CO$_2$Me | Me | SMe | CF$_3$ | |
| 6-161 | CO$_2$Me | Me | SO$_2$CH$_2$CH$_2$OMe | CF$_3$ | |
| 6-162 | CO$_2$Me | Me | pyrazol-1-yl | SO$_2$Me | |
| 6-163 | CO$_2$Me | Me | 4-methoxypyrazol-1-yl | SO$_2$Me | |
| 6-164 | CO$_2$Me | Me | 1,2,3-triazol-1-yl | SO$_2$Me | |
| 6-165 | CO$_2$Me | Me | 1,2,3-triazol-2-yl | SO$_2$Me | |
| 6-166 | CO$_2$Me | Me | Cl | SO$_2$Me | |
| 6-167 | CO$_2$Me | Me | Me | SO$_2$Me | |
| 6-168 | CO$_2$Me | Me | Me | SMe | |
| 6-169 | CO$_2$Me | Me | SO$_2$Me | Cl | |
| 6-170 | CO$_2$Me | Me | NMe$_2$ | SO$_2$Me | |
| 6-171 | CO$_2$Me | Me | NH(CH$_2$)$_2$OMe | SO$_2$Me | |
| 6-172 | CO$_2$Me | CF$_3$ | F | SO$_2$CH$_3$ | |
| 6-173 | CO$_2$Me | CF$_3$ | SMe | SO$_2$CH$_3$ | |
| 6-174 | CO$_2$Me | CF$_3$ | SEt | SO$_2$CH$_3$ | |
| 6-175 | CO$_2$Me | CF$_3$ | S(O)Et | SO$_2$CH$_3$ | |
| 6-176 | CO$_2$Me | CF$_3$ | SO$_2$CH$_3$ | SO$_2$CH$_3$ | |
| 6-177 | CO$_2$Me | CF$_3$ | OCH$_2$CH$_2$OMe | SO$_2$CH$_3$ | |
| 6-178 | CO$_2$Me | CF$_3$ | OCH$_2$(CO)NMe$_2$ | SO2Me | |
| 6-179 | CO$_2$Me | CF$_3$ | CH$_2$O-tetrahydrofuran-2-yl | SO$_2$Et | |
| 6-180 | CO$_2$Me | SMe | SMe | F | |
| 6-181 | CO$_2$Me | SMe | SEt | F | |
| 6-182 | CO$_2$Me | SO$_2$CH$_3$ | F | Cl | |
| 6-183 | CO$_2$Me | F | S(O)Me | CF$_3$ | |
| 6-184 | CO$_2$Me | F | SMe | CF$_3$ | |
| 6-185 | benzyl | NO$_2$ | H | SO$_2$Me | |

TABLE 6-continued

Compounds of the general formula (I) in which A represents CY, V represents hydrogen, W represents fluorine

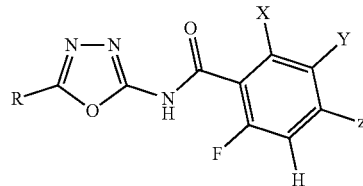

| No. | R | X | Y | Z | Physical data |
|---|---|---|---|---|---|
| 6-186 | benzyl | Cl | H | $SO_2Me$ | |
| 6-187 | benzyl | $SO_2Me$ | H | $CF_3$ | |
| 6-188 | benzyl | $NO_2$ | H | OMe | |
| 6-189 | benzyl | $NO_2$ | H | Br | |
| 6-190 | benzyl | $NO_2$ | H | $CF_3$ | |
| 6-191 | benzyl | $NO_2$ | H | $NO_2$ | |
| 6-192 | benzyl | $NO_2$ | H | Cl | |
| 6-193 | benzyl | $NO_2$ | H | Me | |
| 6-194 | benzyl | $NO_2$ | H | F | |
| 6-195 | benzyl | OMe | H | $SO_2Me$ | |
| 6-196 | benzyl | $CF_3$ | H | $NO_2$ | |
| 6-197 | benzyl | $CH_2SO_2Me$ | H | Br | |
| 6-198 | benzyl | Cl | $CH_2OCH_2CF_3$ | $SO_2Me$ | |
| 6-199 | benzyl | Cl | $CH_2OCH_2CF_3$ | SMe | |
| 6-200 | benzyl | Cl | 5-cyanomethyl-4,5-dihydro-1,2-oxazol-3-yl | $SO_2Et$ | |
| 6-201 | benzyl | Cl | 4,5-dihydro-1,2-oxazol-3-yl | $SO_2Et$ | |
| 6-202 | benzyl | Cl | $CH_2OCH_2$-tetrahydrofuran-2-yl | $SO_2Me$ | |
| 6-203 | benzyl | Cl | SMe | Cl | |
| 6-204 | benzyl | Cl | SMe | $SO_2Me$ | |
| 6-205 | benzyl | Cl | Me | $SO_2Et$ | |
| 6-206 | benzyl | Cl | $O(CH_2)_2OMe$ | Cl | |
| 6-207 | benzyl | Cl | $OCH_2$-cyclopropyl | Cl | |
| 6-208 | benzyl | Cl | OMe | Cl | |
| 6-209 | benzyl | Cl | NHAc | Cl | |
| 6-210 | benzyl | Cl | $OCH_2C(O)NMe_2$ | Cl | |
| 6-211 | benzyl | Cl | Cl | $SO_2Me$ | |
| 6-212 | benzyl | Cl | pyrazol-1-yl | $SO_2Me$ | |
| 6-213 | benzyl | Cl | 4-methoxypyrazol-1-yl | $SO_2Me$ | |
| 6-214 | benzyl | Cl | 1,2,3-triazol-1-yl | $SO_2Me$ | |
| 6-215 | benzyl | Cl | 1,2,3-triazol-2-yl | $SO_2Me$ | |
| 6-216 | benzyl | Cl | F | $SO_2Me$ | |
| 6-217 | benzyl | Me | $SO_2Me$ | $SO_2Me$ | |
| 6-218 | benzyl | Me | $SO_2Me$ | $CF_3$ | |
| 6-219 | benzyl | Me | $NMe_2$ | $SO_2Me$ | |
| 6-220 | benzyl | Me | $S(O)Me$ | $CF_3$ | |
| 6-221 | benzyl | Me | SMe | $CF_3$ | |
| 6-222 | benzyl | Me | $SO_2CH_2CH_2OMe$ | $CF_3$ | |
| 6-223 | benzyl | Me | pyrazol-1-yl | $SO_2Me$ | |
| 6-224 | benzyl | Me | 4-methoxypyrazol-1-yl | $SO_2Me$ | |
| 6-225 | benzyl | Me | 1,2,3-triazol-1-yl | $SO_2Me$ | |
| 6-226 | benzyl | Me | 1,2,3-triazol-2-yl | $SO_2Me$ | |
| 6-227 | benzyl | Me | Cl | $SO_2Me$ | |
| 6-228 | benzyl | Me | Me | $SO_2Me$ | |
| 6-229 | benzyl | Me | Me | SMe | |
| 6-230 | benzyl | Me | $SO_2Me$ | Cl | |
| 6-231 | benzyl | Me | $NMe_2$ | $SO_2Me$ | |
| 6-232 | benzyl | Me | $NH(CH_2)_2OMe$ | $SO_2Me$ | |
| 6-233 | benzyl | $CF_3$ | F | $SO_2CH_3$ | |
| 6-234 | benzyl | $CF_3$ | SMe | $SO_2CH_3$ | |
| 6-235 | benzyl | $CF_3$ | SEt | $SO_2CH_3$ | |
| 6-236 | benzyl | $CF_3$ | $S(O)Et$ | $SO_2CH_3$ | |
| 6-237 | benzyl | $CF_3$ | $SO_2CH_3$ | $SO_2CH_3$ | |
| 6-238 | benzyl | $CF_3$ | $OCH_2CH_2OMe$ | $SO_2CH_3$ | |
| 6-239 | benzyl | $CF_3$ | $OCH_2(CO)NMe_2$ | SO2Me | |
| 6-240 | benzyl | $CF_3$ | $CH_2O$-tetrahydrofuran-2-yl | $SO_2Et$ | |
| 6-241 | benzyl | SMe | SMe | F | |
| 6-242 | benzyl | SMe | SEt | F | |
| 6-243 | benzyl | $SO_2CH_3$ | F | Cl | |
| 6-244 | benzyl | F | $S(O)Me$ | $CF_3$ | |
| 6-245 | benzyl | F | SMe | $CF_3$ | |
| 6-246 | phenyl | $NO_2$ | H | $SO_2Me$ | |

TABLE 6-continued

Compounds of the general formula (I) in which A represents CY, V represents hydrogen, W represents fluorine

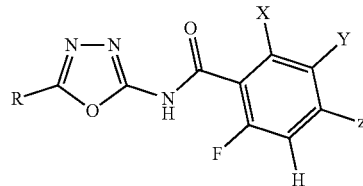

| No. | R | X | Y | Z | Physical data |
|---|---|---|---|---|---|
| 6-247 | phenyl | Cl | H | SO$_2$Me | |
| 6-248 | phenyl | SO$_2$Me | H | CF$_3$ | |
| 6-249 | phenyl | NO$_2$ | H | OMe | |
| 6-250 | phenyl | NO$_2$ | H | Br | |
| 6-251 | phenyl | NO$_2$ | H | CF$_3$ | |
| 6-252 | phenyl | NO$_2$ | H | NO$_2$ | |
| 6-253 | phenyl | NO$_2$ | H | Cl | |
| 6-254 | phenyl | NO$_2$ | H | Me | |
| 6-255 | phenyl | NO$_2$ | H | F | |
| 6-256 | phenyl | OMe | H | SO$_2$Me | |
| 6-257 | phenyl | CF$_3$ | H | NO$_2$ | |
| 6-258 | phenyl | CH$_2$SO$_2$Me | H | Br | |
| 6-259 | phenyl | Cl | CH$_2$OCH$_2$CF$_3$ | SO$_2$Me | |
| 6-260 | phenyl | Cl | CH$_2$OCH$_2$CF$_3$ | SMe | |
| 6-261 | phenyl | Cl | 5-cyanomethyl-4,5-dihydro-1,2-oxazol-3-yl | SO$_2$Et | |
| 6-262 | phenyl | Cl | 4,5-dihydro-1,2-oxazol-3-yl | SO$_2$Et | |
| 6-263 | phenyl | Cl | CH$_2$OCH$_2$-tetrahydrofuran-2-yl | SO$_2$Me | |
| 6-264 | phenyl | Cl | SMe | Cl | |
| 6-265 | phenyl | Cl | SMe | SO$_2$Me | |
| 6-266 | phenyl | Cl | Me | SO$_2$Et | |
| 6-267 | phenyl | Cl | O(CH$_2$)$_2$OMe | Cl | |
| 6-268 | phenyl | Cl | OCH$_2$-cyclopropyl | Cl | |
| 6-269 | phenyl | Cl | OMe | Cl | |
| 6-270 | phenyl | Cl | NHAc | Cl | |
| 6-271 | phenyl | Cl | OCH$_2$C(O)NMe$_2$ | Cl | |
| 6-272 | phenyl | Cl | Cl | SO$_2$Me | |
| 6-273 | phenyl | Cl | pyrazol-1-yl | SO$_2$Me | |
| 6-274 | phenyl | Cl | 4-methoxypyrazol-1-yl | SO$_2$Me | |
| 6-275 | phenyl | Cl | 1,2,3-triazol-1-yl | SO$_2$Me | |
| 6-276 | phenyl | Cl | 1,2,3-triazol-2-yl | SO$_2$Me | |
| 6-277 | phenyl | Cl | F | SO$_2$Me | |
| 6-278 | phenyl | Me | SO$_2$Me | SO$_2$Me | |
| 6-279 | phenyl | Me | SO$_2$Me | CF$_3$ | |
| 6-280 | phenyl | Me | NMe$_2$ | SO$_2$Me | |
| 6-281 | phenyl | Me | S(O)Me | CF$_3$ | |
| 6-282 | phenyl | Me | SMe | CF$_3$ | |
| 6-283 | phenyl | Me | SO$_2$CH$_2$CH$_2$OMe | CF$_3$ | |
| 6-284 | phenyl | Me | pyrazol-1-yl | SO$_2$Me | |
| 6-285 | phenyl | Me | 4-methoxypyrazol-1-yl | SO$_2$Me | |
| 6-286 | phenyl | Me | 1,2,3-triazol-1-yl | SO$_2$Me | |
| 6-287 | phenyl | Me | 1,2,3-triazol-2-yl | SO$_2$Me | |
| 6-288 | phenyl | Me | Cl | SO$_2$Me | |
| 6-289 | phenyl | Me | Me | SO$_2$Me | |
| 6-290 | phenyl | Me | Me | SMe | |
| 6-291 | phenyl | Me | SO$_2$Me | Cl | |
| 6-292 | phenyl | Me | NMe$_2$ | SO$_2$Me | |
| 6-293 | phenyl | Me | NH(CH$_2$)$_2$OMe | SO$_2$Me | |
| 6-294 | phenyl | CF$_3$ | F | SO$_2$CH$_3$ | |
| 6-295 | phenyl | CF$_3$ | SMe | SO$_2$CH$_3$ | |
| 6-296 | phenyl | CF$_3$ | SEt | SO$_2$CH$_3$ | |
| 6-297 | phenyl | CF$_3$ | S(O)Et | SO$_2$CH$_3$ | |
| 6-298 | phenyl | CF$_3$ | SO$_2$CH$_3$ | SO$_2$CH$_3$ | |
| 6-299 | phenyl | CF$_3$ | OCH$_2$CH$_2$OMe | SO$_2$CH$_3$ | |
| 6-300 | phenyl | CF$_3$ | OCH$_2$(CO)NMe$_2$ | SO2Me | |
| 6-301 | phenyl | CF$_3$ | CH$_2$O-tetrahydrofuran-2-yl | SO$_2$Et | |
| 6-302 | phenyl | SMe | SMe | F | |
| 6-303 | phenyl | SMe | SEt | F | |
| 6-304 | phenyl | SO$_2$CH$_3$ | F | Cl | |
| 6-305 | phenyl | F | S(O)Me | CF$_3$ | |
| 6-306 | phenyl | F | SMe | CF$_3$ | |
| 6-307 | pyrazin-2-yl | NO$_2$ | H | SO$_2$Me | |
| 6-308 | pyrazin-2-yl | Cl | H | SO$_2$Me | |

TABLE 6-continued

Compounds of the general formula (I) in which A represents CY, V represents hydrogen, W represents fluorine

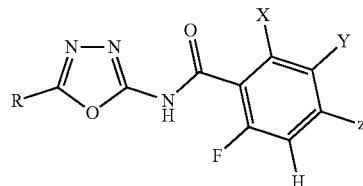

| No. | R | X | Y | Z | Physical data |
|---|---|---|---|---|---|
| 6-309 | pyrazin-2-yl | SO$_2$Me | H | CF$_3$ | |
| 6-310 | pyrazin-2-yl | NO$_2$ | H | OMe | |
| 6-311 | pyrazin-2-yl | NO$_2$ | H | Br | |
| 6-312 | pyrazin-2-yl | NO$_2$ | H | CF$_3$ | |
| 6-313 | pyrazin-2-yl | NO$_2$ | H | NO$_2$ | |
| 6-314 | pyrazin-2-yl | NO$_2$ | H | Cl | |
| 6-315 | pyrazin-2-yl | NO$_2$ | H | Me | |
| 6-316 | pyrazin-2-yl | NO$_2$ | H | F | |
| 6-317 | pyrazin-2-yl | OMe | H | SO$_2$Me | |
| 6-318 | pyrazin-2-yl | CF$_3$ | H | NO$_2$ | |
| 6-319 | pyrazin-2-yl | CH$_2$SO$_2$Me | H | Br | |
| 6-320 | pyrazin-2-yl | Cl | CH$_2$OCH$_2$CF$_3$ | SO$_2$Me | |
| 6-321 | pyrazin-2-yl | Cl | CH$_2$OCH$_2$CF$_3$ | SMe | |
| 6-322 | pyrazin-2-yl | Cl | 5-cyanomethyl-4,5-dihydro-1,2-oxazol-3-yl | SO$_2$Et | |
| 6-323 | pyrazin-2-yl | Cl | 4,5-dihydro-1,2-oxazol-3-yl | SO$_2$Et | |
| 6-324 | pyrazin-2-yl | Cl | CH$_2$OCH$_2$-tetrahydrofuran-2-yl | SO$_2$Me | |
| 6-325 | pyrazin-2-yl | Cl | SMe | Cl | |
| 6-326 | pyrazin-2-yl | Cl | SMe | SO$_2$Me | |
| 6-327 | pyrazin-2-yl | Cl | Me | SO$_2$Et | |
| 6-328 | pyrazin-2-yl | Cl | O(CH$_2$)$_2$OMe | Cl | |
| 6-329 | pyrazin-2-yl | Cl | OCH$_2$-cyclopropyl | Cl | |
| 6-330 | pyrazin-2-yl | Cl | OMe | Cl | |
| 6-331 | pyrazin-2-yl | Cl | NHAc | Cl | |
| 6-332 | pyrazin-2-yl | Cl | OCH$_2$C(O)NMe$_2$ | Cl | |
| 6-333 | pyrazin-2-yl | Cl | Cl | SO$_2$Me | |
| 6-334 | pyrazin-2-yl | Cl | pyrazol-1-yl | SO$_2$Me | |
| 6-335 | pyrazin-2-yl | Cl | 4-methoxypyrazol-1-yl | SO$_2$Me | |
| 6-336 | pyrazin-2-yl | Cl | 1,2,3-triazol-1-yl | SO$_2$Me | |
| 6-337 | pyrazin-2-yl | Cl | 1,2,3-triazol-2-yl | SO$_2$Me | |
| 6-338 | pyrazin-2-yl | Cl | F | SO$_2$Me | |
| 6-339 | pyrazin-2-yl | Me | SO$_2$Me | SO$_2$Me | |
| 6-340 | pyrazin-2-yl | Me | SO$_2$Me | CF$_3$ | |
| 6-341 | pyrazin-2-yl | Me | NMe$_2$ | SO$_2$Me | |
| 6-342 | pyrazin-2-yl | Me | S(O)Me | CF$_3$ | |
| 6-343 | pyrazin-2-yl | Me | SMe | CF$_3$ | |
| 6-344 | pyrazin-2-yl | Me | SO$_2$CH$_2$CH$_2$OMe | CF$_3$ | |
| 6-345 | pyrazin-2-yl | Me | pyrazol-1-yl | SO$_2$Me | |
| 6-346 | pyrazin-2-yl | Me | 4-methoxypyrazol-1-yl | SO$_2$Me | |
| 6-347 | pyrazin-2-yl | Me | 1,2,3-triazol-1-yl | SO$_2$Me | |
| 6-348 | pyrazin-2-yl | Me | 1,2,3-triazol-2-yl | SO$_2$Me | |
| 6-349 | pyrazin-2-yl | Me | Cl | SO$_2$Me | |
| 6-350 | pyrazin-2-yl | Me | Me | SO$_2$Me | |
| 6-351 | pyrazin-2-yl | Me | Me | SMe | |
| 6-352 | pyrazin-2-yl | Me | SO$_2$Me | Cl | |
| 6-353 | pyrazin-2-yl | Me | NMe$_2$ | SO$_2$Me | |
| 6-354 | pyrazin-2-yl | Me | NH(CH$_2$)$_2$OMe | SO$_2$Me | |
| 6-355 | pyrazin-2-yl | CF$_3$ | F | SO$_2$CH$_3$ | |
| 6-356 | pyrazin-2-yl | CF$_3$ | SMe | SO$_2$CH$_3$ | |
| 6-357 | pyrazin-2-yl | CF$_3$ | SEt | SO$_2$CH$_3$ | |
| 6-358 | pyrazin-2-yl | CF$_3$ | S(O)Et | SO$_2$CH$_3$ | |
| 6-359 | pyrazin-2-yl | CF$_3$ | SO$_2$CH$_3$ | SO$_2$CH$_3$ | |
| 6-360 | pyrazin-2-yl | CF$_3$ | OCH$_2$CH$_2$OMe | SO$_2$CH$_3$ | |
| 6-361 | pyrazin-2-yl | CF$_3$ | OCH$_2$(CO)NMe$_2$ | SO2Me | |
| 6-362 | pyrazin-2-yl | CF$_3$ | CH$_2$O-tetrahydrofuran-2-yl | SO$_2$Et | |
| 6-363 | pyrazin-2-yl | SMe | SMe | F | |
| 6-364 | pyrazin-2-yl | SMe | SEt | F | |
| 6-365 | pyrazin-2-yl | SO$_2$CH$_3$ | F | Cl | |
| 6-366 | pyrazin-2-yl | F | S(O)Me | CF$_3$ | |
| 6-367 | pyrazin-2-yl | F | SMe | CF$_3$ | |
| 6-368 | 4-OMe—Ph | NO$_2$ | H | SO$_2$Me | |
| 6-369 | 4-OMe—Ph | Cl | H | SO$_2$Me | |

TABLE 6-continued

Compounds of the general formula (I) in which A represents CY, V represents hydrogen, W represents fluorine

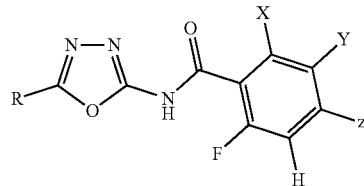

| No. | R | X | Y | Z | Physical data |
|---|---|---|---|---|---|
| 6-370 | 4-OMe—Ph | SO$_2$Me | H | CF$_3$ | |
| 6-371 | 4-OMe—Ph | NO$_2$ | H | OMe | |
| 6-372 | 4-OMe—Ph | NO$_2$ | H | Br | |
| 6-373 | 4-OMe—Ph | NO$_2$ | H | CF$_3$ | |
| 6-374 | 4-OMe—Ph | NO$_2$ | H | NO$_2$ | |
| 6-375 | 4-OMe—Ph | NO$_2$ | H | Cl | |
| 6-376 | 4-OMe—Ph | NO$_2$ | H | Me | |
| 6-377 | 4-OMe—Ph | NO$_2$ | H | F | |
| 6-378 | 4-OMe—Ph | OMe | H | SO$_2$Me | |
| 6-379 | 4-OMe—Ph | CF$_3$ | H | NO$_2$ | |
| 6-380 | 4-OMe—Ph | CH$_2$SO$_2$Me | H | Br | |
| 6-381 | 4-OMe—Ph | Cl | CH$_2$OCH$_2$CF$_3$ | SO$_2$Me | |
| 6-382 | 4-OMe—Ph | Cl | CH$_2$OCH$_2$CF$_3$ | SMe | |
| 6-383 | 4-OMe—Ph | Cl | 5-cyanomethyl-4,5-dihydro-1,2-oxazol-3-yl | SO$_2$Et | |
| 6-384 | 4-OMe—Ph | Cl | 4,5-dihydro-1,2-oxazol-3-yl | SO$_2$Et | |
| 6-385 | 4-OMe—Ph | Cl | CH$_2$OCH$_2$-tetrahydrofuran-2-yl | SO$_2$Me | |
| 6-386 | 4-OMe—Ph | Cl | SMe | Cl | |
| 6-387 | 4-OMe—Ph | Cl | SMe | SO$_2$Me | |
| 6-388 | 4-OMe—Ph | Cl | Me | SO$_2$Et | |
| 6-389 | 4-OMe—Ph | Cl | O(CH$_2$)$_2$OMe | Cl | |
| 6-390 | 4-OMe—Ph | Cl | OCH$_2$-cyclopropyl | Cl | |
| 6-391 | 4-OMe—Ph | Cl | OMe | Cl | |
| 6-392 | 4-OMe—Ph | Cl | NHAc | Cl | |
| 6-393 | 4-OMe—Ph | Cl | OCH$_2$C(O)NMe$_2$ | Cl | |
| 6-394 | 4-OMe—Ph | Cl | Cl | SO$_2$Me | |
| 6-395 | 4-OMe—Ph | Cl | pyrazol-1-yl | SO$_2$Me | |
| 6-396 | 4-OMe—Ph | Cl | 4-methoxypyrazol-1-yl | SO$_2$Me | |
| 6-397 | 4-OMe—Ph | Cl | 1,2,3-triazol-1-yl | SO$_2$Me | |
| 6-398 | 4-OMe—Ph | Cl | 1,2,3-triazol-2-yl | SO$_2$Me | |
| 6-399 | 4-OMe—Ph | Cl | F | SO$_2$Me | |
| 6-400 | 4-OMe—Ph | Me | SO$_2$Me | SO$_2$Me | |
| 6-401 | 4-OMe—Ph | Me | SO$_2$Me | CF$_3$ | |
| 6-402 | 4-OMe—Ph | Me | NMe$_2$ | SO$_2$Me | |
| 6-403 | 4-OMe—Ph | Me | S(O)Me | CF$_3$ | |
| 6-404 | 4-OMe—Ph | Me | SMe | CF$_3$ | |
| 6-405 | 4-OMe—Ph | Me | SO$_2$CH$_2$CH$_2$OMe | CF$_3$ | |
| 6-406 | 4-OMe—Ph | Me | pyrazol-1-yl | SO$_2$Me | |
| 6-407 | 4-OMe—Ph | Me | 4-methoxypyrazol-1-yl | SO$_2$Me | |
| 6-408 | 4-OMe—Ph | Me | 1,2,3-triazol-1-yl | SO$_2$Me | |
| 6-409 | 4-OMe—Ph | Me | 1,2,3-triazol-2-yl | SO$_2$Me | |
| 6-410 | 4-OMe—Ph | Me | Cl | SO$_2$Me | |
| 6-411 | 4-OMe—Ph | Me | Me | SO$_2$Me | |
| 6-412 | 4-OMe—Ph | Me | Me | SMe | |
| 6-413 | 4-OMe—Ph | Me | SO$_2$Me | Cl | |
| 6-414 | 4-OMe—Ph | Me | NMe$_2$ | SO$_2$Me | |
| 6-415 | 4-OMe—Ph | Me | NH(CH$_2$)$_2$OMe | SO$_2$Me | |
| 6-416 | 4-OMe—Ph | CF$_3$ | F | SO$_2$CH$_3$ | |
| 6-417 | 4-OMe—Ph | CF$_3$ | SMe | SO$_2$CH$_3$ | |
| 6-418 | 4-OMe—Ph | CF$_3$ | SEt | SO$_2$CH$_3$ | |
| 6-419 | 4-OMe—Ph | CF$_3$ | S(O)Et | SO$_2$CH$_3$ | |
| 6-420 | 4-OMe—Ph | CF$_3$ | SO$_2$CH$_3$ | SO$_2$CH$_3$ | |
| 6-421 | 4-OMe—Ph | CF$_3$ | OCH$_2$CH$_2$OMe | SO$_2$CH$_3$ | |
| 6-422 | 4-OMe—Ph | CF$_3$ | OCH$_2$(CO)NMe$_2$ | SO2Me | |
| 6-423 | 4-OMe—Ph | CF$_3$ | CH$_2$O-tetrahydrofuran-2-yl | SO$_2$Et | |
| 6-424 | 4-OMe—Ph | SMe | SMe | F | |
| 6-425 | 4-OMe—Ph | SMe | SEt | F | |
| 6-426 | 4-OMe—Ph | SO$_2$CH$_3$ | F | Cl | |
| 6-427 | 4-OMe—Ph | F | S(O)Me | CF$_3$ | |
| 6-428 | 4-OMe—Ph | F | SMe | CF$_3$ | |
| 6-429 | 4-Cl—Ph | NO$_2$ | H | SO$_2$Me | |
| 6-430 | 4-Cl—Ph | Cl | H | SO$_2$Me | |

TABLE 6-continued

Compounds of the general formula (I) in which A represents CY, V represents hydrogen, W represents fluorine

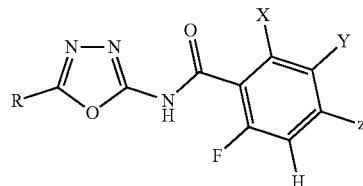

| No. | R | X | Y | Z | Physical data |
|---|---|---|---|---|---|
| 6-431 | 4-Cl—Ph | SO₂Me | H | CF₃ | |
| 6-432 | 4-Cl—Ph | NO₂ | H | OMe | |
| 6-433 | 4-Cl—Ph | NO₂ | H | Br | |
| 6-434 | 4-Cl—Ph | NO₂ | H | CF₃ | |
| 6-435 | 4-Cl—Ph | NO₂ | H | NO₂ | |
| 6-436 | 4-Cl—Ph | NO₂ | H | Cl | |
| 6-437 | 4-Cl—Ph | NO₂ | H | Me | |
| 6-438 | 4-Cl—Ph | NO₂ | H | F | |
| 6-439 | 4-Cl—Ph | OMe | H | SO₂Me | |
| 6-440 | 4-Cl—Ph | CF₃ | H | NO₂ | |
| 6-441 | 4-Cl—Ph | CH₂SO₂Me | H | Br | |
| 6-442 | 4-Cl—Ph | Cl | CH₂OCH₂CF₃ | SO₂Me | |
| 6-443 | 4-Cl—Ph | Cl | CH₂OCH₂CF₃ | SMe | |
| 6-444 | 4-Cl—Ph | Cl | 5-cyanomethyl-4,5-dihydro-1,2-oxazol-3-yl | SO₂Et | |
| 6-445 | 4-Cl—Ph | Cl | 4,5-dihydro-1,2-oxazol-3-yl | SO₂Et | |
| 6-446 | 4-Cl—Ph | Cl | CH₂OCH₂-tetrahydrofuran-2-yl | SO₂Me | |
| 6-447 | 4-Cl—Ph | Cl | SMe | Cl | |
| 6-448 | 4-Cl—Ph | Cl | SMe | SO₂Me | |
| 6-449 | 4-Cl—Ph | Cl | Me | SO₂Et | |
| 6-450 | 4-Cl—Ph | Cl | O(CH₂)₂OMe | Cl | |
| 6-451 | 4-Cl—Ph | Cl | OCH₂-cyclopropyl | Cl | |
| 6-452 | 4-Cl—Ph | Cl | OMe | Cl | |
| 6-453 | 4-Cl—Ph | Cl | NHAc | Cl | |
| 6-454 | 4-Cl—Ph | Cl | OCH₂C(O)NMe₂ | Cl | |
| 6-455 | 4-Cl—Ph | Cl | Cl | SO₂Me | |
| 6-456 | 4-Cl—Ph | Cl | pyrazol-1-yl | SO₂Me | |
| 6-457 | 4-Cl—Ph | Cl | 4-methoxypyrazol-1-yl | SO₂Me | |
| 6-458 | 4-Cl—Ph | Cl | 1,2,3-triazol-1-yl | SO₂Me | |
| 6-459 | 4-Cl—Ph | Cl | 1,2,3-triazol-2-yl | SO₂Me | |
| 6-460 | 4-Cl—Ph | Cl | F | SO₂Me | |
| 6-461 | 4-Cl—Ph | Me | SO₂Me | SO₂Me | |
| 6-462 | 4-Cl—Ph | Me | SO₂Me | CF₃ | |
| 6-463 | 4-Cl—Ph | Me | NMe₂ | SO₂Me | |
| 6-464 | 4-Cl—Ph | Me | S(O)Me | CF₃ | |
| 6-465 | 4-Cl—Ph | Me | SMe | CF₃ | |
| 6-466 | 4-Cl—Ph | Me | SO₂CH₂CH₂OMe | CF₃ | |
| 6-467 | 4-Cl—Ph | Me | pyrazol-1-yl | SO₂Me | |
| 6-468 | 4-Cl—Ph | Me | 4-methoxypyrazol-1-yl | SO₂Me | |
| 6-469 | 4-Cl—Ph | Me | 1,2,3-triazol-1-yl | SO₂Me | |
| 6-470 | 4-Cl—Ph | Me | 1,2,3-triazol-2-yl | SO₂Me | |
| 6-471 | 4-Cl—Ph | Me | Cl | SO₂Me | |
| 6-472 | 4-Cl—Ph | Me | Me | SO₂Me | |
| 6-473 | 4-Cl—Ph | Me | Me | SMe | |
| 6-474 | 4-Cl—Ph | Me | SO₂Me | Cl | |
| 6-475 | 4-Cl—Ph | Me | NMe₂ | SO₂Me | |
| 6-476 | 4-Cl—Ph | Me | NH(CH₂)₂OMe | SO₂Me | |
| 6-477 | 4-Cl—Ph | CF₃ | F | SO₂CH₃ | |
| 6-478 | 4-Cl—Ph | CF₃ | SMe | SO₂CH₃ | |
| 6-479 | 4-Cl—Ph | CF₃ | SEt | SO₂CH₃ | |
| 6-480 | 4-Cl—Ph | CF₃ | S(O)Et | SO₂CH₃ | |
| 6-481 | 4-Cl—Ph | CF₃ | SO₂CH₃ | SO₂CH₃ | |
| 6-482 | 4-Cl—Ph | CF₃ | OCH₂CH₂OMe | SO₂CH₃ | |
| 6-483 | 4-Cl—Ph | CF₃ | OCH₂(CO)NMe₂ | SO2Me | |
| 6-484 | 4-Cl—Ph | CF₃ | CH₂O-tetrahydrofuran-2-yl | SO₂Et | |
| 6-485 | 4-Cl—Ph | SMe | SMe | F | |
| 6-486 | 4-Cl—Ph | SMe | SEt | F | |
| 6-487 | 4-Cl—Ph | SO₂CH₃ | F | Cl | |
| 6-488 | 4-Cl—Ph | F | S(O)Me | CF₃ | |

TABLE 6-continued

Compounds of the general formula (I) in which A represents CY, V represents hydrogen, W represents fluorine

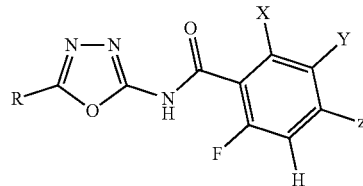

| No. | R | X | Y | Z | Physical data |
|---|---|---|---|---|---|
| 6-489 | 4-Cl—Ph | F | SMe | $CF_3$ | |
| 6-490 | tert-butyl | $NO_2$ | H | $SO_2Me$ | |
| 6-491 | tert-butyl | Cl | H | $SO_2Me$ | |
| 6-492 | tert-butyl | $SO_2Me$ | H | $CF_3$ | |
| 6-493 | tert-butyl | $NO_2$ | H | OMe | |
| 6-494 | tert-butyl | $NO_2$ | H | Br | |
| 6-495 | tert-butyl | $NO_2$ | H | $CF_3$ | |
| 6-496 | tert-butyl | $NO_2$ | H | $NO_2$ | |
| 6-497 | tert-butyl | $NO_2$ | H | Cl | |
| 6-498 | tert-butyl | $NO_2$ | H | Me | |
| 6-499 | tert-butyl | $NO_2$ | H | F | |
| 6-500 | tert-butyl | OMe | H | $SO_2Me$ | |
| 6-501 | tert-butyl | $CF_3$ | H | $NO_2$ | |
| 6-502 | tert-butyl | $CH_2SO_2Me$ | H | Br | |
| 6-503 | tert-butyl | Cl | $CH_2OCH_2CF_3$ | $SO_2Me$ | |
| 6-504 | tert-butyl | Cl | $CH_2OCH_2CF_3$ | SMe | |
| 6-505 | tert-butyl | Cl | 5-cyanomethyl-4,5-dihydro-1,2-oxazol-3-yl | $SO_2Et$ | |
| 6-506 | tert-butyl | Cl | 4,5-dihydro-1,2-oxazol-3-yl | $SO_2Et$ | |
| 6-507 | tert-butyl | Cl | $CH_2OCH_2$-tetrahydrofuran-2-yl | $SO_2Me$ | |
| 6-508 | tert-butyl | Cl | SMe | Cl | |
| 6-509 | tert-butyl | Cl | SMe | $SO_2Me$ | |
| 6-510 | tert-butyl | Cl | Me | $SO_2Et$ | |
| 6-511 | tert-butyl | Cl | $O(CH_2)_2OMe$ | Cl | |
| 6-512 | tert-butyl | Cl | $OCH_2$-cyclopropyl | Cl | |
| 6-513 | tert-butyl | Cl | OMe | Cl | |
| 6-514 | tert-butyl | Cl | NHAc | Cl | |
| 6-515 | tert-butyl | Cl | $OCH_2C(O)NMe_2$ | Cl | |
| 6-516 | tert-butyl | Cl | Cl | $SO_2Me$ | |
| 6-517 | tert-butyl | Cl | pyrazol-1-yl | $SO_2Me$ | |
| 6-518 | tert-butyl | Cl | 4-methoxypyrazol-1-yl | $SO_2Me$ | |
| 6-519 | tert-butyl | Cl | 1,2,3-triazol-1-yl | $SO_2Me$ | |
| 6-520 | tert-butyl | Cl | 1,2,3-triazol-2-yl | $SO_2Me$ | |
| 6-521 | tert-butyl | Cl | F | $SO_2Me$ | |
| 6-522 | tert-butyl | Me | $SO_2Me$ | $SO_2Me$ | |
| 6-523 | tert-butyl | Me | $SO_2Me$ | $CF_3$ | |
| 6-524 | tert-butyl | Me | $NMe_2$ | $SO_2Me$ | |
| 6-525 | tert-butyl | Me | $S(O)Me$ | $CF_3$ | |
| 6-526 | tert-butyl | Me | SMe | $CF_3$ | |
| 6-527 | tert-butyl | Me | $SO_2CH_2CH_2OMe$ | $CF_3$ | |
| 6-528 | tert-butyl | Me | pyrazol-1-yl | $SO_2Me$ | |
| 6-529 | tert-butyl | Me | 4-methoxypyrazol-1-yl | $SO_2Me$ | |
| 6-530 | tert-butyl | Me | 1,2,3-triazol-1-yl | $SO_2Me$ | |
| 6-531 | tert-butyl | Me | 1,2,3-triazol-2-yl | $SO_2Me$ | |
| 6-532 | tert-butyl | Me | Cl | $SO_2Me$ | |
| 6-533 | tert-butyl | Me | Me | $SO_2Me$ | |
| 6-534 | tert-butyl | Me | Me | SMe | |
| 6-535 | tert-butyl | Me | $SO_2Me$ | Cl | |
| 6-536 | tert-butyl | Me | $NMe_2$ | $SO_2Me$ | |
| 6-537 | tert-butyl | Me | $NH(CH_2)_2OMe$ | $SO_2Me$ | |
| 6-538 | tert-butyl | $CF_3$ | F | $SO_2CH_3$ | |
| 6-539 | tert-butyl | $CF_3$ | SMe | $SO_2CH_3$ | |
| 6-540 | tert-butyl | $CF_3$ | SEt | $SO_2CH_3$ | |
| 6-541 | tert-butyl | $CF_3$ | $S(O)Et$ | $SO_2CH_3$ | |
| 6-542 | tert-butyl | $CF_3$ | $SO_2CH_3$ | $SO_2CH_3$ | |
| 6-543 | tert-butyl | $CF_3$ | $OCH_2CH_2OMe$ | $SO_2CH_3$ | |
| 6-544 | tert-butyl | $CF_3$ | $OCH_2(CO)NMe_2$ | SO2Me | |
| 6-545 | tert-butyl | $CF_3$ | $CH_2O$-tetrahydrofuran-2-yl | $SO_2Et$ | |
| 6-546 | tert-butyl | SMe | SMe | F | |
| 6-547 | tert-butyl | SMe | SEt | F | |
| 6-548 | tert-butyl | $SO_2CH_3$ | F | Cl | |
| 6-549 | tert-butyl | F | $S(O)Me$ | $CF_3$ | |
| 6-550 | tert-butyl | F | SMe | $CF_3$ | |
| 6-551 | furan-2-yl | $NO_2$ | H | $SO_2Me$ | |

TABLE 6-continued

Compounds of the general formula (I) in which A represents CY, V represents hydrogen, W represents fluorine

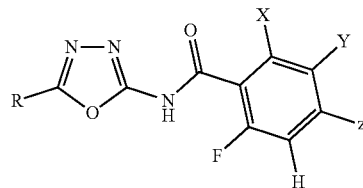

| No. | R | X | Y | Z | Physical data |
|---|---|---|---|---|---|
| 6-552 | furan-2-yl | Cl | H | SO$_2$Me | |
| 6-553 | furan-2-yl | SO$_2$Me | H | CF$_3$ | |
| 6-554 | furan-2-yl | NO$_2$ | H | OMe | |
| 6-555 | furan-2-yl | NO$_2$ | H | Br | |
| 6-556 | furan-2-yl | NO$_2$ | H | CF$_3$ | |
| 6-557 | furan-2-yl | NO$_2$ | H | NO$_2$ | |
| 6-558 | furan-2-yl | NO$_2$ | H | Cl | |
| 6-559 | furan-2-yl | NO$_2$ | H | Me | |
| 6-560 | furan-2-yl | NO$_2$ | H | F | |
| 6-561 | furan-2-yl | OMe | H | SO$_2$Me | |
| 6-562 | furan-2-yl | CF$_3$ | H | NO$_2$ | |
| 6-563 | furan-2-yl | CH$_2$SO$_2$Me | H | Br | |
| 6-564 | furan-2-yl | Cl | CH$_2$OCH$_2$CF$_3$ | SO$_2$Me | |
| 6-565 | furan-2-yl | Cl | CH$_2$OCH$_2$CF$_3$ | SMe | |
| 6-566 | furan-2-yl | Cl | 5-cyanomethyl-4,5-dihydro-1,2-oxazol-3-yl | SO$_2$Et | |
| 6-567 | furan-2-yl | Cl | 4,5-dihydro-1,2-oxazol-3-yl | SO$_2$Et | |
| 6-568 | furan-2-yl | Cl | CH$_2$OCH$_2$-tetrahydrofuran-2-yl | SO$_2$Me | |
| 6-569 | furan-2-yl | Cl | SMe | Cl | |
| 6-570 | furan-2-yl | Cl | SMe | SO$_2$Me | |
| 6-571 | furan-2-yl | Cl | Me | SO$_2$Et | |
| 6-572 | furan-2-yl | Cl | O(CH$_2$)$_2$OMe | Cl | |
| 6-573 | furan-2-yl | Cl | OCH$_2$-cyclopropyl | Cl | |
| 6-574 | furan-2-yl | Cl | OMe | Cl | |
| 6-575 | furan-2-yl | Cl | NHAc | Cl | |
| 6-576 | furan-2-yl | Cl | OCH$_2$C(O)NMe$_2$ | Cl | |
| 6-577 | furan-2-yl | Cl | Cl | SO$_2$Me | |
| 6-578 | furan-2-yl | Cl | pyrazol-1-yl | SO$_2$Me | |
| 6-579 | furan-2-yl | Cl | 4-methoxypyrazol-1-yl | SO$_2$Me | |
| 6-580 | furan-2-yl | Cl | 1,2,3-triazol-1-yl | SO$_2$Me | |
| 6-581 | furan-2-yl | Cl | 1,2,3-triazol-2-yl | SO$_2$Me | |
| 6-582 | furan-2-yl | Cl | F | SO$_2$Me | |
| 6-583 | furan-2-yl | Me | SO$_2$Me | SO$_2$Me | |
| 6-584 | furan-2-yl | Me | SO$_2$Me | CF$_3$ | |
| 6-585 | furan-2-yl | Me | NMe$_2$ | SO$_2$Me | |
| 6-586 | furan-2-yl | Me | S(O)Me | CF$_3$ | |
| 6-587 | furan-2-yl | Me | SMe | CF$_3$ | |
| 6-588 | furan-2-yl | Me | SO$_2$CH$_2$CH$_2$OMe | CF$_3$ | |
| 6-589 | furan-2-yl | Me | pyrazol-1-yl | SO$_2$Me | |
| 6-590 | furan-2-yl | Me | 4-methoxypyrazol-1-yl | SO$_2$Me | |
| 6-591 | furan-2-yl | Me | 1,2,3-triazol-1-yl | SO$_2$Me | |
| 6-592 | furan-2-yl | Me | 1,2,3-triazol-2-yl | SO$_2$Me | |
| 6-593 | furan-2-yl | Me | Cl | SO$_2$Me | |
| 6-594 | furan-2-yl | Me | Me | SO$_2$Me | |
| 6-595 | furan-2-yl | Me | Me | SMe | |
| 6-596 | furan-2-yl | Me | SO$_2$Me | Cl | |
| 6-597 | furan-2-yl | Me | NMe$_2$ | SO$_2$Me | |
| 6-598 | furan-2-yl | Me | NH(CH$_2$)$_2$OMe | SO$_2$Me | |
| 6-599 | furan-2-yl | CF$_3$ | F | SO$_2$CH$_3$ | |
| 6-600 | furan-2-yl | CF$_3$ | SMe | SO$_2$CH$_3$ | |
| 6-601 | furan-2-yl | CF$_3$ | SEt | SO$_2$CH$_3$ | |
| 6-602 | furan-2-yl | CF$_3$ | S(O)Et | SO$_2$CH$_3$ | |
| 6-603 | furan-2-yl | CF$_3$ | SO$_2$CH$_3$ | SO$_2$CH$_3$ | |
| 6-604 | furan-2-yl | CF$_3$ | OCH$_2$CH$_2$OMe | SO$_2$CH$_3$ | |
| 6-605 | furan-2-yl | CF$_3$ | OCH$_2$(CO)NMe$_2$ | SO2Me | |
| 6-606 | furan-2-yl | CF$_3$ | CH$_2$O-tetrahydrofuran-2-yl | SO$_2$Et | |
| 6-607 | furan-2-yl | SMe | SMe | F | |
| 6-608 | furan-2-yl | SMe | SEt | F | |
| 6-609 | furan-2-yl | SO$_2$CH$_3$ | F | Cl | |
| 6-610 | furan-2-yl | F | S(O)Me | CF$_3$ | |
| 6-611 | furan-2-yl | F | SMe | CF$_3$ | |
| 6-612 | isopropyl | NO$_2$ | H | SO$_2$Me | |
| 6-613 | isopropyl | Cl | H | SO$_2$Me | |
| 6-614 | isopropyl | SO$_2$Me | H | CF$_3$ | |

TABLE 6-continued

Compounds of the general formula (I) in which A represents CY, V represents hydrogen, W represents fluorine

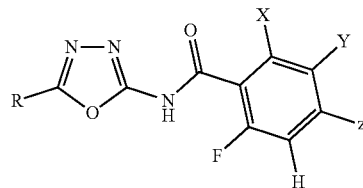

| No. | R | X | Y | Z | Physical data |
|---|---|---|---|---|---|
| 6-615 | isopropyl | $NO_2$ | H | OMe | |
| 6-616 | isopropyl | $NO_2$ | H | Br | |
| 6-617 | isopropyl | $NO_2$ | H | $CF_3$ | |
| 6-618 | isopropyl | $NO_2$ | H | $NO_2$ | |
| 6-619 | isopropyl | $NO_2$ | H | Cl | |
| 6-620 | isopropyl | $NO_2$ | H | Me | |
| 6-621 | isopropyl | $NO_2$ | H | F | |
| 6-622 | isopropyl | OMe | H | $SO_2Me$ | |
| 6-623 | isopropyl | $CF_3$ | H | $NO_2$ | |
| 6-624 | isopropyl | $CH_2SO_2Me$ | H | Br | |
| 6-625 | isopropyl | Cl | $CH_2OCH_2CF_3$ | $SO_2Me$ | |
| 6-626 | isopropyl | Cl | $CH_2OCH_2CF_3$ | SMe | |
| 6-627 | isopropyl | Cl | 5-cyanomethyl-4,5-dihydro-1,2-oxazol-3-yl | $SO_2Et$ | |
| 6-628 | isopropyl | Cl | 4,5-dihydro-1,2-oxazol-3-yl | $SO_2Et$ | |
| 6-629 | isopropyl | Cl | $CH_2OCH_2$-tetrahydrofuran-2-yl | $SO_2Me$ | |
| 6-630 | isopropyl | Cl | SMe | Cl | |
| 6-631 | isopropyl | Cl | SMe | $SO_2Me$ | |
| 6-632 | isopropyl | Cl | Me | $SO_2Et$ | |
| 6-633 | isopropyl | Cl | $O(CH_2)_2OMe$ | Cl | |
| 6-634 | isopropyl | Cl | $OCH_2$-cyclopropyl | Cl | |
| 6-635 | isopropyl | Cl | OMe | Cl | |
| 6-636 | isopropyl | Cl | NHAc | Cl | |
| 6-637 | isopropyl | Cl | $OCH_2C(O)NMe_2$ | Cl | |
| 6-638 | isopropyl | Cl | Cl | $SO_2Me$ | |
| 6-639 | isopropyl | Cl | pyrazol-1-yl | $SO_2Me$ | |
| 6-640 | isopropyl | Cl | 4-methoxypyrazol-1-yl | $SO_2Me$ | |
| 6-641 | isopropyl | Cl | 1,2,3-triazol-1-yl | $SO_2Me$ | |
| 6-642 | isopropyl | Cl | 1,2,3-triazol-2-yl | $SO_2Me$ | |
| 6-643 | isopropyl | Cl | F | $SO_2Me$ | |
| 6-644 | isopropyl | Me | $SO_2Me$ | $SO_2Me$ | |
| 6-645 | isopropyl | Me | $SO_2Me$ | $CF_3$ | |
| 6-646 | isopropyl | Me | $NMe_2$ | $SO_2Me$ | |
| 6-647 | isopropyl | Me | S(O)Me | $CF_3$ | |
| 6-648 | isopropyl | Me | SMe | $CF_3$ | |
| 6-649 | isopropyl | Me | $SO_2CH_2CH_2OMe$ | $CF_3$ | |
| 6-650 | isopropyl | Me | pyrazol-1-yl | $SO_2Me$ | |
| 6-651 | isopropyl | Me | 4-methoxypyrazol-1-yl | $SO_2Me$ | |
| 6-652 | isopropyl | Me | 1,2,3-triazol-1-yl | $SO_2Me$ | |
| 6-653 | isopropyl | Me | 1,2,3-triazol-2-yl | $SO_2Me$ | |
| 6-654 | isopropyl | Me | Cl | $SO_2Me$ | |
| 6-655 | isopropyl | Me | Me | $SO_2Me$ | |
| 6-656 | isopropyl | Me | F | Cl | |
| 6-657 | isopropyl | Me | $SO_2Me$ | Cl | |
| 6-658 | isopropyl | Me | $NMe_2$ | $SO_2Me$ | |
| 6-659 | isopropyl | Me | $NH(CH_2)_2OMe$ | $SO_2Me$ | |
| 6-660 | isopropyl | $CF_3$ | F | $SO_2CH_3$ | |
| 6-661 | isopropyl | $CF_3$ | SMe | $SO_2CH_3$ | |
| 6-662 | isopropyl | $CF_3$ | SEt | $SO_2CH_3$ | |
| 6-663 | isopropyl | $CF_3$ | S(O)Et | $SO_2CH_3$ | |
| 6-664 | isopropyl | $CF_3$ | $SO_2CH_3$ | $SO_2CH_3$ | |
| 6-665 | isopropyl | $CF_3$ | $OCH_2CH_2OMe$ | $SO_2CH_3$ | |
| 6-666 | isopropyl | $CF_3$ | $OCH_2(CO)NMe_2$ | SO2Me | |
| 6-667 | isopropyl | $CF_3$ | $CH_2O$-tetrahydrofuran-2-yl | $SO_2Et$ | |
| 6-668 | isopropyl | SMe | SMe | F | |
| 6-669 | isopropyl | SMe | SEt | F | |
| 6-670 | isopropyl | $SO_2CH_3$ | F | Cl | |
| 6-671 | isopropyl | F | S(O)Me | $CF_3$ | |
| 6-672 | isopropyl | F | SMe | $CF_3$ | |
| 6-673 | $CH_2CH_2OMe$ | $NO_2$ | H | $SO_2Me$ | |
| 6-674 | $CH_2CH_2OMe$ | Cl | H | $SO_2Me$ | |
| 6-675 | $CH_2CH_2OMe$ | $SO_2Me$ | H | $CF_3$ | |
| 6-676 | $CH_2CH_2OMe$ | $NO_2$ | H | OMe | |

TABLE 6-continued

Compounds of the general formula (I) in which A represents CY, V represents hydrogen, W represents fluorine

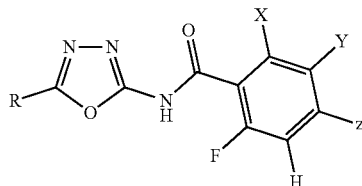

| No. | R | X | Y | Z | Physical data |
|---|---|---|---|---|---|
| 6-677 | CH$_2$CH$_2$OMe | NO$_2$ | H | Br | |
| 6-678 | CH$_2$CH$_2$OMe | NO$_2$ | H | CF$_3$ | |
| 6-679 | CH$_2$CH$_2$OMe | NO$_2$ | H | NO$_2$ | |
| 6-680 | CH$_2$CH$_2$OMe | NO$_2$ | H | Cl | |
| 6-681 | CH$_2$CH$_2$OMe | NO$_2$ | H | Me | |
| 6-682 | CH$_2$CH$_2$OMe | NO$_2$ | H | F | |
| 6-683 | CH$_2$CH$_2$OMe | OMe | H | SO$_2$Me | |
| 6-684 | CH$_2$CH$_2$OMe | CF$_3$ | H | NO$_2$ | |
| 6-685 | CH$_2$CH$_2$OMe | CH$_2$SO$_2$Me | H | Br | |
| 6-686 | CH$_2$CH$_2$OMe | Cl | CH$_2$OCH$_2$CF$_3$ | SO$_2$Me | |
| 6-687 | CH$_2$CH$_2$OMe | Cl | CH$_2$OCH$_2$CF$_3$ | SMe | |
| 6-688 | CH$_2$CH$_2$OMe | Cl | 5-cyanomethyl-4,5-dihydro-1,2-oxazol-3-yl | SO$_2$Et | |
| 6-689 | CH$_2$CH$_2$OMe | Cl | 4,5-dihydro-1,2-oxazol-3-yl | SO$_2$Et | |
| 6-690 | CH$_2$CH$_2$OMe | Cl | CH$_2$OCH$_2$-tetrahydrofuran-2-yl | SO$_2$Me | |
| 6-691 | CH$_2$CH$_2$OMe | Cl | SMe | Cl | |
| 6-692 | CH$_2$CH$_2$OMe | Cl | SMe | SO$_2$Me | |
| 6-693 | CH$_2$CH$_2$OMe | Cl | Me | SO$_2$Et | |
| 6-694 | CH$_2$CH$_2$OMe | Cl | O(CH$_2$)$_2$OMe | Cl | |
| 6-695 | CH$_2$CH$_2$OMe | Cl | OCH$_2$-cyclopropyl | Cl | |
| 6-696 | CH$_2$CH$_2$OMe | Cl | OMe | Cl | |
| 6-697 | CH$_2$CH$_2$OMe | Cl | NHAc | Cl | |
| 6-698 | CH$_2$CH$_2$OMe | Cl | OCH$_2$C(O)NMe$_2$ | Cl | |
| 6-699 | CH$_2$CH$_2$OMe | Cl | Cl | SO$_2$Me | |
| 6-700 | CH$_2$CH$_2$OMe | Cl | pyrazol-1-yl | SO$_2$Me | |
| 6-701 | CH$_2$CH$_2$OMe | Cl | 4-methoxypyrazol-1-yl | SO$_2$Me | |
| 6-702 | CH$_2$CH$_2$OMe | Cl | 1,2,3-triazol-1-yl | SO$_2$Me | |
| 6-703 | CH$_2$CH$_2$OMe | Cl | 1,2,3-triazol-2-yl | SO$_2$Me | |
| 6-704 | CH$_2$CH$_2$OMe | Cl | F | SO$_2$Me | |
| 6-705 | CH$_2$CH$_2$OMe | Me | SO$_2$Me | SO$_2$Me | |
| 6-706 | CH$_2$CH$_2$OMe | Me | SO$_2$Me | CF$_3$ | |
| 6-707 | CH$_2$CH$_2$OMe | Me | NMe$_2$ | SO$_2$Me | |
| 6-708 | CH$_2$CH$_2$OMe | Me | S(O)Me | CF$_3$ | |
| 6-709 | CH$_2$CH$_2$OMe | Me | SMe | CF$_3$ | |
| 6-710 | CH$_2$CH$_2$OMe | Me | SO$_2$CH$_2$CH$_2$OMe | CF$_3$ | |
| 6-711 | CH$_2$CH$_2$OMe | Me | pyrazol-1-yl | SO$_2$Me | |
| 6-712 | CH$_2$CH$_2$OMe | Me | 4-methoxypyrazol-1-yl | SO$_2$Me | |
| 6-713 | CH$_2$CH$_2$OMe | Me | 1,2,3-triazol-1-yl | SO$_2$Me | |
| 6-714 | CH$_2$CH$_2$OMe | Me | 1,2,3-triazol-2-yl | SO$_2$Me | |
| 6-715 | CH$_2$CH$_2$OMe | Me | Cl | SO$_2$Me | |
| 6-716 | CH$_2$CH$_2$OMe | Me | Me | SO$_2$Me | |
| 6-717 | CH$_2$CH$_2$OMe | Me | Me | SMe | |
| 6-718 | CH$_2$CH$_2$OMe | Me | SO$_2$Me | Cl | |
| 6-719 | CH$_2$CH$_2$OMe | Me | NMe$_2$ | SO$_2$Me | |
| 6-720 | CH$_2$CH$_2$OMe | Me | NH(CH$_2$)$_2$OMe | SO$_2$Me | |
| 6-721 | CH$_2$CH$_2$OMe | CF$_3$ | F | SO$_2$CH$_3$ | |
| 6-722 | CH$_2$CH$_2$OMe | CF$_3$ | SMe | SO$_2$CH$_3$ | |
| 6-723 | CH$_2$CH$_2$OMe | CF$_3$ | SEt | SO$_2$CH$_3$ | |
| 6-724 | CH$_2$CH$_2$OMe | CF$_3$ | S(O)Et | SO$_2$CH$_3$ | |
| 6-725 | CH$_2$CH$_2$OMe | CF$_3$ | SO$_2$CH$_3$ | SO$_2$CH$_3$ | |
| 6-726 | CH$_2$CH$_2$OMe | CF$_3$ | OCH$_2$CH$_2$OMe | SO$_2$CH$_3$ | |
| 6-727 | CH$_2$CH$_2$OMe | CF$_3$ | OCH$_2$(CO)NMe$_2$ | SO2Me | |
| 6-728 | CH$_2$CH$_2$OMe | CF$_3$ | CH$_2$O-tetrahydrofuran-2-yl | SO$_2$Et | |
| 6-729 | CH$_2$CH$_2$OMe | SMe | SMe | F | |
| 6-730 | CH$_2$CH$_2$OMe | SMe | SEt | F | |
| 6-731 | CH$_2$CH$_2$OMe | SO$_2$CH$_3$ | F | Cl | |
| 6-732 | CH$_2$CH$_2$OMe | F | S(O)Me | CF$_3$ | |
| 6-733 | CH$_2$CH$_2$OMe | F | SMe | CF$_3$ | |
| 6-734 | CH$_2$CF$_3$ | NO$_2$ | H | SO$_2$Me | |
| 6-735 | CH$_2$CF$_3$ | Cl | H | SO$_2$Me | |
| 6-736 | CH$_2$CF$_3$ | SO$_2$Me | H | CF$_3$ | |
| 6-737 | CH$_2$CF$_3$ | NO$_2$ | H | OMe | |
| 6-738 | CH$_2$CF$_3$ | NO$_2$ | H | Br | |

TABLE 6-continued

Compounds of the general formula (I) in which A represents CY, V represents hydrogen, W represents fluorine

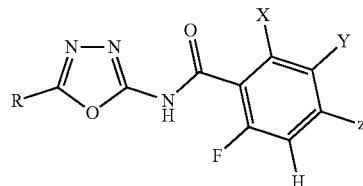

| No. | R | X | Y | Z | Physical data |
|---|---|---|---|---|---|
| 6-739 | $CH_2CF_3$ | $NO_2$ | H | $CF_3$ | |
| 6-740 | $CH_2CF_3$ | $NO_2$ | H | $NO_2$ | |
| 6-741 | $CH_2CF_3$ | $NO_2$ | H | Cl | |
| 6-742 | $CH_2CF_3$ | $NO_2$ | H | Me | |
| 6-743 | $CH_2CF_3$ | $NO_2$ | H | F | |
| 6-744 | $CH_2CF_3$ | OMe | H | $SO_2Me$ | |
| 6-745 | $CH_2CF_3$ | $CF_3$ | H | $NO_2$ | |
| 6-746 | $CH_2CF_3$ | $CH_2SO_2Me$ | H | Br | |
| 6-747 | $CH_2CF_3$ | Cl | $CH_2OCH_2CF_3$ | $SO_2Me$ | |
| 6-748 | $CH_2CF_3$ | Cl | $CH_2OCH_2CF_3$ | SMe | |
| 6-749 | $CH_2CF_3$ | Cl | 5-cyanomethyl-4,5-dihydro-1,2-oxazol-3-yl | $SO_2Et$ | |
| 6-750 | $CH_2CF_3$ | Cl | 4,5-dihydro-1,2-oxazol-3-yl | $SO_2Et$ | |
| 6-751 | $CH_2CF_3$ | Cl | $CH_2OCH_2$-tetrahydrofuran-2-yl | $SO_2Me$ | |
| 6-752 | $CH_2CF_3$ | Cl | SMe | Cl | |
| 6-753 | $CH_2CF_3$ | Cl | SMe | $SO_2Me$ | |
| 6-754 | $CH_2CF_3$ | Cl | Me | $SO_2Et$ | |
| 6-755 | $CH_2CF_3$ | Cl | $O(CH_2)_2OMe$ | Cl | |
| 6-756 | $CH_2CF_3$ | Cl | $OCH_2$-cyclopropyl | Cl | |
| 6-757 | $CH_2CF_3$ | Cl | OMe | Cl | |
| 6-758 | $CH_2CF_3$ | Cl | NHAc | Cl | |
| 6-759 | $CH_2CF_3$ | Cl | $OCH_2C(O)NMe_2$ | Cl | |
| 6-760 | $CH_2CF_3$ | Cl | Cl | $SO_2Me$ | |
| 6-761 | $CH_2CF_3$ | Cl | pyrazol-1-yl | $SO_2Me$ | |
| 6-762 | $CH_2CF_3$ | Cl | 4-methoxypyrazol-1-yl | $SO_2Me$ | |
| 6-763 | $CH_2CF_3$ | Cl | 1,2,3-triazol-1-yl | $SO_2Me$ | |
| 6-764 | $CH_2CF_3$ | Cl | 1,2,3-triazol-2-yl | $SO_2Me$ | |
| 6-765 | $CH_2CF_3$ | Cl | F | $SO_2Me$ | |
| 6-766 | $CH_2CF_3$ | Me | $SO_2Me$ | $SO_2Me$ | |
| 6-767 | $CH_2CF_3$ | Me | $SO_2Me$ | $CF_3$ | |
| 6-768 | $CH_2CF_3$ | Me | $NMe_2$ | $SO_2Me$ | |
| 6-769 | $CH_2CF_3$ | Me | $S(O)Me$ | $CF_3$ | |
| 6-770 | $CH_2CF_3$ | Me | SMe | $CF_3$ | |
| 6-771 | $CH_2CF_3$ | Me | $SO_2CH_2CH_2OMe$ | $CF_3$ | |
| 6-772 | $CH_2CF_3$ | Me | pyrazol-1-yl | $SO_2Me$ | |
| 6-773 | $CH_2CF_3$ | Me | 4-methoxypyrazol-1-yl | $SO_2Me$ | |
| 6-774 | $CH_2CF_3$ | Me | 1,2,3-triazol-1-yl | $SO_2Me$ | |
| 6-775 | $CH_2CF_3$ | Me | 1,2,3-triazol-2-yl | $SO_2Me$ | |
| 6-776 | $CH_2CF_3$ | Me | Cl | $SO_2Me$ | |
| 6-777 | $CH_2CF_3$ | Me | Me | $SO_2Me$ | |
| 6-778 | $CH_2CF_3$ | Me | Me | SMe | |
| 6-779 | $CH_2CF_3$ | Me | $SO_2Me$ | Cl | |
| 6-780 | $CH_2CF_3$ | Me | $NMe_2$ | $SO_2Me$ | |
| 6-781 | $CH_2CF_3$ | Me | $NH(CH_2)_2OMe$ | $SO_2Me$ | |
| 6-782 | $CH_2CF_3$ | $CF_3$ | F | $SO_2CH_3$ | |
| 6-783 | $CH_2CF_3$ | $CF_3$ | SMe | $SO_2CH_3$ | |
| 6-784 | $CH_2CF_3$ | $CF_3$ | SEt | $SO_2CH_3$ | |
| 6-785 | $CH_2CF_3$ | $CF_3$ | $S(O)Et$ | $SO_2CH_3$ | |
| 6-786 | $CH_2CF_3$ | $CF_3$ | $SO_2CH_3$ | $SO_2CH_3$ | |
| 6-787 | $CH_2CF_3$ | $CF_3$ | $OCH_2CH_2OMe$ | $SO_2CH_3$ | |
| 6-788 | $CH_2CF_3$ | $CF_3$ | $OCH_2(CO)NMe_2$ | $SO2Me$ | |
| 6-789 | $CH_2CF_3$ | $CF_3$ | $CH_2O$-tetrahydrofuran-2-yl | $SO_2Et$ | |
| 6-790 | $CH_2CF_3$ | SMe | SMe | F | |
| 6-791 | $CH_2CF_3$ | SMe | SEt | F | |
| 6-792 | $CH_2CF_3$ | $SO_2CH_3$ | F | Cl | |
| 6-793 | $CH_2CF_3$ | F | $S(O)Me$ | $CF_3$ | |
| 6-794 | $CH_2CF_3$ | F | SMe | $CF_3$ | |
| 6-795 | tetrahydrofuran-2-yl | $NO_2$ | H | $SO_2Me$ | |
| 6-796 | tetrahydrofuran-2-yl | Cl | H | $SO_2Me$ | |
| 6-797 | tetrahydrofuran-2-yl | $SO_2Me$ | H | $CF_3$ | |
| 6-798 | tetrahydrofuran-2-yl | $NO_2$ | H | OMe | |
| 6-799 | tetrahydrofuran-2-yl | $NO_2$ | H | Br | |
| 6-800 | tetrahydrofuran-2-yl | $NO_2$ | H | $CF_3$ | |

TABLE 6-continued

Compounds of the general formula (I) in which A represents CY, V represents hydrogen, W represents fluorine

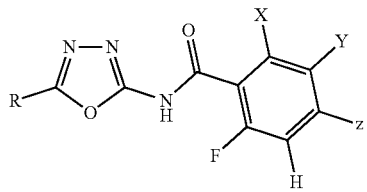

| No. | R | X | Y | Z | Physical data |
|---|---|---|---|---|---|
| 6-801 | tetrahydrofuran-2-yl | $NO_2$ | H | $NO_2$ | |
| 6-802 | tetrahydrofuran-2-yl | $NO_2$ | H | Cl | |
| 6-803 | tetrahydrofuran-2-yl | $NO_2$ | H | Me | |
| 6-804 | tetrahydrofuran-2-yl | $NO_2$ | H | F | |
| 6-805 | tetrahydrofuran-2-yl | OMe | H | $SO_2Me$ | |
| 6-806 | tetrahydrofuran-2-yl | $CF_3$ | H | $NO_2$ | |
| 6-807 | tetrahydrofuran-2-yl | $CH_2SO_2Me$ | H | Br | |
| 6-808 | tetrahydrofuran-2-yl | Cl | $CH_2OCH_2CF_3$ | $SO_2Me$ | |
| 6-809 | tetrahydrofuran-2-yl | Cl | $CH_2OCH_2CF_3$ | SMe | |
| 6-810 | tetrahydrofuran-2-yl | Cl | 5-cyanomethyl-4,5-dihydro-1,2-oxazol-3-yl | $SO_2Et$ | |
| 6-811 | tetrahydrofuran-2-yl | Cl | 4,5-dihydro-1,2-oxazol-3-yl | $SO_2Et$ | |
| 6-812 | tetrahydrofuran-2-yl | Cl | $CH_2OCH_2$-tetrahydrofuran-2-yl | $SO_2Me$ | |
| 6-813 | tetrahydrofuran-2-yl | Cl | SMe | Cl | |
| 6-814 | tetrahydrofuran-2-yl | Cl | SMe | $SO_2Me$ | |
| 6-815 | tetrahydrofuran-2-yl | Cl | Me | $SO_2Et$ | |
| 6-816 | tetrahydrofuran-2-yl | Cl | $O(CH_2)_2OMe$ | Cl | |
| 6-817 | tetrahydrofuran-2-yl | Cl | $OCH_2$-cyclopropyl | Cl | |
| 6-818 | tetrahydrofuran-2-yl | Cl | OMe | Cl | |
| 6-819 | tetrahydrofuran-2-yl | Cl | NHAc | Cl | |
| 6-820 | tetrahydrofuran-2-yl | Cl | $OCH_2C(O)NMe_2$ | Cl | |
| 6-821 | tetrahydrofuran-2-yl | Cl | Cl | $SO_2Me$ | |
| 6-822 | tetrahydrofuran-2-yl | Cl | pyrazol-1-yl | $SO_2Me$ | |
| 6-823 | tetrahydrofuran-2-yl | Cl | 4-methoxypyrazol-1-yl | $SO_2Me$ | |
| 6-824 | tetrahydrofuran-2-yl | Cl | 1,2,3-triazol-1-yl | $SO_2Me$ | |
| 6-825 | tetrahydrofuran-2-yl | Cl | 1,2,3-triazol-2-yl | $SO_2Me$ | |
| 6-826 | tetrahydrofuran-2-yl | Cl | F | $SO_2Me$ | |
| 6-827 | tetrahydrofuran-2-yl | Me | $SO_2Me$ | $SO_2Me$ | |
| 6-828 | tetrahydrofuran-2-yl | Me | $SO_2Me$ | $CF_3$ | |
| 6-829 | tetrahydrofuran-2-yl | Me | $NMe_2$ | $SO_2Me$ | |
| 6-830 | tetrahydrofuran-2-yl | Me | S(O)Me | $CF_3$ | |
| 6-831 | tetrahydrofuran-2-yl | Me | SMe | $CF_3$ | |
| 6-832 | tetrahydrofuran-2-yl | Me | $SO_2CH_2CH_2OMe$ | $CF_3$ | |
| 6-833 | tetrahydrofuran-2-yl | Me | pyrazol-1-yl | $SO_2Me$ | |
| 6-834 | tetrahydrofuran-2-yl | Me | 4-methoxypyrazol-1-yl | $SO_2Me$ | |
| 6-835 | tetrahydrofuran-2-yl | Me | 1,2,3-triazol-1-yl | $SO_2Me$ | |
| 6-836 | tetrahydrofuran-2-yl | Me | 1,2,3-triazol-2-yl | $SO_2Me$ | |
| 6-837 | tetrahydrofuran-2-yl | Me | Cl | $SO_2Me$ | |
| 6-838 | tetrahydrofuran-2-yl | Me | Me | $SO_2Me$ | |
| 6-839 | tetrahydrofuran-2-yl | Me | Me | SMe | |
| 6-840 | tetrahydrofuran-2-yl | Me | $SO_2Me$ | Cl | |
| 6-841 | tetrahydrofuran-2-yl | Me | $NMe_2$ | $SO_2Me$ | |
| 6-842 | tetrahydrofuran-2-yl | Me | $NH(CH_2)_2OMe$ | $SO_2Me$ | |
| 6-843 | tetrahydrofuran-2-yl | $CF_3$ | F | $SO_2CH_3$ | |
| 6-844 | tetrahydrofuran-2-yl | $CF_3$ | SMe | $SO_2CH_3$ | |
| 6-845 | tetrahydrofuran-2-yl | $CF_3$ | SEt | $SO_2CH_3$ | |
| 6-846 | tetrahydrofuran-2-yl | $CF_3$ | S(O)Et | $SO_2CH_3$ | |
| 6-847 | tetrahydrofuran-2-yl | $CF_3$ | $SO_2CH_3$ | $SO_2CH_3$ | |
| 6-848 | tetrahydrofuran-2-yl | $CF_3$ | $OCH_2CH_2OMe$ | $SO_2CH_3$ | |
| 6-849 | tetrahydrofuran-2-yl | $CF_3$ | $OCH_2(CO)NMe_2$ | $SO2Me$ | |
| 6-850 | tetrahydrofuran-2-yl | $CF_3$ | $CH_2O$-tetrahydrofuran-2-yl | $SO_2Et$ | |
| 6-851 | tetrahydrofuran-2-yl | SMe | SMe | F | |
| 6-852 | tetrahydrofuran-2-yl | SMe | SEt | F | |
| 6-853 | tetrahydrofuran-2-yl | $SO_2CH_3$ | F | Cl | |
| 6-854 | tetrahydrofuran-2-yl | F | S(O)Me | $CF_3$ | |
| 6-855 | tetrahydrofuran-2-yl | F | SMe | $CF_3$ | |
| 6-856 | n-Pr | $NO_2$ | H | $SO_2Me$ | |
| 6-857 | n-Pr | Cl | H | $SO_2Me$ | |
| 6-858 | n-Pr | $SO_2Me$ | H | $CF_3$ | |
| 6-859 | n-Pr | $NO_2$ | H | OMe | |
| 6-860 | n-Pr | $NO_2$ | H | Br | |
| 6-861 | n-Pr | $NO_2$ | H | Cl | |
| 6-862 | n-Pr | $NO_2$ | H | $CF_3$ | |

TABLE 6-continued

Compounds of the general formula (I) in which A represents CY, V represents hydrogen, W represents fluorine

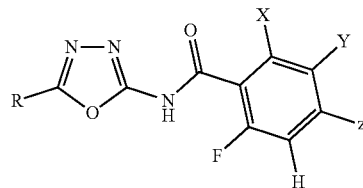

| No. | R | X | Y | Z | Physical data |
|---|---|---|---|---|---|
| 6-863 | n-Pr | $NO_2$ | H | $NO_2$ | |
| 6-864 | n-Pr | $NO_2$ | H | Me | |
| 6-865 | n-Pr | $NO_2$ | H | F | |
| 6-866 | n-Pr | OMe | H | $SO_2Me$ | |
| 6-867 | n-Pr | $CF_3$ | H | $NO_2$ | |
| 6-868 | n-Pr | $CH_2SO_2Me$ | H | Br | |
| 6-869 | n-Pr | Cl | $CH_2OCH_2CF_3$ | $SO_2Me$ | |
| 6-870 | n-Pr | Cl | $CH_2OCH_2CF_3$ | SMe | |
| 6-871 | n-Pr | Cl | 5-cyanomethyl-4,5-dihydro-1,2-oxazol-3-yl | $SO_2Et$ | |
| 6-872 | n-Pr | Cl | 4,5-dihydro-1,2-oxazol-3-yl | $SO_2Et$ | |
| 6-873 | n-Pr | Cl | $CH_2OCH_2$-tetrahydrofuran-2-yl | $SO_2Me$ | |
| 6-874 | n-Pr | Cl | SMe | Cl | |
| 6-875 | n-Pr | Cl | SMe | $SO_2Me$ | |
| 6-876 | n-Pr | Cl | Me | $SO_2Et$ | |
| 6-877 | n-Pr | Cl | $O(CH_2)_2OMe$ | Cl | |
| 6-878 | n-Pr | Cl | $OCH_2$-cyclopropyl | Cl | |
| 6-879 | n-Pr | Cl | OMe | Cl | |
| 6-880 | n-Pr | Cl | NHAc | Cl | |
| 6-881 | n-Pr | Cl | $OCH_2C(O)NMe_2$ | Cl | |
| 6-882 | n-Pr | Cl | Cl | $SO_2Me$ | |
| 6-883 | n-Pr | Cl | pyrazol-1-yl | $SO_2Me$ | |
| 6-884 | n-Pr | Cl | 4-methoxypyrazol-1-yl | $SO_2Me$ | |
| 6-885 | n-Pr | Cl | 1,2,3-triazol-1-yl | $SO_2Me$ | |
| 6-886 | n-Pr | Cl | 1,2,3-triazol-2-yl | $SO_2Me$ | |
| 6-887 | n-Pr | Cl | F | $SO_2Me$ | |
| 6-888 | n-Pr | Me | $SO_2Me$ | $SO_2Me$ | |
| 6-889 | n-Pr | Me | $SO_2Me$ | $CF_3$ | |
| 6-890 | n-Pr | Me | $NMe_2$ | $SO_2Me$ | |
| 6-891 | n-Pr | Me | $S(O)Me$ | $CF_3$ | |
| 6-892 | n-Pr | Me | SMe | $CF_3$ | |
| 6-893 | n-Pr | Me | $SO_2CH_2CH_2OMe$ | $CF_3$ | |
| 6-894 | n-Pr | Me | pyrazol-1-yl | $SO_2Me$ | |
| 6-895 | n-Pr | Me | 4-methoxypyrazol-1-yl | $SO_2Me$ | |
| 6-896 | n-Pr | Me | 1,2,3-triazol-1-yl | $SO_2Me$ | |
| 6-897 | n-Pr | Me | 1,2,3-triazol-2-yl | $SO_2Me$ | |
| 6-898 | n-Pr | Me | Cl | $SO_2Me$ | |
| 6-899 | n-Pr | Me | Me | $SO_2Me$ | |
| 6-900 | n-Pr | Me | Me | SMe | |
| 6-901 | n-Pr | Me | $SO_2Me$ | Cl | |
| 6-902 | n-Pr | Me | $NMe_2$ | $SO_2Me$ | |
| 6-903 | n-Pr | Me | $NH(CH_2)_2OMe$ | $SO_2Me$ | |
| 6-904 | n-Pr | $CF_3$ | F | $SO_2CH_3$ | |
| 6-905 | n-Pr | $CF_3$ | SMe | $SO_2CH_3$ | |
| 6-906 | n-Pr | $CF_3$ | SEt | $SO_2CH_3$ | |
| 6-907 | n-Pr | $CF_3$ | $S(O)Et$ | $SO_2CH_3$ | |
| 6-908 | n-Pr | $CF_3$ | $SO_2CH_3$ | $SO_2CH_3$ | |
| 6-909 | n-Pr | $CF_3$ | $OCH_2CH_2OMe$ | $SO_2CH_3$ | |
| 6-910 | n-Pr | $CF_3$ | $OCH_2(CO)NMe_2$ | $SO2Me$ | |
| 6-911 | n-Pr | $CF_3$ | $CH_2O$-tetrahydrofuran-2-yl | $SO_2Et$ | |
| 6-912 | n-Pr | SMe | SMe | F | |
| 6-913 | n-Pr | SMe | SEt | F | |
| 6-914 | n-Pr | $SO_2CH_3$ | F | Cl | |
| 6-915 | n-Pr | F | $S(O)Me$ | $CF_3$ | |
| 6-916 | n-Pr | F | SMe | $CF_3$ | |
| 6-917 | $CH_2OEt$ | $NO_2$ | H | $SO_2Me$ | |
| 6-918 | $CH_2OEt$ | Cl | H | $SO_2Me$ | |
| 6-919 | $CH_2OEt$ | $SO_2Me$ | H | $CF_3$ | |
| 6-920 | $CH_2OEt$ | $NO_2$ | H | OMe | |
| 6-921 | $CH_2OEt$ | $NO_2$ | H | Br | |
| 6-922 | $CH_2OEt$ | $NO_2$ | H | $CF_3$ | |
| 6-923 | $CH_2OEt$ | $NO_2$ | H | $NO_2$ | |
| 6-924 | $CH_2OEt$ | $NO_2$ | H | Cl | |
| 6-925 | $CH_2OEt$ | $NO_2$ | H | Me | |

TABLE 6-continued

Compounds of the general formula (I) in which A represents CY, V represents hydrogen, W represents fluorine

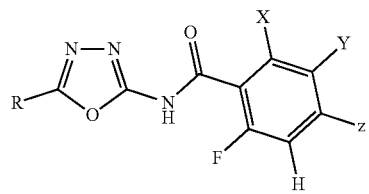

| No. | R | X | Y | Z | Physical data |
|---|---|---|---|---|---|
| 6-926 | CH$_2$OEt | NO$_2$ | H | F | |
| 6-927 | CH$_2$OEt | OMe | H | SO$_2$Me | |
| 6-928 | CH$_2$OEt | CF$_3$ | H | NO$_2$ | |
| 6-929 | CH$_2$OEt | CH$_2$SO$_2$Me | H | Br | |
| 6-930 | CH$_2$OEt | Cl | CH$_2$OCH$_2$CF$_3$ | SO$_2$Me | |
| 6-931 | CH$_2$OEt | Cl | CH$_2$OCH$_2$CF$_3$ | SMe | |
| 6-932 | CH$_2$OEt | Cl | 5-cyanomethyl-4,5-dihydro-1,2-oxazol-3-yl | SO$_2$Et | |
| 6-933 | CH$_2$OEt | Cl | 4,5-dihydro-1,2-oxazol-3-yl | SO$_2$Et | |
| 6-934 | CH$_2$OEt | Cl | CH$_2$OCH$_2$-tetrahydrofuran-2-yl | SO$_2$Me | |
| 6-935 | CH$_2$OEt | Cl | SMe | Cl | |
| 6-936 | CH$_2$OEt | Cl | SMe | SO$_2$Me | |
| 6-937 | CH$_2$OEt | Cl | Me | SO$_2$Et | |
| 6-938 | CH$_2$OEt | Cl | O(CH$_2$)$_2$OMe | Cl | |
| 6-939 | CH$_2$OEt | Cl | OCH$_2$-cyclopropyl | Cl | |
| 6-940 | CH$_2$OEt | Cl | OMe | Cl | |
| 6-941 | CH$_2$OEt | Cl | NHAc | Cl | |
| 6-942 | CH$_2$OEt | Cl | OCH$_2$C(O)NMe$_2$ | Cl | |
| 6-943 | CH$_2$OEt | Cl | Cl | SO$_2$Me | |
| 6-944 | CH$_2$OEt | Cl | pyrazol-1-yl | SO$_2$Me | |
| 6-945 | CH$_2$OEt | Cl | 4-methoxypyrazol-1-yl | SO$_2$Me | |
| 6-946 | CH$_2$OEt | Cl | 1,2,3-triazol-1-yl | SO$_2$Me | |
| 6-947 | CH$_2$OEt | Cl | 1,2,3-triazol-2-yl | SO$_2$Me | |
| 6-948 | CH$_2$OEt | Cl | F | SO$_2$Me | |
| 6-949 | CH$_2$OEt | Me | SO$_2$Me | SO$_2$Me | |
| 6-950 | CH$_2$OEt | Me | SO$_2$Me | CF$_3$ | |
| 6-951 | CH$_2$OEt | Me | NMe$_2$ | SO$_2$Me | |
| 6-952 | CH$_2$OEt | Me | S(O)Me | CF$_3$ | |
| 6-953 | CH$_2$OEt | Me | SMe | CF$_3$ | |
| 6-954 | CH$_2$OEt | Me | SO$_2$CH$_2$CH$_2$OMe | CF$_3$ | |
| 6-955 | CH$_2$OEt | Me | pyrazol-1-yl | SO$_2$Me | |
| 6-956 | CH$_2$OEt | Me | 4-methoxypyrazol-1-yl | SO$_2$Me | |
| 6-957 | CH$_2$OEt | Me | 1,2,3-triazol-1-yl | SO$_2$Me | |
| 6-958 | CH$_2$OEt | Me | 1,2,3-triazol-2-yl | SO$_2$Me | |
| 6-959 | CH$_2$OEt | Me | Cl | SO$_2$Me | |
| 6-960 | CH$_2$OEt | Me | Me | SO$_2$Me | |
| 6-961 | CH$_2$OEt | Me | Me | SMe | |
| 6-962 | CH$_2$OEt | Me | SO$_2$Me | Cl | |
| 6-963 | CH$_2$OEt | Me | NMe$_2$ | SO$_2$Me | |
| 6-964 | CH$_2$OEt | Me | NH(CH$_2$)$_2$OMe | SO$_2$Me | |
| 6-965 | CH$_2$OEt | CF$_3$ | F | SO$_2$CH$_3$ | |
| 6-966 | CH$_2$OEt | CF$_3$ | SMe | SO$_2$CH$_3$ | |
| 6-967 | CH$_2$OEt | CF$_3$ | SEt | SO$_2$CH$_3$ | |
| 6-968 | CH$_2$OEt | CF$_3$ | S(O)Et | SO$_2$CH$_3$ | |
| 6-969 | CH$_2$OEt | CF$_3$ | SO$_2$CH$_3$ | SO$_2$CH$_3$ | |
| 6-970 | CH$_2$OEt | CF$_3$ | OCH$_2$CH$_2$OMe | SO$_2$CH$_3$ | |
| 6-971 | CH$_2$OEt | CF$_3$ | OCH$_2$(CO)NMe$_2$ | SO2Me | |
| 6-972 | CH$_2$OEt | CF$_3$ | CH$_2$O-tetrahydrofuran-2-yl | SO$_2$Et | |
| 6-973 | CH$_2$OEt | SMe | SMe | F | |
| 6-974 | CH$_2$OEt | SMe | SEt | F | |
| 6-975 | CH$_2$OEt | SO$_2$CH$_3$ | F | Cl | |
| 6-976 | CH$_2$OEt | F | S(O)Me | CF$_3$ | |
| 6-977 | CH$_2$OEt | F | SMe | CF$_3$ | |
| 6-978 | cyclobutyl | NO$_2$ | H | SO$_2$Me | |
| 6-979 | cyclobutyl | Cl | H | SO$_2$Me | |
| 6-980 | cyclobutyl | SO$_2$Me | H | CF$_3$ | |
| 6-981 | cyclobutyl | NO$_2$ | H | OMe | |
| 6-982 | cyclobutyl | NO$_2$ | H | Br | |
| 6-983 | cyclobutyl | SMe | H | CF$_3$ | |
| 6-984 | cyclobutyl | NO$_2$ | H | NO$_2$ | |
| 6-985 | cyclobutyl | NO$_2$ | H | Cl | |
| 6-986 | cyclobutyl | NO$_2$ | H | Me | |
| 6-987 | cyclobutyl | NO$_2$ | H | F | |

TABLE 6-continued

Compounds of the general formula (I) in which A represents CY, V represents hydrogen, W represents fluorine

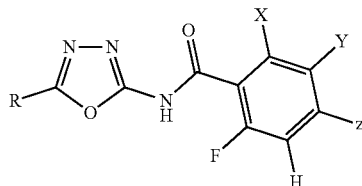

| No. | R | X | Y | Z | Physical data |
|---|---|---|---|---|---|
| 6-988 | cyclobutyl | OMe | H | SO$_2$Me | |
| 6-989 | cyclobutyl | CF$_3$ | H | NO$_2$ | |
| 6-990 | cyclobutyl | CH$_2$SO$_2$Me | H | Br | |
| 6-991 | cyclobutyl | Cl | CH$_2$OCH$_2$CF$_3$ | SO$_2$Me | |
| 6-992 | cyclobutyl | Cl | CH$_2$OCH$_2$CF$_3$ | SMe | |
| 6-993 | cyclobutyl | Cl | 5-cyanomethyl-4,5-dihydro-1,2-oxazol-3-yl | SO$_2$Et | |
| 6-994 | cyclobutyl | Cl | 4,5-dihydro-1,2-oxazol-3-yl | SO$_2$Et | |
| 6-995 | cyclobutyl | Cl | CH$_2$OCH$_2$-tetrahydrofuran-2-yl | SO$_2$Me | |
| 6-996 | cyclobutyl | Cl | SMe | Cl | |
| 6-997 | cyclobutyl | Cl | SMe | SO$_2$Me | |
| 6-998 | cyclobutyl | Cl | Me | SO$_2$Et | |
| 6-999 | cyclobutyl | Cl | O(CH$_2$)$_2$OMe | Cl | |
| 6-1000 | cyclobutyl | Cl | OCH$_2$-cyclopropyl | Cl | |
| 6-1001 | cyclobutyl | Cl | OMe | Cl | |
| 6-1002 | cyclobutyl | Cl | NHAc | Cl | |
| 6-1003 | cyclobutyl | Cl | OCH$_2$C(O)NMe$_2$ | Cl | |
| 6-1004 | cyclobutyl | Cl | Cl | SO$_2$Me | |
| 6-1005 | cyclobutyl | Cl | pyrazol-1-yl | SO$_2$Me | |
| 6-1006 | cyclobutyl | Cl | 4-methoxypyrazol-1-yl | SO$_2$Me | |
| 6-1007 | cyclobutyl | Cl | 1,2,3-triazol-1-yl | SO$_2$Me | |
| 6-1008 | cyclobutyl | Cl | 1,2,3-triazol-2-yl | SO$_2$Me | |
| 6-1009 | cyclobutyl | Cl | F | SO$_2$Me | |
| 6-1010 | cyclobutyl | Me | SO$_2$Me | SO$_2$Me | |
| 6-1011 | cyclobutyl | Me | SO$_2$Me | CF$_3$ | |
| 6-1012 | cyclobutyl | Me | NMe$_2$ | SO$_2$Me | |
| 6-1013 | cyclobutyl | Me | S(O)Me | CF$_3$ | |
| 6-1014 | cyclobutyl | Me | SMe | CF$_3$ | |
| 6-1015 | cyclobutyl | Me | SO$_2$CH$_2$CH$_2$OMe | CF$_3$ | |
| 6-1016 | cyclobutyl | Me | pyrazol-1-yl | SO$_2$Me | |
| 6-1017 | cyclobutyl | Me | 4-methoxypyrazol-1-yl | SO$_2$Me | |
| 6-1018 | cyclobutyl | Me | 1,2,3-triazol-1-yl | SO$_2$Me | |
| 6-1019 | cyclobutyl | Me | 1,2,3-triazol-2-yl | SO$_2$Me | |
| 6-1020 | cyclobutyl | Me | Cl | SO$_2$Me | |
| 6-1021 | cyclobutyl | Me | Me | SO$_2$Me | |
| 6-1022 | cyclobutyl | Me | Me | SMe | |
| 6-1023 | cyclobutyl | Me | SO$_2$Me | Cl | |
| 6-1024 | cyclobutyl | Me | NMe$_2$ | SO$_2$Me | |
| 6-1025 | cyclobutyl | Me | NH(CH$_2$)$_2$OMe | SO$_2$Me | |
| 6-1026 | cyclobutyl | CF$_3$ | F | SO$_2$CH$_3$ | |
| 6-1027 | cyclobutyl | CF$_3$ | SMe | SO$_2$CH$_3$ | |
| 6-1028 | cyclobutyl | CF$_3$ | SEt | SO$_2$CH$_3$ | |
| 6-1029 | cyclobutyl | CF$_3$ | S(O)Et | SO$_2$CH$_3$ | |
| 6-1030 | cyclobutyl | CF$_3$ | SO$_2$CH$_3$ | SO$_2$CH$_3$ | |
| 6-1031 | cyclobutyl | CF$_3$ | OCH$_2$CH$_2$OMe | SO$_2$CH$_3$ | |
| 6-1032 | cyclobutyl | CF$_3$ | OCH$_2$(CO)NMe$_2$ | SO2Me | |
| 6-1033 | cyclobutyl | CF$_3$ | CH$_2$O-tetrahydrofuran-2-yl | SO$_2$Et | |
| 6-1034 | cyclobutyl | SMe | SMe | F | |
| 6-1035 | cyclobutyl | SMe | SEt | F | |
| 6-1036 | cyclobutyl | SO$_2$CH$_3$ | F | Cl | |
| 6-1037 | cyclobutyl | F | S(O)Me | CF$_3$ | |
| 6-1038 | cyclobutyl | F | SMe | CF$_3$ | |
| 6-1039 | cyclopentyl | NO$_2$ | H | SO$_2$Me | |
| 6-1040 | cyclopentyl | Cl | H | SO$_2$Me | |
| 6-1041 | cyclopentyl | SO$_2$Me | H | CF$_3$ | |
| 6-1042 | cyclopentyl | NO$_2$ | H | OMe | |
| 6-1043 | cyclopentyl | NO$_2$ | H | Br | |
| 6-1044 | cyclopentyl | SMe | H | CF$_3$ | |
| 6-1045 | cyclopentyl | NO$_2$ | H | NO$_2$ | |
| 6-1046 | cyclopentyl | NO$_2$ | H | Cl | |
| 6-1047 | cyclopentyl | NO$_2$ | H | Me | |
| 6-1048 | cyclopentyl | NO$_2$ | H | F | |
| 6-1049 | cyclopentyl | OMe | H | SO$_2$Me | |

TABLE 6-continued

Compounds of the general formula (I) in which A represents CY, V represents hydrogen, W represents fluorine

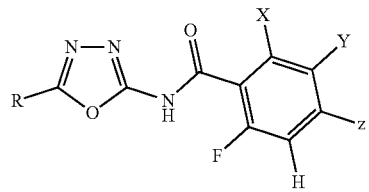

| No. | R | X | Y | Z | Physical data |
|---|---|---|---|---|---|
| 6-1050 | cyclopentyl | $CF_3$ | H | $NO_2$ | |
| 6-1051 | cyclopentyl | $CH_2SO_2Me$ | H | Br | |
| 6-1052 | cyclopentyl | Cl | $CH_2OCH_2CF_3$ | $SO_2Me$ | |
| 6-1053 | cyclopentyl | Cl | $CH_2OCH_2CF_3$ | SMe | |
| 6-1054 | cyclopentyl | Cl | 5-cyanomethyl-4,5-dihydro-1,2-oxazol-3-yl | $SO_2Et$ | |
| 6-1055 | cyclopentyl | Cl | 4,5-dihydro-1,2-oxazol-3-yl | $SO_2Et$ | |
| 6-1056 | cyclopentyl | Cl | $CH_2OCH_2$-tetrahydrofuran-2-yl | $SO_2Me$ | |
| 6-1057 | cyclopentyl | Cl | SMe | Cl | |
| 6-1058 | cyclopentyl | Cl | SMe | $SO_2Me$ | |
| 6-1059 | cyclopentyl | Cl | Me | $SO_2Et$ | |
| 6-1060 | cyclopentyl | Cl | $O(CH_2)_2OMe$ | Cl | |
| 6-1061 | cyclopentyl | Cl | $OCH_2$-cyclopropyl | Cl | |
| 6-1062 | cyclopentyl | Cl | OMe | Cl | |
| 6-1063 | cyclopentyl | Cl | NHAc | Cl | |
| 6-1064 | cyclopentyl | Cl | $OCH_2C(O)NMe_2$ | Cl | |
| 6-1065 | cyclopentyl | Cl | Cl | $SO_2Me$ | |
| 6-1066 | cyclopentyl | Cl | pyrazol-1-yl | $SO_2Me$ | |
| 6-1067 | cyclopentyl | Cl | 4-methoxypyrazol-1-yl | $SO_2Me$ | |
| 6-1068 | cyclopentyl | Cl | 1,2,3-triazol-1-yl | $SO_2Me$ | |
| 6-1069 | cyclopentyl | Cl | 1,2,3-triazol-2-yl | $SO_2Me$ | |
| 6-1070 | cyclopentyl | Cl | F | $SO_2Me$ | |
| 6-1071 | cyclopentyl | Me | $SO_2Me$ | $SO_2Me$ | |
| 6-1072 | cyclopentyl | Me | $SO_2Me$ | $CF_3$ | |
| 6-1073 | cyclopentyl | Me | $NMe_2$ | $SO_2Me$ | |
| 6-1074 | cyclopentyl | Me | S(O)Me | $CF_3$ | |
| 6-1075 | cyclopentyl | Me | SMe | $CF_3$ | |
| 6-1076 | cyclopentyl | Me | $SO_2CH_2CH_2OMe$ | $CF_3$ | |
| 6-1077 | cyclopentyl | Me | pyrazol-1-yl | $SO_2Me$ | |
| 6-1078 | cyclopentyl | Me | 4-methoxypyrazol-1-yl | $SO_2Me$ | |
| 6-1079 | cyclopentyl | Me | 1,2,3-triazol-1-yl | $SO_2Me$ | |
| 6-1080 | cyclopentyl | Me | 1,2,3-triazol-2-yl | $SO_2Me$ | |
| 6-1081 | cyclopentyl | Me | Cl | $SO_2Me$ | |
| 6-1082 | cyclopentyl | Me | Me | $SO_2Me$ | |
| 6-1083 | cyclopentyl | Me | Me | SMe | |
| 6-1084 | cyclopentyl | Me | $SO_2Me$ | Cl | |
| 6-1085 | cyclopentyl | Me | $NMe_2$ | $SO_2Me$ | |
| 6-1086 | cyclopentyl | Me | $NH(CH_2)_2OMe$ | $SO_2Me$ | |
| 6-1087 | cyclopentyl | $CF_3$ | F | $SO_2CH_3$ | |
| 6-1088 | cyclopentyl | $CF_3$ | SMe | $SO_2CH_3$ | |
| 6-1089 | cyclopentyl | $CF_3$ | SEt | $SO_2CH_3$ | |
| 6-1090 | cyclopentyl | $CF_3$ | S(O)Et | $SO_2CH_3$ | |
| 6-1091 | cyclopentyl | $CF_3$ | $SO_2CH_3$ | $SO_2CH_3$ | |
| 6-1092 | cyclopentyl | $CF_3$ | $OCH_2CH_2OMe$ | $SO_2CH_3$ | |
| 6-1093 | cyclopentyl | $CF_3$ | $OCH_2(CO)NMe_2$ | $SO2Me$ | |
| 6-1094 | cyclopentyl | $CF_3$ | $CH_2O$-tetrahydrofuran-2-yl | $SO_2Et$ | |
| 6-1095 | cyclopentyl | SMe | SMe | F | |
| 6-1096 | cyclopentyl | SMe | SEt | F | |
| 6-1097 | cyclopentyl | $SO_2CH_3$ | F | Cl | |
| 6-1098 | cyclopentyl | F | S(O)Me | $CF_3$ | |
| 6-1099 | cyclopentyl | F | SMe | $CF_3$ | |
| 6-1100 | $Me_2N$ | $NO_2$ | H | $SO_2Me$ | |
| 6-1101 | $Me_2N$ | Cl | H | $SO_2Me$ | |
| 6-1102 | $Me_2N$ | $SO_2Me$ | H | $CF_3$ | |
| 6-1103 | $Me_2N$ | $NO_2$ | H | OMe | |
| 6-1104 | $Me_2N$ | $NO_2$ | H | Br | |
| 6-1105 | $Me_2N$ | $NO_2$ | H | $CF_3$ | |
| 6-1106 | $Me_2N$ | $NO_2$ | H | $NO_2$ | |
| 6-1107 | $Me_2N$ | $NO_2$ | H | Cl | |
| 6-1108 | $Me_2N$ | $NO_2$ | H | Me | |
| 6-1109 | $Me_2N$ | $NO_2$ | H | F | |
| 6-1110 | $Me_2N$ | OMe | H | $SO_2Me$ | |
| 6-1111 | $Me_2N$ | $CF_3$ | H | $NO_2$ | |

TABLE 6-continued

Compounds of the general formula (I) in which A represents CY, V represents hydrogen, W represents fluorine

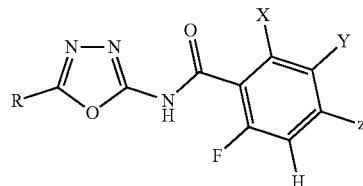

| No. | R | X | Y | Z | Physical data |
|---|---|---|---|---|---|
| 6-1112 | Me₂N | CH₂SO₂Me | H | Br | |
| 6-1113 | Me₂N | Cl | CH₂OCH₂CF₃ | SO₂Me | |
| 6-1114 | Me₂N | Cl | CH₂OCH₂CF₃ | SMe | |
| 6-1115 | Me₂N | Cl | 5-cyanomethyl-4,5-dihydro-1,2-oxazol-3-yl | SO₂Et | |
| 6-1116 | Me₂N | Cl | 4,5-dihydro-1,2-oxazol-3-yl | SO₂Et | |
| 6-1117 | Me₂N | Cl | CH₂OCH₂-tetrahydrofuran-2-yl | SO₂Me | |
| 6-1118 | Me₂N | Cl | SMe | Cl | |
| 6-1119 | Me₂N | Cl | SMe | SO₂Me | |
| 6-1120 | Me₂N | Cl | Me | SO₂Et | |
| 6-1121 | Me₂N | Cl | O(CH₂)₂OMe | Cl | |
| 6-1122 | Me₂N | Cl | OCH₂-cyclopropyl | Cl | |
| 6-1123 | Me₂N | Cl | OMe | Cl | |
| 6-1124 | Me₂N | Cl | NHAc | Cl | |
| 6-1125 | Me₂N | Cl | OCH₂C(O)NMe₂ | Cl | |
| 6-1126 | Me₂N | Cl | Cl | SO₂Me | |
| 6-1127 | Me₂N | Cl | pyrazol-1-yl | SO₂Me | |
| 6-1128 | Me₂N | Cl | 4-methoxypyrazol-1-yl | SO₂Me | |
| 6-1129 | Me₂N | Cl | 1,2,3-triazol-1-yl | SO₂Me | |
| 6-1130 | Me₂N | Cl | 1,2,3-triazol-2-yl | SO₂Me | |
| 6-1131 | Me₂N | Cl | F | SO₂Me | |
| 6-1132 | Me₂N | Me | SO₂Me | SO₂Me | |
| 6-1133 | Me₂N | Me | SO₂Me | CF₃ | |
| 6-1134 | Me₂N | Me | NMe₂ | SO₂Me | |
| 6-1135 | Me₂N | Me | S(O)Me | CF₃ | |
| 6-1136 | Me₂N | Me | SMe | CF₃ | |
| 6-1137 | Me₂N | Me | SO₂CH₂CH₂OMe | CF₃ | |
| 6-1138 | Me₂N | Me | pyrazol-1-yl | SO₂Me | |
| 6-1139 | Me₂N | Me | 4-methoxypyrazol-1-yl | SO₂Me | |
| 6-1140 | Me₂N | Me | 1,2,3-triazol-1-yl | SO₂Me | |
| 6-1141 | Me₂N | Me | 1,2,3-triazol-2-yl | SO₂Me | |
| 6-1142 | Me₂N | Me | Cl | SO₂Me | |
| 6-1143 | Me₂N | Me | Me | SO₂Me | |
| 6-1144 | Me₂N | Me | Me | SMe | |
| 6-1145 | Me₂N | Me | SO₂Me | Cl | |
| 6-1146 | Me₂N | Me | NMe₂ | SO₂Me | |
| 6-1147 | Me₂N | Me | NH(CH₂)₂OMe | SO₂Me | |
| 6-1148 | Me₂N | CF₃ | F | SO₂CH₃ | |
| 6-1149 | Me₂N | CF₃ | SMe | SO₂CH₃ | |
| 6-1150 | Me₂N | CF₃ | SEt | SO₂CH₃ | |
| 6-1151 | Me₂N | CF₃ | S(O)Et | SO₂CH₃ | |
| 6-1152 | Me₂N | CF₃ | SO₂CH₃ | SO₂CH₃ | |
| 6-1153 | Me₂N | CF₃ | OCH₂CH₂OMe | SO₂CH₃ | |
| 6-1154 | Me₂N | CF₃ | OCH₂(CO)NMe₂ | SO2Me | |
| 6-1155 | Me₂N | CF₃ | CH₂O-tetrahydrofuran-2-yl | SO₂Et | |
| 6-1156 | Me₂N | SMe | SMe | F | |
| 6-1157 | Me₂N | SMe | SEt | F | |
| 6-1158 | Me₂N | SO₂CH₃ | F | Cl | |
| 6-1159 | Me₂N | F | S(O)Me | CF₃ | |
| 6-1160 | Me₂N | F | SMe | CF₃ | |
| 6-1161 | Ph—NH | NO₂ | H | SO₂Me | |
| 6-1162 | Ph—NH | Cl | H | SO₂Me | |
| 6-1163 | Ph—NH | SO₂Me | H | CF₃ | |
| 6-1164 | Ph—NH | NO₂ | H | OMe | |
| 6-1165 | Ph—NH | NO₂ | H | Br | |
| 6-1166 | Ph—NH | NO₂ | H | CF₃ | |
| 6-1167 | Ph—NH | NO₂ | H | NO₂ | |
| 6-1168 | Ph—NH | NO₂ | H | Cl | |
| 6-1169 | Ph—NH | NO₂ | H | Me | |
| 6-1170 | Ph—NH | NO₂ | H | F | |
| 6-1171 | Ph—NH | OMe | H | SO₂Me | |
| 6-1172 | Ph—NH | CF₃ | H | NO₂ | |

TABLE 6-continued

Compounds of the general formula (I) in which A represents CY, V represents hydrogen, W represents fluorine

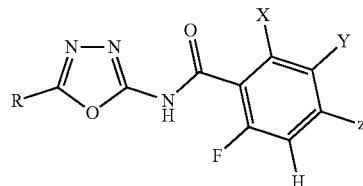

| No. | R | X | Y | Z | Physical data |
|---|---|---|---|---|---|
| 6-1173 | Ph—NH | CH$_2$SO$_2$Me | H | Br | |
| 6-1174 | Ph—NH | Cl | CH$_2$OCH$_2$CF$_3$ | SO$_2$Me | |
| 6-1175 | Ph—NH | Cl | CH$_2$OCH$_2$CF$_3$ | SMe | |
| 6-1176 | Ph—NH | Cl | 5-cyanomethyl-4,5-dihydro-1,2-oxazol-3-yl | SO$_2$Et | |
| 6-1177 | Ph—NH | Cl | 4,5-dihydro-1,2-oxazol-3-yl | SO$_2$Et | |
| 6-1178 | Ph—NH | Cl | CH$_2$OCH$_2$-tetrahydrofuran-2-yl | SO$_2$Me | |
| 6-1179 | Ph—NH | Cl | SMe | Cl | |
| 6-1180 | Ph—NH | Cl | SMe | SO$_2$Me | |
| 6-1181 | Ph—NH | Cl | Me | SO$_2$Et | |
| 6-1182 | Ph—NH | Cl | O(CH$_2$)$_2$OMe | Cl | |
| 6-1183 | Ph—NH | Cl | OCH$_2$-cyclopropyl | Cl | |
| 6-1184 | Ph—NH | Cl | OMe | Cl | |
| 6-1185 | Ph—NH | Cl | NHAc | Cl | |
| 6-1186 | Ph—NH | Cl | OCH$_2$C(O)NMe$_2$ | Cl | |
| 6-1187 | Ph—NH | Cl | Cl | SO$_2$Me | |
| 6-1188 | Ph—NH | Cl | pyrazol-1-yl | SO$_2$Me | |
| 6-1189 | Ph—NH | Cl | 4-methoxypyrazol-1-yl | SO$_2$Me | |
| 6-1190 | Ph—NH | Cl | 1,2,3-triazol-1-yl | SO$_2$Me | |
| 6-1191 | Ph—NH | Cl | 1,2,3-triazol-2-yl | SO$_2$Me | |
| 6-1192 | Ph—NH | Cl | F | SO$_2$Me | |
| 6-1193 | Ph—NH | Me | SO$_2$Me | SO$_2$Me | |
| 6-1194 | Ph—NH | Me | SO$_2$Me | CF$_3$ | |
| 6-1195 | Ph—NH | Me | NMe$_2$ | SO$_2$Me | |
| 6-1196 | Ph—NH | Me | S(O)Me | CF$_3$ | |
| 6-1197 | Ph—NH | Me | SMe | CF$_3$ | |
| 6-1198 | Ph—NH | Me | SO$_2$CH$_2$CH$_2$OMe | CF$_3$ | |
| 6-1199 | Ph—NH | Me | pyrazol-1-yl | SO$_2$Me | |
| 6-1200 | Ph—NH | Me | 4-methoxypyrazol-1-yl | SO$_2$Me | |
| 6-1201 | Ph—NH | Me | 1,2,3-triazol-1-yl | SO$_2$Me | |
| 6-1202 | Ph—NH | Me | 1,2,3-triazol-2-yl | SO$_2$Me | |
| 6-1203 | Ph—NH | Me | Cl | SO$_2$Me | |
| 6-1204 | Ph—NH | Me | Me | SO$_2$Me | |
| 6-1205 | Ph—NH | Me | Me | SMe | |
| 6-1206 | Ph—NH | Me | SO$_2$Me | Cl | |
| 6-1207 | Ph—NH | Me | NMe$_2$ | SO$_2$Me | |
| 6-1208 | Ph—NH | Me | NH(CH$_2$)$_2$OMe | SO$_2$Me | |
| 6-1209 | Ph—NH | CF$_3$ | F | SO$_2$CH$_3$ | |
| 6-1210 | Ph—NH | CF$_3$ | SMe | SO$_2$CH$_3$ | |
| 6-1211 | Ph—NH | CF$_3$ | SEt | SO$_2$CH$_3$ | |
| 6-1212 | Ph—NH | CF$_3$ | S(O)Et | SO$_2$CH$_3$ | |
| 6-1213 | Ph—NH | CF$_3$ | SO$_2$CH$_3$ | SO$_2$CH$_3$ | |
| 6-1214 | Ph—NH | CF$_3$ | OCH$_2$CH$_2$OMe | SO$_2$CH$_3$ | |
| 6-1215 | Ph—NH | CF$_3$ | OCH$_2$(CO)NMe$_2$ | SO2Me | |
| 6-1216 | Ph—NH | CF$_3$ | CH$_2$O-tetrahydrofuran-2-yl | SO$_2$Et | |
| 6-1217 | Ph—NH | SMe | SMe | F | |
| 6-1218 | Ph—NH | SMe | SEt | F | |
| 6-1219 | Ph—NH | SO$_2$CH$_3$ | F | Cl | |
| 6-1220 | Ph—NH | F | S(O)Me | CF$_3$ | |
| 6-1221 | Ph—NH | F | SMe | CF$_3$ | |
| 6-1222 | morpholin-1-yl | NO$_2$ | H | SO$_2$Me | |
| 6-1223 | morpholin-1-yl | Cl | H | SO$_2$Me | |
| 6-1224 | morpholin-1-yl | SO$_2$Me | H | CF$_3$ | |
| 6-1225 | morpholin-1-yl | NO$_2$ | H | OMe | |
| 6-1226 | morpholin-1-yl | NO$_2$ | H | Br | |
| 6-1227 | morpholin-1-yl | NO$_2$ | H | CF$_3$ | |
| 6-1228 | morpholin-1-yl | NO$_2$ | H | NO$_2$ | |
| 6-1229 | morpholin-1-yl | NO$_2$ | H | Cl | |
| 6-1230 | morpholin-1-yl | NO$_2$ | H | Me | |
| 6-1231 | morpholin-1-yl | NO$_2$ | H | F | |
| 6-1232 | morpholin-1-yl | OMe | H | SO$_2$Me | |
| 6-1233 | morpholin-1-yl | CF$_3$ | H | NO$_2$ | |
| 6-1234 | morpholin-1-yl | CH$_2$SO$_2$Me | H | Br | |

TABLE 6-continued

Compounds of the general formula (I) in which A represents CY, V represents hydrogen, W represents fluorine

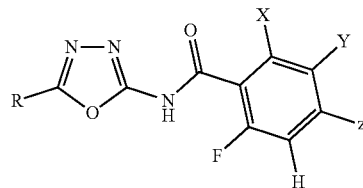

| No. | R | X | Y | Z | Physical data |
|---|---|---|---|---|---|
| 6-1235 | morpholin-1-yl | Cl | CH$_2$OCH$_2$CF$_3$ | SO$_2$Me | |
| 6-1236 | morpholin-1-yl | Cl | CH$_2$OCH$_2$CF$_3$ | SMe | |
| 6-1237 | morpholin-1-yl | Cl | 5-cyanomethyl-4,5-dihydro-1,2-oxazol-3-yl | SO$_2$Et | |
| 6-1238 | morpholin-1-yl | Cl | 4,5-dihydro-1,2-oxazol-3-yl | SO$_2$Et | |
| 6-1239 | morpholin-1-yl | Cl | CH$_2$OCH$_2$-tetrahydrofuran-2-yl | SO$_2$Me | |
| 6-1240 | morpholin-1-yl | Cl | SMe | Cl | |
| 6-1241 | morpholin-1-yl | Cl | SMe | SO$_2$Me | |
| 6-1242 | morpholin-1-yl | Cl | Me | SO$_2$Et | |
| 6-1243 | morpholin-1-yl | Cl | O(CH$_2$)$_2$OMe | Cl | |
| 6-1244 | morpholin-1-yl | Cl | OCH$_2$-cyclopropyl | Cl | |
| 6-1245 | morpholin-1-yl | Cl | OMe | Cl | |
| 6-1246 | morpholin-1-yl | Cl | NHAc | Cl | |
| 6-1247 | morpholin-1-yl | Cl | OCH$_2$C(O)NMe$_2$ | Cl | |
| 6-1248 | morpholin-1-yl | Cl | Cl | SO$_2$Me | |
| 6-1249 | morpholin-1-yl | Cl | pyrazol-1-yl | SO$_2$Me | |
| 6-1250 | morpholin-1-yl | Cl | 4-methoxypyrazol-1-yl | SO$_2$Me | |
| 6-1251 | morpholin-1-yl | Cl | 1,2,3-triazol-1-yl | SO$_2$Me | |
| 6-1252 | morpholin-1-yl | Cl | 1,2,3-triazol-2-yl | SO$_2$Me | |
| 6-1253 | morpholin-1-yl | Cl | F | SO$_2$Me | |
| 6-1254 | morpholin-1-yl | Me | SO$_2$Me | SO$_2$Me | |
| 6-1255 | morpholin-1-yl | Me | SO$_2$Me | CF$_3$ | |
| 6-1256 | morpholin-1-yl | Me | NMe$_2$ | SO$_2$Me | |
| 6-1257 | morpholin-1-yl | Me | S(O)Me | CF$_3$ | |
| 6-1258 | morpholin-1-yl | Me | SMe | CF$_3$ | |
| 6-1259 | morpholin-1-yl | Me | SO$_2$CH$_2$CH$_2$OMe | CF$_3$ | |
| 6-1260 | morpholin-1-yl | Me | pyrazol-1-yl | SO$_2$Me | |
| 6-1261 | morpholin-1-yl | Me | 4-methoxypyrazol-1-yl | SO$_2$Me | |
| 6-1262 | morpholin-1-yl | Me | 1,2,3-triazol-1-yl | SO$_2$Me | |
| 6-1263 | morpholin-1-yl | Me | 1,2,3-triazol-2-yl | SO$_2$Me | |
| 6-1264 | morpholin-1-yl | Me | Cl | SO$_2$Me | |
| 6-1265 | morpholin-1-yl | Me | Me | SO$_2$Me | |
| 6-1266 | morpholin-1-yl | Me | Me | SMe | |
| 6-1267 | morpholin-1-yl | Me | SO$_2$Me | Cl | |
| 6-1268 | morpholin-1-yl | Me | NMe$_2$ | SO$_2$Me | |
| 6-1269 | morpholin-1-yl | Me | NH(CH$_2$)$_2$OMe | SO$_2$Me | |
| 6-1270 | morpholin-1-yl | CF$_3$ | F | SO$_2$CH$_3$ | |
| 6-1271 | morpholin-1-yl | CF$_3$ | SMe | SO$_2$CH$_3$ | |
| 6-1272 | morpholin-1-yl | CF$_3$ | SEt | SO$_2$CH$_3$ | |
| 6-1273 | morpholin-1-yl | CF$_3$ | S(O)Et | SO$_2$CH$_3$ | |
| 6-1274 | morpholin-1-yl | CF$_3$ | SO$_2$CH$_3$ | SO$_2$CH$_3$ | |
| 6-1275 | morpholin-1-yl | CF$_3$ | OCH$_2$CH$_2$OMe | SO$_2$CH$_3$ | |
| 6-1276 | morpholin-1-yl | CF$_3$ | OCH$_2$(CO)NMe$_2$ | SO2Me | |
| 6-1277 | morpholin-1-yl | CF$_3$ | CH$_2$O-tetrahydrofuran-2-yl | SO$_2$Et | |
| 6-1278 | morpholin-1-yl | SMe | SMe | F | |
| 6-1279 | morpholin-1-yl | SMe | SEt | F | |
| 6-1280 | morpholin-1-yl | SO$_2$CH$_3$ | F | Cl | |
| 6-1281 | morpholin-1-yl | F | S(O)Me | CF$_3$ | |
| 6-1282 | morpholin-1-yl | F | SMe | CF$_3$ | |
| 6-1283 | sec-Bu | NO$_2$ | H | SO$_2$Me | |
| 6-1284 | sec-Bu | Cl | H | SO$_2$Me | |
| 6-1285 | sec-Bu | SO$_2$Me | H | CF$_3$ | |
| 6-1286 | sec-Bu | NO$_2$ | H | OMe | |
| 6-1287 | sec-Bu | NO$_2$ | H | Br | |
| 6-1288 | sec-Bu | NO$_2$ | H | CF$_3$ | |
| 6-1289 | sec-Bu | NO$_2$ | H | NO$_2$ | |
| 6-1290 | sec-Bu | NO$_2$ | H | Cl | |
| 6-1291 | sec-Bu | NO$_2$ | H | Me | |
| 6-1292 | sec-Bu | NO$_2$ | H | F | |
| 6-1293 | sec-Bu | OMe | H | SO$_2$Me | |
| 6-1294 | sec-Bu | CF$_3$ | H | NO$_2$ | |
| 6-1295 | sec-Bu | CH$_2$SO$_2$Me | H | Br | |
| 6-1296 | sec-Bu | Cl | CH$_2$OCH$_2$CF$_3$ | SO$_2$Me | |

TABLE 6-continued

Compounds of the general formula (I) in which A represents CY, V represents hydrogen, W represents fluorine

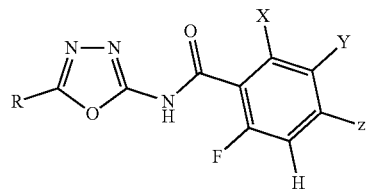

| No. | R | X | Y | Z | Physical data |
|---|---|---|---|---|---|
| 6-1297 | sec-Bu | Cl | $CH_2OCH_2CF_3$ | SMe | |
| 6-1298 | sec-Bu | Cl | 5-cyanomethyl-4,5-dihydro-1,2-oxazol-3-yl | $SO_2Et$ | |
| 6-1299 | sec-Bu | Cl | 4,5-dihydro-1,2-oxazol-3-yl | $SO_2Et$ | |
| 6-1300 | sec-Bu | Cl | $CH_2OCH_2$-tetrahydrofuran-2-yl | $SO_2Me$ | |
| 6-1301 | sec-Bu | Cl | SMe | Cl | |
| 6-1302 | sec-Bu | Cl | SMe | $SO_2Me$ | |
| 6-1303 | sec-Bu | Cl | Me | $SO_2Et$ | |
| 6-1304 | sec-Bu | Cl | $O(CH_2)_2OMe$ | Cl | |
| 6-1305 | sec-Bu | Cl | $OCH_2$-cyclopropyl | Cl | |
| 6-1306 | sec-Bu | Cl | OMe | Cl | |
| 6-1307 | sec-Bu | Cl | NHAc | Cl | |
| 6-1308 | sec-Bu | Cl | $OCH_2C(O)NMe_2$ | Cl | |
| 6-1309 | sec-Bu | Cl | Cl | $SO_2Me$ | |
| 6-1310 | sec-Bu | Cl | pyrazol-1-yl | $SO_2Me$ | |
| 6-1311 | sec-Bu | Cl | 4-methoxypyrazol-1-yl | $SO_2Me$ | |
| 6-1312 | sec-Bu | Cl | 1,2,3-triazol-1-yl | $SO_2Me$ | |
| 6-1313 | sec-Bu | Cl | 1,2,3-triazol-2-yl | $SO_2Me$ | |
| 6-1314 | sec-Bu | Cl | F | $SO_2Me$ | |
| 6-1315 | sec-Bu | Me | $SO_2Me$ | $SO_2Me$ | |
| 6-1316 | sec-Bu | Me | $SO_2Me$ | $CF_3$ | |
| 6-1317 | sec-Bu | Me | $NMe_2$ | $SO_2Me$ | |
| 6-1318 | sec-Bu | Me | S(O)Me | $CF_3$ | |
| 6-1319 | sec-Bu | Me | SMe | $CF_3$ | |
| 6-1320 | sec-Bu | Me | $SO_2CH_2CH_2OMe$ | $CF_3$ | |
| 6-1321 | sec-Bu | Me | pyrazol-1-yl | $SO_2Me$ | |
| 6-1322 | sec-Bu | Me | 4-methoxypyrazol-1-yl | $SO_2Me$ | |
| 6-1323 | sec-Bu | Me | 1,2,3-triazol-1-yl | $SO_2Me$ | |
| 6-1324 | sec-Bu | Me | 1,2,3-triazol-2-yl | $SO_2Me$ | |
| 6-1325 | sec-Bu | Me | Cl | $SO_2Me$ | |
| 6-1326 | sec-Bu | Me | Me | $SO_2Me$ | |
| 6-1327 | sec-Bu | Me | Me | SMe | |
| 6-1328 | sec-Bu | Me | $SO_2Me$ | Cl | |
| 6-1329 | sec-Bu | Me | $NMe_2$ | $SO_2Me$ | |
| 6-1330 | sec-Bu | Me | $NH(CH_2)_2OMe$ | $SO_2Me$ | |
| 6-1331 | sec-Bu | $CF_3$ | F | $SO_2CH_3$ | |
| 6-1332 | sec-Bu | $CF_3$ | SMe | $SO_2CH_3$ | |
| 6-1333 | sec-Bu | $CF_3$ | SEt | $SO_2CH_3$ | |
| 6-1334 | sec-Bu | $CF_3$ | S(O)Et | $SO_2CH_3$ | |
| 6-1335 | sec-Bu | $CF_3$ | $SO_2CH_3$ | $SO_2CH_3$ | |
| 6-1336 | sec-Bu | $CF_3$ | $OCH_2CH_2OMe$ | $SO_2CH_3$ | |
| 6-1337 | sec-Bu | $CF_3$ | $OCH_2(CO)NMe_2$ | $SO_2Me$ | |
| 6-1338 | sec-Bu | $CF_3$ | $CH_2O$-tetrahydrofuran-2-yl | SO2Et | |
| 6-1339 | sec-Bu | SMe | SMe | F | |
| 6-1340 | sec-Bu | SMe | SEt | F | |
| 6-1341 | sec-Bu | $SO_2CH_3$ | F | Cl | |
| 6-1342 | sec-Bu | F | S(O)Me | $CF_3$ | |
| 6-1343 | sec-Bu | F | SMe | $CF_3$ | |

TABLE 7

Compounds of the general formula (I) according to the invention in which A represents nitrogen, V represents hydrogen, W represents fluorine

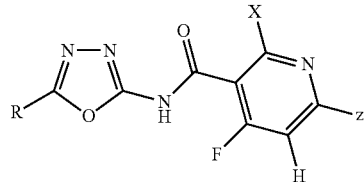

| No. | R | X | Z | Physical data ($^1$H-NMR, DMSO-$d_6$, 400 MHz) |
|---|---|---|---|---|
| 7-1 | H | Cl | CF$_3$ | |
| 7-2 | Me | Cl | CF$_3$ | |
| 7-3 | Et | Cl | CF$_3$ | |
| 7-4 | CF$_3$ | Cl | CF$_3$ | |
| 7-5 | CH$_2$OMe | Cl | CF$_3$ | |
| 7-6 | c-Pr | Cl | CF$_3$ | |
| 7-7 | CO$_2$Et | Cl | CF$_3$ | |
| 7-8 | CO$_2$Me | Cl | CF$_3$ | |
| 7-9 | benzyl | Cl | CF$_3$ | |
| 7-10 | phenyl | Cl | CF$_3$ | |
| 7-11 | pyrazin-2-yl | Cl | CF$_3$ | |
| 7-12 | 4-OMe—Ph | Cl | CF$_3$ | |
| 7-13 | 4-Cl—Ph | Cl | CF$_3$ | |
| 7-14 | t-Bu | Cl | CF$_3$ | |
| 7-15 | furan-2-yl | Cl | CF$_3$ | |
| 7-16 | i-Pr | Cl | CF$_3$ | |
| 7-17 | CH$_2$CH$_2$OMe | Cl | CF$_3$ | |
| 7-18 | CH$_2$CF$_3$ | Cl | CF$_3$ | |
| 7-19 | tetrahydrofuran-2-yl | Cl | CF$_3$ | |
| 7-20 | n-Pr | Cl | CF$_3$ | |
| 7-21 | CH$_2$OEt | Cl | CF$_3$ | |
| 7-22 | cyclobutyl | Cl | CF$_3$ | |
| 7-23 | cyclopentyl | Cl | CF$_3$ | |
| 7-24 | Me$_2$N | Cl | CF$_3$ | |
| 7-25 | Ph—NH | Cl | CF$_3$ | |
| 7-26 | morpholin-1-yl | Cl | CF$_3$ | |
| 7-27 | H | Cl | Cl | |
| 7-28 | Me | Cl | Cl | |
| 7-29 | Et | Cl | Cl | |
| 7-30 | CF$_3$ | Cl | Cl | |
| 7-31 | CH$_2$OMe | Cl | Cl | |
| 7-32 | c-Pr | Cl | Cl | |
| 7-33 | CO$_2$Et | Cl | Cl | |
| 7-34 | CO$_2$Me | Cl | Cl | |
| 7-35 | benzyl | Cl | Cl | |
| 7-36 | phenyl | Cl | Cl | |
| 7-37 | pyrazin-2-yl | Cl | Cl | |
| 7-38 | 4-OMe—Ph | Cl | Cl | |
| 7-39 | 4-Cl—Ph | Cl | Cl | |
| 7-40 | t-Bu | Cl | Cl | |
| 7-41 | furan-2-yl | Cl | Cl | |
| 7-42 | i-Pr | Cl | Cl | |
| 7-43 | CH$_2$CH$_2$OMe | Cl | Cl | |
| 7-44 | CH$_2$CF$_3$ | Cl | Cl | |
| 7-45 | tetrahydrofuran-2-yl | Cl | Cl | |
| 7-46 | n-Pr | Cl | Cl | |
| 7-47 | CH$_2$OEt | Cl | Cl | |
| 7-48 | cyclobutyl | Cl | Cl | |
| 7-49 | cyclopentyl | Cl | Cl | |
| 7-50 | Me$_2$N | Cl | Cl | |
| 7-51 | Ph—NH | Cl | Cl | |
| 7-52 | morpholin-1-yl | Cl | Cl | |
| 7-53 | H | Me | Cl | |
| 7-54 | Me | Me | Cl | |
| 7-55 | Et | Me | Cl | |
| 7-56 | CF$_3$ | Me | Cl | |
| 7-57 | CH$_2$OMe | Me | Cl | |
| 7-58 | c-Pr | Me | Cl | |
| 7-59 | CO$_2$Et | Me | Cl | |
| 7-60 | CO$_2$Me | Me | Cl | |

TABLE 7-continued

Compounds of the general formula (I) according to the invention in which A represents nitrogen, V represents hydrogen, W represents fluorine

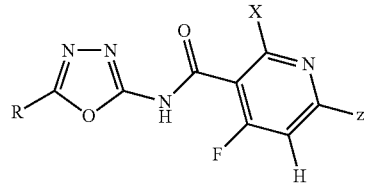

| No. | R | X | Z | Physical data ($^1$H-NMR, DMSO-$d_6$, 400 MHz) |
|---|---|---|---|---|
| 7-61 | benzyl | Me | Cl | |
| 7-62 | phenyl | Me | Cl | |
| 7-63 | pyrazin-2-yl | Me | Cl | |
| 7-64 | 4-OMe—Ph | Me | Cl | |
| 7-65 | 4-Cl—Ph | Me | Cl | |
| 7-66 | t-Bu | Me | Cl | |
| 7-67 | furan-2-yl | Me | Cl | |
| 7-68 | i-Pr | Me | Cl | |
| 7-69 | CH$_2$CH$_2$OMe | Me | Cl | |
| 7-70 | CH$_2$CF$_3$ | Me | Cl | |
| 7-71 | tetrahydrofuran-2-yl | Me | Cl | |
| 7-72 | n-Pr | Me | Cl | |
| 7-73 | CH$_2$OEt | Me | Cl | |
| 7-74 | cyclobutyl | Me | Cl | |
| 7-75 | cyclopentyl | Me | Cl | |
| 7-76 | Me$_2$N | Me | Cl | |
| 7-77 | Ph—NH | Me | Cl | |
| 7-78 | morpholin-1-yl | Me | Cl | |
| 7-79 | H | Cl | SMe | |
| 7-80 | Me | Cl | SMe | |
| 7-81 | Et | Cl | SMe | |
| 7-82 | CF$_3$ | Cl | SMe | |
| 7-83 | CH$_2$OMe | Cl | SMe | |
| 7-84 | c-Pr | Cl | SMe | |
| 7-85 | CO$_2$Et | Cl | SMe | |
| 7-86 | CO$_2$Me | Cl | SMe | |
| 7-87 | benzyl | Cl | SMe | |
| 7-88 | phenyl | Cl | SMe | |
| 7-89 | pyrazin-2-yl | Cl | SMe | |
| 7-90 | 4-OMe—Ph | Cl | SMe | |
| 7-91 | 4-Cl—Ph | Cl | SMe | |
| 7-92 | t-Bu | Cl | SMe | |
| 7-93 | furan-2-yl | Cl | SMe | |
| 7-94 | i-Pr | Cl | SMe | |
| 7-95 | CH$_2$CH$_2$OMe | Cl | SMe | |
| 7-96 | CH$_2$CF$_3$ | Cl | SMe | |
| 7-97 | tetrahydrofuran-2-yl | Cl | SMe | |
| 7-98 | n-Pr | Cl | SMe | |
| 7-99 | CH$_2$OEt | Cl | SMe | |
| 7-100 | cyclobutyl | Cl | SMe | |
| 7-101 | cyclopentyl | Cl | SMe | |
| 7-102 | Me$_2$N | Cl | SMe | |
| 7-103 | Ph—NH | Cl | SMe | |
| 7-104 | morpholin-1-yl | Cl | SMe | |
| 7-105 | H | Cl | SO$_2$Me | |
| 7-106 | Me | Cl | SO$_2$Me | |
| 7-107 | Et | Cl | SO$_2$Me | |
| 7-108 | CF$_3$ | Cl | SO$_2$Me | |
| 7-109 | CH$_2$OMe | Cl | SO$_2$Me | |
| 7-110 | c-Pr | Cl | SO$_2$Me | |
| 7-111 | CO$_2$Et | Cl | SO$_2$Me | |
| 7-112 | CO$_2$Me | Cl | SO$_2$Me | |
| 7-113 | benzyl | Cl | SO$_2$Me | |
| 7-114 | phenyl | Cl | SO$_2$Me | |
| 7-115 | pyrazin-2-yl | Cl | SO$_2$Me | |
| 7-116 | 4-OMe—Ph | Cl | SO$_2$Me | |
| 7-117 | 4-Cl—Ph | Cl | SO$_2$Me | |
| 7-118 | t-Bu | Cl | SO$_2$Me | |
| 7-119 | furan-2-yl | Cl | SO$_2$Me | |
| 7-120 | i-Pr | Cl | SO$_2$Me | |

TABLE 7-continued

Compounds of the general formula (I) according to the invention in which A represents nitrogen, V represents hydrogen, W represents fluorine

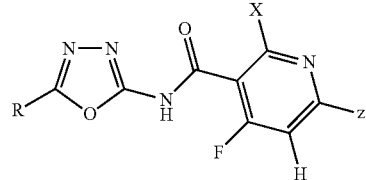
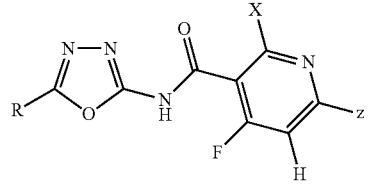

| No. | R | X | Z | Physical data ($^1$H-NMR, DMSO-$d_6$, 400 MHz) |
|---|---|---|---|---|
| 7-121 | CH$_2$CH$_2$OMe | Cl | SO$_2$Me | |
| 7-122 | CH$_2$CF$_3$ | Cl | SO$_2$Me | |
| 7-123 | tetrahydrofuran-2-yl | Cl | SO$_2$Me | |
| 7-124 | n-Pr | Cl | SO$_2$Me | |
| 7-125 | CH$_2$OEt | Cl | SO$_2$Me | |
| 7-126 | cyclobutyl | Cl | SO$_2$Me | |
| 7-127 | cyclopentyl | Cl | SO$_2$Me | |
| 7-128 | Me$_2$N | Cl | SO$_2$Me | |
| 7-129 | Ph—NH | Cl | SO$_2$Me | |
| 7-130 | morpholin-1-yl | Cl | SO$_2$Me | |
| 7-131 | H | Me | CF$_3$ | |
| 7-132 | Me | Me | CF$_3$ | |
| 7-133 | Et | Me | CF$_3$ | |
| 7-134 | CF$_3$ | Me | CF$_3$ | |
| 7-135 | CH$_2$OMe | Me | CF$_3$ | |
| 7-136 | c-Pr | Me | CF$_3$ | |
| 7-137 | CO$_2$Et | Me | CF$_3$ | |
| 7-138 | CO$_2$Me | Me | CF$_3$ | |
| 7-139 | benzyl | Me | CF$_3$ | |
| 7-140 | phenyl | Me | CF$_3$ | |
| 7-141 | pyrazin-2-yl | Me | CF$_3$ | |
| 7-142 | 4-OMe—Ph | Me | CF$_3$ | |
| 7-143 | 4-Cl—Ph | Me | CF$_3$ | |
| 7-144 | t-Bu | Me | CF$_3$ | |
| 7-145 | furan-2-yl | Me | CF$_3$ | |
| 7-146 | i-Pr | Me | CF$_3$ | |
| 7-147 | CH$_2$CH$_2$OMe | Me | CF$_3$ | |
| 7-148 | CH$_2$CF$_3$ | Me | CF$_3$ | |
| 7-149 | tetrahydrofuran-2-yl | Me | CF$_3$ | |
| 7-150 | n-Pr | Me | CF$_3$ | |
| 7-151 | CH$_2$OEt | Me | CF$_3$ | |
| 7-152 | cyclobutyl | Me | CF$_3$ | |
| 7-153 | cyclopentyl | Me | CF$_3$ | |
| 7-154 | Me$_2$N | Me | CF$_3$ | |
| 7-155 | Ph—NH | Me | CF$_3$ | |
| 7-156 | morpholin-1-yl | Me | CF$_3$ | |
| 7-157 | H | CH$_2$OMe | CF$_3$ | |
| 7-158 | Me | CH$_2$OMe | CF$_3$ | |
| 7-159 | Et | CH$_2$OMe | CF$_3$ | |
| 7-160 | CF$_3$ | CH$_2$OMe | CF$_3$ | |
| 7-161 | CH$_2$OMe | CH$_2$OMe | CF$_3$ | |
| 7-162 | c-Pr | CH$_2$OMe | CF$_3$ | |
| 7-163 | CO$_2$Et | CH$_2$OMe | CF$_3$ | |
| 7-164 | CO$_2$Me | CH$_2$OMe | CF$_3$ | |
| 7-165 | benzyl | CH$_2$OMe | CF$_3$ | |
| 7-166 | phenyl | CH$_2$OMe | CF$_3$ | |
| 7-167 | pyrazin-2-yl | CH$_2$OMe | CF$_3$ | |
| 7-168 | 4-OMe—Ph | CH$_2$OMe | CF$_3$ | |
| 7-169 | 4-Cl—Ph | CH$_2$OMe | CF$_3$ | |
| 7-170 | t-Bu | CH$_2$OMe | CF$_3$ | |
| 7-171 | furan-2-yl | CH$_2$OMe | CF$_3$ | |
| 7-172 | i-Pr | CH$_2$OMe | CF$_3$ | |
| 7-173 | CH$_2$CH$_2$OMe | CH$_2$OMe | CF$_3$ | |
| 7-174 | CH$_2$CF$_3$ | CH$_2$OMe | CF$_3$ | |
| 7-175 | tetrahydrofuran-2-yl | CH$_2$OMe | CF$_3$ | |
| 7-176 | n-Pr | CH$_2$OMe | CF$_3$ | |
| 7-177 | CH$_2$OEt | CH$_2$OMe | CF$_3$ | |
| 7-178 | cyclobutyl | CH$_2$OMe | CF$_3$ | |
| 7-179 | cyclopentyl | CH$_2$OMe | CF$_3$ | |
| 7-180 | Me$_2$N | CH$_2$OMe | CF$_3$ | |
| 7-181 | Ph—NH | CH$_2$OMe | CF$_3$ | |
| 7-182 | morpholin-1-yl | CH$_2$OMe | CF$_3$ | |
| 7-183 | H | CH$_2$SMe | CF$_3$ | |
| 7-184 | Me | CH$_2$SMe | CF$_3$ | |
| 7-185 | Et | CH$_2$SMe | CF$_3$ | |
| 7-186 | CF$_3$ | CH$_2$SMe | CF$_3$ | |
| 7-187 | CH$_2$OMe | CH$_2$SMe | CF$_3$ | |
| 7-188 | c-Pr | CH$_2$SMe | CF$_3$ | |
| 7-189 | CO$_2$Et | CH$_2$SMe | CF$_3$ | |
| 7-190 | CO$_2$Me | CH$_2$SMe | CF$_3$ | |
| 7-191 | benzyl | CH$_2$SMe | CF$_3$ | |
| 7-192 | phenyl | CH$_2$SMe | CF$_3$ | |
| 7-193 | pyrazin-2-yl | CH$_2$SMe | CF$_3$ | |
| 7-194 | 4-OMe—Ph | CH$_2$SMe | CF$_3$ | |
| 7-195 | 4-Cl—Ph | CH$_2$SMe | CF$_3$ | |
| 7-196 | t-Bu | CH$_2$SMe | CF$_3$ | |
| 7-197 | furan-2-yl | CH$_2$SMe | CF$_3$ | |
| 7-198 | i-Pr | CH$_2$SMe | CF$_3$ | |
| 7-199 | CH$_2$CH$_2$OMe | CH$_2$SMe | CF$_3$ | |
| 7-200 | CH$_2$CF$_3$ | CH$_2$SMe | CF$_3$ | |
| 7-201 | tetrahydrofuran-2-yl | CH$_2$SMe | CF$_3$ | |
| 7-202 | n-Pr | CH$_2$SMe | CF$_3$ | |
| 7-203 | CH$_2$OEt | CH$_2$SMe | CF$_3$ | |
| 7-204 | cyclobutyl | CH$_2$SMe | CF$_3$ | |
| 7-205 | cyclopentyl | CH$_2$SMe | CF$_3$ | |
| 7-206 | Me$_2$N | CH$_2$SMe | CF$_3$ | |
| 7-207 | Ph—NH | CH$_2$SMe | CF$_3$ | |
| 7-208 | morpholin-1-yl | CH$_2$SMe | CF$_3$ | |
| 7-209 | H | CH$_2$SO$_2$Me | CF$_3$ | |
| 7-210 | Me | CH$_2$SO$_2$Me | CF$_3$ | |
| 7-211 | Et | CH$_2$SO$_2$Me | CF$_3$ | |
| 7-212 | CF$_3$ | CH$_2$SO$_2$Me | CF$_3$ | |
| 7-213 | CH$_2$OMe | CH$_2$SO$_2$Me | CF$_3$ | |
| 7-214 | c-Pr | CH$_2$SO$_2$Me | CF$_3$ | |
| 7-215 | CO$_2$Et | CH$_2$SO$_2$Me | CF$_3$ | |
| 7-216 | CO$_2$Me | CH$_2$SO$_2$Me | CF$_3$ | |
| 7-217 | benzyl | CH$_2$SO$_2$Me | CF$_3$ | |
| 7-218 | phenyl | CH$_2$SO$_2$Me | CF$_3$ | |
| 7-219 | pyrazin-2-yl | CH$_2$SO$_2$Me | CF$_3$ | |
| 7-220 | 4-OMe—Ph | CH$_2$SO$_2$Me | CF$_3$ | |
| 7-221 | 4-Cl—Ph | CH$_2$SO$_2$Me | CF$_3$ | |
| 7-222 | t-Bu | CH$_2$SO$_2$Me | CF$_3$ | |
| 7-223 | furan-2-yl | CH$_2$SO$_2$Me | CF$_3$ | |
| 7-224 | i-Pr | CH$_2$SO$_2$Me | CF$_3$ | |
| 7-225 | CH$_2$CH$_2$OMe | CH$_2$SO$_2$Me | CF$_3$ | |
| 7-226 | CH$_2$CF$_3$ | CH$_2$SO$_2$Me | CF$_3$ | |
| 7-227 | tetrahydrofuran-2-yl | CH$_2$SO$_2$Me | CF$_3$ | |
| 7-228 | n-Pr | CH$_2$SO$_2$Me | CF$_3$ | |
| 7-229 | CH$_2$OEt | CH$_2$SO$_2$Me | CF$_3$ | |
| 7-230 | cyclobutyl | CH$_2$SO$_2$Me | CF$_3$ | |
| 7-231 | cyclopentyl | CH$_2$SO$_2$Me | CF$_3$ | |
| 7-232 | Me$_2$N | CH$_2$SO$_2$Me | CF$_3$ | |
| 7-233 | Ph—NH | CH$_2$SO$_2$Me | CF$_3$ | |
| 7-234 | morpholin-1-yl | CH$_2$SO$_2$Me | CF$_3$ | |
| 7-235 | H | CH$_2$OC$_2$H$_4$OMe | CF$_3$ | |
| 7-236 | Me | CH$_2$OC$_2$H$_4$OMe | CF$_3$ | |
| 7-237 | Et | CH$_2$OC$_2$H$_4$OMe | CF$_3$ | |
| 7-238 | CF$_3$ | CH$_2$OC$_2$H$_4$OMe | CF$_3$ | |
| 7-239 | CH$_2$OMe | CH$_2$OC$_2$H$_4$OMe | CF$_3$ | |

TABLE 7-continued

Compounds of the general formula (I) according to the invention in which A represents nitrogen, V represents hydrogen, W represents fluorine

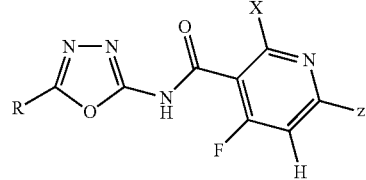

| No. | R | X | Z | Physical data ($^1$H-NMR, DMSO-$d_6$, 400 MHz) |
|---|---|---|---|---|
| 7-240 | c-Pr | CH$_2$OC$_2$H$_4$OMe | CF$_3$ | |
| 7-241 | CO$_2$Et | CH$_2$OC$_2$H$_4$OMe | CF$_3$ | |
| 7-242 | CO$_2$Me | CH$_2$OC$_2$H$_4$OMe | CF$_3$ | |
| 7-243 | benzyl | CH$_2$OC$_2$H$_4$OMe | CF$_3$ | |
| 7-244 | phenyl | CH$_2$OC$_2$H$_4$OMe | CF$_3$ | |
| 7-245 | pyrazin-2-yl | CH$_2$OC$_2$H$_4$OMe | CF$_3$ | |
| 7-246 | 4-OMe—Ph | CH$_2$OC$_2$H$_4$OMe | CF$_3$ | |
| 7-247 | 4-Cl—Ph | CH$_2$OC$_2$H$_4$OMe | CF$_3$ | |
| 7-248 | t-Bu | CH$_2$OC$_2$H$_4$OMe | CF$_3$ | |
| 7-249 | furan-2-yl | CH$_2$OC$_2$H$_4$OMe | CF$_3$ | |
| 7-250 | i-Pr | CH$_2$OC$_2$H$_4$OMe | CF$_3$ | |
| 7-251 | CH$_2$CH$_2$OMe | CH$_2$OC$_2$H$_4$OMe | CF$_3$ | |
| 7-252 | CH$_2$CF$_3$ | CH$_2$OC$_2$H$_4$OMe | CF$_3$ | |
| 7-253 | tetrahydrofuran-2-yl | CH$_2$OC$_2$H$_4$OMe | CF$_3$ | |
| 7-254 | n-Pr | CH$_2$OC$_2$H$_4$OMe | CF$_3$ | |
| 7-255 | CH$_2$OEt | CH$_2$OC$_2$H$_4$OMe | CF$_3$ | |
| 7-256 | cyclobutyl | CH$_2$OC$_2$H$_4$OMe | CF$_3$ | |
| 7-257 | cyclopentyl | CH$_2$OC$_2$H$_4$OMe | CF$_3$ | |
| 7-258 | Me$_2$N | CH$_2$OC$_2$H$_4$OMe | CF$_3$ | |
| 7-259 | Ph—NH | CH$_2$OC$_2$H$_4$OMe | CF$_3$ | |
| 7-260 | morpholin-1-yl | CH$_2$OC$_2$H$_4$OMe | CF$_3$ | |
| 7-261 | H | OCH$_2$-tetrahydrofuran-2-yl | CF$_3$ | |
| 7-262 | Me | OCH$_2$-tetrahydrofuran-2-yl | CF$_3$ | |
| 7-263 | Et | OCH$_2$-tetrahydrofuran-2-yl | CF$_3$ | |
| 7-264 | CF$_3$ | OCH$_2$-tetrahydrofuran-2-yl | CF$_3$ | |
| 7-265 | CH$_2$OMe | OCH$_2$-tetrahydrofuran-2-yl | CF$_3$ | |
| 7-266 | c-Pr | OCH$_2$-tetrahydrofuran-2-yl | CF$_3$ | |
| 7-267 | CO$_2$Et | OCH$_2$-tetrahydrofuran-2-yl | CF$_3$ | |
| 7-268 | CO$_2$Me | OCH$_2$-tetrahydrofuran-2-yl | CF$_3$ | |
| 7-269 | benzyl | OCH$_2$-tetrahydrofuran-2-yl | CF$_3$ | |
| 7-270 | phenyl | OCH$_2$-tetrahydrofuran-2-yl | CF$_3$ | |
| 7-271 | pyrazin-2-yl | OCH$_2$-tetrahydrofuran-2-yl | CF$_3$ | |
| 7-272 | 4-OMe—Ph | OCH$_2$-tetrahydrofuran-2-yl | CF$_3$ | |
| 7-273 | 4-Cl—Ph | OCH$_2$-tetrahydrofuran-2-yl | CF$_3$ | |
| 7-274 | t-Bu | OCH$_2$-tetrahydrofuran-2-yl | CF$_3$ | |
| 7-275 | furan-2-yl | OCH$_2$-tetrahydrofuran-2-yl | CF$_3$ | |
| 7-276 | i-Pr | OCH$_2$-tetrahydrofuran-2-yl | CF$_3$ | |
| 7-277 | CH$_2$CH$_2$OMe | OCH$_2$-tetrahydrofuran-2-yl | CF$_3$ | |
| 7-278 | CH$_2$CF$_3$ | OCH$_2$-tetrahydrofuran-2-yl | CF$_3$ | |
| 7-279 | tetrahydrofuran-2-yl | OCH$_2$-tetrahydrofuran-2-yl | CF$_3$ | |
| 7-280 | n-Pr | OCH$_2$-tetrahydrofuran-2-yl | CF$_3$ | |
| 7-281 | CH$_2$OEt | OCH$_2$-tetrahydrofuran-2-yl | CF$_3$ | |
| 7-282 | cyclobutyl | OCH$_2$-tetrahydrofuran-2-yl | CF$_3$ | |
| 7-283 | cyclopentyl | OCH$_2$-tetrahydrofuran-2-yl | CF$_3$ | |
| 7-284 | Me$_2$N | OCH$_2$-tetrahydrofuran-2-yl | CF$_3$ | |
| 7-285 | Ph—NH | OCH$_2$-tetrahydrofuran-2-yl | CF$_3$ | |
| 7-286 | morpholin-1-yl | OCH$_2$-tetrahydrofuran-2-yl | CF$_3$ | |
| 7-287 | H | (1,1-dioxido-1,2-thiadiazolidin-1-yl)methyl | CF$_3$ | |
| 7-288 | Me | (1,1-dioxido-1,2-thiadiazolidin-1-yl)methyl | CF$_3$ | |
| 7-289 | Et | (1,1-dioxido-1,2-thiadiazolidin-1-yl)methyl | CF$_3$ | |
| 7-290 | CF$_3$ | (1,1-dioxido-1,2-thiadiazolidin-1-yl)methyl | CF$_3$ | |
| 7-291 | CH$_2$OMe | (1,1-dioxido-1,2-thiadiazolidin-1-yl)methyl | CF$_3$ | |
| 7-292 | c-Pr | (1,1-dioxido-1,2-thiadiazolidin-1-yl)methyl | CF$_3$ | |
| 7-293 | CO$_2$Et | (1,1-dioxido-1,2-thiadiazolidin-1-yl)methyl | CF$_3$ | |

TABLE 7-continued

Compounds of the general formula (I) according to the invention in which A represents nitrogen, V represents hydrogen, W represents fluorine

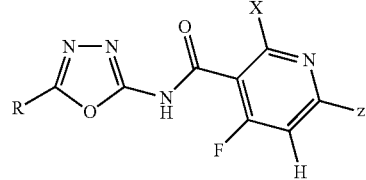

| No. | R | X | Z | Physical data ($^1$H-NMR, DMSO-$d_6$, 400 MHz) |
|---|---|---|---|---|
| 7-294 | CO$_2$Me | (1,1-dioxido-1,2-thiadiazolidin-1-yl)methyl | CF$_3$ | |
| 7-295 | benzyl | (1,1-dioxido-1,2-thiadiazolidin-1-yl)methyl | CF$_3$ | |
| 7-296 | phenyl | (1,1-dioxido-1,2-thiadiazolidin-1-yl)methyl | CF$_3$ | |
| 7-297 | pyrazin-2-yl | (1,1-dioxido-1,2-thiadiazolidin-1-yl)methyl | CF$_3$ | |
| 7-298 | 4-OMe—Ph | (1,1-dioxido-1,2-thiadiazolidin-1-yl)methyl | CF$_3$ | |
| 7-299 | 4-Cl—Ph | (1,1-dioxido-1,2-thiadiazolidin-1-yl)methyl | CF$_3$ | |
| 7-300 | t-Bu | (1,1-dioxido-1,2-thiadiazolidin-1-yl)methyl | CF$_3$ | |
| 7-301 | furan-2-yl | (1,1-dioxido-1,2-thiadiazolidin-1-yl)methyl | CF$_3$ | |
| 7-302 | i-Pr | (1,1-dioxido-1,2-thiadiazolidin-1-yl)methyl | CF$_3$ | |
| 7-303 | CH$_2$CH$_2$OMe | (1,1-dioxido-1,2-thiadiazolidin-1-yl)methyl | CF$_3$ | |
| 7-304 | CH$_2$CF$_3$ | (1,1-dioxido-1,2-thiadiazolidin-1-yl)methyl | CF$_3$ | |
| 7-305 | tetrahydrofuran-2-yl | (1,1-dioxido-1,2-thiadiazolidin-1-yl)methyl | CF$_3$ | |
| 7-306 | n-Pr | (1,1-dioxido-1,2-thiadiazolidin-1-yl)methyl | CF$_3$ | |
| 7-307 | CH$_2$OEt | (1,1-dioxido-1,2-thiadiazolidin-1-yl)methyl | CF$_3$ | |
| 7-308 | cyclobutyl | (1,1-dioxido-1,2-thiadiazolidin-1-yl)methyl | CF$_3$ | |
| 7-309 | cyclopentyl | (1,1-dioxido-1,2-thiadiazolidin-1-yl)methyl | CF$_3$ | |
| 7-310 | Me$_2$N | (1,1-dioxido-1,2-thiadiazolidin-1-yl)methyl | CF$_3$ | |
| 7-311 | Ph—NH | (1,1-dioxido-1,2-thiadiazolidin-1-yl)methyl | CF$_3$ | |
| 7-312 | morpholin-1-yl | (1,1-dioxido-1,2-thiadiazolidin-1-yl)methyl | CF$_3$ | |
| 7-313 | H | (3-methyl-2-oxoimidazolidin-1-yl)methyl | CF$_3$ | |
| 7-314 | Me | (3-methyl-2-oxoimidazolidin-1-yl)methyl | CF$_3$ | |
| 7-315 | Et | (3-methyl-2-oxoimidazolidin-1-yl)methyl | CF$_3$ | |
| 7-316 | CF$_3$ | (3-methyl-2-oxoimidazolidin-1-yl)methyl | CF$_3$ | |
| 7-317 | CH$_2$OMe | (3-methyl-2-oxoimidazolidin-1-yl)methyl | CF$_3$ | |
| 7-318 | c-Pr | (3-methyl-2-oxoimidazolidin-1-yl)methyl | CF$_3$ | |
| 7-319 | CO$_2$Et | (3-methyl-2-oxoimidazolidin-1-yl)methyl | CF$_3$ | |
| 7-320 | CO$_2$Me | (3-methyl-2-oxoimidazolidin-1-yl)methyl | CF$_3$ | |
| 7-321 | benzyl | (3-methyl-2-oxoimidazolidin-1-yl)methyl | CF$_3$ | |
| 7-322 | phenyl | (3-methyl-2-oxoimidazolidin-1-yl)methyl | CF$_3$ | |
| 7-323 | pyrazin-2-yl | (3-methyl-2-oxoimidazolidin-1-yl)methyl | CF$_3$ | |
| 7-324 | 4-OMe—Ph | (3-methyl-2-oxoimidazolidin-1-yl)methyl | CF$_3$ | |
| 7-325 | 4-Cl—Ph | (3-methyl-2-oxoimidazolidin-1-yl)methyl | CF$_3$ | |
| 7-326 | t-Bu | (3-methyl-2-oxoimidazolidin-1-yl)methyl | CF$_3$ | |
| 7-327 | furan-2-yl | (3-methyl-2-oxoimidazolidin-1-yl)methyl | CF$_3$ | |
| 7-328 | i-Pr | (3-methyl-2-oxoimidazolidin-1-yl)methyl | CF$_3$ | |
| 7-329 | CH$_2$CH$_2$OMe | (3-methyl-2-oxoimidazolidin-1-yl)methyl | CF$_3$ | |
| 7-330 | CH$_2$CF$_3$ | (3-methyl-2-oxoimidazolidin-1-yl)methyl | CF$_3$ | |
| 7-331 | tetrahydrofuran-2-yl | (3-methyl-2-oxoimidazolidin-1-yl)methyl | CF$_3$ | |
| 7-332 | n-Pr | (3-methyl-2-oxoimidazolidin-1-yl)methyl | CF$_3$ | |
| 7-333 | CH$_2$OEt | (3-methyl-2-oxoimidazolidin-1-yl)methyl | CF$_3$ | |

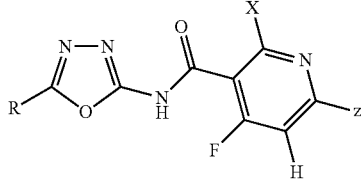

TABLE 7-continued

Compounds of the general formula (I) according to the invention in which A represents nitrogen, V represents hydrogen, W represents fluorine

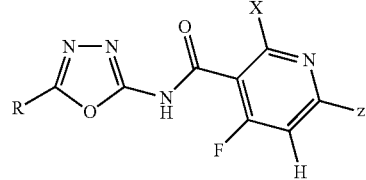

| No. | R | X | Z | Physical data ($^1$H-NMR, DMSO-$d_6$, 400 MHz) |
|---|---|---|---|---|
| 7-334 | cyclobutyl | (3-methyl-2-oxoimidazolidin-1-yl)methyl | CF$_3$ | |
| 7-335 | cyclopentyl | (3-methyl-2-oxoimidazolidin-1-yl)methyl | CF$_3$ | |
| 7-336 | Me$_2$N | (3-methyl-2-oxoimidazolidin-1-yl)methyl | CF$_3$ | |
| 7-337 | Ph—NH | (3-methyl-2-oxoimidazolidin-1-yl)methyl | CF$_3$ | |
| 7-338 | morpholin-1-yl | (3-methyl-2-oxoimidazolidin-1-yl)methyl | CF$_3$ | |
| 7-339 | H | (3-methoxy-4-methyl-5-oxo-4,5-dihydro-1H-1,2,4-triazol-1-yl)methyl | CF$_3$ | |
| 7-340 | Me | (3-methoxy-4-methyl-5-oxo-4,5-dihydro-1H-1,2,4-triazol-1-yl)methyl | CF$_3$ | |
| 7-341 | Et | (3-methoxy-4-methyl-5-oxo-4,5-dihydro-1H-1,2,4-triazol-1-yl)methyl | CF$_3$ | |
| 7-342 | CF$_3$ | (3-methoxy-4-methyl-5-oxo-4,5-dihydro-1H-1,2,4-triazol-1-yl)methyl | CF$_3$ | |
| 7-343 | CH$_2$OMe | (3-methoxy-4-methyl-5-oxo-4,5-dihydro-1H-1,2,4-triazol-1-yl)methyl | CF$_3$ | |
| 7-344 | c-Pr | (3-methoxy-4-methyl-5-oxo-4,5-dihydro-1H-1,2,4-triazol-1-yl)methyl | CF$_3$ | |
| 7-345 | CO$_2$Et | (3-methoxy-4-methyl-5-oxo-4,5-dihydro-1H-1,2,4-triazol-1-yl)methyl | CF$_3$ | |
| 7-346 | CO$_2$Me | (3-methoxy-4-methyl-5-oxo-4,5-dihydro-1H-1,2,4-triazol-1-yl)methyl | CF$_3$ | |
| 7-347 | benzyl | (3-methoxy-4-methyl-5-oxo-4,5-dihydro-1H-1,2,4-triazol-1-yl)methyl | CF$_3$ | |

TABLE 7-continued

Compounds of the general formula (I) according to the invention in which A represents nitrogen, V represents hydrogen, W represents fluorine

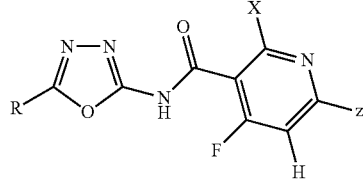

| No. | R | X | Z | Physical data ($^1$H-NMR, DMSO-$d_6$, 400 MHz) |
|---|---|---|---|---|
| 7-348 | phenyl | (3-methoxy-4-methyl-5-oxo-4,5-dihydro-1H-1,2,4-triazol-1-yl)methyl | CF$_3$ | |
| 7-349 | pyrazin-2-yl | (3-methoxy-4-methyl-5-oxo-4,5-dihydro-1H-1,2,4-triazol-1-yl)methyl | CF$_3$ | |
| 7-350 | 4-OMe—Ph | (3-methoxy-4-methyl-5-oxo-4,5-dihydro-1H-1,2,4-triazol-1-yl)methyl | CF$_3$ | |
| 7-351 | 4-Cl—Ph | (3-methoxy-4-methyl-5-oxo-4,5-dihydro-1H-1,2,4-triazol-1-yl)methyl | CF$_3$ | |
| 7-352 | t-Bu | (3-methoxy-4-methyl-5-oxo-4,5-dihydro-1H-1,2,4-triazol-1-yl)methyl | CF$_3$ | |
| 7-353 | furan-2-yl | (3-methoxy-4-methyl-5-oxo-4,5-dihydro-1H-1,2,4-triazol-1-yl)methyl | CF$_3$ | |
| 7-354 | i-Pr | (3-methoxy-4-methyl-5-oxo-4,5-dihydro-1H-1,2,4-triazol-1-yl)methyl | CF$_3$ | |
| 7-355 | CH$_2$CH$_2$OMe | (3-methoxy-4-methyl-5-oxo-4,5-dihydro-1H-1,2,4-triazol-1-yl)methyl | CF$_3$ | |
| 7-356 | CH$_2$CF$_3$ | (3-methoxy-4-methyl-5-oxo-4,5-dihydro-1H-1,2,4-triazol-1-yl)methyl | CF$_3$ | |
| 7-357 | tetrahydrofuran-2-yl | (3-methoxy-4-methyl-5-oxo-4,5-dihydro-1H-1,2,4-triazol-1-yl)methyl | CF$_3$ | |
| 7-358 | n-Pr | (3-methoxy-4-methyl-5-oxo-4,5-dihydro-1H-1,2,4-triazol-1-yl)methyl | CF$_3$ | |
| 7-359 | CH$_2$OEt | (3-methoxy-4-methyl-5-oxo-4,5-dihydro-1H-1,2,4-triazol-1-yl)methyl | CF$_3$ | |

TABLE 7-continued

Compounds of the general formula (I) according to the invention in which A represents nitrogen, V represents hydrogen, W represents fluorine

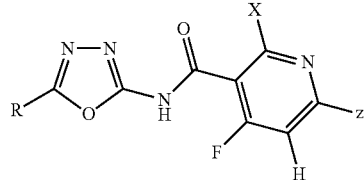

| No. | R | X | Z | Physical data ($^1$H-NMR, DMSO-$d_6$, 400 MHz) |
|---|---|---|---|---|
| 7-360 | cyclobutyl | (3-methoxy-4-methyl-5-oxo-4,5-dihydro-1H-1,2,4-triazol-1-yl)methyl | $CF_3$ | |
| 7-361 | cyclopentyl | (3-methoxy-4-methyl-5-oxo-4,5-dihydro-1H-1,2,4-triazol-1-yl)methyl | $CF_3$ | |
| 7-362 | $Me_2N$ | (3-methoxy-4-methyl-5-oxo-4,5-dihydro-1H-1,2,4-triazol-1-yl)methyl | $CF_3$ | |
| 7-363 | Ph—NH | (3-methoxy-4-methyl-5-oxo-4,5-dihydro-1H-1,2,4-triazol-1-yl)methyl | $CF_3$ | |
| 7-364 | morpholin-1-yl | (3-methoxy-4-methyl-5-oxo-4,5-dihydro-1H-1,2,4-triazol-1-yl)methyl | $CF_3$ | |
| 7-365 | i-Pr | Cl | Me | |

TABLE 8

Compounds according to the invention of the general formula (I), in which A represents CY, Z represents trifluoromethyl and R represents methyl

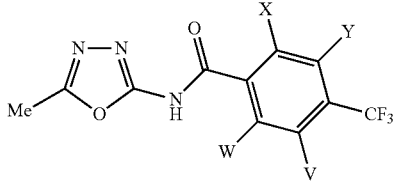

| No. | X | Y | V | W | Physical data |
|---|---|---|---|---|---|
| 8-1 | Cl | SOMe | H | Cl | |
| 8-2 | Cl | SOMe | H | Br | |
| 8-3 | Cl | SOMe | H | CN | |
| 8-4 | Cl | SOMe | H | $NO_2$ | |
| 8-5 | Cl | SOMe | H | Me | |
| 8-6 | Cl | SOMe | H | Et | |
| 8-7 | Cl | SOMe | H | iPr | |
| 8-8 | Cl | SOMe | H | cPr | |
| 8-9 | Cl | SOMe | H | tBu | |
| 8-10 | Cl | SOMe | H | $CF_3$ | |
| 8-11 | Cl | SOMe | H | $CHF_2t$ | |
| 8-12 | Cl | SOMe | H | $C_2F_5$ | |
| 8-13 | Cl | SOMe | H | $CH_2OMe$ | |
| 8-14 | Cl | SOMe | H | OMe | |
| 8-15 | Cl | SOMe | H | OEt | |
| 8-16 | Cl | SOMe | H | $OCF_3$ | |
| 8-17 | Cl | SOMe | H | SMe | |
| 8-18 | Cl | SOMe | H | SOMe | |
| 8-19 | Cl | SOMe | H | $SO_2Me$ | |
| 8-20 | Cl | SOMe | Cl | H | |
| 8-21 | Cl | SOMe | Br | H | |
| 8-22 | Cl | SOMe | CN | H | |
| 8-23 | Cl | SOMe | $NO_2$ | H | |
| 8-24 | Cl | SOMe | Me | H | |
| 8-25 | Cl | SOMe | Et | H | |
| 8-26 | Cl | SOMe | iPr | H | |
| 8-27 | Cl | SOMe | cPr | H | |
| 8-28 | Cl | SOMe | tBu | H | |
| 8-29 | Cl | SOMe | $CF_3$ | H | |
| 8-30 | Cl | SOMe | $CHF_2t$ | H | |
| 8-31 | Cl | SOMe | $C_2F_5$ | H | |
| 8-32 | Cl | SOMe | $CH_2OMe$ | H | |
| 8-33 | Cl | SOMe | OMe | H | |
| 8-34 | Cl | SOMe | OEt | H | |
| 8-35 | Cl | SOMe | $OCF_3$ | H | |
| 8-36 | Cl | SOMe | SMe | H | |
| 8-37 | Cl | SOMe | SOMe | H | |
| 8-38 | Cl | SOMe | $SO_2Me$ | H | |
| 8-39 | Me | $SO_2Me$ | H | Cl | |
| 8-40 | Me | $SO_2Me$ | H | Br | |
| 8-41 | Me | $SO_2Me$ | H | CN | |
| 8-42 | Me | $SO_2Me$ | H | $NO_2$ | |
| 8-43 | Me | $SO_2Me$ | H | Me | |
| 8-44 | Me | $SO_2Me$ | H | Et | |
| 8-45 | Me | $SO_2Me$ | H | iPr | |
| 8-46 | Me | $SO_2Me$ | H | cPr | |
| 8-47 | Me | $SO_2Me$ | H | tBu | |
| 8-48 | Me | $SO_2Me$ | H | $CF_3$ | |
| 8-49 | Me | $SO_2Me$ | H | $CHF_2t$ | |
| 8-50 | Me | $SO_2Me$ | H | $C_2F_5$ | |
| 8-51 | Me | $SO_2Me$ | H | $CH_2OMe$ | |
| 8-52 | Me | $SO_2Me$ | H | OMe | |
| 8-53 | Me | $SO_2Me$ | H | OEt | |
| 8-54 | Me | $SO_2Me$ | H | $OCF_3$ | |
| 8-55 | Me | $SO_2Me$ | H | SMe | |
| 8-56 | Me | $SO_2Me$ | H | SOMe | |
| 8-57 | Me | $SO_2Me$ | H | $SO_2Me$ | |
| 8-58 | Me | $SO_2Me$ | Cl | H | |
| 8-59 | Me | $SO_2Me$ | Br | H | |
| 8-60 | Me | $SO_2Me$ | CN | H | |
| 8-61 | Me | $SO_2Me$ | $NO_2$ | H | |
| 8-62 | Me | $SO_2Me$ | Me | H | |
| 8-63 | Me | $SO_2Me$ | Et | H | |
| 8-64 | Me | $SO_2Me$ | iPr | H | |
| 8-65 | Me | $SO_2Me$ | cPr | H | |
| 8-66 | Me | $SO_2Me$ | tBu | H | |
| 8-67 | Me | $SO_2Me$ | $CF_3$ | H | |
| 8-68 | Me | $SO_2Me$ | $CHF_2t$ | H | |
| 8-69 | Me | $SO_2Me$ | $C_2F_5$ | H | |
| 8-70 | Me | $SO_2Me$ | $CH_2OMe$ | H | |
| 8-71 | Me | $SO_2Me$ | OMe | H | |
| 8-72 | Me | $SO_2Me$ | OEt | H | |
| 8-73 | Me | $SO_2Me$ | $OCF_3$ | H | |
| 8-74 | Me | $SO_2Me$ | SMe | H | |
| 8-75 | Me | $SO_2Me$ | SOMe | H | |
| 8-76 | Me | $SO_2Me$ | $SO_2Me$ | H | |

B. FORMULATION EXAMPLES a) A dusting product is obtained by mixing 10 parts by weight of a compound of the formula (I) and/or salts thereof and 90 parts by weight of talc as an inert substance and comminuting the mixture in a hammer mill.

b) A readily water-dispersible, wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277 C), and grinding the mixture in a friction ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing
   75 parts by weight of a compound of the formula (I) and/or salts thereof,
   10 parts by weight of calcium lignosulfonate,
   5 parts by weight of sodium lauryl sulfate,
   3 parts by weight of polyvinyl alcohol and
   7 parts by weight of kaolin,
   grinding the mixture in a pinned-disk mill, and granulating the powder in a fluidized bed by spray application of water as a granulating liquid.

f) Water-dispersible granules are also obtained by homogenizing and precomminuting, in a colloid mill,
   25 parts by weight of a compound of the formula (I) and/or salts thereof,
   5 parts by weight of sodium 2,2'-dinaphthylmethane-6,6'-disulfonate
   2 parts by weight of sodium oleoylmethyltaurate,
   1 part by weight of polyvinyl alcohol,
   17 parts by weight of calcium carbonate and
   50 parts by weight of water,
   then grinding the mixture in a bead mill and atomizing and drying the resulting suspension in a spray tower by means of a one-phase nozzle.

C. BIOLOGICAL EXAMPLES

1. Pre-Emergence Herbicidal Action Against Harmful Plants

Seeds of monocotyledonous and dicotyledonous weed plants and crop plants are laid out in sandy loam soil in wood-fiber pots and covered with soil. The compounds of the invention, formulated in the form of wettable powders (WP) or as emulsion concentrates (EC), are then applied to the surface of the covering soil in the form of an aqueous suspension or emulsion at a water application rate equating to 600 to 800 l/ha, with addition of 0.2% wetting agent. After the treatment, the pots are placed in a greenhouse and kept under good growth conditions for the trial plants. The damage to the test plants is scored visually after a test period of 3 weeks by comparison with untreated controls (herbicidal activity in percent (%): 100% activity=the plants have died, 0% activity=like control plants).

In this test, for example, compounds no. 2-242 and 2-243 at an application rate of 320 g/ha each show at least 80% efficacy against *Echinochloa crus galli, Setaria viridis, Amaranthus retroflexus, Stellaria media, Veronica persica* and *Viola tricolor.*

2. Post-Emergence Herbicidal Action Against Harmful Plants

Seeds of monocotyledonous and dicotyledonous weed and crop plants are laid out in sandy loam soil in wood-fiber pots, covered with soil and cultivated in a greenhouse under good growth conditions. 2 to 3 weeks after sowing, the test plants are treated at the one-leaf stage. The compounds of the invention, formulated in the form of wettable powders (WP) or as emulsion concentrates (EC), are then sprayed onto the green parts of the plants in the form of an aqueous suspension or emulsion at a water application rate equating to 600 to 800 l/ha, with addition of 0.2% wetting agent. After the test plants have been left to stand in the greenhouse under optimal growth conditions for about 3 weeks, the action of the preparations is assessed visually in comparison to untreated controls (herbicidal action in percent (%): 100% activity=the plants have died, 0% activity=like control plants).

In this test, for example, compounds no. 2-242 and 2-243 at an application rate of 80 g/ha each show at least 80% efficacy against *Echinochloa crus galli, Setaria viridis, Abutilon theophrasti, Amaranthus retroflexus, Stellaria media* and *Viola tricolor.*

The invention claimed is:

1. An N-(1,3,4-oxadiazol-2-yl)arylcarboxamide of formula (I) or salt thereof

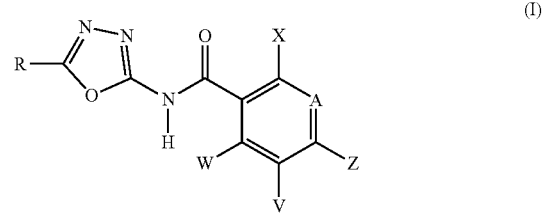

wherein the substituents have the following meanings:
A represents N or C—Y,
R represents hydrogen or $(C_1-C_6)$-alkyl,
X represents halogen or $(C_1-C_6)$-alkyl,
Y represents halogen, $(C_1-C_6)$-alkyl, $C(O)N(R^1)_2$, $S(O)_nR^2$, or 2-oxoazetidin-1-yl,
Z represents halogen, $(C_1-C_6)$-alkyl, halo-$(C_1-C_6)$-alkyl, or $R^2(O)_nS$,
V represents hydrogen, halogen or $(C_1-C_6)$-alkyl,
W represents hydrogen, halogen or $(C_1-C_6)$-haloalkyl,
with the proviso that in each case at least one of the radicals V and W does not represent hydrogen,
$R^1$ represents hydrogen, $(C_1-C_6)$-alkyl, $(C_1-C_6)$-haloalkyl, or $(C_3-C_6)$-cycloalkyl-$(C_1-C_6)$-alkyl,
$R^2$ represents $(C_1-C_6)$-alkyl, and
n represents 0, 1 or 2,
with the proviso that the compounds
4-bromo-2,6-difluoro-2-N-(5-methyl-1,3,4-oxadiazol-2-yl)benzamide and
4-bromo-2,6-difluoro-2-N-(5-cyclopropyl-1,3,4-oxadiazol-2-yl)benzamide
are excluded.

2. The N-(1,3,4-oxadiazol-2-yl)arylcarboxamide as claimed in claim 1, wherein
R represents hydrogen, or $(C_1-C_4)$-alkyl,
V represents hydrogen, halogen, or $(C_1-C_4)$-alkyl, and
W represents halogen or $(C_1-C_4)$-haloalkyl.

3. The N-(1,3,4-oxadiazol-2-yl)arylcarboxamide as claimed in claim 1, wherein
R represents hydrogen, methyl, or ethyl,
X represents fluorine, chlorine, bromine, iodine, methyl, ethyl, n-propyl, or isopropyl,
Y represents fluorine, chlorine, bromine, iodine, $(C_1-C_6)$-alkyl, or 2-oxoazetidin-1-yl,
Z represents fluorine, chlorine, bromine iodine, methyl, ethyl, n-propyl, isopropyl, trifluoromethyl, difluoromethyl, chlorodifluoromethyl, dichlorofluoromethyl, trichloromethyl, pentafluoroethyl, or heptafluoroisopropyl,
V represents hydrogen, fluorine, or methyl and,
W represents fluorine.

4. The N-(1,3,4-oxadiazol-2-yl)arylcarboxamide as claimed in claim 1, wherein
A represents C—Y,
V represents hydrogen, and
W represents fluorine.

5. The N-(1,3,4-oxadiazol-2-yl)arylcarboxamide as claimed in claim 1, wherein
A represents C—Y,
R represents hydrogen, methyl, or ethyl,
X represents fluorine, chlorine, bromine, iodine, methyl, ethyl, n-propyl, or isopropyl,
V represents hydrogen, and
W represents fluorine.

6. The N-(1,3,4-oxadiazol-2-yl)arylcarboxamide as claimed in claim 5, wherein
Y represents $S(O)_n R^2$, and
Z represents trifluoromethyl, difluoromethyl or pentafluoroethyl.

7. The N-(1,3,4-oxadiazol-2-yl)arylcarboxamide as claimed in claim 5, wherein
X represents fluorine, chlorine, bromine, methyl, ethyl, n-propyl, or isopropyl,
Y represents fluorine, chlorine, methyl ethyl, propyl, isopropyl, $CONMe_2$, $S(O)Me$, $S(O)Et$, $So_2Me$, or $SO_2Et$,
and
Z represents fluorine, chlorine, bromine, iodine, $CF_3$, SMe, SEt, SOMe, SOEt, $SO_2Me$, or $SO_2Et$.

8. The N-(1,3,4-oxadiazol-2-yl)arylcarboxamide as claimed in claim 1, wherein
A represents N,
V represents hydrogen,
W represents fluorine, and
Z represents $CF_3$.

9. An herbicidal composition, comprising an herbicidally active content of at least one compound of formula (I) as claimed in claim 1.

10. The herbicidal composition as claimed in claim 9 in a mixture with one or more formulation auxiliaries.

11. The herbicidal composition as claimed in claim 9, comprising at least one further pesticidally active substance from the group consisting of insecticides, acaricides, herbicides, fungicides, safeners, and growth regulators.

12. The herbicidal composition as claimed in claim 11, comprising a safener.

13. The herbicidal composition as claimed in claim 12, comprising cyprosulfamide, cloquintocet-mexyl, mefenpyr-diethyl or isoxadifen-ethyl.

14. The herbicidal composition as claimed in claim 9, comprising a further herbicide.

15. A method for controlling monocotyledonous or dicotyledonous weeds, comprising applying an effective amount of at least one compound of formula (I) as claimed in claim 1 or of a herbicidal composition comprising the at least one compound of formula (I) is applied to the weeds or to the site of the weeds.

16. A product comprising the compound of formula (I) as claimed in claim 1 or an herbicidal composition comprising the compound of formula (I) for controlling one or more monocotyledonous or dicotyledonous weeds.

* * * * *